US012767694B2

(12) United States Patent
Plasterk

(10) Patent No.: US 12,767,694 B2
(45) Date of Patent: Oct. 20, 2026

(54) CANCER VACCINES FOR KIDNEY CANCER

(71) Applicant: CureVac Netherlands B.V., Amsterdam (NL)

(72) Inventor: Ronald Hans Anton Plasterk, Amsterdam (NL)

(73) Assignee: CureVac Netherlands B.V., Amsterdam (NL)

( * ) Notice: Subject to any disclaimer, the term of this patent is extended or adjusted under 35 U.S.C. 154(b) by 1115 days.

(21) Appl. No.: 17/263,287

(22) PCT Filed: Jul. 25, 2019

(86) PCT No.: PCT/NL2019/050493
§ 371 (c)(1),
(2) Date: Jan. 26, 2021

(87) PCT Pub. No.: WO2020/022900
PCT Pub. Date: Jan. 30, 2020

(65) Prior Publication Data

US 2021/0213116 A1 Jul. 15, 2021

(30) Foreign Application Priority Data

Jul. 26, 2018 (NL) .................................... 2021400
Jan. 24, 2019 (NL) .................................... 2022447
Apr. 5, 2019 (EP) .................................... 19167617

(51) Int. Cl.
*C07K 14/47* (2006.01)
*A61K 39/00* (2006.01)
*A61K 40/11* (2025.01)
*A61K 40/42* (2025.01)
*C07K 16/30* (2006.01)
*C12N 5/0783* (2010.01)
*C12Q 1/6886* (2018.01)

(52) U.S. Cl.
CPC ...... *C07K 14/4748* (2013.01); *A61K 39/0011* (2013.01); *A61K 40/11* (2025.01); *A61K 40/4201* (2025.01); *C07K 16/3038* (2013.01); *C12N 5/0636* (2013.01); *C12Q 1/6886* (2013.01); *A61K 2039/868* (2018.08); *C12Q 2600/156* (2013.01)

(58) Field of Classification Search
CPC .......... A61K 39/0011; A61K 2039/868; A61K 39/4611; A61K 39/464401; A61K 2039/812; A61K 2039/836; C07K 14/4748; C07K 16/3038; C12N 5/0636; C12Q 1/6886; C12Q 2600/156; G01N 33/57438
See application file for complete search history.

(56) References Cited

U.S. PATENT DOCUMENTS

| | | | |
|---|---|---|---|
| 2007/0083334 | A1 | 4/2007 | Mintz et al. |
| 2016/0069895 | A1 | 3/2016 | Delamarre et al. |
| 2016/0101170 | A1 | 4/2016 | Hacohen et al. |
| 2017/0028043 | A1 | 2/2017 | Benz et al. |
| 2017/0028044 | A1 | 2/2017 | Soon-Shiong et al. |
| 2017/0032082 | A1 | 2/2017 | Nguyen et al. |
| 2017/0032103 | A1 | 2/2017 | Nguyen et al. |
| 2017/0202939 | A1 | 7/2017 | Carreno et al. |
| 2017/0312351 | A1 | 11/2017 | Niazi et al. |
| 2018/0064793 | A1 | 3/2018 | Mcgranahan et al. |
| 2018/0078624 | A1 | 3/2018 | Zhou et al. |
| 2018/0078625 | A1 | 3/2018 | Moon et al. |
| 2018/0318409 | A1 | 11/2018 | Valiante et al. |
| 2018/0340944 | A1 | 11/2018 | Han et al. |
| 2019/0022202 | A1 | 1/2019 | Granum et al. |
| 2019/0030147 | A1 | 1/2019 | Artomov et al. |
| 2019/0060428 | A1 | 2/2019 | Fritsch et al. |
| 2019/0083593 | A1 | 3/2019 | Sahin et al. |
| 2019/0091316 | A1 | 3/2019 | Soon-Shiong et al. |

FOREIGN PATENT DOCUMENTS

| | | | |
|---|---|---|---|
| WO | 1995032731 | A2 | 12/1995 |
| WO | 20040111075 | A2 | 12/2004 |
| WO | 2011143656 | A2 | 11/2011 |
| WO | 2012159754 | A2 | 11/2012 |
| WO | 2014168874 | A2 | 10/2014 |
| WO | 2015095811 | A2 | 6/2015 |
| WO | 2016040900 | A1 | 3/2016 |
| WO | 2016154544 | A1 | 9/2016 |
| WO | 2016172722 | A1 | 10/2016 |
| WO | 2016187508 | A2 | 11/2016 |
| WO | 2016201049 | A2 | 12/2016 |
| WO | 2017020026 | A1 | 2/2017 |

(Continued)

OTHER PUBLICATIONS

Hurley et al., Tissue Antigens; 1997, 50:401 (Year: 1997).*
Hurley et al., Tissue Antigens; 1997, 50:401 (Year: 2014).*
Orfanelli, T. et al., "Shared tumor antigens in uterine cancers with microsatellite instability: Putative targets for immunotherapeutic approaches", Gynecologic Oncology, Jun. 2019, 154(1):91, DOI: 10.1016/j.ygyno.2019.04.214.

(Continued)

*Primary Examiner* — Julie Wu
*Assistant Examiner* — Sydney Van Druff
(74) *Attorney, Agent, or Firm* — Adams & Reese LLP

(57) ABSTRACT

The invention relates to the field of cancer, in particular kidney cancer. In particular, it relates to the field of immune system directed approaches for tumor reduction and control. Some aspects of the invention relate to vaccines, vaccinations and other means of stimulating an antigen specific immune response against a tumor in individuals. Such vaccines comprise neoantigens resulting from frameshift mutations that bring out-of-frame sequences of the BAP1, PBRM1, SETD2, and VHL genes in-frame. Such vaccines are also useful for 'off the shelf' use.

11 Claims, 35 Drawing Sheets

Specification includes a Sequence Listing.

(56) References Cited

FOREIGN PATENT DOCUMENTS

| | | | | |
|---|---|---|---|---|
| WO | 2017106638 A1 | | 6/2017 | |
| WO | 2017118702 A1 | | 7/2017 | |
| WO | 2017139694 A1 | | 8/2017 | |
| WO | 2017177207 A1 | | 10/2017 | |
| WO | WO-2017173321 A1 | * | 10/2017 | ......... A61K 39/0011 |
| WO | 2017194170 A1 | | 11/2017 | |
| WO | 2017223085 A2 | | 12/2017 | |
| WO | 2018015433 A2 | | 1/2018 | |
| WO | 2018026896 A1 | | 2/2018 | |
| WO | 2018102584 A1 | | 6/2018 | |
| WO | 2018136664 A1 | | 7/2018 | |
| WO | 2018144082 A1 | | 8/2018 | |
| WO | 2018144775 A1 | | 8/2018 | |
| WO | 2018195357 A1 | | 10/2018 | |
| WO | 2018200389 A1 | | 11/2018 | |
| WO | 2018213803 A1 | | 11/2018 | |
| WO | 2018223092 A1 | | 12/2018 | |
| WO | 2018223094 A1 | | 12/2018 | |
| WO | 2018224405 A1 | | 12/2018 | |
| WO | 2018234516 A2 | | 12/2018 | |
| WO | 2019008364 A1 | | 1/2019 | |
| WO | 2019012082 A1 | | 1/2019 | |
| WO | 2019036043 A2 | | 2/2019 | |
| WO | 2019126186 A1 | | 6/2019 | |

OTHER PUBLICATIONS

Roudko, V. et al., "Widespread immunogenic poly-epitope frameshift mutations in microsatellite unstable tumors", bioRxiv 2019; doi: https://doi.org/10.1101/662262; pp. 1-53.

Hartmaier, R. et al., "Genomic analysis of 63,220 tumors reveals insights into tumor uniqueness and targeted cancer immunotherapy strategies", Genome Medicine, BioMed Central, vol. 9, Article No. 16 (2017), pp. 1-9.

Batista, M.T. et al., "Abstract 1463: Fast vaccines based on frameshift neoantigens may have advantages over personal vaccines", Proceedings of American Association for Cancer Research Annual Meeting 2019, Mar. 29, 2019, vol. 79, Nr.:13, p. 1463.

Zhang, J. et al., "Using Frameshift Peptide Arrays for Cancer Neo-Antigens Screening", Scientific Reports, vol. 8, No. 1, (2018), pp. 1-10.

Koster, J. et al., "A library of Neo Open Reading Frame peptides (NOPs) as a sustainable resource of common neoantigens in up to 50% of cancer patients", Scientific Reports, 2019, vol. 9, Nr: 1.

Fisher, R. et al., "Cancer heterogeneity: implications for targeted therapeutics", British Journal of Cancer, Feb. 1, 2013, Nature Publishing Group, GB—ISSN 0007-0920, vol. 108, Nr:3, pp. 479-485.

Schwitalle, Y. et al., "Immunogenic peptides generated by frameshift mutations in DNA mismatch repair-deficient cancer cells", Cancer Immun. 2004 Academy of Cancer Immunology, CH-ISSN 1424-9734, vol. 4, Nr:1, pp. 1-10.

Luhui, S. et al., "Abstract 469: Progress towards developing a universal, prophylactic cancer vaccine.", American Association for Cancer Research; vol. 73, No. 8, Suppl. 1, Apr. 2013 (Apr. 1, 2013).

Linnebacher et al., "Frameshift peptide-derived T-cell epitopes: a source of novel tumor-specific antigens", Int. J. Cancer: 93, pp. 6-11 (2001).

Schumacher et al., "Neoantigens in cancer immunotherapy", Science, 2015, vol. 348, Issue 6230, pp. 69-74.

Rahma et al., "A pilot clinical trial testing mutant von Hippel-Lindau peptide as a novel immune therapy in metastatic Renal Cell Carcinoma", Journal of Translational Medicine, 2010, 8:8, 9 pages.

Hacohen et al., "Getting Personal with Neoantigen-Based Therapeutic Cancer Vaccines", Cancer Immunol. Res., Jul. 2013; 1(1): 11-15, pp. 1-8.

Ito et al., "Cancer Neoantigens: A Promising Source of Immunogens for Cancer Immunotherapy", J Clin Cell Immunol 2015, 6:2, pp. 1-7.

Tomczak et al., "The Cancer Genome Atlas (TCGA): an immeasurable source of knowledge", Contemp Oncol (Pozn). 2015, 19 (1A): A68-A77.

The Cancer Genome Atlas Research Network. "Comprehensive molecular characterization of clear cell renal cell carcinoma", Nature (2013), 499, pp. 43-49.

Pavlopoulou et al., "Human cancer databases (review)", Oncology Reports, 33: pp. 3-18, 2015.

Rammensee, H-G et al., "Cancer Vaccines: Some Basic Considerations", Genomic and Personalized Medicine, 2009, Elsevier, pp. 573-589.

Rajasagi, M. et al., "Systematic identification of personal tumor-specific neoantigens in chronic lymphocytic leukemia", Blood, 2014, ISSN 0006-4971, vol. 124, Nr: 3, pp. 453-462.

Van Vught, R. et al., "Site-Specific Functionalization of Proteins and Their Applications to Therapeutic Antibodies", Computational and Structural Biotechnology Journal, (2014), 9(14), 13 pgs. (Copy A).

Boutureira, O. et al., "Advances in Chemical Protein Modification", Chemical Reviews, (2015), 115, pp. 2174-2195.

Yu, K. et al., "Synthetic Fusion Protein Design and Applications", Biotechnology Advances, (2015), 33, 155-164 (abstract only).

Kosobokova, E. N. et al., "Overview of Fusion Tags for Recombinant Proteins", Biochemistry (Moscow), (2016), (81)3, pp. 1357-1369 (abstract only).

Chen, X. et al., "Fusion Protein Linkers: Property, Design and Functionality", Advanced Drug Delivery Reviews, (2013), 65(10); pp. 1357-1369.

Ebina, T. et al., "Loop-Length-Dependent SVM Prediction of Domain Linkers for High-Throughput Structural Proteomics", Biopolymers, (2009), 92(1), pp. 1-8 (abstract only).

Richman, S. A. et al., "Structural Features of T Cell Receptor Variable Regions That Enhance Domain Stability and Enable Expression as Single-Chain VaVB Fragments", Molecular Immunology, (2009), 46(5), pp. 902-916.

Guedan, S. et al., "Engineering and Design of Chimeric Antigen Receptors", Molecular Therapy: Methods and Clinical Development, (2019), 12, pp. 145-156.

Van Vught, R. et al., "Site-Specific Functionalization of Proteins and Their Applications to Therapeutic Antibodies", Computational and Structural Biotechnology Journal, (2014), 9(14), 12 pgs. (Copy B).

* cited by examiner

Fig. 8 (Cont. I)
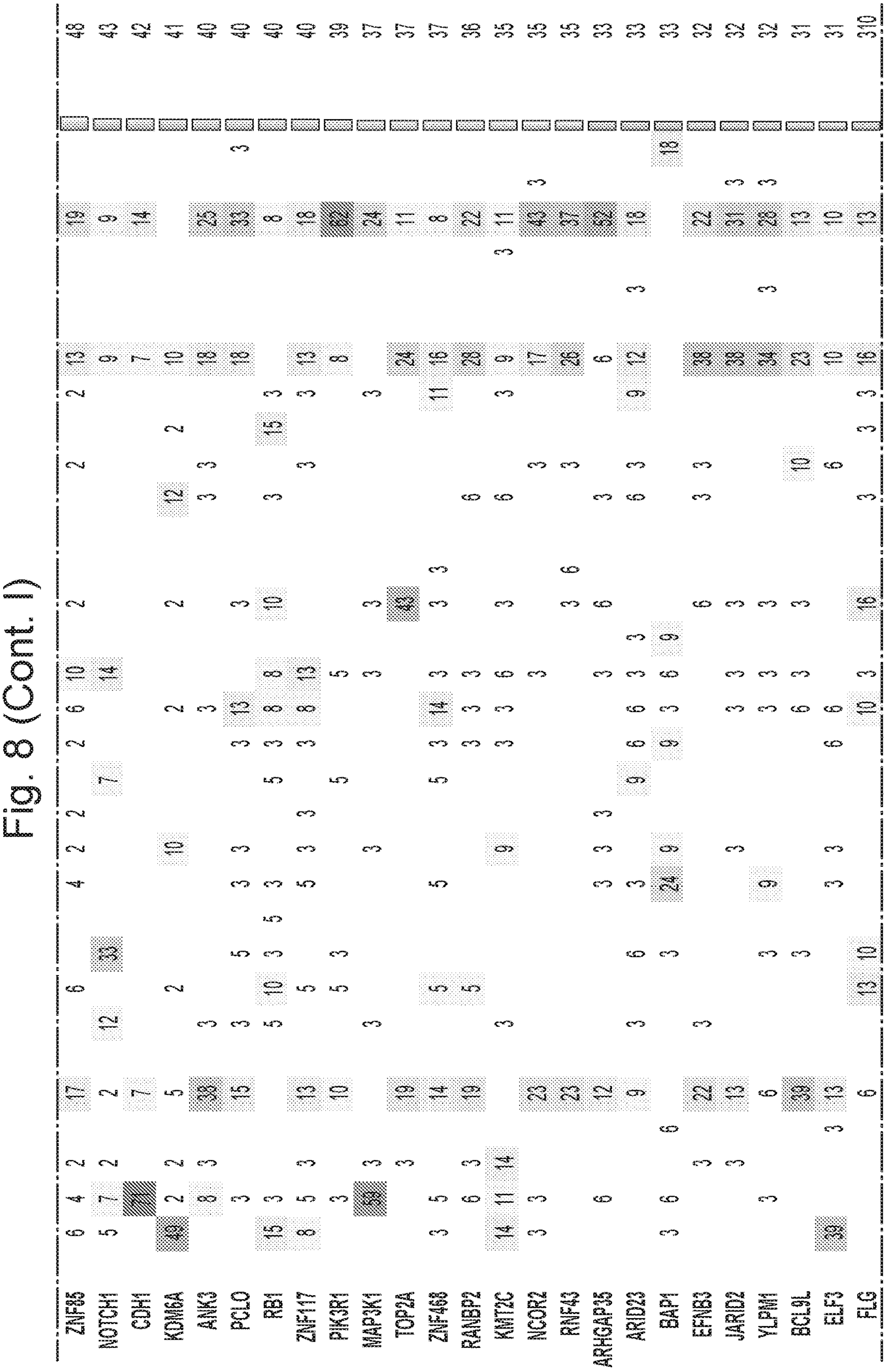

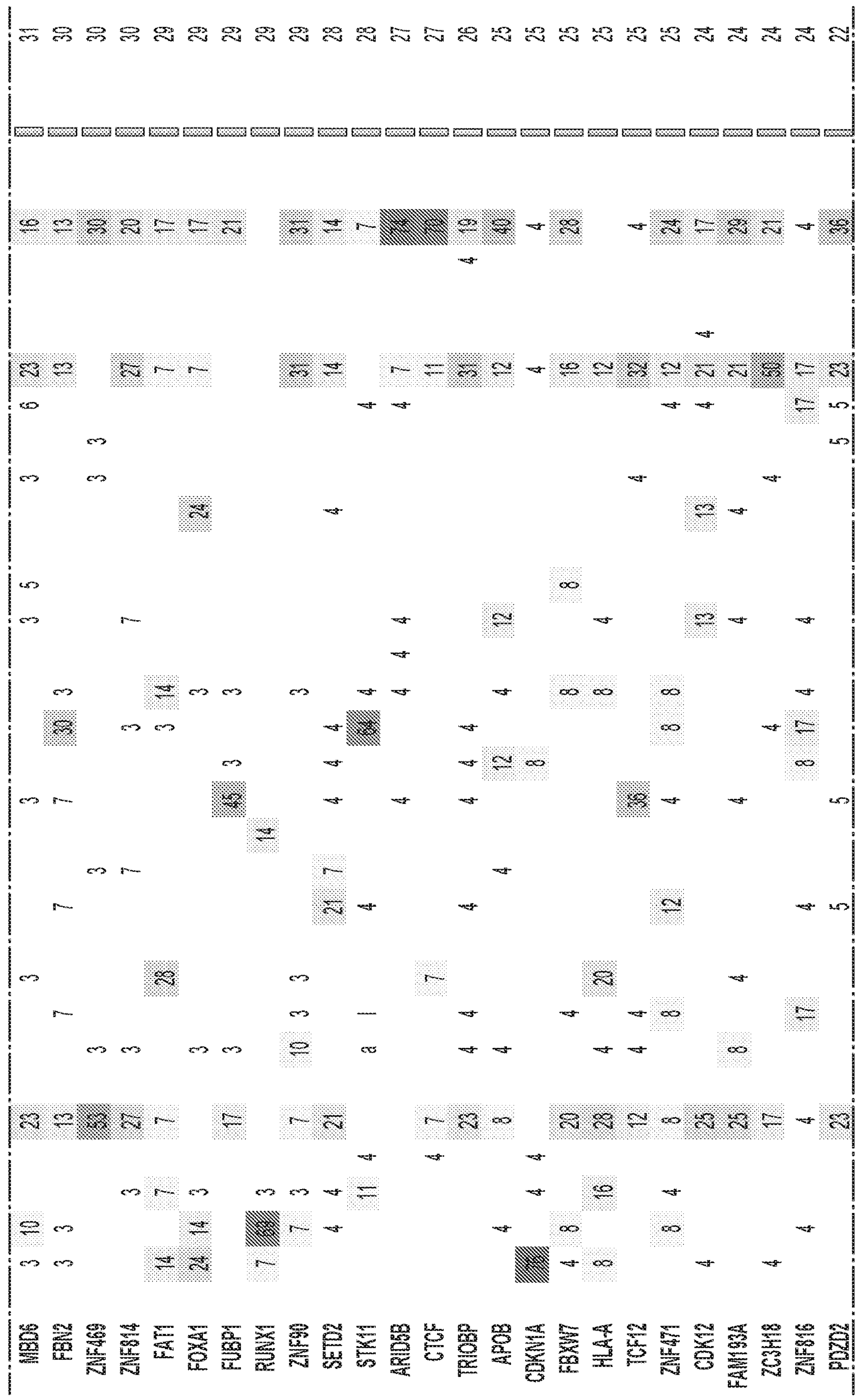
Fig. 8 (Cont. II)

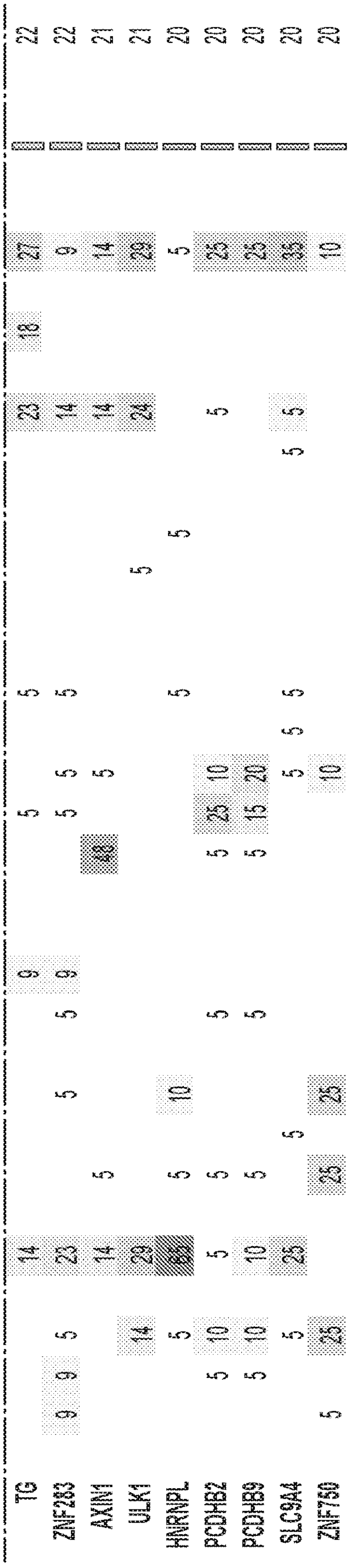
Fig. 8 (Cont. III)

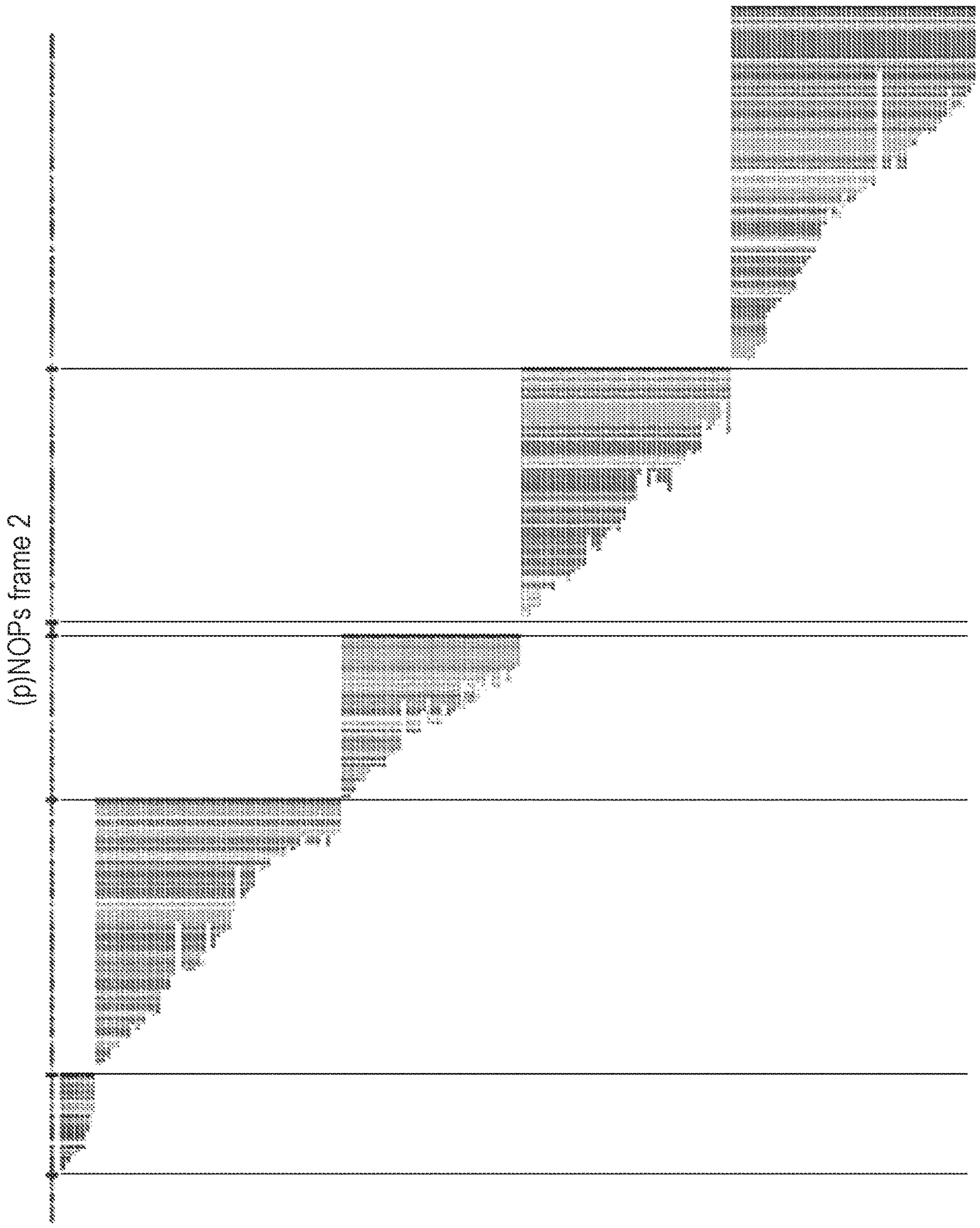
Fig. 9D (Cont. I)

Fig. 9D. (Cont II)
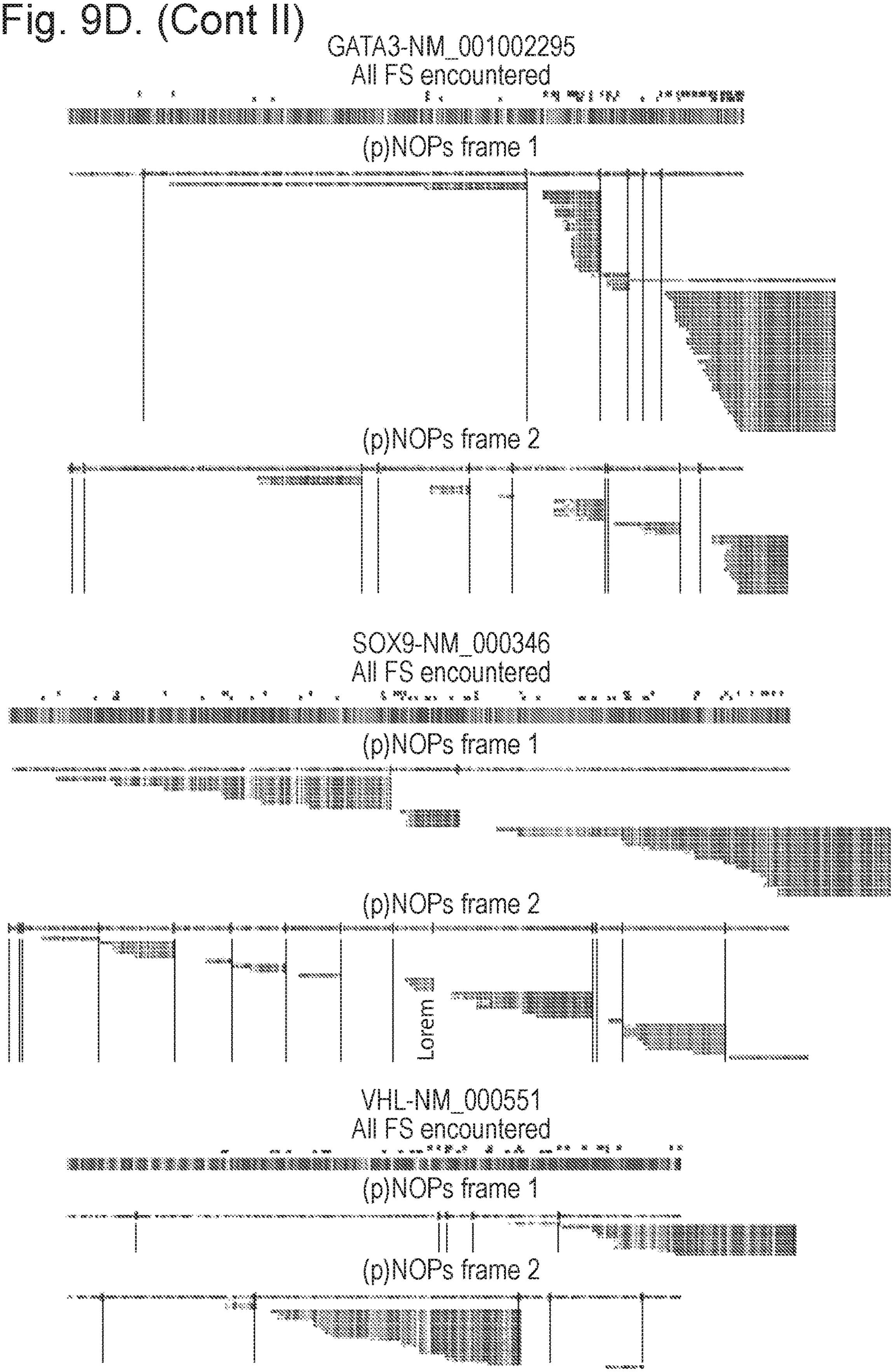

CANCER VACCINES FOR KIDNEY CANCER

FIELD OF THE INVENTION

The invention relates to the field of cancer, in particular kidney cancer. In particular, it relates to the field of immune system directed approaches for tumor reduction and control. Some aspects of the invention relate to vaccines, vaccinations and other means of stimulating an antigen specific immune response against a tumor in individuals. Such vaccines comprise neoantigens resulting from frameshift mutations that bring out-of-frame sequences of the BAP1, PBRM1, SETD2, and VHL genes in-frame. Such vaccines are also useful for 'off the shelf' use.

BACKGROUND OF THE INVENTION

There are a number of different existing cancer therapies, including ablation techniques (e.g., surgical procedures and radiation) and chemical techniques (e.g., pharmaceutical agents and antibodies), and various combinations of such techniques. Despite intensive research such therapies are still frequently associated with serious risk, adverse or toxic side effects, as well as varying efficacy.

There is a growing interest in cancer therapies that aim to target cancer cells with a patient's own immune system (such as cancer vaccines or checkpoint inhibitors, or T-cell based immunotherapy). Such therapies may indeed eliminate some of the known disadvantages of existing therapies, or be used in addition to the existing therapies for additional therapeutic effect. Cancer vaccines or immunogenic compositions intended to treat an existing cancer by strengthening the body's natural defenses against the cancer and based on tumor-specific neoantigens hold great promise as next-generation of personalized cancer immunotherapy. Evidence shows that such neoantigen-based vaccination can elicit T-cell responses and can cause tumor regression in patients.

Typically the immunogenic compositions/vaccines are composed of tumor antigens (antigenic peptides or nucleic acids encoding them) and may include immune stimulatory molecules like cytokines that work together to induce antigen-specific cytotoxic T-cells that target and destroy tumor cells. Vaccines containing tumor-specific and patient-specific neoantigens require the sequencing of the patients' genome and tumor genome in order to determine whether the neoantigen is tumor specific, followed by the production of personalized compositions. Sequencing, identifying the patient's specific neoantigens and preparing such personalized compositions may require a substantial amount of time, time which may unfortunately not be available to the patient, given that for some tumors the average survival time after diagnosis is short, sometimes around a year or less.

Accordingly, there is a need for improved methods and compositions for providing subject-specific immunogenic compositions/cancer vaccines. In particular it would be desirable to have available a vaccine for use in the treatment of cancer, wherein such vaccine is suitable for treatment of a larger number of patients, and can thus be prepared in advance and provided off the shelf. There is a clear need in the art for personalized vaccines which induce an immune response to tumor specific neoantigens. One of the objects of the present disclosure is to provide personalized cancer vaccines that can be provided off the shelf. An additional object of the present disclosure is to provide cancer vaccines that can be provided prophylactically. Such vaccines are especially useful for individuals that are at risk of developing cancer.

SUMMARY OF THE INVENTION

In a preferred embodiment, the disclosure provides a vaccine for use in the treatment of kidney cancer, said vaccine comprising:

(i) a peptide, or a collection of tiled peptides, having the amino acid sequence selected from Sequence 1, an amino acid sequence having 90% identity to Sequence 1, or a fragment thereof comprising at least 10 consecutive amino acids of Sequence 1; and a peptide, or a collection of tiled peptides, having the amino acid sequence selected from Sequence 2, an amino acid sequence having 90% identity to Sequence 2, or a fragment thereof comprising at least 10 consecutive amino acids of Sequence 2; preferably also comprising a peptide, or a collection of tiled peptides, having the amino acid sequence selected from Sequence 3, an amino acid sequence having 90% identity to Sequence 3, or a fragment thereof comprising at least 10 consecutive amino acids of Sequence 3;

a peptide, or a collection of tiled peptides, having the amino acid sequence selected from Sequence 4, an amino acid sequence having 90% identity to Sequence 4, or a fragment thereof comprising at least 10 consecutive amino acids of Sequence 4;

a peptide, or a collection of tiled peptides, having the amino acid sequence selected from Sequence 5, an amino acid sequence having 90% identity to Sequence 5, or a fragment thereof comprising at least 10 consecutive amino acids of Sequence 5;

a peptide, or a collection of tiled peptides, having the amino acid sequence selected from Sequence 6, an amino acid sequence having 90% identity to Sequence 6, or a fragment thereof comprising at least 10 consecutive amino acids of Sequence 6; and/or a peptide, or a collection of tiled peptides, having the amino acid sequence selected from Sequence 7, an amino acid sequence having 90% identity to Sequence 7, or a fragment thereof comprising at least 10 consecutive amino acids of Sequence 7;

(ii) a peptide, or a collection of tiled peptides, having the amino acid sequence selected from Sequence 19, an amino acid sequence having 90% identity to Sequence 19, or a fragment thereof comprising at least 10 consecutive amino acids of Sequence 19; and a peptide, or a collection of tiled peptides, having the amino acid sequence selected from Sequence 20, an amino acid sequence having 90% identity to Sequence 20, or a fragment thereof comprising at least 10 consecutive amino acids of Sequence 20;

(iii) a peptide, or a collection of tiled peptides, having the amino acid sequence selected from Sequence 189, an amino acid sequence having 90% identity to Sequence 189, or a fragment thereof comprising at least 10 consecutive amino acids of Sequence 189; and a peptide, or a collection of tiled peptides, having the amino acid sequence selected from any one of Sequences 190-192, an amino acid sequence having 90% identity to Sequences 190-192, or a fragment thereof comprising at least 10 consecutive amino acids of Sequences 190-192; and/or (iv) a peptide, or a collection of tiled peptides, having the amino acid sequence selected from Sequence 311, an amino acid sequence having 90% identity to Sequence 311, or a fragment thereof comprising at least 10 consecutive amino acids of Sequence 311; and a peptide, or a collection of tiled peptides, having the amino acid sequence selected from Sequence 312, an amino acid sequence having 90% identity to Sequence 312, or a fragment thereof comprising at least 10 consecutive amino acids of Sequence 312; preferably also comprising a peptide, or a collection of tiled peptides, having the amino acid sequence selected from Sequence 313, an amino acid sequence having 90% identity to Sequence 313, or a fragment thereof comprising at least 10 consecutive amino acids of Sequence 313.

In a preferred embodiment, the disclosure provides a collection of frameshift-mutation peptides comprising:

(i) a peptide, or a collection of tiled peptides, having the amino acid sequence selected from Sequence 1, an amino acid sequence having 90% identity to Sequence 1, or a fragment thereof comprising at least 10 consecutive amino acids of Sequence 1; and a peptide, or a collection of tiled peptides, having the amino acid sequence selected from Sequence 2, an amino acid sequence having 90% identity to Sequence 2, or a fragment thereof comprising at least 10 consecutive amino acids of Sequence 2; preferably also comprising a peptide, or a collection of tiled peptides, having the amino acid sequence selected from Sequence 3, an amino acid sequence having 90% identity to Sequence 3, or a fragment thereof comprising at least 10 consecutive amino acids of Sequence 3;

a peptide, or a collection of tiled peptides, having the amino acid sequence selected from Sequence 4, an amino acid sequence having 90% identity to Sequence 4, or a fragment thereof comprising at least 10 consecutive amino acids of Sequence 4;

a peptide, or a collection of tiled peptides, having the amino acid sequence selected from Sequence 5, an amino acid sequence having 90% identity to Sequence 5, or a fragment thereof comprising at least 10 consecutive amino acids of Sequence 5;

a peptide, or a collection of tiled peptides, having the amino acid sequence selected from Sequence 6, an amino acid sequence having 90% identity to Sequence 6, or a fragment thereof comprising at least 10 consecutive amino acids of Sequence 6; and/or a peptide, or a collection of tiled peptides, having the amino acid sequence selected from Sequence 7, an amino acid sequence having 90% identity to Sequence 7, or a fragment thereof comprising at least 10 consecutive amino acids of Sequence 7;

(ii) a peptide, or a collection of tiled peptides, having the amino acid sequence selected from Sequence 19, an amino acid sequence having 90% identity to Sequence 19, or a fragment thereof comprising at least 10 consecutive amino acids of Sequence 19; and a peptide, or a collection of tiled peptides, having the amino acid sequence selected from Sequence 20, an amino acid sequence having 90% identity to Sequence 20, or a fragment thereof comprising at least 10 consecutive amino acids of Sequence 20;

(iii) a peptide, or a collection of tiled peptides, having the amino acid sequence selected from Sequence 189, an amino acid sequence having 90% identity to Sequence 189, or a fragment thereof comprising at least 10 consecutive amino acids of Sequence 189; and a peptide, or a collection of tiled peptides, having the amino acid sequence selected from any one of Sequences 190-192, an amino acid sequence having 90% identity to Sequences 190-192, or a fragment thereof comprising at least 10 consecutive amino acids of Sequences 190-192; and/or (iv) a peptide, or a collection of tiled peptides, having the amino acid sequence selected from Sequence 311, an amino acid sequence having 90% identity to Sequence 311, or a fragment thereof comprising at least 10 consecutive amino acids of Sequence 311; and a peptide, or a collection of tiled peptides, having the amino acid sequence selected from Sequence 312, an amino acid sequence having 90% identity to Sequence 312, or a fragment thereof comprising at least 10 consecutive amino acids of Sequence 312; preferably also comprising a peptide, or a collection of tiled peptides, having the amino acid sequence selected from Sequence 313, an amino acid sequence having 90% identity to Sequence 313, or a fragment thereof comprising at least 10 consecutive amino acids of Sequence 313.

In a preferred embodiment, the disclosure provides a peptide comprising an amino acid sequence selected from the groups:

(i) Sequences 1-18, an amino acid sequence having 90% identity to Sequences 1-18, or a fragment thereof comprising at least 10 consecutive amino acids of Sequences 1-18;

(ii) Sequences 19-188, an amino acid sequence having 90% identity to Sequences 19-188, or a fragment thereof comprising at least 10 consecutive amino acids of Sequences 19-188;

(iii) Sequences 189-310, an amino acid sequence having 90% identity to Sequences 189-310, or a fragment thereof comprising at least 10 consecutive amino acids of Sequences 189-310; and (iv) Sequences 311-352, an amino acid sequence having 90% identity to Sequences 311-352, or a fragment thereof comprising at least 10 consecutive amino acids of Sequences 311-352.

In some embodiments of the disclosure, the peptides are linked, preferably wherein said peptides are comprised within the same polypeptide.

In a preferred embodiment, the disclosure provides one more isolated nucleic acid molecules encoding the peptides or collection of peptides as disclosed herein. In a preferred embodiment, the disclosure provides one or more vectors comprising the nucleic acid molecules disclosed herein, preferably wherein the vector is a viral vector. In a preferred embodiment, the disclosure provides a host cell comprising the isolated nucleic acid molecules or the vectors as disclosed herein.

In a preferred embodiment, the disclosure provides a binding molecule or a collection of binding molecules that bind the peptide or collection of peptides disclosed herein, where in the binding molecule is an antibody, a T-cell receptor, or an antigen binding fragment thereof.

In a preferred embodiment, the disclosure provides a chimeric antigen receptor or collection of chimeric antigen receptors each comprising i) a T cell activation molecule; ii) a transmembrane region; and iii) an antigen recognition moiety; wherein said antigen recognition moieties bind the peptide or collection of peptides disclosed herein. In a preferred embodiment, the disclosure provides a host cell or combination of host cells that express the binding molecule or collection of binding molecules, or the chimeric antigen receptor or collection of chimeric antigen receptors as disclosed herein.

In a preferred embodiment, the disclosure provides a vaccine or collection of vaccines comprising the peptide or collection of peptides, the nucleic acid molecules, the vectors, or the host cells as disclosed herein; and a pharmaceutically acceptable excipient and/or adjuvant, preferably an immune-effective amount of adjuvant.

In a preferred embodiment, the disclosure provides the vaccines as disclosed herein for use in the treatment of kidney cancer in an individual. In a preferred embodiment, the disclosure provides the vaccines as disclosed herein for prophylactic use in the prevention of kidney cancer in an individual. In a preferred embodiment, the disclosure provides the vaccines as disclosed herein for use in the preparation of a medicament for treatment of kidney cancer in an individual or for prophylactic use. In a preferred embodiment, the disclosure provides methods of treating an individual for kidney cancer or reducing the risk of developing said cancer, the method comprising administering to the individual in need thereof a therapeutically effective amount of a vaccine as disclosed herein. In some embodiments, the individual prophylactically administered a vaccine as disclosed herein has not been diagnosed with cancer.

In a preferred embodiment, the individual has kidney cancer and one or more cancer cells of the individual:

(i) expresses a peptide having the amino acid sequence selected from Sequences 1-352, an amino acid sequence having 90% identity to any one of Sequences 1-352, or a fragment thereof comprising at least 10 consecutive amino acids of amino acid sequence selected from Sequences 1-352;

(ii) or comprises a DNA or RNA sequence encoding an amino acid sequences of (i).

In a preferred embodiment, the disclosure provides a method of stimulating the proliferation of human T-cells, comprising contacting said T-cells with the peptide or collection of peptides, the nucleic acid molecules, the vectors, the host cell, or the vaccine as disclosed herein.

In a preferred embodiment, the disclosure provides a storage facility for storing vaccines. Preferably the facility stores at least two different cancer vaccines as disclosed herein. Preferably the storing facility stores:

a vaccine comprising:

(i) a peptide, or a collection of tiled peptides, having the amino acid sequence selected from Sequence 1, an amino acid sequence having 90% identity to Sequence 1, or a fragment thereof comprising at least 10 consecutive amino acids of Sequence 1; and a peptide, or a collection of tiled peptides, having the amino acid sequence selected from Sequence 2, an amino acid sequence having 90% identity to Sequence 2, or a fragment thereof comprising at least 10 consecutive amino acids of Sequence 2; preferably also comprising a peptide, or a collection of tiled peptides, having the amino acid sequence selected from Sequence 3, an amino acid sequence having 90% identity to Sequence 3, or a fragment thereof comprising at least 10 consecutive amino acids of Sequence 3;

a peptide, or a collection of tiled peptides, having the amino acid sequence selected from Sequence 4, an amino acid sequence having 90% identity to Sequence 4, or a fragment thereof comprising at least 10 consecutive amino acids of Sequence 4;

a peptide, or a collection of tiled peptides, having the amino acid sequence selected from Sequence 5, an amino acid sequence having 90% identity to Sequence 5, or a fragment thereof comprising at least 10 consecutive amino acids of Sequence 5;

a peptide, or a collection of tiled peptides, having the amino acid sequence selected from Sequence 6, an amino acid sequence having 90% identity to Sequence 6, or a fragment thereof comprising at least 10 consecutive amino acids of Sequence 6; and/or a peptide, or a collection of tiled peptides, having the amino acid sequence selected from Sequence 7, an amino acid sequence having 90% identity to Sequence 7, or a fragment thereof comprising at least 10 consecutive amino acids of Sequence 7;

and one or more vaccines selected from:

a vaccine comprising:

(ii) a peptide, or a collection of tiled peptides, having the amino acid sequence selected from Sequence 19, an amino acid sequence having 90% identity to Sequence 19, or a fragment thereof comprising at least 10 consecutive amino acids of Sequence 19; and a peptide, or a collection of tiled peptides, having the amino acid sequence selected from Sequence 20, an amino acid sequence having 90% identity to Sequence 20, or a fragment thereof comprising at least 10 consecutive amino acids of Sequence 20;

a vaccine comprising:

(iii) a peptide, or a collection of tiled peptides, having the amino acid sequence selected from Sequence 189, an amino acid sequence having 90% identity to Sequence 189, or a fragment thereof comprising at least 10 consecutive amino acids of Sequence 189; and a peptide, or a collection of tiled peptides, having the amino acid sequence selected from any one of Sequences 190-192, an amino acid sequence having 90% identity to Sequences 190-192, or a fragment thereof comprising at least 10 consecutive amino acids of Sequences 190-192; and/or a vaccine comprising:

(iv) a peptide, or a collection of tiled peptides, having the amino acid sequence selected from Sequence 311, an amino acid sequence having 90% identity to Sequence 311, or a fragment thereof comprising at least 10 consecutive amino acids of Sequence 311; and a peptide, or a collection of tiled peptides, having the amino acid sequence selected from Sequence 312, an amino acid sequence having 90% identity to Sequence 312, or a fragment thereof comprising at least 10 consecutive amino acids of Sequence 312; preferably also comprising a peptide, or a collection of tiled peptides, having the amino acid sequence selected from Sequence 313, an amino acid sequence having 90% identity to Sequence 313, or a fragment thereof comprising at least 10 consecutive amino acids of Sequence 313.

In a preferred embodiment, the disclosure provides a method for providing a vaccine for immunizing a patient against a cancer in said patient comprising determining the sequence of BAP1, PBRM1, SETD2, and/or VHL in cancer cells of said cancer and when the determined sequence comprises a frameshift mutation that produces a neoantigen of Sequence 1-352 or a fragment thereof, providing a vaccine comprising said neoantigen or a fragment thereof. Preferably, the vaccine is obtained from a storage facility as disclosed herein.

REFERENCE TO A SEQUENCE LISTING

The Sequence listing, which is a part of the present disclosure, includes a text file comprising amino acid and/or nucleic acid sequences. The subject matter of the Sequence listing is incorporated herein by reference in its entirety. The information recorded in computer readable form is identical to the written sequence listing. In the event of a discrepancy between the Sequence listing and the description, e.g., in regard to a sequence or sequence numbering, the description (e.g., Table 1) is leading.

DETAILED DESCRIPTION OF THE DISCLOSED EMBODIMENTS

One issue that may arise when considering personalized cancer vaccines is that once a tumor from a patient has been analysed (e.g. by whole genome or exome sequencing), neoantigens need to be selected and made in a vaccine. This may be a time consuming process, while time is something the cancer patient usually lacks as the disease progresses.

Somatic mutations in cancer can result in neoantigens against which patients can be vaccinated. Unfortunately, the quest for tumor specific neoantigens has yielded no targets that are common to all tumors, yet foreign to healthy cells. Single base pair substitutions (SNVs) at best can alter 1 amino acid which can result in a neoantigen. However, with the exception of rare site-specific oncogenic driver mutations (such as RAS or BRAF) such mutations are private and thus not generalizable.

An “off-the-shelf” solution, where vaccines are available against each potential-neoantigen would be beneficial. The present disclosure is based on the surprising finding that, despite the fact that there are infinite possibilities for frame shift mutations in the human genome, a vaccine can be developed that targets the novel amino acid sequence following a frame shift mutation in a tumor with potential use in a large population of cancer patients.

Neoantigens resulting from frame shift mutations have been previously described as potential cancer vaccines. See, for example, WO95/32731, WO2016172722 (Nantomics), WO2016/187508 (Broad), WO2017/173321 (Neon Therapeutics), US2018340944 (University of Connecticut), and WO2019/012082 (Nouscom), as well as Rahma et al. (Journal of Translational Medicine 2010 8:8) which describes peptides resulting from frame shift mutations in the von Hippel-Lindau tumor suppressor gene (VHL) and Rajasagi et al. (Blood 2014 124(3):453-462) which reports the systematic identification of personal tumor specific neoantigens.

The present disclosure provides a unique set of sequences resulting from frame shift mutations and that are shared among kidney cancer patients. The finding of shared frame shift sequences is used to define an off-the-shelf kidney cancer vaccine that can be used for both therapeutic and prophylactic use in a large number of individuals.

In the present disclosure we provide a source of common neoantigens induced by frame shift mutations, based on analysis of 10,186 TCGA tumor samples and 2774 tumor samples (see Priestley et al. 2019 at https://doi.org/10.1101/415133). We find that these frame shift mutations can produce long neoantigens. These neoantigens are typically new to the body, and can be highly immunogenic. The heterogeneity in the mutations that are found in tumors of different organs or tumors from a single organ in different individuals has always hampered the development of specific medicaments directed towards such mutations. The number of possible different tumorigenic mutations, even in a single gene as P53 was regarded prohibitive for the development of specific treatments. In the present disclosure it was found that many of the possible different frame shift mutations in a gene converge to the same small set of 3' neo open reading frame peptides (neopeptides or NOPs). We find a fixed set of only 1,244 neopeptides in as much as 30% of all TCGA cancer patients. For some tumor classes this is higher; e.g. for colon and cervical cancer, peptides derived from only ten genes (saturated at 90 peptides) can be applied to 39% of all patients. 50% of all TCGA patients can be targeted at saturation (using all those peptides in the library found more than once). A pre-fabricated library of vaccines (peptide, RNA or DNA) based on this set can provide off the shelf, quality certified, ‘personalized’ vaccines within hours, saving months of vaccine preparation. This is important for critically ill cancer patients with short average survival expectancy after diagnosis.

The concept of utilizing the immune system to battle cancer is very attractive and studied extensively. Indeed, neoantigens can result from somatic mutations, against which patients can be vaccinated1-11. Recent evidence suggests that frame shift mutations, that result in peptides which are completely new to the body, can be highly immunogenic12-15. The immune response to neoantigen vaccination, including the possible predictive value of epitope selection has been studied in great detail8, 13, 16-21 and WO2007/101227, and there is no doubt about the promise of neoantigen-directed immunotherapy. Some approaches find subject-specific neoantigens based on alternative reading frames caused by errors in translation/transcription (WO2004/111075). Others identify subject specific neoantigens based on mutational analysis of the subjects tumor that is to be treated (WO1999/058552; WO2011/143656; US20140170178; WO2016/187508; WO2017/173321). The quest for common antigens, however, has been disappointing, since virtually all mutations are private. For SNV-derived amino acid changes, one can derive algorithms that predict likely good epitopes, but still every case is different.

A change of one amino acid in an otherwise wild-type protein may or may not be immunogenic. The antigenicity depends on a number of factors including the degree of fit of the proteasome-produced peptides in the MHC and ultimately on the repertoire of the finite T-cell system of the patient. In regards to both of these points, novel peptide sequences resulting from a frame shift mutation (referred to herein as novel open reading frames or pNOPs) are a priori expected to score much higher. For example, a fifty amino acid long novel open reading frame sequence is as foreign to the body as a viral antigen. In addition, novel open reading frames can be processed by the proteasome in many ways, thus increasing the chance of producing peptides that bind MHC molecules, and increasing the number of epitopes will be seen by T-cell in the body repertoire.

It is has been established that novel proteins/peptides can arise from frameshift mutations[32,36]. Furthermore, tumors with a high load of frameshift mutations (micro-satellite instable tumors) have a high density of tumor infiltrating CD8+ T cells[33]. In fact, it has been shown that neo-antigens derived from frameshift mutations can elicit cytotoxic T cell responses[32,34,33]. A recent study demonstrated that a high load of frameshift indels or other mutation types correlates with response to checkpoint inhibitors[35].

Binding affinity to MHC class-I molecules was systematically predicted for frameshift indel and point mutations derived neoantigens[35]. Based on this analysis, neoantigens derived from frameshifts indels result in 3 times more high-affinity MHC binders compared to point mutation derived neoantigens, consistent with earlier work[31]. Almost all frameshift derived neoantigens are so-called mutant-specific binders, which means that cells with reactive T cell receptors for those frameshift neoantigens are (likely) not cleared by immune tolerance mechanisms[35]. These data are all in favour of neo-peptides from frameshift being superior antigens.

Here we report that frame shift mutations, which are also mostly unique among patients and tumors, nevertheless converge to neo open reading frame peptides (NOPs) from their translation products that surprisingly result in common neoantigens in large groups of cancer patients. The disclosure is based, in part, on the identification of common, tumor specific novel open reading frames resulting from frame shift mutations. Accordingly, the present disclosure provides novel tumor neoantigens and vaccines for the treatment of cancer. In some embodiments, multiple neoantigens corresponding to multiple NOPs can be combined, preferably within a single peptide or a nucleic acid molecule encoding such single peptide. This has the advantage that a large percentage of the patients can be treated with a single vaccine.

While not wishing to be bound by theory, the surprisingly high number of frame shift induced novel open reading frames shared by cancer patients can be explained, at least in part, as follows. Firstly, on the molecular level, different frame shift mutations can lead to the generation of shared novel open reading frames (or sharing at least part of a novel open reading frame). Secondly, the data presented herein suggests that frame shift mutations are strong loss-of-function mutations. This is illustrated in FIG. 2A, where it can be seen that the SNVs in the TCGA database are clustered within the p53 gene, presumably because mutations elsewhere in the gene do not inactive gene function. In contrast, frame shift mutations occur throughout the p53 gene (FIG. 2B). This suggests that frame shift mutations virtually anywhere in the p53 ORF reduce function (splice variants possibly excluded), while not all point mutations in p53 are expected to reduce function. Finally, the process of tumorigenesis naturally selects for loss of function mutations in genes that may suppress tumorigenesis. Interestingly, the present disclosure identifies frame shift mutations in genes that were not previously known as classic tumor suppressors, or that apparently do so only in some tissue tumor types (see, e.g., FIG. 8). These three factors are likely to contribute to the surprisingly high number of frame shift induced novel open reading frames shared by cancer patients; in particular, while frame shift mutations generally represent less than 10% of the mutations in cancer cells, their contribution to neoantigens and potential as vaccines is much higher. The high immunogenic potential of peptides resulting from frameshifts is to a large part attributable to their unique sequence, which is not part of any native protein sequence in humans, and would therefore not be recognised as 'self' by the immune system, which would lead to immune tolerance effects. The high immunogenic potential of out-of-frame peptides has been demonstrated in several recent papers.

Neoantigens are antigens that have at least one alteration that makes them distinct from the corresponding wild-type, parental antigen, e.g., via mutation in a tumor cell. A neoantigen can include a polypeptide sequence or a nucleotide sequence As used herein the term "ORF" refers to an open reading frame. As used herein the term "neoORF" is a tumor-specific ORF (i.e., neoantigen) arising from a frame shift mutation. Peptides arising from such neo ORFs are also referred to herein as neo open reading frame peptides (NOPs) and neoantigens.

A "frame shift mutation" is a mutation causing a change in the frame of the protein, for example as the consequence of an insertion or deletion mutation (other than insertion or deletion of 3 nucleotides, or multitudes thereof). Such frameshift mutations result in new amino acid sequences in the C-terminal part of the protein. These new amino acid sequences generally do not exist in the absence of the frameshift mutation and thus only exist in cells having the mutation (e.g., in tumor cells and pre-malignant progenitor cells).

FIGS. 3 and 4 and the data discussed above provide the answer to the question: how many cancer patients exhibit in their tumor a frame shift in region x or gene y of the genome. The patterns result from the summation of all cancer patients. The disclosure surprisingly demonstrates that within a single cancer type (i.e. kidney cancer), the fraction of patients with a frame shift in a subset of genes is much higher than the fractions identified when looking at all cancer patients. We find that careful analysis of the data shows that frame shift mutations in only 4 genes together are found in 27% of all kidney cancers.

Novel 3' neo open reading frame peptides (i.e., NOPs) of BAP1, PBRM1, SETD2, and VHL are depicted in table 1. The NOPs, are defined as the amino acid sequences encoded by the longest neo open reading frame sequence identified. Sequences of these NOPs are represented in table 1 as follows:

VHL: Sequences 1-18.

SETD2: Sequences 19-188.

PBRM1: Sequences 189-310.

BAP1: Sequences 311-352.

The most preferred neoantigens are VHL frameshift mutation peptides, followed by PBRM1 frameshift mutation peptides, followed by BAP1 frameshift mutation peptides, followed by SETD2 frameshift mutation peptides. The preference for individual neoantigens directly correlates with the frequency of their occurrence in kidney cancer patients, with VHL frameshift mutation peptides covering up to 23% of kidney cancer patients, PBRM1 frameshift mutation peptides covering up to 9.1% of kidney cancer patients, BAP1 frameshift mutation peptides covering up to 4.4% of kidney cancer patients, SETD2 frameshift mutation peptides covering up to 4.2% of kidney cancer patients. In preferred embodiments, collections are provided comprising PBRM1 frameshift mutation peptides and SETD2 frameshift mutation peptides. In preferred embodiments, collections are provided comprising PBRM1 frameshift mutation peptides and BAP1 frameshift mutation peptides. In preferred embodiments, collections are provided comprising SETD2 frameshift mutation peptides and BAP1 frameshift mutation peptides.

TABLE 1

Library of NOP sequences
Sequences of NOPs including the percentage of kidney cancer patients identified in the present study with each NOP. The sequences referred to herein correspond to the sequence numbering in the table below. Different predicted alternative splice forms are indicated as "alt splice x".

| Sequence | PeptideID | geen | PeptideSeq | % Kidney Cancer Patients |
|---|---|---|---|---|
| 1 | pNOP42302 alt splice a | VHL | TRASPPRSSSAIAVRASCCPYGSTSTASRSPTQRCRLARAAASTATEVTFG SSEMQGHTMGFWLTKLNYLCHLSMLTDSLFLPISHCQCIL | 6.18 |
| 2 | pNOP279502 | VHL | SSLRITGDWTSSGRSTKIWKTTQMCRKTWSG | 3.64 |
| 3 | pNOP29645 alt splice b | VHL | RRRRGGVGRRGVRPGRVRPGGTGRRGGDGGRAAAARAALGELARALPGHLL QSQSARRAARMAQLRRRAAALPNAAAWHGPPHPQLPSVYSERAMPPGCPEP SQA | 3.45 |
| 4 | pNOP30388 alt splice b | VHL | RRRRGGVGRRGVRPGRVRPGGTGRRGGDGGRAAAARAALGELARALPGHLL QSQSARRAARMAQLRRRAAALPNAAAWHGPPHPQLPRSPLALQRCRDTRWA SG | 3.45 |
| 5 | pNOP140916 alt splice a | VHL | TRASPPRSSSAIAVRASCCPYGSTSTASRSPTQRCRLARAAASTATECIL | 2.55 |
| 6 | pNOP54515 | VHL | ELQETGHRQVALRRSGRPPKCAERPGAADTGAHCTSTDGRLKISVETYTVS SQLLMVLMSLDLDTGLVPSLVSKCLILRVK | 2.00 |
| 7 | pNOP301515 | VHL | RTAYFCQYHTASVYSERAMPPGCPEPSQA | 1.27 |
| 8 | pNOP700435 | VHL | KSDASRLSGA | 0.55 |
| 9 | pNOP10058 alt splice b | VHL | RRRRGGVGRRGVRPGRVRPGGTGRRGGDGGRAAAARAALGELARALPGHLL QSQSARRAARMAQLRRRAAALPNAAAWHGPPHPQLPSPHDSSGPVLRSPCP RGEHIPPGETDRCKDRNKPGSCWRRKSRPCVAWEIDLPACWEMEGLRLCGFS | <0.1 |
| 10 | pNOP128393 | VHL | ARRRQASKSTALKKTAGRSRAPRSPARKSPARRNWAPRRRWRPGGRGPCCAR | <0.1 |
| 11 | pNOP145743 alt splice a | VHL | TRASPPRSSSAIAVRASCCPYGSTSTASRSPTQRCRLARAAASTATESS | <0.1 |
| 12 | pNOP265165 | VHL | LTCLLGDGGVAVVWFQLRSTSRRRKRAGWSRN | <0.1 |
| 13 | pNOP352529 | VHL | NAPEGGELGRGRGRRGGGRRRRVRP | <0.1 |
| 14 | pNOP369816 | VHL | QMQRQEQARVMLAPEEPTVCGVGN | <0.1 |
| 15 | pNOP472058 | VHL | GALPGEGREQDGVGTSQP | <0.1 |
| 16 | pNOP519384 | VHL | HRSALHINGWEIEDFC | <0.1 |
| 17 | pNOP614216 | SETD2 | SLPSWRTHSSWGD | <0.1 |
| 18 | pNOP622782 | SETD2 | CPGGRRTGTRPR | <0.1 |
| 19 | pNOP42654 | SETD2 | ETSASCNIQATAGYYHSSSISTYSCSTITSSDSRINNCRLTALISASTASTC PSHNTLITSTSNRASGLATYTNNSSNGSTSTLTSRCSS | 1.27 |
| 20 | pNOP36509 | SETD2 | CLGFKPTVCQCTAAVLSCTVSSNHILSRTDMSNSLWCDITLFTDNSTNCTEL CPAKSSVYPGATDFHSSSTRSGGTASRSSDYNSCTRAASALAAI | 0.55 |
| 21 | pNOP127387 | SETD2 | SLGSAAPLSSQTKNHCLTSQLEDSSRSRREDLLLPCDHKADSVGSSYLGKPRR | 0.36 |
| 22 | pNOP169956 | SETD2 | KPKYLLGSKKSCQFILLILKMSQISLGNRPLSKTGQIVDWEKQN | 0.36 |
| 23 | pNOP102433 | SETD2 | YTKTPALLSCQCRPPAQFRDRIIVFGIQTNSLSVYSSSTLLHSLKQPYIIKDR HVQQSMV | 0.18 |
| 24 | pNOP163115 | SETD2 | FISTYWEFRYCFISSESSTRNKGGQSNSLEMRREHISSSGCSAKE | 0.18 |
| 25 | pNOP175535 | SETD2 | HHLIHRQLHQLYRVMPSQVFSISRGNRFSQLIHKEWWYSQPQQ | 0.18 |
| 26 | pNOP212518 | SETD2 | QUISWICRPPLLPNQKPLSYLPTGRQLEIQKGRFITTM | 0.18 |
| 27 | pNOP238211 | SETD2 | RLWNTCPFLLKICWRKAKYFQLFNAGLRLRLLSLR | 0.18 |
| 28 | pNOP244560 | SETD2 | KNLLMKKHHPKMKRRVCLMWRVKGAKNSQIKQWI | 0.18 |
| 29 | pNOP310885 | SETD2 | MSKQIFPQKKKIPILGRMKKFQIVLRLV | 0.18 |

TABLE 1 -continued

Library of NOP sequences
Sequences of NOPs including the percentage of kidney cancer patients identified in the present study with each NOP. The sequences referred to herein correspond to the sequence numbering in the table below. Different predicted alternative splice forms are indicated as "alt splice x".

| Sequence | PeptideID | geen | PeptideSeq | % Kidney Cancer Patients |
|---|---|---|---|---|
| 30 | pNOP516328 | SETD2 | EVHAEVWGCLQTQRGH | 0.18 |
| 31 | pNOP91847 | SETD2 | LDRNYPLWSKHACFHQMDFRILVGAKKKTWMIPACCIRSQKAHLEKQNLWCHH<br>TKINSCLCQL | 0.18 |
| 32 | pNOP129693 | SETD2 | IRVTVGPGWEDGWSGKTDSRERKSCGPFCPTPVSTVLLMIHHPGEFNPADVN | <0.1 |
| 33 | pNOP140653 | SETD2 | SRERHQCPQVQHWLGPPVSWMTSGTHSDGRNVPSKGKCHVTLILLKKMFI | <0.1 |
| 34 | pNOP149559 | SETD2 | QITQNLHVKNISRASVALVQLLLIILMIYINLLGVQVLLHLFRVFHQE | <0.1 |
| 35 | pNOP151102 | SETD2 | VVTFLIQERDLLPGRTGVIMGYLGNVCKRLKKKGIPYCLKEEEDQKSL | <0.1 |
| 36 | pNOP164732 | SETD2 | LSVPEIWKRSPEMFLRISQLPGLPGRRKQSQHQSSRRENEEGTIS | <0.1 |
| 37 | pNOP172893<br>alt splice a | SETD2 | TVSEKTACRCGSHTHRKERLGLESCQRPSFEHLCPRILWRGTRS | <0.1 |
| 38 | pNOP18146 | SETD2 | RRYIEFQRKVKLKRKTQQLNEEGMLLASEIKHLPRRLLIGQERETQTSKLKIK<br>RKGNEEAPSHHPLLPMSGEQKGQMTDMIHQLLKRKYELKTAINFLQRNAGSCLS<br>KRWLNGRLRNNSNRCRTWE | <0.1 |
| 39 | pNOP189678 | SETD2 | NFGAETYLSGTHTEHTLTVLPEVLSGTSWAVFVVDLDGRAR | <0.1 |
| 40 | pNOP191028 | SETD2 | RLTISSRDMEKKPRNVSADQPIAGVTWEEKTESASEQQEGK | <0.1 |
| 41 | pNOP197618 | SETD2 | QMIVKKRRIGINRMDPIFQTSPINFFYPFRKTRGQCKHLK | <0.1 |
| 42 | pNOP198489 | SETD2 | SCSALGGTFYRTPFCPSTSTSGATCGSSCGSFQFPVCGPE | <0.1 |
| 43 | pNOP201541<br>alt splice b | SETD2 | ELPKTFLQKKPRNVSADQPIAGVTWEEKTESASEQQEGK | <0.1 |
| 44 | pNOP204603 | SETD2 | PLPPTPSYCWLLSALHLIFRKLSFLRAGMLLYSNLVSSP | <0.1 |
| 45 | pNOP208142 | SETD2 | AVKKQVLRRNPHNLKASFLVQNLMKILYGLLQVKDHMI | <0.1 |
| 46 | pNOP21038 | SETD2 | GNLHDLKQTEMINILAIQNLKEILGMYLPDVDQKESDGGADLTLGLREALELIYP<br>IPGQNDLIIMTLIVATIGAPLIERGRAILGHTQITEHERVLTQKKSIRRHTQGVP<br>HLIPLLTET | <0.1 |
| 47 | pNOP213911 | SETD2 | SQGRLSGILLLGKAQEMMPALSMKLRWTWELQHMMKTP | <0.1 |
| 48 | pNOP219165 | SETD2 | LNVLLGVQMGIIVPIDGFRENSMQMWKSYSQKRKAGA | <0.1 |
| 49 | pNOP237811 | SETD2 | QYSKKPSPVCCGCAKEFYFAHGRNKSLFFSEQSKL | <0.1 |
| 50 | pNOP244795 | SETD2 | KWKLVIPYLLQKNLPHQSQGWNWAKFILRNICFM | <0.1 |
| 51 | pNOP261712 | SETD2 | DTTCGWLALIRRAQKLRLGLLSRKAFYHVSAT | <0.1 |
| 52 | pNOP267031 | SETD2 | QVKPVLKLISFSFIKEQRRIRKFLLHSPVENK | <0.1 |
| 53 | pNOP272114 | SETD2 | EGFKHTLTVLPEVLSGTSWAVFVVDLQGRAR | <0.1 |
| 54 | pNOP27510<br>alt splice c | SETD2 | SSCSRSRLRRWGISTTRSTRPLKKKKMRQRLKMCRKQVSSKDQCSKVLLLVDFCPK<br>APKQKLIWKNRDDRRCHSASALQRKLCRIGFSLHLAMKSKVILQTLQLYLFR | <0.1 |
| 55 | pNOP277421 | SETD2 | QKERRINLIEILSECSVSVHLFLKMKELKVK | <0.1 |
| 56 | pNOP292377 | SETD2 | YDSSHEKPDHCLLLHLIVGFFLPYTLYSGS | <0.1 |
| 57 | pNOP311275 | SETD2 | NPKMDCERTTEGWVFYHQTGSFRLRVNV | <0.1 |
| 58 | pNOP329486 | SETD2 | TSKEKQRSIQKRDVPVHRPVPEPLPET | <0.1 |
| 59 | pNOP331645 | SETD2 | ARGGSTGGSETTATDAEPGNDITTAL | <0.1 |

TABLE 1 -continued

Library of NOP sequences
Sequences of NOPs including the percentage of kidney cancer patients identified in the present study with each NOP. The sequences referred to herein correspond to the sequence numbering in the table below. Different predicted alternative splice forms are indicated as "alt splice x".

| Sequence | PeptideID | geen | PeptideSeq | % Kidney Cancer Patients |
|---|---|---|---|---|
| 60 | pNOP33233 | SETD2 | HHHCPMTLLVIMPR/IPLLVTHQVIPCRPMWIPATLMLERCSCPHPAWTQCVLLLL MIMLSPWWDILQNPFLPLHQYQWCHMWQLLWKFPVPSMWPRVMV | <0.1 |
| 61 | pNOP33646 | SETD2 | SVTVVVMPQKLCLQFMKIILALLKVQMMKVIQKIQIRMIAVFQETVSSLLWLCQRI LLCPWKKQVLVLLGAVKVIDTILTIGKMRDWSQGDICMRKNLKV | <0.1 |
| 62 | pNOP338557 | SETD2 | NTKPRSTLRSTCRSLGLFTNPKRTLN | <0.1 |
| 63 | pNOP340580 | SETD2 | RKRKNCSHNSYSHNSCLNAKLIVKPT | <0.1 |
| 64 | pNOP342316 alt splice c | SETD2 | SSCSRSRLRRWGISTTRSTRPLSFLG | <0.1 |
| 65 | pNOP343672 | SETD2 | VKEMGILVRIHRVLIHHSTHLILPPS | <0.1 |
| 66 | pNOP357840 | SETD2 | TLTGNLTAKWEELPQLKTLNIWLAS | <0.1 |
| 67 | pNOP358911 | SETD2 | WCSTPRLQRCCLASAGPRPSSGTEL | <0.1 |
| 68 | pNOP359043 | SETD2 | WLELKLWSRNLPVWNSYRTHTHSPA | <0.1 |
| 69 | pNOP360928 | SETD2 | CPASSLCWLPTRLSHAGLCGSQQP | <0.1 |
| 70 | pNOP362588 | SETD2 | FGHQTPGQLERPKGGISNSKEKSN | <0.1 |
| 71 | pNOP371897 | SETD2 | SGGRAGRDISAPRFSTGWALLCHG | <0.1 |
| 72 | pNOP372037 | SETD2 | SIRKCPCRGRGRIAVTTATPTTAA | <0.1 |
| 73 | pNOP373154 | SETD2 | THRPHLRLHRLHLPKPQHSHHQHQ | <0.1 |
| 74 | pNOP376360 | SETD2 | CDWIGIIPFGQSMHAFIKWISEY | <0.1 |
| 75 | pNOP377069 | SETD2 | DEAAAAAAASEDGGFLRPGAPDP | <0.1 |
| 76 | pNOP377612 | SETD2 | EDILKAYLISFLFLQRPKDIILF | <0.1 |
| 77 | pNOP383516 | SETD2 | MKEEKEDMCILLMTQKLYFLLVI | <0.1 |
| 78 | pNOP394982 | SETD2 | FGRTGTTEGVIQLQPYKENFAE | <0.1 |
| 79 | pNOP397465 | SETD2 | HIACLNFLILRVMGLIVQVIQM | <0.1 |
| 80 | pNOP399481 | SETD2 | LKNQLIRGFLAAKPKIQTYTVL | <0.1 |
| 81 | pNOP407617 | SETD2 | VFLPLVRYHMWMACTHQKSSET | <0.1 |
| 82 | pNOP409009 | SETD2 | YLIYCRRIFPTKVKGGIGQNSF | <0.1 |
| 83 | pNOP418203 | SETD2 | MDLLGQNLIWQHFALLKLMLF | <0.1 |
| 84 | pNOP418296 | SETD2 | MKKSNSLILLVYRHLVQKVVN | <0.1 |
| 85 | pNOP424480 | SETD2 | SSSEGVCTKQKHPLLFHGPEE | <0.1 |
| 86 | pNOP429517 | SETD2 | CWKGAPAHTQHGPSVFSCSL | <0.1 |
| 87 | pNOP429922 | SETD2 | DLLLRDGKKRQVFFKTRKRI | <0.1 |
| 88 | pNOP432391 | SETD2 | GQGCCFIQIWSPALSTRRRK | <0.1 |
| 89 | pNOP436619 | SETD2 | LQGPTAMEGMCQARENAMLL | <0.1 |
| 90 | pNOP437076 | SETD2 | LWSLWWTQVSAKCRTVWWDT | <0.1 |
| 91 | pNOP44117 | SETD2 | MEIEKKKMRQRLKMCRKQVSSKDQCSKVLLLVDFCPKAPKQKLIWKNRDDRRCHSASAL QRKLCRIGFSLHLAMKSKVILQTLQLYLFR | <0.1 |
| 92 | pNOP443088 | SETD2 | SIKKFLSHRIKYKWISWGRI | <0.1 |

TABLE 1 -continued

| Library of NOP sequences Sequences of NOPs including the percentage of kidney cancer patients identified in the present study with each NOP. The sequences referred to herein correspond to the sequence numbering in the table below. Different predicted alternative splice forms are indicated as "alt splice x". | | | | |
|---|---|---|---|---|
| Sequence | PeptideID | geen | PeptideSeq | % Kidney Cancer Patients |
| 93 | pNOP460543 | SETD2 | QRKAKKYSEKRCPSSSSSA | <0.1 |
| 94 | pNOP462663 | SETD2 | RVILKVMVSFRTERKLEWR | <0.1 |
| 95 | pNOP46371 | SETD2 | HKKKKMRQRLKMCRKQVSSKDQCSKVLLLVDFCPKAPKQKLIWKNRDDRRCHSASALQR KLCRIGFSLHLAMKSKVILQTLQLYLFR | <0.1 |
| 96 | pNOP464819 | SETD2 | TIATLLCVTLKLKILSLQL | <0.1 |
| 97 | pNOP467110 | SETD2 | WVIWEMFARGSRRREFHIA | <0.1 |
| 98 | pNOP467219 | SETD2 | YEGFLLQNQRFRHILYFER | <0.1 |
| 99 | pNOP470113 | SETD2 | DNRCHSKRKLLSFHESQL | <0.1 |
| 100 | pNOP472466 | SETD2 | GHHPILNLIGTVKLRPLT | <0.1 |
| 101 | pNOP474911 | SETD2 | ISERTTNYNCTRIFRSRY | <0.1 |
| 102 | pNOP475195 | SETD2 | KCAENRFHQRTNVQRCCF | <0.1 |
| 103 | pNOP475627 | SETD2 | KKFRVFKACRERNNSRSR | <0.1 |
| 104 | pNOP475977 | SETD2 | KPHEGLEKAQDSRSRHLQ | <0.1 |
| 105 | pNOP476615 | SETD2 | KYVGGKQSTSNYSTLVSD | <0.1 |
| 106 | pNOP477103 | SETD2 | LIKILKEKRLGLQLHQID | <0.1 |
| 107 | pNOP478859 | SETD2 | NFQQALKRKEILKRAQHL | <0.1 |
| 108 | pNOP479862 | SETD2 | PEASGRDYKDFGTLAHSY | <0.1 |
| 109 | pNOP483413 | SETD2 | RRGELGSTGWIPFFRPVR | <0.1 |
| 110 | pNOP485089 | SETD2 | SPFWNVMGCLCCGSGWQS | <0.1 |
| 111 | pNOP486790 | SETD2 | TRKGCCWLQRSNTCPEDS | <0.1 |
| 112 | pNOP488264 | SETD2 | WKMVRVSLIKTRCSAYPG | <0.1 |
| 113 | pNOP497968 | SETD2 | KKMISKIEGLLKKGGRK | <0.1 |
| 114 | pNOP503210 | SETD2 | PSGSPKFRGNRESQNTF | <0.1 |
| 115 | pNOP506077 alt splice d | SETD2 | RRNDLVRRIQTHTHSPA | <0.1 |
| 116 | pNOP513180 | SETD2 | ASRYFLKKRRFPYWEG | <0.1 |
| 117 | pNOP515847 | SETD2 | ELPLSREDALFSAIHR | <0.1 |
| 118 | pNOP519358 | SETD2 | HRHSQETNVSQTENYK | <0.1 |
| 119 | pNOP528494 | SETD2 | REKETKKLPLTTLFCL | <0.1 |
| 120 | pNOP529595 | SETD2 | RPRKSPRQQKQTPPVN | <0.1 |
| 121 | pNOP533091 | SETD2 | THVYASYDCGLFQNSS | <0.1 |
| 122 | pNOP540029 | SETD2 | EGFSGWRARSSDGKW | <0.1 |
| 123 | pNOP542259 | SETD2 | GLGFLPPNWFLQAQS | <0.1 |
| 124 | pNOP545135 | SETD2 | ISSIPSERQGVSAST | <0.1 |
| 125 | pNOP546281 | SETD2 | KLVSYLHLNQKLTLK | <0.1 |
| 126 | pNOP547748 | SETD2 | LHQGSLSPCSHLKWL | <0.1 |

TABLE 1 -continued

Library of NOP sequences
Sequences of NOPs including the percentage of kidney cancer patients identified in the present study with each NOP. The sequences referred to herein correspond to the sequence numbering in the table below. Different predicted alternative splice forms are indicated as "alt splice x".

| Sequence | PeptideID | geen | PeptideSeq | % Kidney Cancer Patients |
|---|---|---|---|---|
| 127 | pNOP549104 | SETD2 | MCIWNQNQLYVIVEI | <0.1 |
| 128 | pNOP550126 | SETD2 | NIVERYSIIKSLKLE | <0.1 |
| 129 | pNOP550494 | SETD2 | NRAQREQRHKTRRTY | <0.1 |
| 130 | pNOP555604 | SETD2 | RSMHETKTSITISWP | <0.1 |
| 131 | pNOP560211 | SETD2 | VKIAWTVQSLMQPVS | <0.1 |
| 132 | pNOP562314 | SETD2 | YSKPSSCTSSGRLDS | <0.1 |
| 133 | pNOP571897 | SETD2 | ITAVNQIVKPKNGL | <0.1 |
| 134 | pNOP573430 | SETD2 | KRKGWVSSSIKSIK | <0.1 |
| 135 | pNOP582365 | SETD2 | RNREESGNFFYTVQ | <0.1 |
| 136 | pNOP582849 alt splice d | SETD2 | RRNDLVRRIQWMES | <0.1 |
| 137 | pNOP585794 | SETD2 | STVRILRTWSAMRM | <0.1 |
| 138 | pNOP588522 | SETD2 | VTAGKVTRSFRKRL | <0.1 |
| 139 | pNOP603675 | SETD2 | LLARQWLLGSKIR | <0.1 |
| 140 | pNOP604883 | SETD2 | LYECAFGIKTSYM | <0.1 |
| 141 | pNOP605041 | SETD2 | MFFSVSKWGLLFQ | <0.1 |
| 142 | pNOP605550 | SETD2 | NAERTHLQFWMQC | <0.1 |
| 143 | pNOP606242 | SETD2 | NLTLWVTQIQRKP | <0.1 |
| 144 | pNOP613396 | SETD2 | SDCWARVGGWVVR | <0.1 |
| 145 | pNOP617878 | SETD2 | VIWPPNSWTVGKT | <0.1 |
| 146 | pNOP625134 alt splice b | SETD2 | ELPKTFLRTPLS | <0.1 |
| 147 | pNOP625852 | SETD2 | EYIACSYTTQHT | <0.1 |
| 148 | pNOP626121 | SETD2 | FILFQVRTISLL | <0.1 |
| 149 | pNOP626457 | SETD2 | FRKGICFQGEQA | <0.1 |
| 150 | pNOP629408 | SETD2 | HLHLLMQHHYQQ | <0.1 |
| 151 | pNOP630920 | SETD2 | IRKRATAEQISL | <0.1 |
| 152 | pNOP632708 | SETD2 | KQILSRTLYLIV | <0.1 |
| 153 | pNOP641668 | SETD2 | RFCTDFFKSKIT | <0.1 |
| 154 | pNOP645655 | SETD2 | SNSRTSTRFPNR | <0.1 |
| 155 | pNOP647445 | SETD2 | TGKNRIEFFFLL | <0.1 |
| 156 | pNOP648378 | SETD2 | TSGSQADSRCYE | <0.1 |
| 157 | pNOP649199 | SETD2 | VKRERPRQANSK | <0.1 |
| 158 | pNOP649226 | SETD2 | VLATDHFPKQAR | <0.1 |
| 159 | pNOP652844 | SETD2 | AQKLTQTLPRN | <0.1 |
| 160 | pNOP661751 | SETD2 | HPGHCWLLPQQ | <0.1 |

TABLE 1 -continued

Library of NOP sequences
Sequences of NOPs including the percentage of kidney cancer patients identified in the present study with each NOP. The sequences referred to herein correspond to the sequence numbering in the table below. Different predicted alternative splice forms are indicated as "alt splice x".

| Sequence | PeptideID | geen | PeptideSeq | % Kidney Cancer Patients |
|---|---|---|---|---|
| 161 | pNOP662108 | SETD2 | HVGKIVLIVFS | <0.1 |
| 162 | pNOP663661 | SETD2 | KARMAKRILIN | <0.1 |
| 163 | pNOP663940 | SETD2 | KERFFKKLRKK | <0.1 |
| 164 | pNOP665029 | SETD2 | KPGAQLIPANG | <0.1 |
| 165 | pNOP668907 | SETD2 | MPLKKEIALVS | <0.1 |
| 166 | pNOP675389 | SETD2 | RKCLFNRKKEE | <0.1 |
| 167 | pNOP676055 | SETD2 | RNRTSGVTTPR | <0.1 |
| 168 | pNOP677462 | SETD2 | RWKEEASILQN | <0.1 |
| 169 | pNOP678458 | SETD2 | SIFAQRHQNKS | <0.1 |
| 170 | pNOP684868 | SETD2 | WSCPRNCVYSS | <0.1 |
| 171 | pNOP686009 | SETD2 | AARRAANLFF | <0.1 |
| 172 | pNOP687273 | SETD2 | ARRQGWQRGS | <0.1 |
| 173 | pNOP690677 | SETD2 | ECETQNQGVH | <0.1 |
| 174 | pNOP692910 | SETD2 | FRRTRNSNIE | <0.1 |
| 175 | pNOP696399 | SETD2 | HMIAMIVLRN | <0.1 |
| 176 | pNOP698375 | SETD2 | IYPFKTYTQV | <0.1 |
| 177 | pNOP698819 | SETD2 | KFDRSLKICM | <0.1 |
| 178 | pNOP699449 | SETD2 | KKRKTRNLFR | <0.1 |
| 179 | pNOP700367 | SETD2 | KRRRRTCAYF | <0.1 |
| 180 | pNOP700416 | SETD2 | KRYSVCIFPM | <0.1 |
| 181 | pNOP704029 | SETD2 | MNCLFLSPNL | <0.1 |
| 182 | pNOP709667 | SETD2 | QSQWPCHIHQ | <0.1 |
| 183 | pNOP71440 | SETD2 | VGTSLKKSLLPRISNLTVAMELVVDTSISKMQNSMVGHVITGKAMVTGIQDQVDLLELG LCMIELKDKYQIP | <0.1 |
| 184 | pNOP717155 | SETD2 | TFYRGTPEVV | <0.1 |
| 185 | pNOP717203 | SETD2 | TGIPTRVIIF | <0.1 |
| 186 | pNOP80237 alt splice a | SETD2 | TVSEKTACRCGSHTHRKERLGLESCQRPSFKRSPEMFLRISQLPGLPGRRKQSQHQSSR RENEEGTIS | <0.1 |
| 187 | pNOP85768 | SETD2 | CSKVLLLVDFCPKAPKQKLIWKNRDDRRCHSASALQRKLCRIGFSLHLAMKSKVILQTL QLYLFR | <0.1 |
| 188 | pNOP91732 | SETD2 | KENLKGLQKMKQLKDVVLPLMNWDSDEGHHILSMTVVLPVINLPFQNLYPSLINLKILS VVQN | <0.1 |
| 189 | pNOP100723 | PBRM1 | LLTSSFFLTMQSPIISQILLNIKPLANSGICTFEQEMSLFRKEKQMTKMMMKMGKTIRAQ | 1.82 |
| 190 | pNOP136779 | PBRM1 | WVAIRQAFHLCRAQLMALLAWAACSHFTLGGLHPTIFRQVCLASRASHHRV | 0.55 |
| 191 | pNOP152717 | PBRM1 | GLQHQVEVHMDNRWEFWGLQGSRHHLHIPAHIQLDPLSYSSQQHPCL | 0.55 |
| 192 | pNOP18284 | PBRM1 | ASVWSCLSRNTLSYAQKTSEMRMFLSVNHGILPKPNLLRKLNCGPCPSAQSGLSLGMCL CLWFAWPLYLQMQIKVMMRRIQTTQRTVELKTILTWKRKKKMSLWKCPMVNQVATTLSS SITMTCG | 0.55 |

TABLE 1 -continued

Library of NOP sequences
Sequences of NOPs including the percentage of kidney cancer patients identified in the present study with each NOP. The sequences referred to herein correspond to the sequence numbering in the table below. Different predicted alternative splice forms are indicated as "alt splice x".

| Sequence | PeptideID | geen | PeptideSeq | % Kidney Cancer Patients |
|---|---|---|---|---|
| 193 | pNOP108150 | PBRM1 | RLATVSSSSPMAWCVLVWAELKKYGFEMELHIFMAPSSFTQKKQSMSPQKCSTKKKYF | 0.36 |
| 194 | pNOP143190 | PBRM1 | ILLPCAMNSIIPSETIRMNRADFSVSSSLGHQSEEINQTIMKWFLSPLT | 0.36 |
| 195 | pNOP146830 | PBRM1 | CSGMPGTIMRRAPRFIMMHISWRSYSRRKGKSWAHCLMMMTWLLPNSS | 0.36 |
| 196 | pNOP245326 alt splice a | PBRM1 | LRPNTQTTLSGSSAAWWGQNGEILRQPRKQNMKA | 0.36 |
| 197 | pNOP297770 | PBRM1 | LGRMLKIIATVGLIYFKSICLKYWNEQEG | 0.36 |
| 198 | pNOP302582 | PBRM1 | STKMLLFYTKSCLKHAETWREMRTLMSQM | 0.36 |
| 199 | pNOP323570 | PBRM1 | LQIHQDVSLANFFRNCLLKCNIQIIMQ | 0.36 |
| 200 | pNOP46601 alt splice b | PBRM1 | NEKKKKEKLKRVKIPLVLQASQAYIAHTARTVALKTACTMLEITSMWNLQRPTYNHISS VLKDCGRIQLKKKFLRVTITTKFQLVKF | 0.36 |
| 201 | pNOP139958 | PBRM1 | QVLHTVKAALVKREIPLASITVIKEQYKEVVYQQLQWHENMAQKVKKMLL | 0.18 |
| 202 | pNOP154131 | PBRM1 | NFSSFLLKFVMNSAKMERFFFHRHSAIPQNICIMMWRKRERKNCQKK | 0.18 |
| 203 | pNOP188417 | PBRM1 | HVFSESVLCCHSRTSSPAGQLKYQKMTFCFVRAATMRATSR | 0.18 |
| 204 | pNOP264907 | PBRM1 | LNLFTICLQRKNTLIITSKLKCPYHYNRSEQN | 0.18 |
| 205 | pNOP303604 | PBRM1 | VIKEQYKEVVYQQLQWHFNMAQKVKKMLL | 0.18 |
| 206 | pNOP324121 | PBRM1 | MMKFTTSENQLFLRRSHHLCWKRRSSC | 0.18 |
| 207 | pNOP367819 | PBRM1 | NCSKLCRQRRKSLPGETISRTETA | 0.18 |
| 208 | pNOP396093 | PBRM1 | GPTPRLLFRGAQPPGGDRMEKS | 0.18 |
| 209 | pNOP504975 | PBRM1 | RGNDRRHEADVPECQAL | 0.18 |
| 210 | pNOP520755 | PBRM1 | KEHKKAANENLIQCCS | 0.18 |
| 211 | pNOP547617 | PBRM1 | LGKGKRRCPCGNVQW | 0.18 |
| 212 | pNOP548688 | PBRM1 | LSITSAMTNMLVKRE | 0.18 |
| 213 | pNOP592499 | PBRM1 | CLIMPVHTMSRSL | 0.18 |
| 214 | pNOP613848 | PBRM1 | SHSCSYKSIRTSH | 0.18 |
| 215 | pNOP83912 | PBRM1 | KMFNHIITFLLYRSIKSCGSVAILVTGGGGKEQRRIIFIAFYCTSQGHFYIRTLLISY FNLFVILS | 0.18 |
| 216 | pNOP150133 | PBRM1 | RSWIPWVPREEELPPLPAVSAGTLMMGTILCQHQAQAGKGGDFPIFQL | <0.1 |
| 217 | pNOP155811 | PBRM1 | SWIPWVPREEELPPLPAVSAGTLMMGTILCQHQAQAGKGGDFPIFQL | <0.1 |
| 218 | pNOP170046 | PBRM1 | KSYSMLFLKLESQVQAEDFVTYLWLNHPKRTILIIIKSSWSQWT | <0.1 |
| 219 | pNOP179578 | PBRM1 | WVPREEELPPLPAVSAGTLMMGTILCQHQAQAGKGGDFPIFQL | <0.1 |
| 220 | pNOP180157 | PBRM1 | CAQFSHLQASSKIAASYAGKEERACQERRYRGRRQHDLFSHL | <0.1 |
| 221 | pNOP18247 alt splice c | PBRM1 | AAGERASSTATAAECFSPSRHPCGGSHGGGATTNTNGDAQSAVDTCCRCDEPRSGPYG RDSSTRWKSIWTTGGSFGASRAAGTTSISRPTSSWTPCHTAANNTHVCSSPTKDPAAS SLRGLPEIH | <0.1 |
| 222 | pNOP189150 | PBRM1 | LLHAMKRESQKQKASLPLWMFQILFISFMTQLGVVGITKGS | <0.1 |
| 223 | pNOP189879 | PBRM1 | NTLKDSVRSPTALASGIRHWQLEDATSICRKNRRAAYPLTG | <0.1 |
| 224 | pNOP196761 alt splice d | PBRM1 | NEETGFSRRWLCSGKAEEVGFHGFQEKKSYLPFQQCQRGL | <0.1 |

TABLE 1 -continued

Library of NOP sequences
Sequences of NOPs including the percentage of kidney cancer patients identified in the present study with each NOP. The sequences referred to herein correspond to the sequence numbering in the table below. Different predicted alternative splice forms are indicated as "alt splice x".

| Sequence | PeptideID | geen | PeptideSeq | % Kidney Cancer Patients |
|---|---|---|---|---|
| 225 | pNOP200354 | PBRM1 | AGPHALHTPTVYPKVCQRQCKEGRLQTENQHEWLHPVQQ | <0.1 |
| 226 | pNOP217261 | PBRM1 | GAYRSQDHCPEDTEWKLQKYSCNGQRYRSPRKKCQNL | <0.1 |
| 227 | pNOP219611 alt splice d | PBRM1 | NEETGFSRRWLCSEEVGFHGFQEKKSYLPFQQCQRGL | <0.1 |
| 228 | pNOP227023 alt splice e | PBRM1 | KVEMMILKRWEKKIVSLPQSLPKAVQRRKAPNGKST | <0.1 |
| 229 | pNOP227832 alt splice d | PBRM1 | NEETGFSRRWLCSEVGFHGFQEKKSYLPFQQCQRGL | <0.1 |
| 230 | pNOP245327 alt splice a | PBRM1 | LRPNTQTTLSGSSAAWWGQNGEILRQPRKQNMKV | <0.1 |
| 231 | pNOP258302 alt splice f | PBRM1 | SLQPPLILVVPKEKGTLMTVRCWVSGGYPVKRT | <0.1 |
| 232 | pNOP27190 | PBRM1 | HGQHAATSPWGASTPPSSARCAWPPGHPTTGCDEPRSGPYGRDSSTRWKSIWTTGGS FGASRAAGTTSISRPTSSWTPCHTAANNTHVCSSPTKDPAASSLRGLPEIH | <0.1 |
| 233 | pNOP280248 | PBRM1 | TVDHAHQLSQVCPSGCASACGSRGLCICKCR | <0.1 |
| 234 | pNOP291935 | PBRM1 | WAPFCVNTRPKQEKEETFQSSNCRSYCRVP | <0.1 |
| 235 | pNOP296775 | PBRM1 | ISSQKMPKLIMSLALKYSRMQIQLKKYFI | <0.1 |
| 236 | pNOP303912 | PBRM1 | VYPKVCQRQCKEGRLQTENQHEWLHPVQQ | <0.1 |
| 237 | pNOP314359 | PBRM1 | SGRNLPHDMYSRKVCCVVIQGLPLLQAN | <0.1 |
| 238 | pNOP320508 | PBRM1 | GLSCPKCDFADSRAYPQSFCVSHESSG | <0.1 |
| 239 | pNOP324586 | PBRM1 | NLLLQKTNCSSEGAITFAGKEDPVARS | <0.1 |
| 240 | pNOP336473 | PBRM1 | KQHVPCWRLRLCGTCRGQPTTTYRLY | <0.1 |
| 241 | pNOP364497 | PBRM1 | HVAEGWRLCLHQVPWPGASSCGQN | <0.1 |
| 242 | pNOP365921 | PBRM1 | KSMGSRWSCIFLWPHLHSPRRNRA | <0.1 |
| 243 | pNOP370708 | PBRM1 | RKSTFFSTLPVFSSLLEGDPGAAS | <0.1 |
| 244 | pNOP380983 | PBRM1 | ISRPLPRGYRMEATKVFMQWPKI | <0.1 |
| 245 | pNOP386577 | PBRM1 | RGRVRSRKHHFLYGCFKSFLSAL | <0.1 |
| 246 | pNOP39757 alt splice b | PBRM1 | NEKKKKEKLKRVKIPLVLQASQAYIAHTARTVALKTACTMLEITSMWNLQRPTYNHI SSVLKDCGRIQLVKNGCMAVGFTDQMKHSTWLHENF | <0.1 |
| 247 | pNOP407746 | PBRM1 | VKSSNEDSIQLGCSQTDRSFTQ | <0.1 |
| 248 | pNOP40838 alt splice b | PBRM1 | NEKKKKELKRVKIPLVLQASQAYIAHTARTVALKTACTMLEITSMWNLQRPTYNHIS SVLKDCGRIQLVKNGCMAVGFTDQMKHSTWLHENF | <0.1 |
| 249 | pNOP416668 | PBRM1 | KSSTRRSFISNYNGTSIWLRK | <0.1 |
| 250 | pNOP425265 | PBRM1 | TLQKWRDSSFTGTQLYHKTFA | <0.1 |
| 251 | pNOP434493 | PBRM1 | KAHGHGKNSKSHDGQQVPRY | <0.1 |
| 252 | pNOP448870 | PBRM1 | CLKMPNAIMCPIQPSTSEF | <0.1 |
| 253 | pNOP449322 | PBRM1 | CTYPGEVTQGEKERAGPTA | <0.1 |
| 254 | pNOP452067 | PBRM1 | GKMLQRFFSRNSCCGSQLS | <0.1 |
| 255 | pNOP453139 | PBRM1 | HGFQEKKSYLPFQQCQRGL | <0.1 |

TABLE 1 -continued

Library of NOP sequences
Sequences of NOPs including the percentage of kidney cancer patients identified in the present study with each NOP. The sequences referred to herein correspond to the sequence numbering in the table below. Different predicted alternative splice forms are indicated as "alt splice x".

| Sequence | PeptideID | geen | PeptideSeq | % Kidney Cancer Patients |
|---|---|---|---|---|
| 256 | pNOP460219 | PBRM1 | QKFLLWIPTFLTNHPLHLT | <0.1 |
| 257 | pNOP461097 | PBRM1 | RFLWCCRPLRLTSHIQPGL | <0.1 |
| 258 | pNOP471164 | PBRM1 | ERQADEEIQRIEEVFTLC | <0.1 |
| 259 | pNOP475150 | PBRM1 | KAKGPTPPWQMPSGAFEI | <0.1 |
| 260 | pNOP475643 | PBRM1 | KKKFLRVTITTKFQLVKF | <0.1 |
| 261 | pNOP484932 alt splice f | PBRM1 | SLQPPLILVVPKEKVKRT | <0.1 |
| 262 | pNOP489695 | PBRM1 | AGVFDLQRCSCSTQSPA | <0.1 |
| 263 | pNOP499515 | PBRM1 | LKEKYFFLHITSLLQLT | <0.1 |
| 264 | pNOP501126 | PBRM1 | NAHITTTDPNKTEESRI | <0.1 |
| 265 | pNOP505051 | PBRM1 | RHDGWLSARPSTFAGPS | <0.1 |
| 266 | pNOP513619 | PBRM1 | CGEREKGKIAKRNRGR | <0.1 |
| 267 | pNOP51984 alt splice a | PBRM1 | LRPNTQTTLSGSSAAWWGQNGEILRQPRKQNMKSGQLKLLSSRRESEQHSNSSRVLLP EQAPLWGLSWGWCHHQHQWGCSISS | <0.1 |
| 268 | pNOP521733 | PBRM1 | KRLKLNIMKWLSQVFE | <0.1 |
| 269 | pNOP531143 | PBRM1 | SIGTSKKDESDRFRNI | <0.1 |
| 270 | pNOP535461 | PBRM1 | WPTSTKILTLWLRTLS | <0.1 |
| 271 | pNOP548322 | PBRM1 | LPHQRPSGFFTQRPT | <0.1 |
| 272 | pNOP550107 | PBRM1 | NIPPGYTKISRKRSF | <0.1 |
| 273 | pNOP554243 | PBRM1 | RIFSSLLEGDPGAAS | <0.1 |
| 274 | pNOP555796 | PBRM1 | RTILIRGVAASVPYF | <0.1 |
| 275 | pNOP566375 | PBRM1 | EGSPPQCHISEASL | <0.1 |
| 276 | pNOP574911 | PBRM1 | LLKSPWTWKKFEVT | <0.1 |
| 277 | pNOP577711 | PBRM1 | NSRQVCGHVCQGIL | <0.1 |
| 278 | pNOP585233 | PBRM1 | SRLQTLGFVPSNKK | <0.1 |
| 279 | pNOP590879 | PBRM1 | AHKNVLQKRSISE | <0.1 |
| 280 | pNOP592931 | PBRM1 | CSGTPSTFAKHTT | <0.1 |
| 281 | pNOP60025 | PBRM1 | RCDEPRSGPYGRDSSTRWKSIWTTGGSFGASRAAGTTSISRPTSSWTPCHTAANNTH VCSSPTKDPAASSLRGLPEIH | <0.1 |
| 282 | pNOP601294 | PBRM1 | KIKIHDSNAAETK | <0.1 |
| 283 | pNOP603087 | PBRM1 | LDENPTETKNGRV | <0.1 |
| 284 | pNOP617063 | PBRM1 | TSFSTSASDPPGQ | <0.1 |
| 285 | pNOP617777 | PBRM1 | VGRVAFLLKNQNT | <0.1 |
| 286 | pNOP617867 | PBRM1 | VIRMMREDATAIL | <0.1 |
| 287 | pNOP622052 | PBRM1 | AWLSSIQGCKEN | <0.1 |
| 288 | pNOP626183 | PBRM1 | FKSLSTIFLCQS | <0.1 |

TABLE 1 -continued

Library of NOP sequences
Sequences of NOPs including the percentage of kidney cancer patients identified in the present study with each NOP. The sequences referred to herein correspond to the sequence numbering in the table below. Different predicted alternative splice forms are indicated as "alt splice x".

| Sequence | PeptideID | geen | PeptideSeq | % Kidney Cancer Patients |
|---|---|---|---|---|
| 289 | pNOP626974 alt splice g | PBRM1 | GDWLFEALVVLW | <0.1 |
| 290 | pNOP627099 | PBRM1 | GFPLDLSCLTTI | <0.1 |
| 291 | pNOP632437 | PBRM1 | KMVVWLLVLPTK | <0.1 |
| 292 | pNOP63453 | PBRM1 | QVGSDTGSSKTRRPFVERTGEPPTLSLAEKQRGPHHHGRCPLAPSRFDAPGHPQHSPSIQPRKCLITSLRFFYIEA | <0.1 |
| 293 | pNOP647364 | PBRM1 | TFLPFAFKEKIP | <0.1 |
| 294 | pNOP656432 | PBRM1 | EEYRQLRGQSS | <0.1 |
| 295 | pNOP659059 alt splice g | PBRM1 | GDWLFEALVVL | <0.1 |
| 296 | pNOP660715 | PBRM1 | GTKAKKSTRLL | <0.1 |
| 297 | pNOP662459 | PBRM1 | IGQIQKYMKMQ | <0.1 |
| 298 | pNOP669764 | PBRM1 | NHLGANGLENN | <0.1 |
| 299 | pNOP679970 | PBRM1 | SSRARFRQKTL | <0.1 |
| 300 | pNOP694253 | PBRM1 | GLHPTWLQPD | <0.1 |
| 301 | pNOP698245 | PBRM1 | ITVFCQNQIF | <0.1 |
| 302 | pNOP700951 | PBRM1 | KWKSMMMLIC | <0.1 |
| 303 | pNOP710206 | PBRM1 | RCSRTSAVFY | <0.1 |
| 304 | pNOP712256 | PBRM1 | RRCCFSCCTL | <0.1 |
| 305 | pNOP712598 | PBRM1 | RRSWSSFLKP | <0.1 |
| 306 | pNOP713384 | PBRM1 | RWARQSGHSD | <0.1 |
| 307 | pNOP713614 | PBRM1 | SAISRLLCNN | <0.1 |
| 308 | pNOP717507 | PBRM1 | TKTRRRKKRS | <0.1 |
| 309 | pNOP88057 alt splice c | PBRM1 | AAGERASSTATAAECFSPSRHPCGGSHGGGATTNTNGDAQSAVDTCCRHDGWLSARPSTFAGPS | <0.1 |
| 310 | pNOP91822 alt splice e | PBRM1 | KVEMMILKRWEKKIVRSLNLLLYLSFRPPWPVSWTSCPTHPHSLPQSLPKAVQRRKAPNGKST | <0.1 |
| 311 | pNOP13160 | BAP1 | AVLLMGNCQCCSPTPSTSWLRSSKSPRRTSQFLCPSRLAAGLGVRLWQCPHTRSPHPPPAMRVQTRPLRSAVLSTRHCARLSAQPTRRGPPALSPPTSPRCFLERMTACCVLTAYATTVLSVIWVLSSAQACCTWLRMGC | 1.09 |
| 312 | pNOP179558 | BAP1 | WSRTSPCGGAKGSASAGSTSSGSLTGGNALAPTRPSASEDCWP | 0.73 |
| 313 | pNOP403156 | BAP1 | QRGWESGCGSAHTLAALTHPQQ | 0.55 |
| 314 | pNOP185542 | BAP1 | VHLHLYLHAGSGRHAGQPSGAEHLRAAAPRGQHRPAPQAAEA | 0.36 |
| 315 | pNOP82605 | BAP1 | TITIMPSPPCRRKKTWRQVWAAAEFQSAHPSSTQMMRMTMRMTRRMTCRTPTLPLGIRGREQGSQGH | 0.36 |
| 316 | pNOP144488 alt splice a | BAP1 | PWALGGGRGVDRQGPAGHHGAYRPRHCRGALPRHPLQPDGSGARPQDQV | 0.18 |
| 317 | pNOP372160 | BAP1 | SLQAAASMGFTPTPLPLSSGCRPF | 0.18 |
| 318 | pNOP396500 | BAP1 | GVQVSQQQVPAGAGSKQGPCSL | 0.18 |

TABLE 1 -continued

Library of NOP sequences
Sequences of NOPs including the percentage of kidney cancer patients identified in the present study with each NOP. The sequences referred to herein correspond to the sequence numbering in the table below. Different predicted alternative splice forms are indicated as "alt splice x".

| Sequence | PeptideID | geen | PeptideSeq | % Kidney Cancer Patients |
|---|---|---|---|---|
| 319 | pNOP42739 | BAP1 | GQPHRWCRGGGWFMRTSPIPQPSQQTQASGEASRQQPQWGSPQPHSHCPAAAGLSRQSQLCQVPHAGGRRPGGRCGPQPSSSPPTPAVLR | 0.18 |
| 320 | pNOP492413 | BAP1 | EAQRVPEGPLNSSVHQD | 0.18 |
| 321 | pNOP64587 alt splice b | BAP1 | GWGAESPGADRGWEGFLALHQTNPRQPGVQQPSGEGGRGSHGQQREDGDGEAWRALEWGEILTQGAAGTAEVCGG | 0.18 |
| 322 | pNOP91275 | BAP1 | FRPTSLKSHSCLRSPSQPATSPRWCWKQTGPLQPLRATTQMVQRRRLVHAHKPHPTALPINPS | 0.18 |
| 323 | pNOP100199 alt splice b | BAP1 | GWGAESPGADRGWEGFLALHQTNPRQPGVQQPSGEGGRGSHGQQREDGDGAAGTAEVCGG | <0.1 |
| 324 | pNOP159625 | BAP1 | PAETLSPLQGQAPVRTAGPDSAAHSCRVALTRVLPCPTSPFPSITE | <0.1 |
| 325 | pNOP163874 | BAP1 | HVLCPPADTQLLCNSCLAERAPELQQRGPGTHPESHEGLHQGFQP | <0.1 |
| 326 | pNOP165665 alt splice c | BAP1 | QRVGRVPRPPSDQSKAARGPAAQWRRRSWKPRTAERRRGWSCWHC | <0.1 |
| 327 | pNOP178195 alt splice d | BAP1 | RSTPLTMGPGGRTRSGQTRPGGSSWSVSASPLQGSPTTTSAST | <0.1 |
| 328 | pNOP178196 alt splice d | BAP1 | RSTPLTMGPGGRTRSGQTRPGGSSWSVSASPLQGSSMRPGCMC | <0.1 |
| 329 | pNOP194903 | BAP1 | GQAACAEGEPSDSTRGSAAADKSNTARADSDPQVSRVTAA | <0.1 |
| 330 | pNOP197712 alt splice c | BAP1 | QRVGRVPRPPSDQSKAARGPAAQWRRRSWKPRTAERRRGW | <0.1 |
| 331 | pNOP216613 | BAP1 | DRQCFQLATALAYPLSQPDAALQPCHLPHLQGAFWRG | <0.1 |
| 332 | pNOP229607 | BAP1 | RRGRSSRLMTREGPTTTMSSSAPLSPCWLRKACWPT | <0.1 |
| 333 | pNOP231133 alt splice e | BAP1 | VGRNTHPSCLLLVGLCCWPAPIRGAMLGFGRSCWHC | <0.1 |
| 334 | pNOP277235 alt splice a | BAP1 | PWALGGGRGVDRQGPAGHHGAYRPRHCRDQV | <0.1 |
| 335 | pNOP34900 alt splice b | BAP1 | GWGAESPGADRGWEGFLALHQTNPRQPGVQQPSGEGGRGSHGQQREDGDGEAWRALEWGEILTQAAYCSWGFVAGPPRSEVQCWVLAGAAGTAEVCGG | <0.1 |
| 336 | pNOP410821 | BAP1 | CSADHGGVPLCQLCAYHRPAL | <0.1 |
| 337 | pNOP508542 | BAP1 | SVWRLRLQTMRRASRRR | <0.1 |
| 338 | pNOP511363 | BAP1 | WQWCPTAGSSMRPGCMC | <0.1 |
| 339 | pNOP516062 | BAP1 | EQRICDWQCPGVGQGP | <0.1 |
| 340 | pNOP51715 alt splice b | BAP1 | GWGAESPGADRGWEGFLALHQTNPRQPGVQQPSGEGGRGSHGQQREDGDAAYCSWGFVAGPPRSEVQCWVLAGAAGTAEVCGG | <0.1 |
| 341 | pNOP543182 | BAP1 | GVPQGGGREEEEVQD | <0.1 |
| 342 | pNOP560984 | BAP1 | WATVSAAAQHHQRLG | <0.1 |
| 343 | pNOP568350 | BAP1 | GEGNREARGIERFC | <0.1 |
| 344 | pNOP613742 | BAP1 | SGSCHQHRPAAPG | <0.1 |
| 345 | pNOP617773 alt splice e | BAP1 | VGRNTHPRSCWHC | <0.1 |
| 346 | pNOP706421 | BAP1 | PCQARATPPP | <0.1 |

TABLE 1 -continued

Library of NOP sequences
Sequences of NOPs including the percentage of kidney cancer patients identified in the present study with each NOP. The sequences referred to herein correspond to the sequence numbering in the table below. Different predicted alternative splice forms are indicated as "alt splice x".

| Sequence | PeptideID | geen | PeptideSeq | % Kidney Cancer Patients |
|---|---|---|---|---|
| 347 | pNOP716714 | BAP1 | TAAAWTWDPP | <0.1 |
| 348 | pNOP722094 | BAP1 | YPTLVQLMPC | <0.1 |
| 349 | pNOP75322 | BAP1 | RTSPRVSALRAKDMRLAMPRSWPRPIIAMPGPSHATSLRSRMALVQCGPWRRSTLSAMCLSQAGSLSWMG | <0.1 |
| 350 | pNOP76739 | BAP1 | IRAGWSWRATQASSPCSWKISVSRGCKWRRSTTFRANVRALYMDLSSCSNGSKSAGPGERSLPWWMIRP | <0.1 |
| 351 | pNOP79648 alt splice c | BAP1 | QRVGRVPRPPSDQSKAARGPAAQWRRRSWKPRTAERRRGCCLLLVGLCCWPAPIRGAMLGFGRSCWHC | <0.1 |
| 352 | pNOP88716 | BAP1 | GLAGAGERPRPLHPARGRFRCQGGASGGDLRPSEQMSGPCIWIYLPVQMDRRAPVPAKGLYLGG | <0.1 |

In a preferred embodiment the disclosure provides one or more frameshift-mutation peptides (also referred to herein as 'neoantigens') comprising an amino acid sequence selected from the groups:

(i) Sequences 1-18, an amino acid sequence having 90% identity to Sequences 1-18, or a fragment thereof comprising at least 10 consecutive amino acids of Sequences 1-18;
(ii) Sequences 19-188, an amino acid sequence having 90% identity to Sequences 19-188, or a fragment thereof comprising at least 10 consecutive amino acids of Sequences 19-188;
(iii) Sequences 189-310, an amino acid sequence having 90% identity to Sequences 189-310, or a fragment thereof comprising at least 10 consecutive amino acids of Sequences 189-310; and
(iv) Sequences 311-352, an amino acid sequence having 90% identity to Sequences 311-352, or a fragment thereof comprising at least 10 consecutive amino acids of Sequences 311-352.

As will be clear to a skilled person, the preferred amino acid sequences may also be provided as a collection of tiled sequences, wherein such a collection comprises two or more peptides that have an overlapping sequence. Such 'tiled' peptides have the advantage that several peptides can be easily synthetically produced, while still covering a large portion of the NOP. In an exemplary embodiment, a collection comprising at least 3, 4, 5, 6, 10, or more tiled peptides each having between 10-50, preferably 12-45, more preferably 15-35 amino acids, is provided. As described further herein, such tiled peptides are preferably directed to the C-terminus of a pNOP. As will be clear to a skilled person, a collection of tiled peptides comprising an amino acid sequence of Sequence X, indicates that when aligning the tiled peptides and removing the overlapping sequences, the resulting tiled peptides provide the amino acid sequence of Sequence X, albeit present on separate peptides. As is also clear to a skilled person, a collection of tiled peptides comprising a fragment of 10 consecutive amino acids of Sequence X, indicates that when aligning the tiled peptides and removing the overlapping sequences, the resulting tiled peptides provide the amino acid sequence of the fragment, albeit present on separate peptides. When providing tiled peptides, the fragment preferably comprises at least 20 consecutive amino acids of a sequence as disclosed herein.

Specific NOP sequences cover a large percentage of kidney cancer patients. Preferred NOP sequences, or subsequences of NOP sequence, are those that target the largest percentage of kidney cancer patients. Preferred sequences are, preferably in this order of preference, Sequence 1 (6.2% of kidney cancer patients) and Sequence 2 (3.6% of kidney cancer patients), Sequence 3, 4 (each covering 3.5% of kidney cancer patients), Sequence 5 (2.6% of kidney cancer patients), Sequence 6 (2% of kidney cancer patients), Sequence 189 (1.8% of kidney cancer patients), Sequence 7, 19 (each covering 1.3% of kidney cancer patients), Sequence 311 (1.1% of kidney cancer patients), Sequence 312 (0.7% of kidney cancer patients), Sequence 8, 20, 190-192, 313 (each covering 0.6% of kidney cancer patients), Sequence 21-22, 193-200, 314-315 (each covering 0.4% of kidney cancer patients), Sequence 23-31, 201-215, 316-322 (each covering 0.2% of kidney cancer patients), and all other Sequences listed in Table 1 and not mentioned in this paragraph (each covering <0.1% of kidney cancer patients).

As discussed further herein, neoantigens also include the nucleic acid molecules (such as DNA and RNA) encoding said amino acid sequences. The preferred sequences listed above are also the preferred sequences for the embodiments described further herein.

Preferably, the neoantigens and vaccines disclosed herein induce an immune response, or rather the neoantigens are immunogenic. Preferably, the neoantigens bind to an antibody or a T-cell receptor. In preferred embodiments, the neoantigens comprise an MHCI or MHCII ligand.

The major histocompatibility complex (MHC) is a set of cell surface molecules encoded by a large gene family in vertebrates. In humans, MHC is also referred to as human leukocyte antigen (HLA). An MHC molecule displays an antigen and presents it to the immune system of the vertebrate. Antigens (also referred to herein as 'MHC ligands') bind MHC molecules via a binding motif specific for the MHC molecule. Such binding motifs have been characterized and can be identified in proteins. See for a review Meydan et al. 2013 BMC Bioinformatics 14:S13.

MHC-class I molecules typically present the antigen to CD8 positive T-cells whereas MHC-class II molecules present the antigen to CD4 positive T-cells. The terms "cellular immune response" and "cellular response" or similar terms refer to an immune response directed to cells characterized by presentation of an antigen with class I or class II MHC involving T cells or T-lymphocytes which act as either "helpers" or "killers". The helper T cells (also termed CD4+ T cells) play a central role by regulating the immune response and the killer cells (also termed cytotoxic T cells, cytolytic T cells, CD8+ T cells or CTLs) kill diseased cells such as cancer cells, preventing the production of more diseased cells.

In preferred embodiments, the present disclosure involves the stimulation of an anti-tumor CTL response against tumor cells expressing one or more tumor-expressed antigens (i.e., NOPs) and preferably presenting such tumor-expressed antigens with class I MHC.

In some embodiments, an entire NOP (e.g., Sequence 1) may be provided as the neoantigen (i.e., peptide). The length of the NOPs identified herein vary from around 10 to around 140 amino acids. Preferred NOPs are at least 20 amino acids in length, more preferably at least 30 amino acids, and most preferably at least 50 amino acids in length. While not wishing to be bound by theory, it is believed that neoantigens longer than 10 amino acids can be processed into shorter peptides, e.g., by antigen presenting cells, which then bind to MHC molecules.

In some embodiments, fragments of a NOP can also be presented as the neoantigen. The fragments comprise at least 8 consecutive amino acids of the NOP, preferably at least 10 consecutive amino acids, and more preferably at least 20 consecutive amino acids, and most preferably at least 30 amino acids. In some embodiments, the fragments can be about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, or about 120 amino acids or greater. Preferably, the fragment is between 8-50, between 8-30, or between 10-20 amino acids. As will be understood by the skilled person, fragments greater than about 10 amino acids can be processed to shorter peptides, e.g., by antigen presenting cells.

The specific mutations resulting in the generation of a neo open reading frame may differ between individuals resulting in differing NOP lengths. However, as depicted in, e.g., FIG. 2, such individuals share common NOP sequences, in particular at the C-terminus of an NOP. While suitable fragments for use as neoantigens may be located at any position along the length of an NOP, fragments located near the C-terminus are preferred as they are expected to benefit a larger number of patients. Preferably, fragments of a NOP correspond to the C-terminal (3') portion of the NOP, preferably the C-terminal 10 consecutive amino acids, more preferably the C-terminal 20 consecutive amino acids, more preferably the C-terminal 30 consecutive amino acids, more preferably the C-terminal 40 consecutive amino acids, more preferably the C-terminal 50 consecutive amino acids, more preferably the C-terminal 60 consecutive amino acids, more preferably the C-terminal 70 consecutive amino acids, more preferably the C-terminal 80 consecutive amino acids, more preferably the C-terminal 90 consecutive amino acids, and most preferably the C-terminal 100 or more consecutive amino acids. As is clear to a skilled person, the C-terminal amino acids need not include the, e.g., 1-most C-terminal amino acids. In some embodiments a subsequence of the preferred C-terminal portion of the NOP may be highly preferred for reasons of manufacturability, solubility and MHC binding strength.

Suitable fragments for use as neoantigens can be readily determined. The NOPs disclosed herein may be analysed by known means in the art in order to identify potential MHC binding peptides (i.e., MHC ligands). Suitable methods are described herein in the examples and include in silico prediction methods (e.g., ANNPRED, BIMAS, EPIMHC, HLABIND, IEDB, KISS, MULTIPRED, NetMHC, PEPVAC, POPI, PREDEP, RANKPEP, SVMHC, SVRMHC, and SYFFPEITHI, see Lundegaard 2010 130:309-318 for a review). MHC binding predictions depend on HLA genotypes, furthermore it is well known in the art that different MHC binding prediction programs predict different MHC affinities for a given epitope. While not wishing to be limited by such predictions, at least 60% of NOP sequences as 15 defined herein, contain one or more predicted high affinity MHC class I binding epitope of 10 amino acids, based on allele HLA-A0201 and using NetMHC4.0.

A skilled person will appreciate that natural variations may occur in the genome resulting in variations in the sequence of an NOP. Accordingly, a neoantigen of the disclosure may comprise minor sequence variations, including, e.g., conservative amino acid substitutions. Conservative substitutions are well known in the art and refer to the substitution of one or more amino acids by similar amino acids. For example, a conservative substitution can be the substitution of an amino acid for another amino acid within the same general class (e.g., an acidic amino acid, a basic amino acid, or a neutral amino acid). A skilled person can readily determine whether such variants retain their immunogenicity, e.g., by determining their ability to bind MHC molecules.

Preferably, a neoantigen has at least 90% sequence identity to the NOPs disclosed herein. Preferably, the neoantigen has at least 95% or 98% sequence identity. The term "% sequence identity" is defined herein as the percentage of nucleotides in a nucleic acid sequence, or amino acids in an amino acid sequence, that are identical with the nucleotides, resp. amino acids, in a nucleic acid or amino acid sequence of interest, after aligning the sequences and optionally introducing gaps, if necessary, to achieve the maximum percent sequence identity. The skilled person understands that consecutive amino acid residues in one amino acid sequence are compared to consecutive amino acid residues in another amino acid sequence. Methods and computer programs for alignments are well known in the art. Sequence identity is calculated over substantially the whole length, preferably the whole (full) length, of a sequence of interest.

The disclosure also provides at least two frameshift-mutation derived peptides (i.e., neoantigens), also referred to herein as a 'collection' of peptides. Preferably the collection comprises at least 3, at least 4, at least 5, at least 10, at least 15, or at least 20, or at least 50 neoantigens. In some embodiments, the collections comprise less than 20, preferably less than 15 neoantigens. Preferably, the collections comprise the top 20, more preferably the top 15 most frequently occurring neoantigens in cancer patients. The neoantigens are selected from (i) Sequences 1-18, an amino acid sequence having 90% identity to Sequences 1-18, or a fragment thereof comprising at least 10 consecutive amino acids of Sequences 1-18;

(ii) Sequences 19-188, an amino acid sequence having 90% identity to Sequences 19-188, or a fragment thereof comprising at least 10 consecutive amino acids of Sequences 19-188;

(iii) Sequences 189-310, an amino acid sequence having 90% identity to Sequences 189-310, or a fragment thereof comprising at least 10 consecutive amino acids of Sequences 189-310; and (iv) Sequences 311-352, an amino acid sequence having 90% identity to Sequences 311-352, or a fragment thereof comprising at least 10 consecutive amino acids of Sequences 311-352.

Preferably, the collection comprises at least two frameshift-mutation derived peptides corresponding to the same gene. Preferably, a collection is provided comprising:

(i) at least two frameshift-mutation derived peptides, wherein each peptide, or collection of tiled peptides, comprises a different amino acid sequence selected from Sequences 1-18, an amino acid sequence having 90% identity to Sequences 1-18, or a fragment thereof comprising at least 10 consecutive amino acids of Sequences 1-18;

(ii) at least two frameshift-mutation derived peptides, wherein each peptide, or collection of tiled peptides, comprises a different amino acid sequence selected from Sequences 19-188, an amino acid sequence having 90% identity to Sequences 19-188, or a fragment thereof comprising at least 10 consecutive amino acids of Sequences 19-188;

(iii) at least two frameshift-mutation derived peptides, wherein each peptide, or collection of tiled peptides, comprises a different amino acid sequence selected from Sequences 189-310, an amino acid sequence having 90% identity to Sequences 189-310, or a fragment thereof comprising at least 10 consecutive amino acids of Sequences 189-310; or (iv) at least two frameshift-mutation derived peptides, wherein each peptide, or collection of tiled peptides, comprises a different amino acid sequence selected from Sequences 311-352, an amino acid sequence having 90% identity to Sequences 311-352, or a fragment thereof comprising at least 10 consecutive amino acids of Sequences 311-352.

In some embodiments, the collection comprises two or more neoantigens corresponding to the same NOP. For example, the collection may comprise two (or more) fragments of Sequence 1 or the collection may comprise a peptide having Sequence 1 and a peptide having 95% identity to Sequence 1.

Preferably, the collection comprises two or more neoantigens corresponding to different NOPs. In some embodiments, the collection comprises two or more neoantigens corresponding to different NOPs of the same gene. For example the peptide may comprise the amino acid sequence of Sequence 1 (or a fragment or collection of tiled fragments thereof) and the amino acid sequence of Sequence 2 (or a fragment or collection of tiled fragments thereof).

Preferably, the collection comprises Sequences 1-4, preferably 1-7, more preferably 1-18 (or a fragment or collection of tiled fragments thereof).

Preferably, the collection comprises Sequences 19-20, preferably 19-31, more preferably 19-188 (or a fragment or collection of tiled fragments thereof).

Preferably, the collection comprises Sequences 189-192, preferably 189-215, more preferably 189-310 (or a fragment or collection of tiled fragments thereof).

Preferably, the collection comprises Sequences 311-313, preferably 311-322, more preferably 311-352 (or a fragment or collection of tiled fragments thereof).

In some embodiments, the collection comprises two or more neoantigens corresponding to different NOPs of different genes. For example the collection may comprise a peptide having the amino acid sequence of Sequence 1 (or a fragment or collection of tiled fragments thereof) and a peptide having the amino acid sequence of Sequence 19 (or a fragment or collection of tiled fragments thereof). Preferably, the collection comprises at least one neoantigen from group (i) and at least one neoantigen from group (ii); at least one neoantigen from group (i) and at least one neoantigen from group (iii); at least one neoantigen from group (i) and at least one neoantigen from group (iv); at least one neoantigen from group (i) and at least one neoantigen from group (v); at least one neoantigen from group (ii) and at least one neoantigen from group (iii); at least one neoantigen from group (ii) and at least one neoantigen from group (iv); or at least one neoantigen from group (iii) and at least one neoantigen from group (iv). Preferably, the collection comprises at least one neoantigen from group (i), at least one neoantigen from group (ii), and at least one neoantigen from group (iii). Preferably, the collection comprises at least one neoantigen from each of groups (i) to (iv).

In a preferred embodiment, the collections disclosed herein include Sequence 1 and Sequence 2 (or a variant or fragment or collection of tiled fragments thereof as disclosed herein). In preferred embodiments, the collection further includes one or both of Sequence 3 and 4 (or a variant or fragment or collection of tiled fragments thereof as disclosed herein). In preferred embodiments, the collection further includes, Sequence 5 (or a variant or fragment or collection of tiled fragments thereof as disclosed herein). In preferred embodiments, the collection even further includes Sequence 6 (or a variant or fragment or collection of tiled fragments thereof as disclosed herein). In preferred embodiments, the collection even further includes Sequence 189 (or a variant or fragment or collection of tiled fragments thereof as disclosed herein). In preferred embodiments, the collection even further includes one or both of Sequence 7 and 19 (or a variant or fragment or collection of tiled fragments thereof as disclosed herein). In preferred embodiments, the collection even further includes Sequence 311 (or a variant or fragment or collection of tiled fragments thereof as disclosed herein). In preferred embodiments, the collection even further includes Sequence 312 (or a variant or fragment or collection of tiled fragments thereof as disclosed herein). In preferred embodiments, the collection even further includes Sequence 8, 20, 190-192, 313 (or a variant or fragment or collection of tiled fragments thereof as disclosed herein). In preferred embodiments, the collection even further includes Sequence 21-22, 193-200, 314-315 (or a variant or fragment or collection of tiled fragments thereof as disclosed herein). In preferred embodiments, the collection even further includes Sequence 23-31, 201-215, 316-322 (or a variant or fragment or collection of tiled fragments thereof as disclosed herein). In preferred embodiments, the collection even further includes all other Sequences listed in Table 1 and not mentioned in this paragraph (or a variant or fragment or collection of tiled fragments thereof as disclosed herein).

Such collections comprising multiple neoantigens have the advantage that a single collection (e.g, when used as a vaccine) can benefit a larger group of patients having different frameshift mutations. This makes it feasible to construct and/or test the vaccine in advance and have the vaccine available for off-the-shelf use. This also greatly reduces the time from screening a tumor from a patient to administering a potential vaccine for said tumor to the patient, as it eliminates the time of production, testing and approval. In addition, a single collection consisting of multiple neoantigens corresponding to different genes will limit possible resistance mechanisms of the tumor, e.g. by losing one or more of the targeted neoantigens.

In preferred embodiments, the neoantigens (i.e., peptides) are directly linked. Preferably, the neoantigens are linked by peptide bonds, or rather, the neoantigens are present in a single polypeptide. Accordingly, the disclosure provides polypeptides comprising at least two peptides (i.e., neoantigens) as disclosed herein. In some embodiments, the polypeptide comprises 3, 4, 5, 6, 7, 8, 9, 10 or more peptides as disclosed herein (i.e., neoantigens). Such polypeptides are also referred to herein as 'polyNOPs'. A collection of peptides can have one or more peptides and one or more polypeptides comprising the respective neoantigens.

In an exemplary embodiment, a polypeptide of the disclosure may comprise different neoantigens, each neoantigen having between 10-400 amino acids. Thus, the polypeptide of the disclosure may comprise between 100-4000 amino acids, or more. As is clear to a skilled person, the final length of the polypeptide is determined by the number of neoantigens selected and their respective lengths. A collection may comprise two or more polypeptides comprising the neoantigens which can be used to reduce the size of each of the polypeptides.

In some embodiments, the amino acid sequences of the neoantigens are located directly adjacent to each other in the polypeptide. For example, a nucleic acid molecule may be provided that encodes multiple neoantigens in the same reading frame. In some embodiments, a linker amino acid sequence may be present. Preferably a linker has a length of 1, 2, 3, 4 or 5, or more amino acids. The use of linker may be beneficial, for example for introducing, among others, signal peptides or cleavage sites. In some embodiments at least one, preferably all of the linker amino acid sequences have the amino acid sequence VDD.

As will be appreciated by the skilled person, the peptides and polypeptides disclosed herein may contain additional amino acids, for example at the N- or C-terminus. Such additional amino acids include, e.g., purification or affinity tags or hydrophilic amino acids in order to decrease the hydrophobicity of the peptide. In some embodiments, the neoantigens may comprise amino acids corresponding to the adjacent, wild-type amino acid sequences of the relevant gene, i.e., amino acid sequences located 5' to the frame shift mutation that results in the neo open reading frame. Preferably, each neoantigen comprises no more than 20, more preferably no more than 10, and most preferably no more than 5 of such wild-type amino acid sequences.

In preferred embodiments, the peptides and polypeptides disclosed herein have a sequence depicted as follows:

$A\text{-}B\text{-}C\text{-}(D\text{-}E)_n$, wherein

A, C, and E are independently 0-100 amino acids

B and D are amino acid sequences as disclosed herein and selected from sequences 1-352, or an amino acid sequence having 90% identity to Sequences 1-352, or a fragment thereof comprising at least 10 consecutive amino acids of Sequences 1-352, n is an integer from 0 to 500.

Preferably, B and D are different amino acid sequences. Preferably, n is an integer from 0-200. Preferably A, C, and E are independently 0-50 amino acids, more preferably independently 0-20 amino acids.

The peptides and polypeptides disclosed herein can be produced by any method known to a skilled person. In some embodiments, the peptides and polypeptide are chemically synthesized. The peptides and polypeptide can also be produced using molecular genetic techniques, such as by inserting a nucleic acid into an expression vector, introducing the expression vector into a host cell, and expressing the peptide. Preferably, such peptides and polypeptide are isolated, or rather, substantially isolated from other polypeptides, cellular components, or impurities. The peptide and polypeptide can be isolated from other (poly) peptides as a result of solid phase protein synthesis, for example. Alternatively, the peptides and polypeptide can be substantially isolated from other proteins after cell lysis from recombinant production (e.g., using HPLC).

The disclosure further provides nucleic acid molecules encoding the peptides and polypeptide disclosed herein. Based on the genetic code, a skilled person can determine the nucleic acid sequences which encode the (poly) peptides disclosed herein. Based on the degeneracy of the genetic code, sixty-four codons may be used to encode twenty amino acids and translation termination signal.

In a preferred embodiment, the nucleic acid molecules are codon optimized. As is known to a skilled person, codon usage bias in different organisms can effect gene expression level. Various computational tools are available to the skilled person in order to optimize codon usage depending on which organism the desired nucleic acid will be expressed. Preferably, the nucleic acid molecules are optimized for expression in mammalian cells, preferably in human cells. Table 2 lists for each acid amino acid (and the stop codon) the most frequently used codon as encountered in the human exome.

TABLE 2

| most frequently used codon for each amino acid and most frequently used stop codon. | |
|---|---|
| A | GCC |
| C | TGC |
| D | GAC |
| E | GAG |
| F | TTC |
| G | GGC |
| H | CAC |
| I | ATC |
| K | AAG |
| L | CTG |
| M | ATG |
| N | AAC |
| P | CCC |
| Q | CAG |
| R | CGG |
| S | AGC |

TABLE 2-continued

| most frequently used codon for each amino acid and most frequently used stop codon. | |
|---|---|
| T | ACC |
| V | GTG |
| W | TGG |
| Y | TAC |
| Stop | TGA |

In preferred embodiments, at least 50%, 60%, 70%, 80%, 90%, or 100% of the amino acids are encoded by a codon corresponding to a codon presented in Table 2.

In preferred embodiments, the nucleic acid molecule encodes for a linker amino acid sequence in the peptide. Preferably, the nucleic acid sequence encoding the linker comprises at least one codon triplet that codes for a stop codon when a frameshift occurs. Preferably, said codon triplet is chosen from the group consisting of: ATA, CTA, GTA, TTA, ATG, CTG, GTG, TTG, AAA, AAC, AAG, AAT, AGA, AGC, AGG, AGT, GAA, GAC, GAG, and GAT. These codons do not code for a stop codon, but could create a stop codon in case of a frame shift, such as when read in the +1, +2, +4, +, 5, etc. reading frame. For example, two amino acid encoding sequences are linked by a linker amino acid encoding sequence as follows (linker amino acid encoding sequence in bold):

CTATACAGGCGAATGAGATTATG

Resulting in the following amino acid sequence (amino acid linker sequence in bold): LYRRMRL In case of a +1 frame shift, the following sequence is encoded:

YTGE[stop]DY

This embodiment has the advantage that if a frame shift occurs in the nucleotide sequence encoding the peptide, the nucleic acid sequence encoding the linker will terminate translation, thereby preventing expression of (part of) the native protein sequence for the gene related to peptide sequence encoded by the nucleotide sequence.

In some preferred embodiments, the linker amino acid sequences are encoded by the nucleotide sequence GTAGATGAC. This linker has the advantage that it contains two out of frame stop codons (TAG and TGA), one in the +1 and one in the −1 reading frame. The amino acid sequence encoded by this nucleotide sequence is VDD. The added advantage of using a nucleotide sequence encoding for this linker amino acid sequence is that any frame shift will result in a stop codon.

The disclosure also provides binding molecules and a collection of binding molecules that bind the neoantigens disclosed herein and or a neoantigen/MHC complex. In some embodiments the binding molecule is an antibody, a T-cell receptor, or an antigen binding fragment thereof. In some embodiments the binding molecule is a chimeric antigen receptor comprising i) a T cell activation molecule; ii) a transmembrane region; and iii) an antigen recognition moiety; wherein said antigen recognition moieties bind the neoantigens disclosed herein and or a neoantigen/MHC complex.

The term "antibody" as used herein refers to an immunoglobulin molecule that is typically composed of two identical pairs of polypeptide chains, each pair of chains consisting of one "heavy" chain with one "light" chain. The human light chains are classified as kappa and lambda. The heavy chains comprise different classes namely: mu, delta, gamma, alpha or epsilon. These classes define the isotype of the antibody, such as IgM, IgD, IgG IgA and IgE, respectively. These classes are important for the function of the antibody and help to regulate the immune response. Both the heavy chain and the light chain comprise a variable domain and a constant region. Each heavy chain variable region (VH) and light chain variable region (VL) comprises complementary determining regions (CDR) interspersed by framework regions (FR). The variable region has in total four FRs and three CDRs. These are arranged from the amino- to the carboxyl-terminus as follows: FR1, CDR1, FR2, CDR2, FR3, CDR3, FR4. The variable regions of the light and heavy chain together form the antibody binding site and define the specificity for the epitope.

The term "antibody" encompasses murine, humanized, deimmunized, human, and chimeric antibodies, and an antibody that is a multimeric form of antibodies, such as dimers, trimers, or higher-order multimers of monomeric antibodies. The term antibody also encompasses monospecific, bispecific or multi-specific antibodies, and any other modified configuration of the immunoglobulin molecule that comprises an antigen recognition site of the required specificity.

Preferably, an antibody or antigen binding fragment thereof as disclosed herein is a humanized antibody or antigen binding fragment thereof. The term "humanized antibody" refers to an antibody that contains some or all of the CDRs from a non-human animal antibody while the framework and constant regions of the antibody contain amino acid residues derived from human antibody sequences. Humanized antibodies are typically produced by grafting CDRs from a mouse antibody into human framework sequences followed by back substitution of certain human framework residues for the corresponding mouse residues from the source antibody. The term "deimmunized antibody" also refers to an antibody of non-human origin in which, typically in one or more variable regions, one or more epitopes have been removed, that have a high propensity of constituting a human T-cell and/or B-cell epitope, for purposes of reducing immunogenicity. The amino acid sequence of the epitope can be removed in full or in part. However, typically the amino acid sequence is altered by substituting one or more of the amino acids constituting the epitope for one or more other amino acids, thereby changing the amino acid sequence into a sequence that does not constitute a human T-cell and/or B-cell epitope. The amino acids are substituted by amino acids that are present at the corresponding position(s) in a corresponding human variable heavy or variable light chain as the case may be.

In some embodiments, an antibody or antigen binding fragment thereof as disclosed herein is a human antibody or antigen binding fragment thereof. The term "human antibody" refers to an antibody consisting of amino acid sequences of human immunoglobulin sequences only. Human antibodies may be prepared in a variety of ways known in the art.

As used herein, antigen-binding fragments include Fab, F(ab'), F(ab') 2, complementarity determining region (CDR) fragments, single-chain antibodies (scFv), bivalent single-chain antibodies, and other antigen recognizing immunoglobulin fragments.

In some embodiments, the antibody or antigen binding fragment thereof is an isolated antibody or antigen binding fragment thereof. The term "isolated" as used herein refer to material which is substantially or essentially free from components which normally accompany it in nature.

In some embodiments, the antibody or antigen binding fragment thereof is linked or attached to a non-antibody moiety. In preferred embodiments, the non-antibody moiety is a cytotoxic moiety such as auristatins, maytanasines, calicheasmicins, duocarymycins, a-amanitin, doxorubicin, and centanamycin. Other suitable cytotoxins and methods for preparing such antibody drug conjugates are known in the art; see, e.g., WO2013085925A1 and WO2016133927A1.

Antibodies which bind a particular epitope can be generated by methods known in the art. For example, polyclonal antibodies can be made by the conventional method of immunizing a mammal (e.g., rabbits, mice, rats, sheep, goats). Polyclonal antibodies are then contained in the sera of the immunized animals and can be isolated using standard procedures (e.g., affinity chromatography, immunoprecipitation, size exclusion chromatography, and ion exchange chromatography). Monoclonal antibodies can be made by the conventional method of immunization of a mammal, followed by isolation of plasma B cells producing the monoclonal antibodies of interest and fusion with a myeloma cell (see, e.g., Mishell, B. B., et al., Selected Methods In Cellular Immunology, (W.H. Freeman, ed.) San Francisco (1980)). Peptides corresponding to the neoantiens disclosed herein may be used for immunization in order to produce antibodies which recognize a particular epitope. Screening for recognition of the epitope can be performed using standard immunoassay methods including ELISA techniques, radioimmunoassays, immunofluorescence, immunohistochemistry, and Western blotting. See, Short Protocols in Molecular Biology, Chapter 11, Green Publishing Associates and John Wiley & Sons, Edited by Ausubel, F. M et al., 1992. In vitro methods of antibody selection, such as antibody phage display, may also be used to generate antibodies recognizing the neoantigens disclosed herein (see, e.g., Schirrmann et al. Molecules 2011 16:412-426).

T-cell receptors (TCRs) are expressed on the surface of T-cells and consist of an $\alpha$ chain and a $\beta$ chain. TCRs recognize antigens bound to MHC molecules expressed on the surface of antigen-presenting cells. The T-cell receptor (TCR) is a heterodimeric protein, in the majority of cases (95%) consisting of a variable alpha ($\alpha$) and beta ($\beta$) chain, and is expressed on the plasma membrane of T-cells. The TCR is subdivided in three domains: an extracellular domain, a transmembrane domain and a short intracellular domain. The extracellular domain of both a and B chains have an immunoglobulin-like structure, containing a variable and a constant region. The variable region recognizes processed peptides, among which neoantigens, presented by major histocompatibility complex (MHC) molecules, and is highly variable. The intracellular domain of the TCR is very short, and needs to interact with CD33 to allow for signal propagation upon ligation of the extracellular domain.

With the focus of cancer treatment shifted towards more targeted therapies, among which immunotherapy, the potential of therapeutic application of tumor-directed T-cells is increasingly explored. One such application is adoptive T-cell therapy (ATCT) using genetically modified T-cells that carry chimeric antigen receptors (CARs) recognizing a particular epitope (Ref Gomes-Silva 2018). The extracellular domain of the CAR is commonly formed by the antigen-specific subunit of (scFv) of a monoclonal antibody that recognizes a tumor-antigen (Ref Abate-Daga 2016). This enables the CAR T-cell to recognize epitopes independent of MHC-molecules, thus widely applicable, as their functionality is not restricted to individuals expressing the specific MHC-molecule recognized by the TCR. Methods for engineering TCRs that bind a particular epitope are known to a skilled person. See, for example, US20100009863A1, which describes methods of modifying one or more structural loop regions. The intracellular domain of the CAR can be a TCR intracellular domain or a modified peptide to enable induction of a signaling cascade without the need for interaction with accessory proteins. This is accomplished by inclusion of the CD33-signalling domain, often in combination with one or more co-stimulatory domains, such as CD28 and 4-1BB, which further enhance CAR T-cell functioning and persistence (Ref Abate-Daga 2016).

The engineering of the extracellular domain towards an scFv limits CAR T-cell to the recognition of molecules that are expressed on the cell-surface. Peptides derived from proteins that are expressed intracellularly can be recognized upon their presentation on the plasma membrane by MHC molecules, of which human form is called human leukocyte antigen (HLA). The HLA-haplotype generally differs among individuals, but some HLA types, like HLA-A*02:01, are globally common. Engineering of CAR T-cell extracellular domains recognizing tumor-derived peptides or neoantigens presented by a commonly shared HLA molecule enables recognition of tumor antigens that remain intracellular. Indeed CAR T-cells expressing a CAR with a TCR-like extracellular domain have been shown to be able to recognize tumor-derived antigens in the context of HLA-A*02:01 (Refs Zhang 2014, Ma 2016, Liu 2017).

In some embodiments, the binding molecules are mono-specific, or rather they bind one of the neoantigens disclosed herein. In some embodiments, the binding molecules are bispecific, e.g., bispecific antibodies and bispecific chimeric antigen receptors.

In some embodiments, the disclosure provides a first antigen binding domain that binds a first neoantigen described herein and a second antigen binding domain that binds a second neoantigen described herein. The first and second antigen binding domains may be part of a single molecule, e.g., as a bispecific antibody or bispecific chimeric antigen receptor or they may be provided on separate molecules, e.g., as a collection of antibodies, T-cell receptors, or chimeric antigen receptors. In some embodiments, 3, 4, 5 or more antigen binding domains are provided each binding a different neoantigen disclosed herein. As used herein, an antigen binding domain includes the variable (antigen binding) domain of a T-cell receptor and the variable domain of an antibody (e.g., comprising a light chain variable region and a heavy chain variable region).

The disclosure further provides nucleic acid molecules encoding the antibodies, TCRs, and CARs disclosed herein. In a preferred embodiment, the nucleic acid molecules are codon optimized as disclosed herein.

The disclosure further provides vectors comprising the nucleic acids molecules disclosed herein. A "vector" is a recombinant nucleic acid construct, such as plasmid, phase genome, virus genome, cosmid, or artificial chromosome, to which another nucleic acid segment may be attached. The term "vector" includes both viral and non-viral means for introducing the nucleic acid into a cell in vitro, ex vivo or in vivo. The disclosure contemplates both DNA and RNA vectors. The disclosure further includes self-replicating RNA with (virus-derived) replicons, including but not limited to mRNA molecules derived from mRNA molecules from alphavirus genomes, such as the Sindbis, Semliki Forest and Venezuelan equine encephalitis viruses.

Vectors, including plasmid vectors, eukaryotic viral vectors and expression vectors are known to the skilled person.

Vectors may be used to express a recombinant gene construct in eukaryotic cells depending on the preference and judgment of the skilled practitioner (see, for example, Sambrook et al., Chapter 16). For example, many viral vectors are known in the art including, for example, retroviruses, adeno-associated viruses, and adenoviruses. Other viruses useful for introduction of a gene into a cell include, but a not limited to, arenavirus, herpes virus, mumps virus, poliovirus, Sindbis virus, and vaccinia virus, such as, canary pox virus. The methods for producing replication-deficient viral particles and for manipulating the viral genomes are well known. In preferred embodiments, the vaccine comprises an attenuated or inactivated viral vector comprising a nucleic acid disclosed herein.

Preferred vectors are expression vectors. It is within the purview of a skilled person to prepare suitable expression vectors for expressing the inhibitors disclosed hereon. An "expression vector" is generally a DNA element, often of circular structure, having the ability to replicate autonomously in a desired host cell, or to integrate into a host cell genome and also possessing certain well-known features which, for example, permit expression of a coding DNA inserted into the vector sequence at the proper site and in proper orientation. Such features can include, but are not limited to, one or more promoter sequences to direct transcription initiation of the coding DNA and other DNA elements such as enhancers, polyadenylation sites and the like, all as well known in the art. Suitable regulatory sequences including enhancers, promoters, translation initiation signals, and polyadenylation signals may be included. Additionally, depending on the host cell chosen and the vector employed, other sequences, such as an origin of replication, additional DNA restriction sites, enhancers, and sequences conferring inducibility of transcription may be incorporated into the expression vector. The expression vectors may also contain a selectable marker gene which facilitates the selection of host cells transformed or transfected. Examples of selectable marker genes are genes encoding a protein such as G418 and hygromycin which confer resistance to certain drugs, 6-galactosidase, chloramphenicol acetyltransferase, and firefly luciferase.

The expression vector can also be an RNA element that contains the sequences required to initiate translation in the desired reading frame, and possibly additional elements that are known to stabilize or contribute to replicate the RNA molecules after administration. Therefore when used herein the term DNA when referring to an isolated nucleic acid encoding the peptide according to the invention should be interpreted as referring to DNA from which the peptide can be transcribed or RNA molecules from which the peptide can be translated.

Also provided for is a host cell comprising an nucleic acid molecule or a vector as disclosed herein. The nucleic acid molecule may be introduced into a cell (prokaryotic or eukaryotic) by standard methods. As used herein, the terms "transformation" and "transfection" are intended to refer to a variety of art recognized techniques to introduce a DNA into a host cell. Such methods include, for example, transfection, including, but not limited to, liposome-polybrene, DEAE dextran-mediated transfection, electroporation, calcium phosphate precipitation, microinjection, or velocity driven microprojectiles ("biolistics"). Such techniques are well known by one skilled in the art. See, Sambrook et al. (1989) Molecular Cloning: A Laboratory Manual (2 ed. Cold Spring Harbor Lab Press, Plainview, N.Y.). Alternatively, one could use a system that delivers the DNA construct in a gene delivery vehicle. The gene delivery vehicle may be viral or chemical. Various viral gene delivery vehicles can be used with the present invention. In general, viral vectors are composed of viral particles derived from naturally occurring viruses. The naturally occurring virus has been genetically modified to be replication defective and does not generate additional infectious viruses, or it may be a virus that is known to be attenuated and does not have unacceptable side effects.

Preferably, the host cell is a mammalian cell, such as MRC5 cells (human cell line derived from lung tissue), HuH7 cells (human liver cell line), CHO-cells (Chinese Hamster Ovary), COS-cells (derived from monkey kidney (African green monkey), Vero-cells (kidney epithelial cells extracted from African green monkey), Hela-cells (human cell line), BHK-cells (baby hamster kidney cells, HEK-cells (Human Embryonic Kidney), NSO-cells (Murine myeloma cell line), C127-cells (nontumorigenic mouse cell line), PerC6®-cells (human cell line, Crucell), and Madin-Darby Canine Kidney (MDCK) cells. In some embodiments, the disclosure comprises an in vitro cell culture of mammalian cells expressing the neoantigens disclosed herein. Such cultures are useful, for example, in the production of cell-based vaccines, such as viral vectors expressing the neoantigens disclosed herein.

In some embodiments the host cells express the antibodies, TCRs, or CARs as disclosed herein. As will be clear to a skilled person, individual polypeptide chains (e.g., immunoglobulin heavy and light chains) may be provided on the same or different nucleic acid molecules and expressed by the same or different vectors. For example, in some embodiments, a host cell is transfected with a nucleic acid encoding an α-TCR polypeptide chain and a nucleic acid encoding a β-polypeptide chain.

In preferred embodiments, the disclosure provides T-cells expressing a TCR or CAR as disclosed herein. T cells may be obtained from, e.g., peripheral blood mononuclear cells, bone marrow, lymph node tissue, cord blood, thymus tissue, spleen tissue, and tumors. Preferably, the T-cells are obtained from the individual to be treated (autologous T-cells). T-cells may also be obtained from healthy donors (allogenic T-cells). Isolated T-cells are expanded in vitro using established methods, such as stimulation with cytokines (IL-2). Methods for obtaining and expanding T-cells for adoptive therapy are well known in the art and are also described, e.g., in EP2872533A1.

The disclosure also provides vaccines comprising one or more neoantigens as disclosed herein. In particular, the vaccine comprises one or more (poly) peptides, antibodies or antigen binding fragments thereof, TCRs, CARS, nucleic acid molecules, vectors, or cells (or cell cultures) as disclosed herein.

The vaccine may be prepared so that the selection, number and/or amount of neoantigens (e.g., peptides or nucleic acids encoding said peptides) present in the composition is patient-specific. Selection of one or more neoantigens may be based on sequencing information from the tumor of the patient. For any frame shift mutation found, a corresponding NOP is selected. Preferably, the vaccine comprises more than one neoantigen corresponding to the NOP selected. In case multiple frame shift mutations (multiple NOPs) are found, multiple neoantigens corresponding to each NOP may be selected for the vaccine.

The selection may also be dependent on the specific type of cancer, the status of the disease, earlier treatment regimens, the immune status of the patient, and, HLA-haplotype of the patient. Furthermore, the vaccine can contain individualized components, according to personal needs of the particular patient.

As is clear to a skilled person, if multiple neoantigens are used, they may be provided in a single vaccine composition or in several different vaccines to make up a vaccine collection. The disclosure thus provides vaccine collections comprising a collection of tiled peptides, collection of peptides as disclosed herein, as well as nucleic acid molecules, vectors, or host cells as disclosed herein. As is clear to a skilled person, such vaccine collections may be administered to an individual simultaneously or consecutively (e.g., on the same day) or they may be administered several days or weeks apart.

Various known methods may be used to administer the vaccines to an individual in need thereof. For instance, one or more neoantigens can be provided as a nucleic acid molecule directly, as "naked DNA". Neoantigens can also be expressed by attenuated viral hosts, such as vaccinia or fowlpox. This approach involves the use of a virus as a vector to express nucleotide sequences that encode the neoantigen. Upon introduction into the individual, the recombinant virus expresses the neoantigen peptide, and thereby elicits a host CTL response. Vaccination using viral vectors is well-known to a skilled person and vaccinia vectors and methods useful in immunization protocols are described in, e.g., U.S. Pat. No. 4,722,848. Another vector is BCG (Bacille Calmette Guerin) as described in Stover et al. (Nature 351:456-460 (1991)).

Preferably, the vaccine comprises a pharmaceutically acceptable excipient and/or an adjuvant. The compositions may contain pharmaceutically acceptable auxiliary substances as required to approximate physiological conditions, such as pH adjusting and buffering agents, tonicity adjusting agents, wetting agents and the like. Suitable adjuvants are well-known in the art and include, aluminum (or a salt thereof, e.g., aluminium phosphate and aluminium hydroxide), monophosphoryl lipid A, squalene (e.g., MF59), and cytosine phosphoguanine (CpG), montanide, liposomes (e.g. CAF adjuvants, cationic adjuvant formulations and variations thereof), lipoprotein conjugates (e.g. Amplivant), Resiquimod, Iscomatrix, hiltonol, poly-ICLC (polyriboinosinic-polyribocytidylic acid-polylysine carboxymethylcellulose). A skilled person is able to determine the appropriate adjuvant, if necessary, and an immune-effective amount thereof. As used herein, an immune-effective amount of adjuvant refers to the amount needed to increase the vaccine's immunogenicity in order to achieve the desired effect.

The disclosure also provides the use of the neoantigens disclosed herein for the treatment of disease, in particular for the treatment of kidney cancer (also referred to as renal cancer) in an individual. In preferred embodiments, the cancer is renal clear cell carcinoma (KIRC). Approximately 70% of all kidney cancer is renal clear cell carcinoma. It is within the purview of a skilled person to diagnose an individual with as having kidney cancer.

As used herein, the terms "treatment," "treat," and "treating" refer to reversing, alleviating, or inhibiting the progress of a disease, or reversing, alleviating, delaying the onset of, or inhibiting one or more symptoms thereof. Treatment includes, e.g., slowing the growth of a tumor, reducing the size of a tumor, and/or slowing or preventing tumor metastasis.

The term 'individual' includes mammals, both humans and non-humans and includes but is not limited to humans, non-human primates, canines, felines, murines, bovines, equines, and porcines. Preferably, the human is a mammal.

As used herein, administration or administering in the context of treatment or therapy of a subject is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners.

The optimum amount of each neoantigen to be included in the vaccine composition and the optimum dosing regimen can be determined by one skilled in the art without undue experimentation. The composition may be prepared for injection of the peptide, nucleic acid molecule encoding the peptide, or any other carrier comprising such (such as a virus or liposomes). For example, doses of between 1 and 500 mg 50 μg and 1.5 mg, preferably 125 μg to 500 μg, of peptide or DNA may be given and will depend from the respective peptide or DNA. Other methods of administration are known to the skilled person. Preferably, the vaccines may be administered parenterally, e.g., intravenously, subcutaneously, intradermally, intramuscularly, or otherwise.

For therapeutic use, administration may begin at or shortly after the surgical removal of tumors. This can be followed by boosting doses until at least symptoms are substantially abated and for a period thereafter.

In some embodiments, the vaccines may be provided as a neoadjuvant therapy, e.g., prior to the removal of tumors or prior to treatment with radiation or chemotherapy. Neoadjuvant therapy is intended to reduce the size of the tumor before more radical treatment is used. For that reason being able to provide the vaccine off-the-shelf or in a short period of time is very important.

Also disclosed herein, the vaccine is capable of initiating a specific T-cell response. It is within the purview of a skilled person to measure such T-cell responses either in vivo or in vitro, e.g. by analyzing IFN-γ production or tumor killing by T-cells. In therapeutic applications, vaccines are administered to a patient in an amount sufficient to elicit an effective CTL response to the tumor antigen and to cure or at least partially arrest symptoms and/or complications.

The vaccine disclosed herein can be administered alone or in combination with other therapeutic agents. The therapeutic agent is for example, a chemotherapeutic agent, radiation, or immunotherapy, including but not limited to checkpoint inhibitors, such as nivolumab, ipilimumab, pembrolizumab, or the like. Any suitable therapeutic treatment for a particular, cancer may be administered.

The term "chemotherapeutic agent" refers to a compound that inhibits or prevents the viability and/or function of cells, and/or causes destruction of cells (cell death), and/or exerts anti-tumor/anti-proliferative effects. The term also includes agents that cause a cytostatic effect only and not a mere cytotoxic effect. Examples of chemotherapeutic agents include, but are not limited to bleomycin, capecitabine, carboplatin, cisplatin, cyclophosphamide, docetaxel, doxorubicin, etoposide, interferon alpha, irinotecan, lansoprazole, levamisole, methotrexate, metoclopramide, mitomycin, omeprazole, ondansetron, paclitaxel, pilocarpine, rituxitnab, tamoxifen, taxol, trastuzumab, vinblastine, and vinorelbine tartrate.

Preferably, the other therapeutic agent is an anti-immunosuppressive/immunostimulatory agent, such as anti-CTLA antibody or anti-PD-1 or anti-PD-L1. Blockade of CTLA-4 or PD-L1 by antibodies can enhance the immune response to cancerous cells. In particular, CTLA-4 blockade has been shown effective when following a vaccination protocol.

As is understood by a skilled person the vaccine and other therapeutic agents may be provided simultaneously, separately, or sequentially. In some embodiments, the vaccine may be provided several days or several weeks prior to or following treatment with one or more other therapeutic agents. The combination therapy may result in an additive or synergistic therapeutic effect.

As disclosed herein, the present disclosure provides vaccines which can be prepared as off-the-shelf vaccines. As used herein "off-the-shelf" means a vaccine as disclosed herein that is available and ready for administration to a patient. For example, when a certain frame shift mutation is identified in a patient, the term "off-the-shelf" would refer to a vaccine according to the disclosure that is ready for use in the treatment of the patient, meaning that, if the vaccine is peptide based, the corresponding polyNOP peptide may, for example already be expressed and for example stored with the required excipients and stored appropriately, for example at −20 °C or −80 °C. Preferably the term "off-the-shelf" also means that the vaccine has been tested, for example for safety or toxicity. More preferably the term also means that the vaccine has also been approved for use in the treatment or prevention in a patient. Accordingly, the disclosure also provides a storage facility for storing the vaccines disclosed herein. Depending on the final formulation, the vaccines may be stored frozen or at room temperature, e.g., as dried preparations. Preferably, the storage facility stores at least 20 or at least 50 different vaccines, each recognizing a neoantigen disclosed herein.

The present disclosure also contemplates methods which include determining the presence of NOPs in a tumor sample. In a preferred embodiment, a tumor of a patient can be screened for the presence of frame shift mutations and an NOP can be identified that results from such a frame shift mutation. Based on the NOP(s) identified in the tumor, a vaccine comprising the relevant NOP(s) can be provided to immunize the patient, so the immune system of the patient will target the tumor cells expressing the neoantigen. An exemplary workflow for providing a neoantigen as disclosed herein is as follows. When a patient is diagnosed with a cancer, a biopsy may be taken from the tumor or a sample set is taken of the tumor after resection. The genome, exome and/or transcriptome is sequenced by any method known to a skilled person. The outcome is compared, for example using a web interface or software, to the library of NOPs disclosed herein. A patient whose tumor expresses one of the NOPs disclosed herein is thus a candidate for a vaccine comprising the NOP (or a fragment thereof).

Accordingly, the disclosure provides a method for determining a therapeutic treatment for an individual afflicted with cancer, said method comprising determining the presence of a frame shift mutation which results in the expression of an NOP selected from sequences 1-352. Identification of the expression of an NOP indicates that said individual should be treated with a vaccine corresponding to the identified NOP. For example, if it is determined that tumor cells from an individual express Sequence 1, then a vaccine comprising Sequence 1 or a fragment thereof is indicated as a treatment for said individual.

Accordingly, the disclosure provides a method for determining a therapeutic treatment for an individual afflicted with cancer, said method comprising a. performing complete, targeted or partial genome, exome, ORFeome, or transcriptome sequencing of at least one tumor sample obtained from the individual to obtain a set of sequences of the subject-specific tumor genome, exome, ORFeome, or transcriptome;
b. comparing at least one sequence or portion thereof from the set of sequences with one or more sequences selected from:
(i) Sequences 1-18;
(ii) Sequences 19-188;
(iii) Sequences 189-310; and
(iv) Sequences 311-352;
c. identifying a match between the at least one sequence or portion thereof from the set of sequences and a sequence from groups (i) to (v) when the sequences have a string in common representative of at least 8 amino acids to identify a neoantigen encoded by a frameshift mutation;
wherein a match indicates that said individual is to be treated with the vaccine as disclosed herein.

As used herein the term "sequence" can refer to a peptide sequence, DNA sequence or RNA sequence. The term "sequence" will be understood by the skilled person to mean either or any of these, and will be clear in the context provided. For example, when comparing sequences to identify a match, the comparison may be between DNA sequences, RNA sequences or peptide sequences, but also between DNA sequences and peptide sequences. In the latter case the skilled person is capable of first converting such DNA sequence or such peptide sequence into, respectively, a peptide sequence and a DNA sequence in order to make the comparison and to identify the match. As is clear to a skilled person, when sequences are obtained from the genome or exome, the DNA sequences are preferably converted to the predicted peptide sequences. In this way, neo open reading frame peptides are identified.

As used herein the term "exome" is a subset of the genome that codes for proteins. An exome can be the collective exons of a genome, or also refer to a subset of the exons in a genome, for example all exons of known cancer genes.

As used herein the term "transcriptome" is the set of all RNA molecules is a cell or population of cells. In a preferred embodiment the transcriptome refers to all mRNA.

In some preferred embodiments the genome is sequenced. In some preferred embodiments the exome is sequenced. In some preferred embodiments the transcriptome is sequenced. In some preferred embodiments a panel of genes is sequenced, for example BAP1, PBRM1, SETD2, and VHL. In some preferred embodiments a single gene is sequenced. Preferably the transcriptome is sequenced, in particular the mRNA present in a sample from a tumor of the patient. The transcriptome is representative of genes and neo open reading frame peptides as defined herein being expressed in the tumor in the patient.

As used herein the term "sample" can include a single cell or multiple cells or fragments of cells or an aliquot of body fluid, taken from an individual, by means including venipuncture, excretion, ejaculation, massage, biopsy, needle aspirate, lavage sample, scraping, surgical incision, or intervention or other means known in the art. The DNA and/or RNA for sequencing is preferably obtained by taking a sample from a tumor of the patient. The skilled person knowns how to obtain samples from a tumor of a patient and depending on the nature, for example location or size, of the tumor. Preferably the tumor is a kidney tumor. Preferably the sample is obtained from the patient by biopsy or resection.

The sample is obtained in such manner that is allows for sequencing of the genetic material obtained therein. In order to prevent a less accurate identification of at least one antigen, preferably the sequence of the tumor sample obtained from the patient is compared to the sequence of other non-tumor tissue of the patient, usually blood, obtained by known techniques (e.g. venipuncture).

Identification of frame shift mutations can be done by sequencing of RNA or DNA using methods known to the skilled person. Sequencing of the genome, exome, ORFeome, or transcriptome may be complete, targeted or partial. In some embodiments the sequencing is complete (whole sequencing). In some embodiments the sequencing is targeted. With targeted sequencing is meant that purposively certain region or portion of the genome, exome, ORFeome or transcriptome are sequenced. For example targeted sequencing may be directed to only sequencing for sequences in the set of sequences obtained from the cancer patient that would provide for a match with one or more of the sequences in the sequence listing, for example by using specific primers. In some embodiment only portion of the genome, exome, ORFeome or transcriptome is sequenced. The skilled person is well-aware of methods that allow for whole, targeted or partial sequencing of the genome, exome, ORFeome or transcriptome of a tumor sample of a patient. For example any suitable sequencing-by-synthesis platform can be used including the Genome Sequencers from Illumina/Solexa, the Ion Torrent system from Applied BioSystems, and the RSII or Sequel systems from Pacific Biosciences. Alternatively Nanopore sequencing may be used, such as the MinION, GridION or PromethION platform offered by Oxford Nanopore Technologies. The method of sequencing the genome, exome, ORFeome or transcriptome is not in particular limited within the context of the present invention.

Sequence comparison can be performed by any suitable means available to the skilled person. Indeed the skilled person is well equipped with methods to perform such comparison, for example using software tools like BLAST and the like, or specific software to align short or long sequence reads, accurate or noisy sequence reads to a reference genome, e.g. the human reference genome GRCh37 or GRCh38. A match is identified when a sequence identified in the patients material and a sequence as disclosed herein have a string, i.e. a peptide sequence (or RNA or DNA sequence encoding such peptide (sequence) in case the comparison is on the level of RNA or DNA) in common representative of at least 8, preferably at least 10 adjacent amino acids. Furthermore, sequence reads derived from a patients cancer genome (or transcriptome) can partially match the genomic DNA sequences encoding the amino acid sequences as disclosed herein, for example if such sequence reads are derived from exon/intron boundaries or exon/exon junctions, or if part of the sequence aligns upstream (to the 5' end of the gene) of the position of a frameshift mutation. Analysis of sequence reads and identification of frameshift mutations will occur through standard methods in the field. For sequence alignment, aligners specific for short or long reads can be used, e.g. BWA (Li and Durbin, Bioinformatics. 2009 Jul. 15; 25(14):1754-60) or Minimap2 (Li, Bioinformatics. 2018 Sep. 15; 34(18):3094-3100). Subsequently, frameshift mutations can be derived from the read alignments and their comparison to a reference genome sequence (e.g. the human reference genome GRCh37) using variant calling tools, for example Genome Analysis ToolKit (GATK), and the like (McKenna et al. Genome Res. 2010 September; 20(9):1297-303).

A match between an individual patient's tumor sample genome or transcriptome sequence and one or more NOPs disclosed herein indicates that said tumor expresses said NOP and that said patient would likely benefit from treatment with a vaccine comprising said NOP (or a fragment thereof). More specifically, a match occurs if a frameshift mutation is identified in said patient's tumor genome sequence and said frameshift leads to a novel reading frame (+1 or −1 with respect to the native reading from of a gene). In such instance, the predicted out-of-frame peptide derived from the frameshift mutation matches any of the sequences 1-352 as disclosed herein. In some embodiments, said patient is administered said NOP (e.g., by administering the peptides, nucleic acid molecules, vectors, host cells or vaccines as disclosed herein).

In some embodiments, the methods further comprise sequencing the genome, exome, ORFeome, or transcriptome (or a part thereof) from a normal, non-tumor sample from said individual and determining whether there is a match with one or more NOPs identified in the tumor sample. Although the neoantigens disclosed herein appear to be specific to tumors, such methods may be employed to confirm that the neoantigen is tumor specific and not, e.g., a germline mutation.

The disclosure further provides the use of the neoantigens and vaccines disclosed herein in prophylactic methods from preventing or delaying the onset of kidney cancer. Approximately 1.5-2% of individuals will develop kidney cancer and the neo open reading frames disclosed herein occur in up to 27% of kidney cancer patients. Prophylactic vaccination based on frameshift resulting peptides disclosed herein would thus provide protection to approximately 0.5% of the general population. The vaccine may be specifically used in a prophylactic setting for individuals that have an increased risk of developing kidney cancer. For example, prophylactic vaccination is expected to provide possible protection to around 22% of individuals having a germline predisposition mutation as referred to in Table 3 and who would have developed kidney cancer as a result of their predisposing mutation. In some embodiments, the prophylactic methods are useful for individuals who are genetically related to individuals afflicted with kidney cancer. In some embodiments, the prophylactic methods are useful for the general population.

In some embodiments, the individual is at risk of developing cancer. It is understood to a skilled person that being at risk of developing cancer indicates that the individual has a higher risk of developing cancer than the general population; or rather the individual has an increased risk over the average of developing cancer. Such risk factors are known to a skilled person and include being a male, increased age, in particular being 40 years or older; smoking, having advanced kidney disease, having von Hippel-Lindau (VHL) disease or inherited papillary renal cell carcinoma, having a family history of kidney cancer, asbestos exposure, and having a mutation in a gene that predisposes an individual to kidney cancer.

In some embodiments, said individual has a germline mutation in a gene that increases the chance that the individual will develop kidney cancer, preferably the mutation is in the ATM, ATR, BRCA1, BRIP1, CBL, CHEK2, DROSHA, FANCL, FH, FLCN, GJB2, MUTYH, PRDM9, RECQL, RECQL3, SDHA, and/or SPC gene. Predisposing mutations in the ATM, ATR, BRCA1, BRIP1, CBL, CHEK2, DROSHA, FANCL, FH, FLCN, GJB2, MUTYH, PRDM9, RECQL, RECQL3, SDHA, and SPC genes are known to a skilled person and such mutations can be identified in individuals. Preferably, the prophylactic methods disclosed herein comprise determining the presence of a predisposing mutation in one or more of the ATM, ATR, BRCA1, BRIP1, CBL, CHEK2, DROSHA, FANCL, FH, FLCN, GJB2, MUTYH, PRDM9, RECQL, RECQL3, SDHA, and SPC genes and prophylactically administering the vaccine disclosed herein to an individual having said predisposing mutation in one or more of the ATM, ATR, BRCA1, BRIP1, CBL, CHEK2, DROSHA, FANCL, FH, FLCN, GJB2, MUTYH, PRDM9, RECQL, RECQL3, SDHA, and SPC genes.

As used herein, "to comprise" and its conjugations is used in its non-limiting sense to mean that items following the word are included, but items not specifically mentioned are not excluded. In addition, the verb "to consist" may be replaced by "to consist essentially of" meaning that a compound or adjunct compound as defined herein may comprise additional component(s) than the ones specifically identified, said additional component(s) not altering the unique characteristic of the invention.

The articles "a" and "an" are used herein to refer to one or to more than one (i.e., to at least one) of the grammatical object of the article. By way of example, "an element" means one element or more than one element.

The word "approximately" or "about" when used in association with a numerical value (approximately 10, about 10) preferably means that the value may be the given value of 10 more or less 1% of the value.

All patent and literature references cited in the present specification are hereby incorporated by reference in their entirety.

For the purpose of clarity and a concise description features are described herein as part of the same or separate embodiments, however, it will be appreciated that the scope of the invention may include embodiments having combinations of all or some of the features described.

a. Cumulative counting of RNAseq allele frequency (Samtools mpileup (XO:1/all)) at the genomic position of DNA detected frame shift mutations.

b. IGV examples of frame shift mutations in the BAM files of CCLE cell lines.

Figure 7:
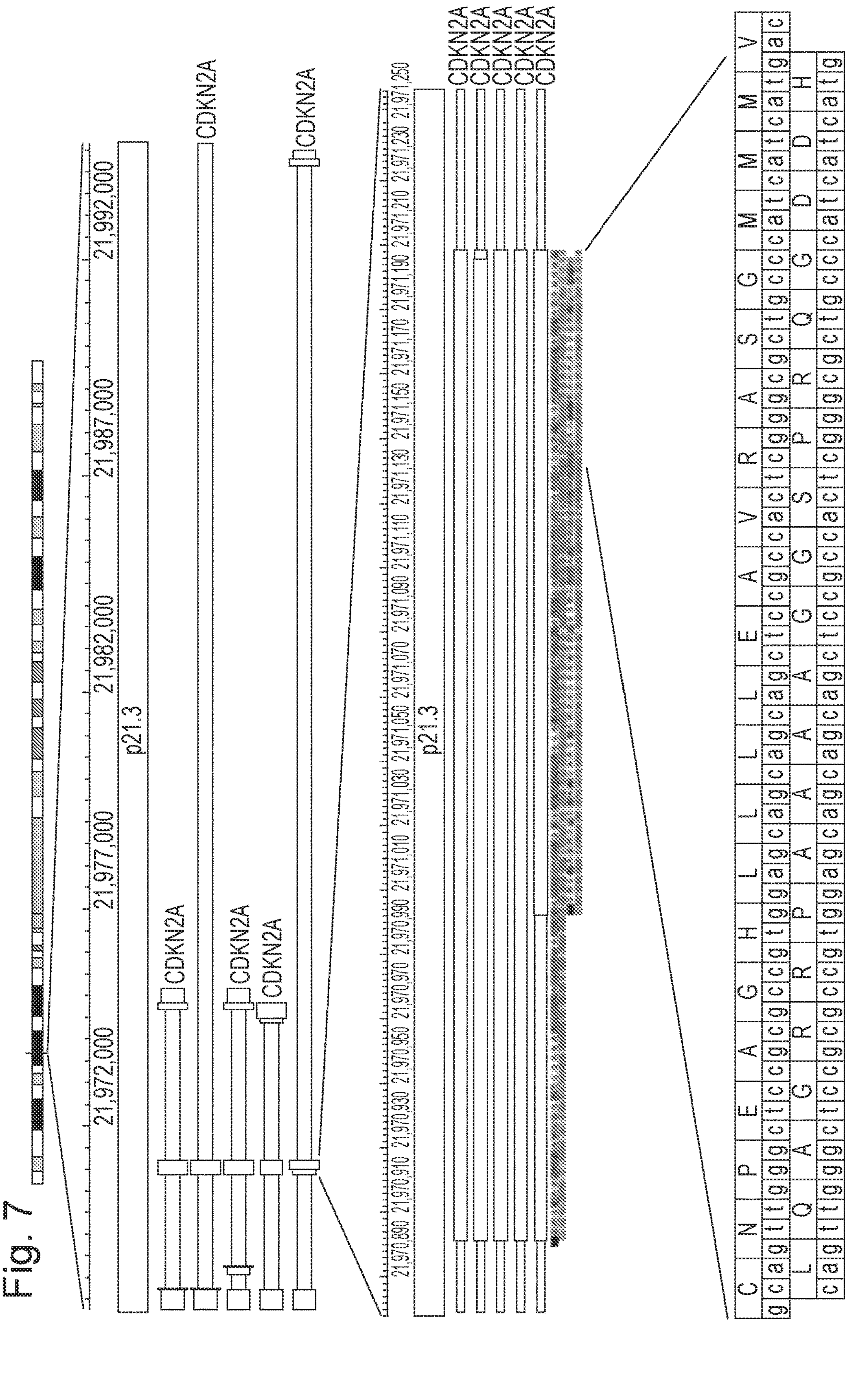

FIG. 7 Example of normal isoforms, using shifted frame. Genome model of CDKN2A with the different isoforms are shown on the minus strand of the genome. Zoom of the middle exon depicts the 2 reading frames that are encountered in the different isoforms.

Figure 8:
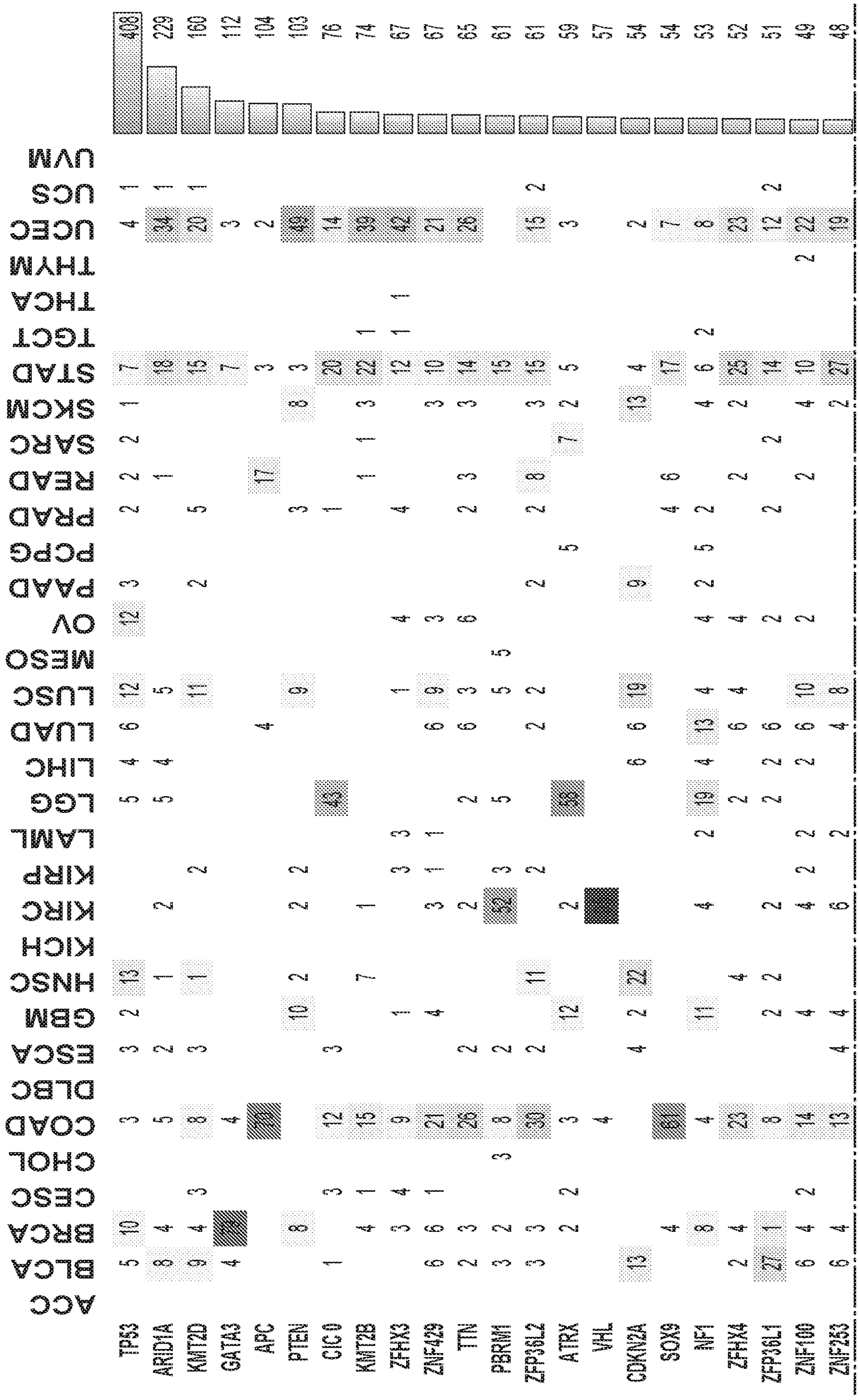
Figure 9A:
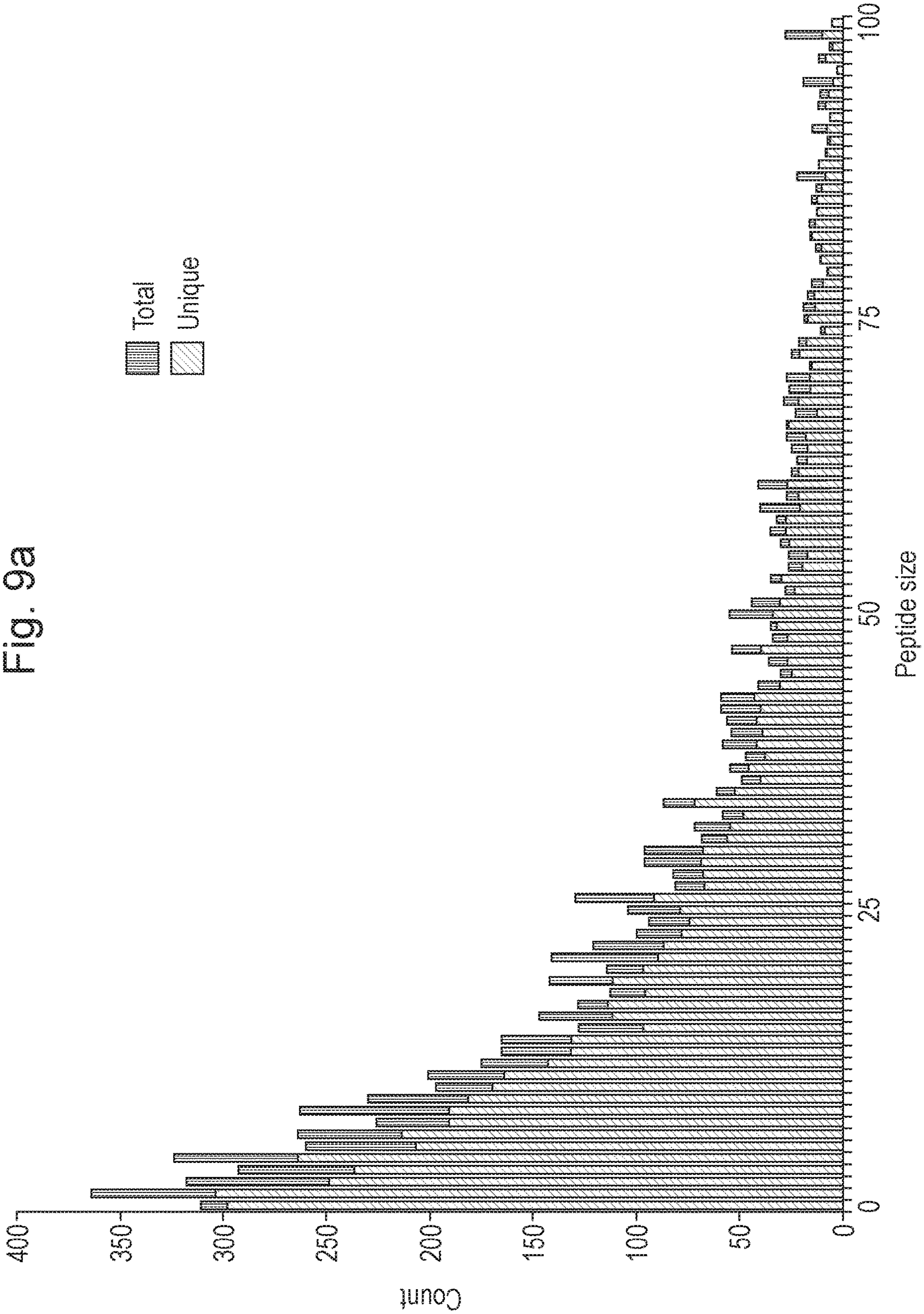
Figure 9B:
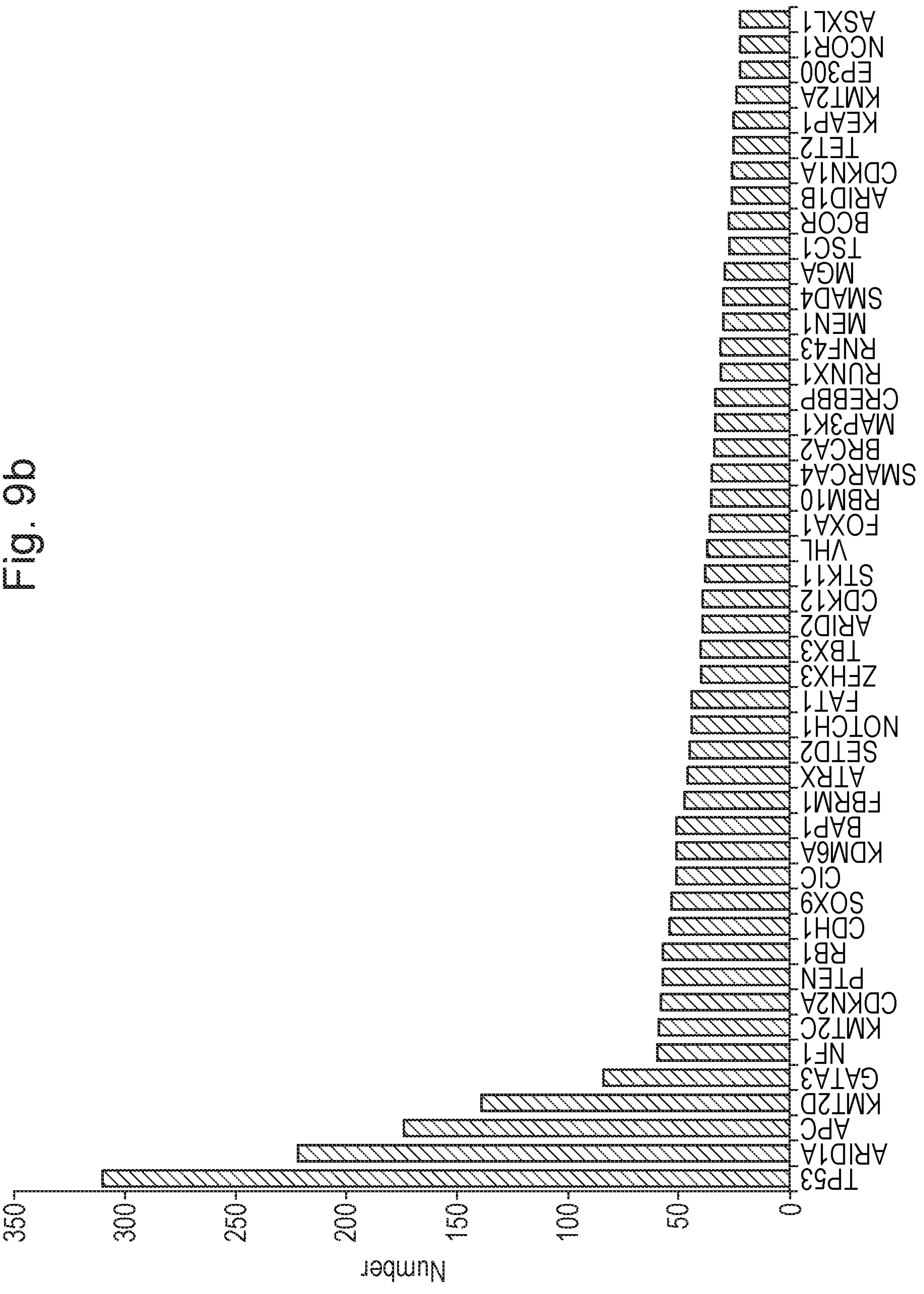
Figure 9C:
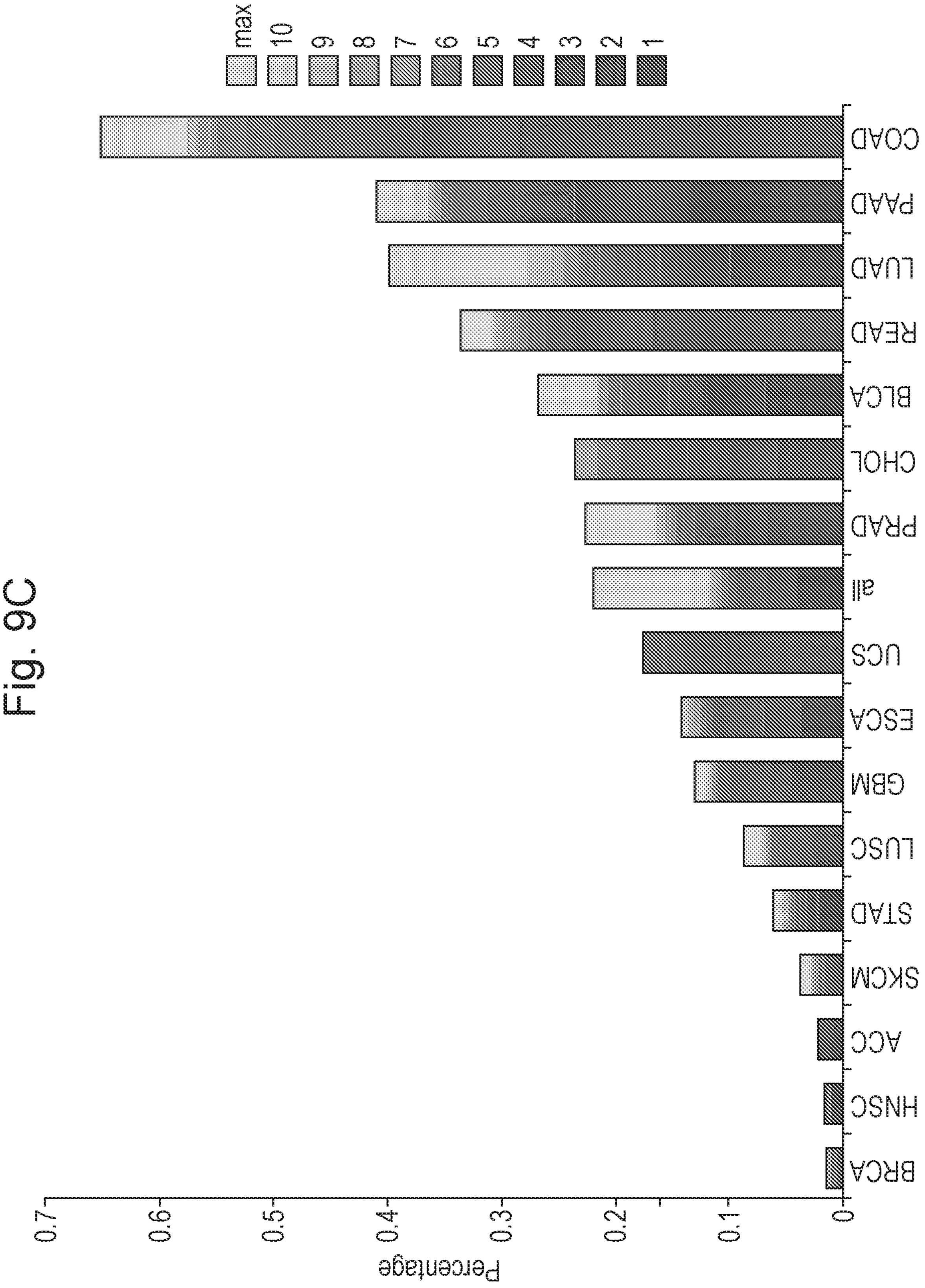
Figure 9D:
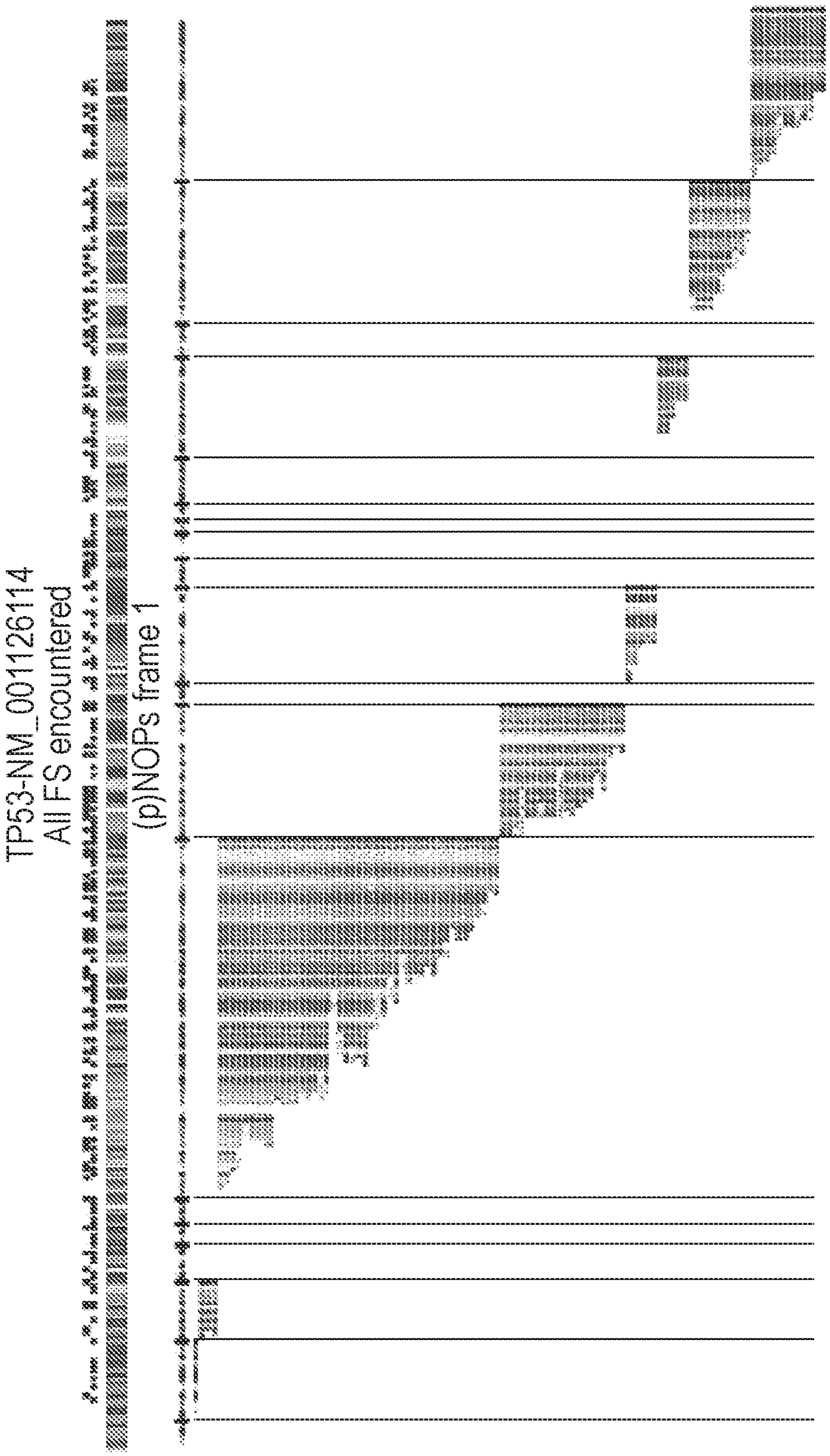

FIG. 8 Gene prevalence vs Cancer type.

Percentage of frameshift mutations (resulting in peptides of 10 aa or longer), assessed by the type of cancer in the TCGA cohort. Genes where 50% or more of the frameshifts occur within a single tumor type are indicated in bold. Cancer type abbreviations are as follows:

LAML Acute Myeloid Leukemia
ACC Adrenocortical carcinoma
BLCA Bladder Urothelial Carcinoma
LGG Brain Lower Grade Glioma
BRCA Breast invasive carcinoma
CESC Cervical squamous cell carcinoma and endocervical adenocarcinoma
CHOL Cholangiocarcinoma
LCML Chronic Myelogenous Leukemia
COAD Colon adenocarcinoma
CNTL Controls
ESCA Esophageal carcinoma
GBM Glioblastoma multiforme
HNSC Head and Neck squamous cell carcinoma
KICH Kidney Chromophobe
KIRC Kidney renal clear cell carcinoma
KIRP Kidney renal papillary cell carcinoma
LIHC Liver hepatocellular carcinoma
LUAD Lung adenocarcinoma
LUSC Lung squamous cell carcinoma
DLBC Lymphoid Neoplasm Diffuse Large B-cell Lymphoma
MESO Mesothelioma
MISC Miscellaneous
OV Ovarian serous cystadenocarcinoma
PAAD Pancreatic adenocarcinoma
PCPG Pheochromocytoma and Paraganglioma
PRAD Prostate adenocarcinoma
READ Rectum adenocarcinoma
SARC Sarcoma
SKCM Skin Cutaneous Melanoma
STAD Stomach adenocarcinoma TGCT Testicular Germ Cell Tumors
THYM Thymoma
THCA Thyroid carcinoma
UCS Uterine Carcinosarcoma
UCEC Uterine Corpus Endometrial Carcinoma
UVM Uveal Melanoma FIG. 9 NOPs in the MSK-IMPACT study Frame shift analysis in the targeted sequencing panel of the MSK-IMPACT study, covering up to 410 genes in more 10,129 patients (with at least 1 somatic mutation). a. FS peptide length distribution, b. Gene count of patients containing NOPs of 10 or more amino acids. c. Ratio of patients separated by tumor type that possess a neo epitope using optimally selected peptides for genes encountered most often within a cancer. Coloring represents the ratio, using 1, 2 . . . 10 genes, or using all encountered genes (lightest shade) d. Examples of NOPs for 4 genes.

Figure 10:
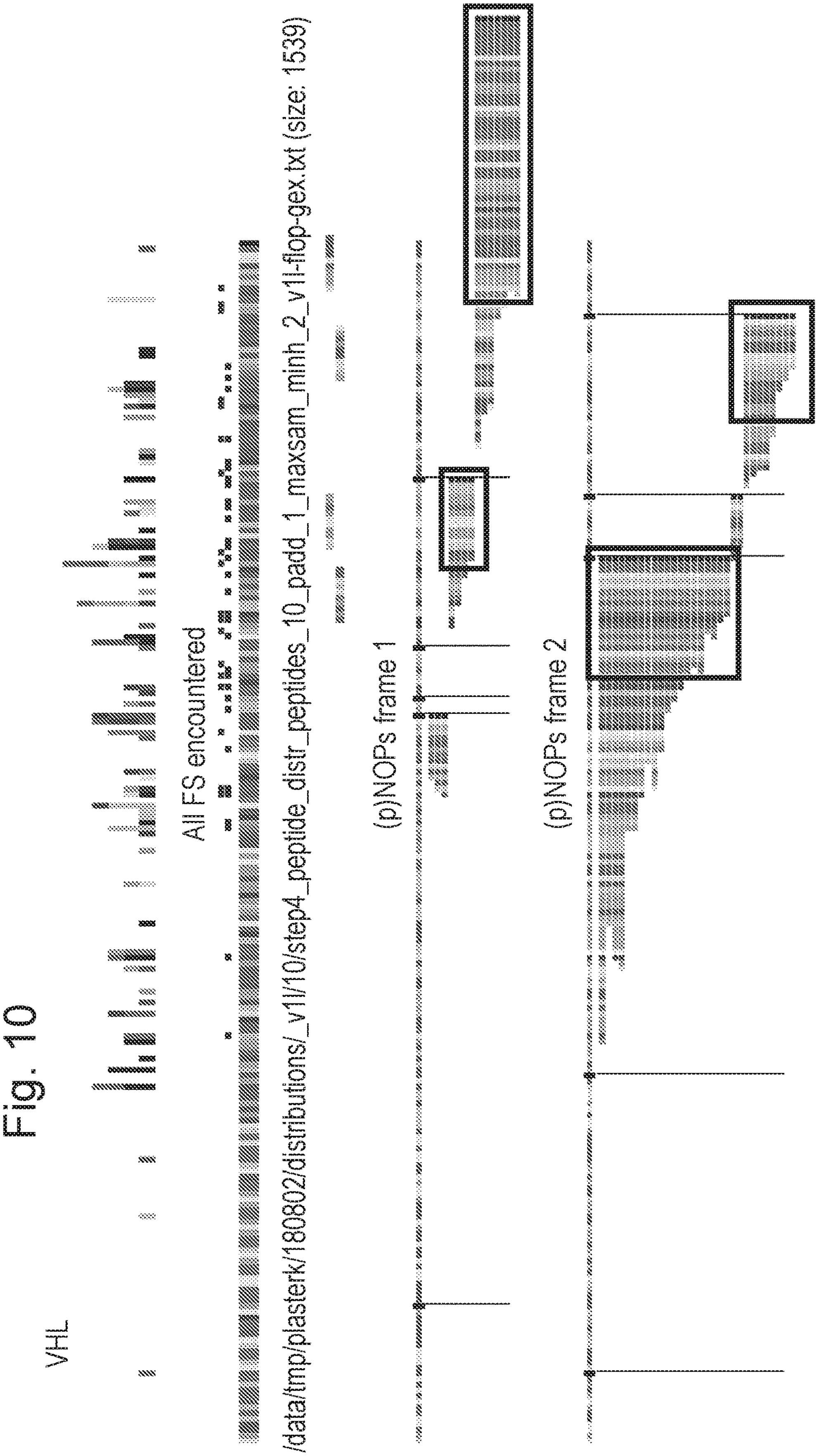
Figure 11:
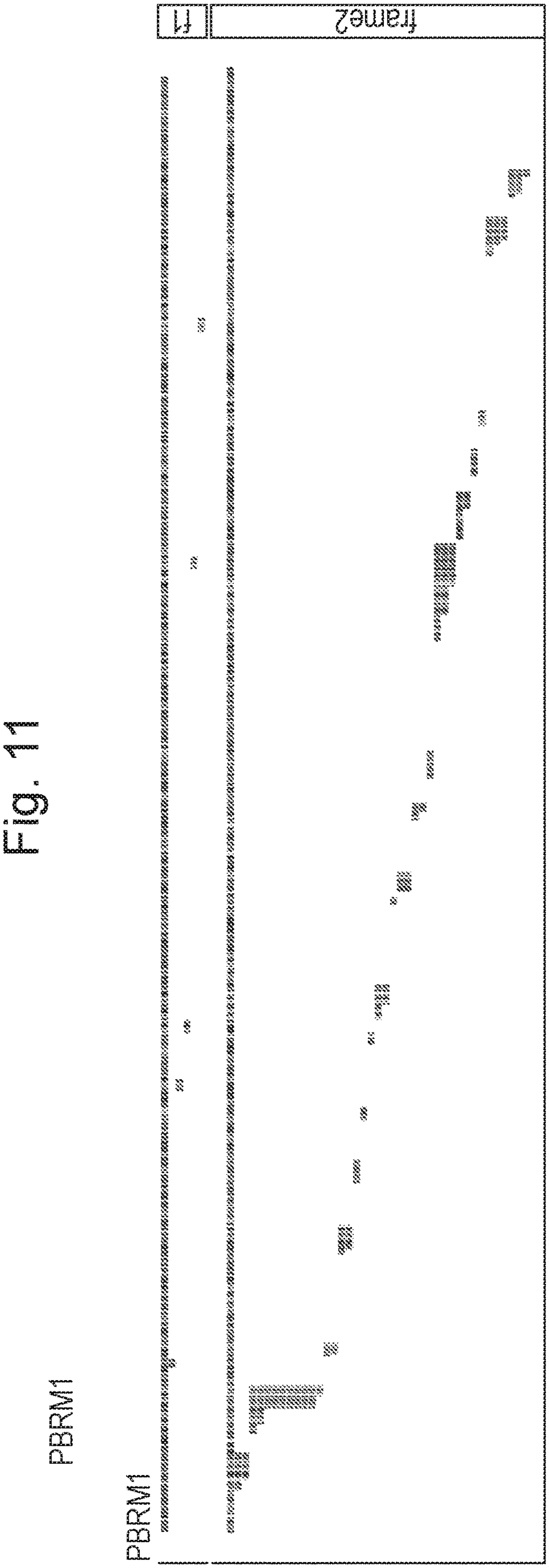
Figure 12:
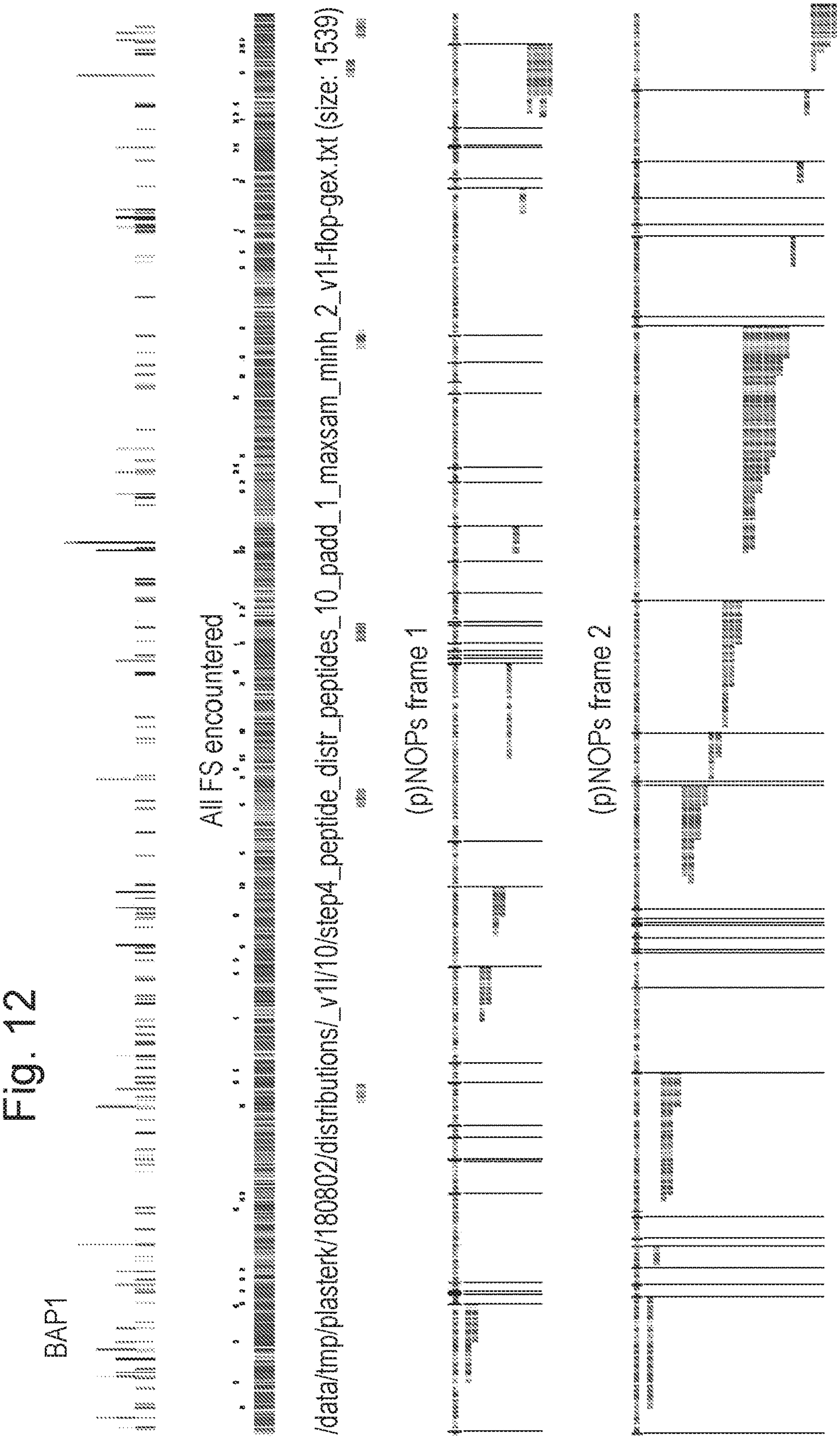
Figure 13:
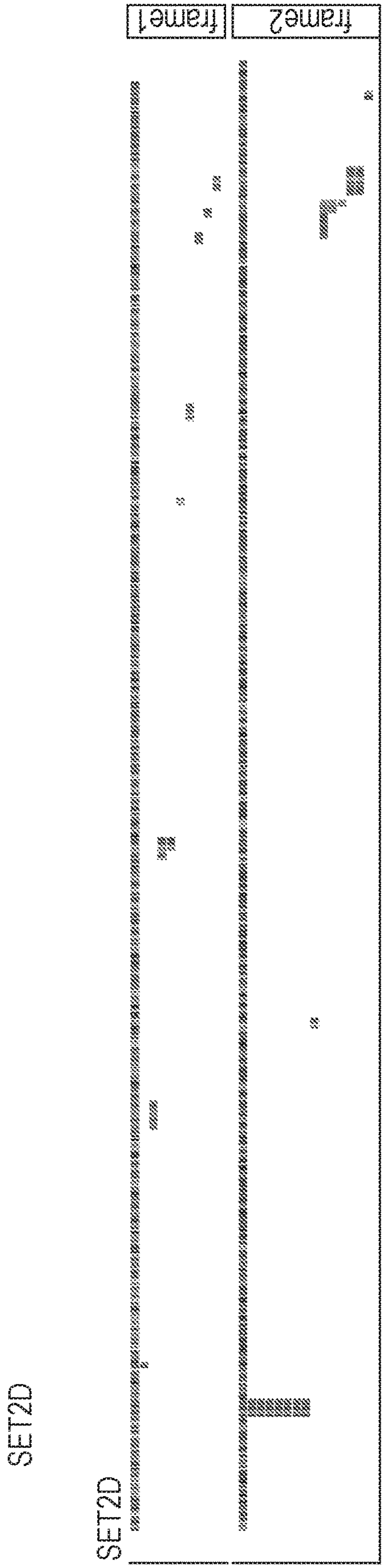

FIG. 10-13 Out-of-frame peptide sequences based on frameshift mutations in kidney cancer patients, for FIG. 10 (VHL), FIG. 11 (PBRM1), FIG. 12 (BAP1), and FIG. 13 (SET2D).

EXAMPLES

Figure 1A:
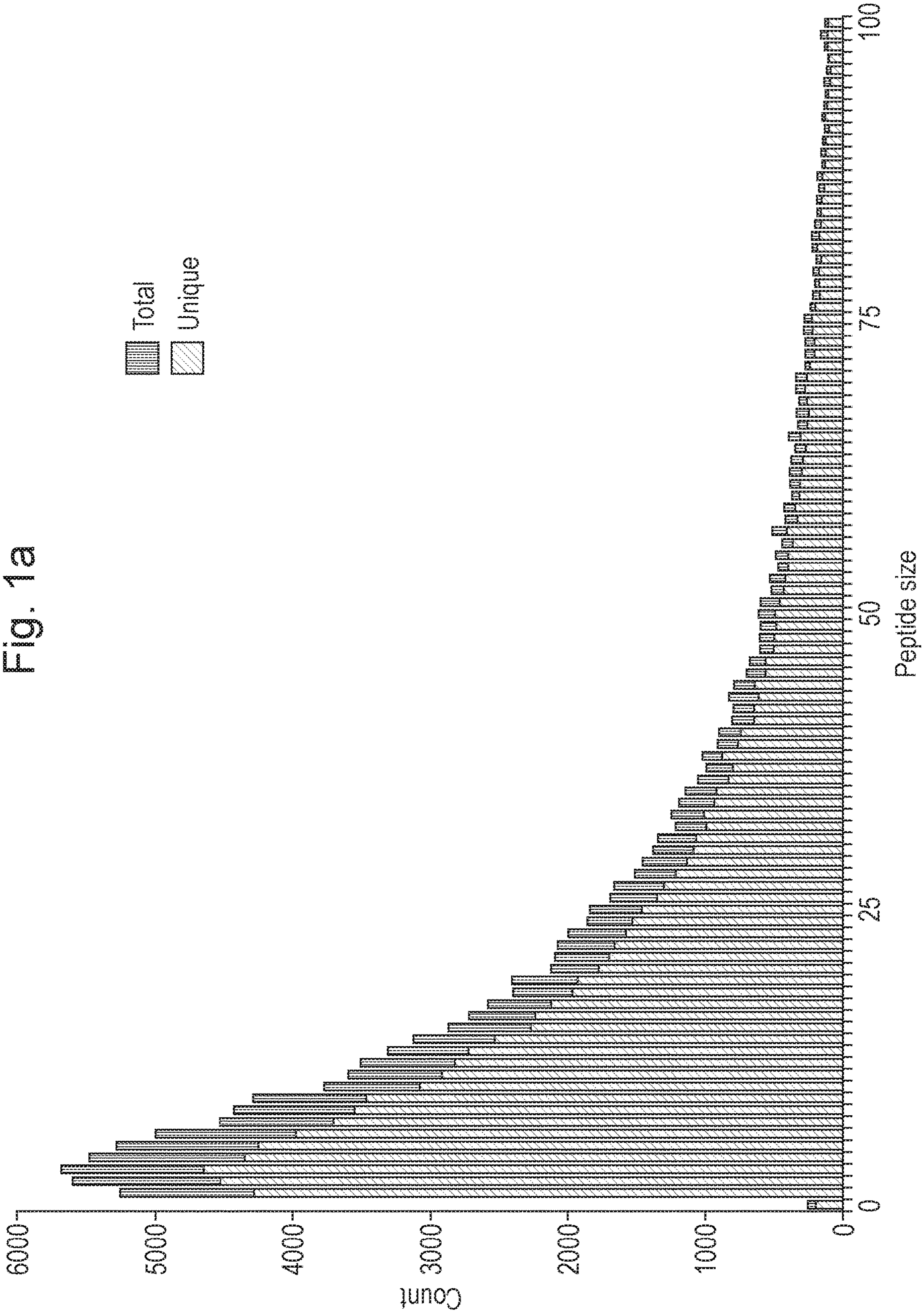
FIG. 1 Frame shift initiated translation in the TCGA (n=10, 186) cohort is of sufficient size for immune presentation. A. Peptide length distribution of frame shift mutation initiated translation up to the first encountered stop codon. Dark shades are unique peptide sequences derived from frameshift mutations, light shade indicates the total sum (unique peptides derived from frameshifts multiplied by number of patients containing that frameshift). B. Gene distribution of peptides with length 10 or longer and encountered in up to 10 patients.
Figure 1B:
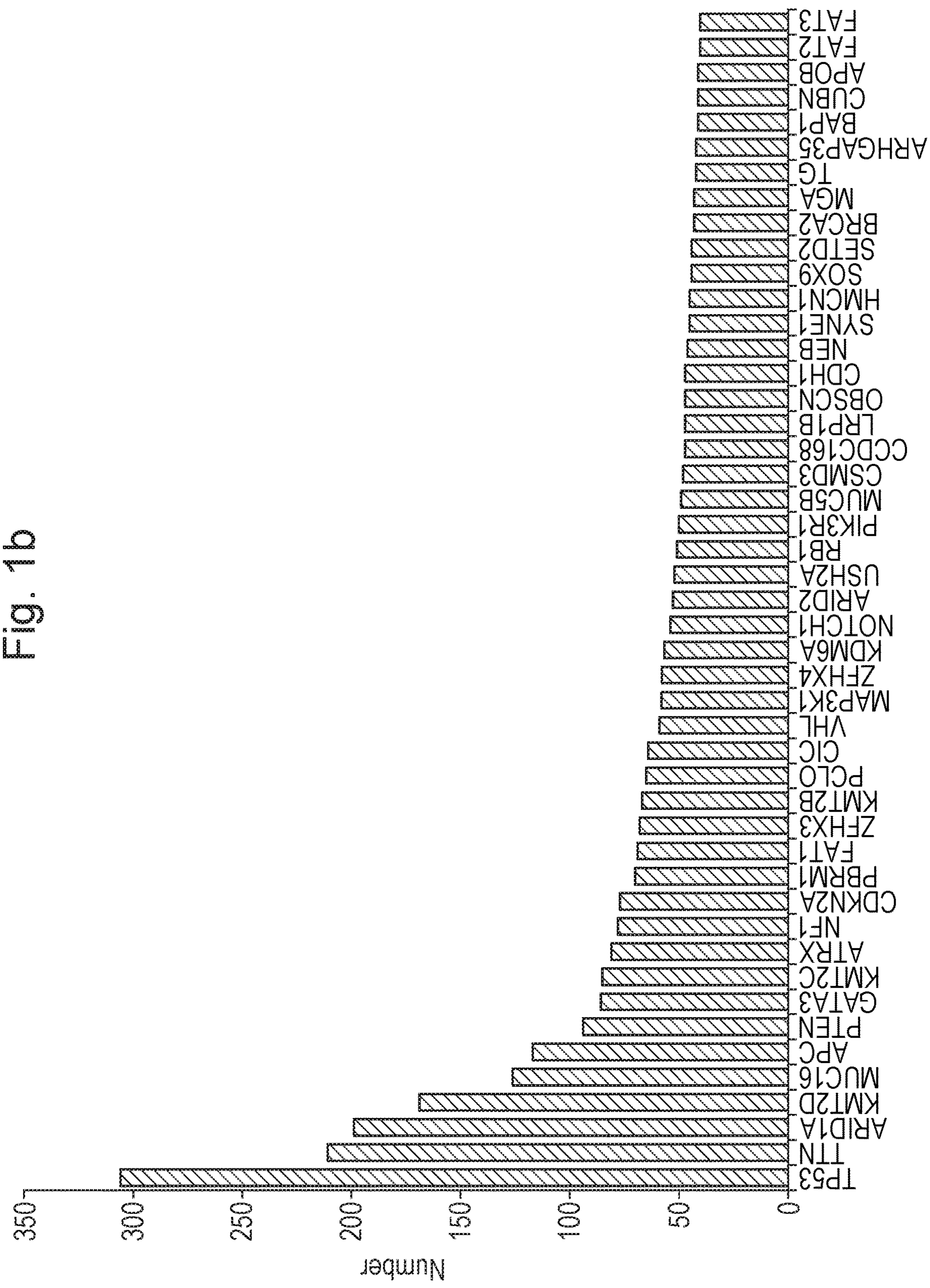
Figures 2A, 2B, 2C, 2D:
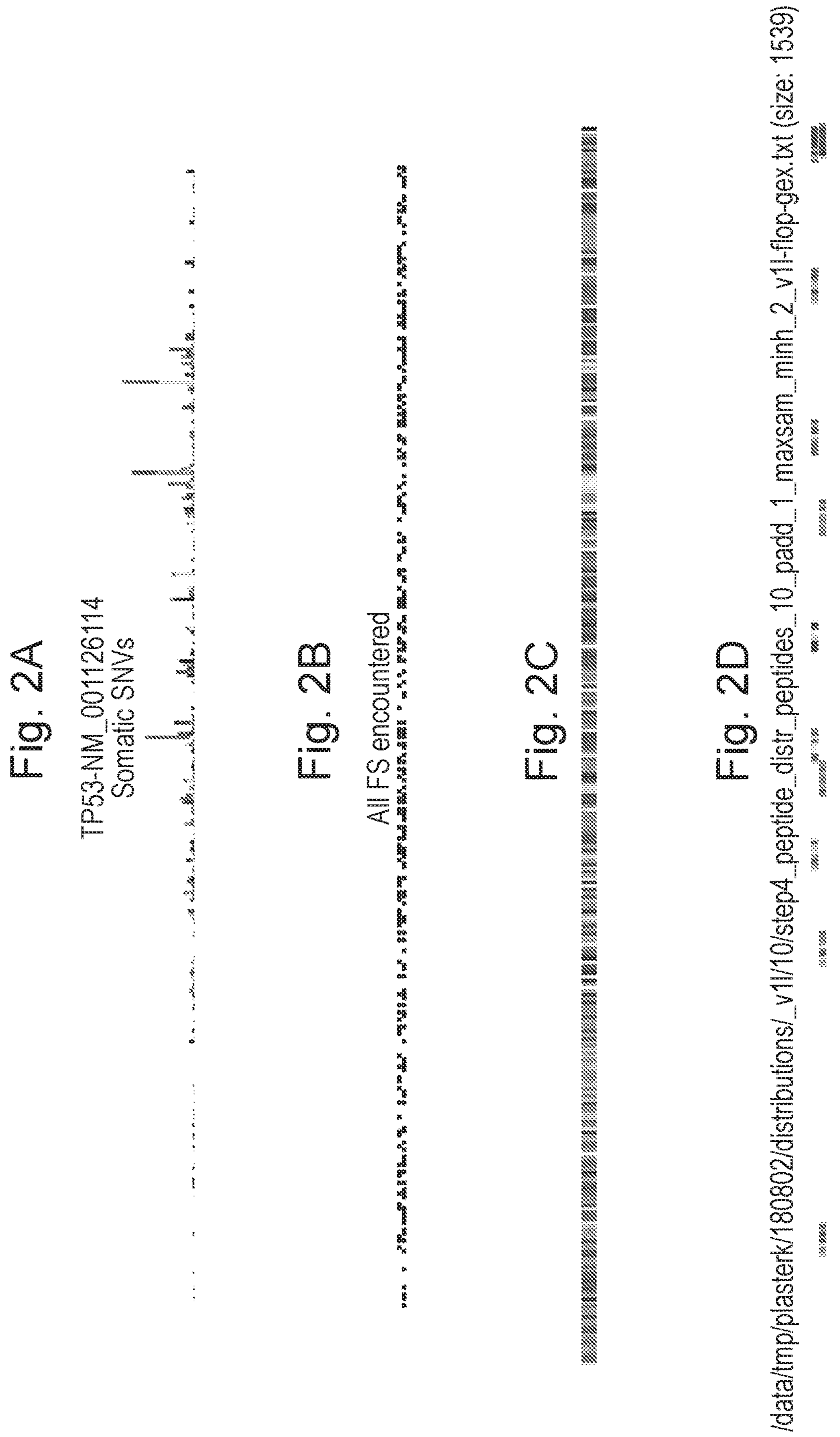
FIG. 2 Neo open reading frame peptides (TCGA cohort) converge on common peptide sequences. Graphical representation in an isoform of TP53, where amino acids are colored distinctly. A. somatic single nucleotide variants, B. positions of frame shift mutations on the −1 and the +1 frame. C. amino acid sequence of TP53. D. Peptide (10aa) library (n=1,000) selection. Peptides belonging to −1 or +1 frame are separated vertically E,F pNOPs for the different frames followed by all encountered frame shift mutations (rows), translated to a stop codon (lines) colored by amino acid.
Figure 2E:
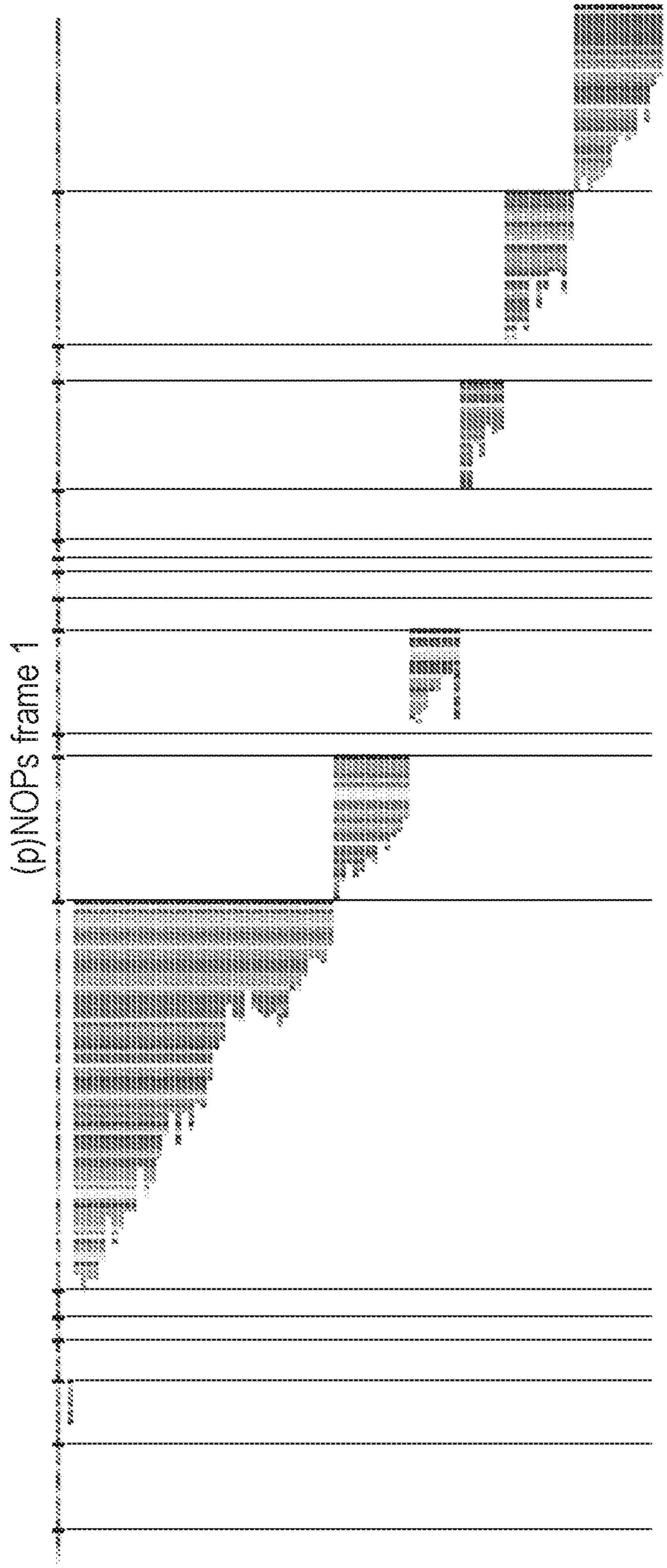
Figure 2F:
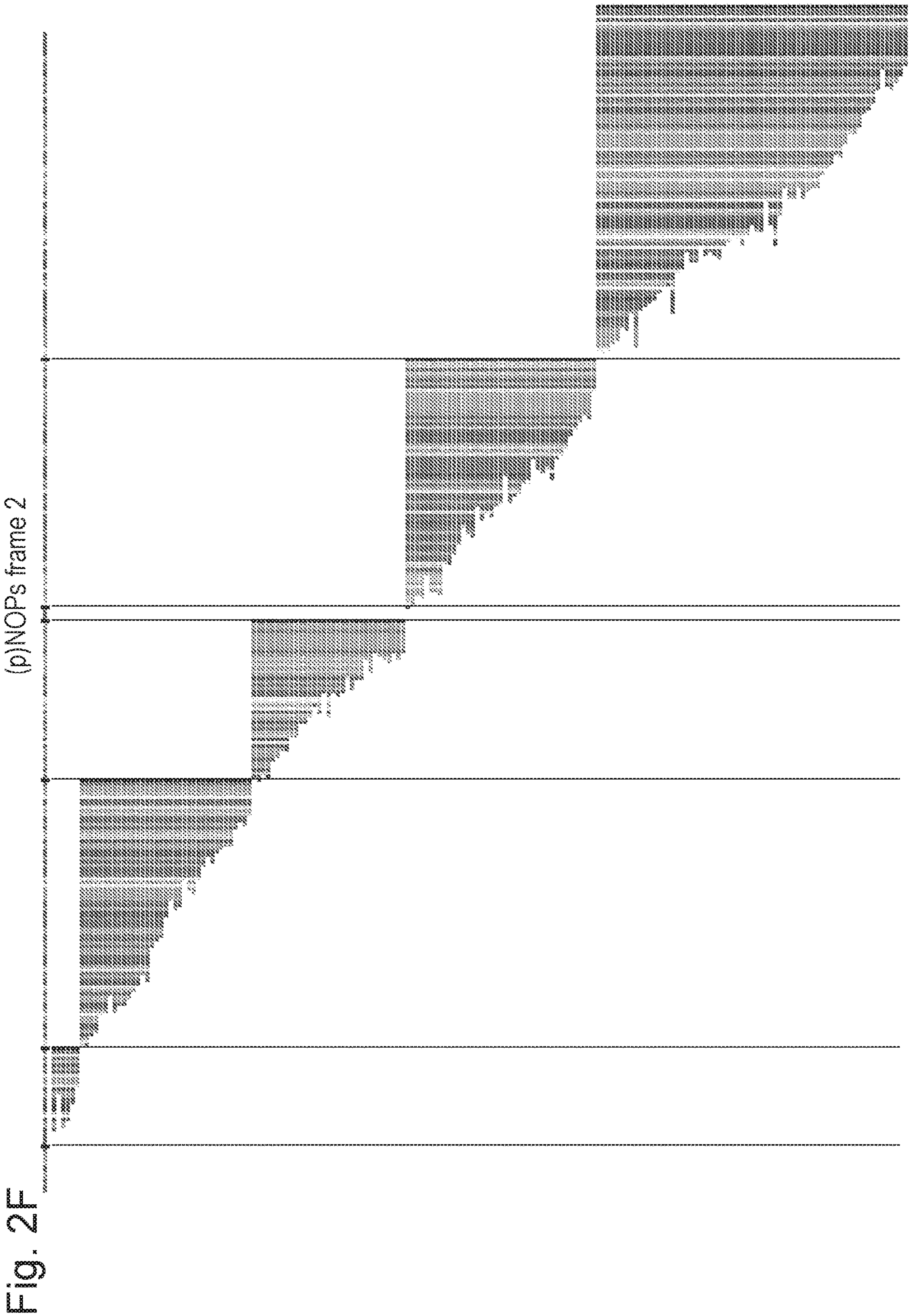
Figure 3:
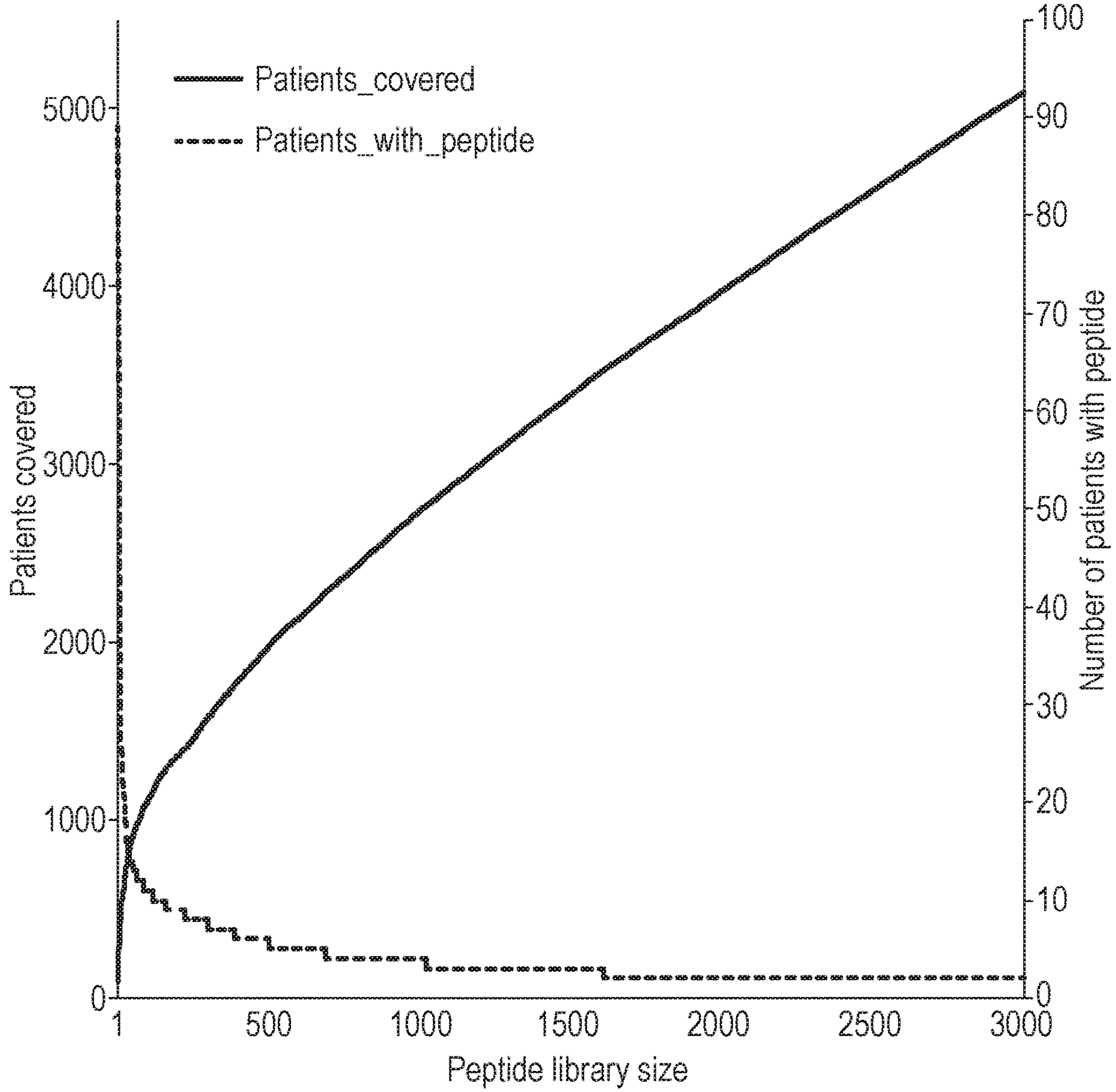
FIG. 3A recurrent peptide selection procedure can generate a 'fixed' library to cover up to 50% of the TCGA cohort. Graph depicts the number of unique patients from the TCGA cohort (10,186 patients) accommodated by a growing library of 10-mer peptides, picked in descending order of the number patients with that sequence in their NOPs. A peptide is only added if it adds a new patient from the TCGA cohort. The dark blue line shows that an increasing number of 10-mer peptides covers an increasing number of patients from the TCGA cohort (up to 50% if using 3000 unique 10-mer peptides). Light shaded blue line depicts the number of patients containing the peptide that was included (right Y-axis). The best peptide covers 89 additional patients from the TCGA cohort (left side of the blue line), the worst peptide includes only 1 additional patient (right side of the blue line).
Figure 4:
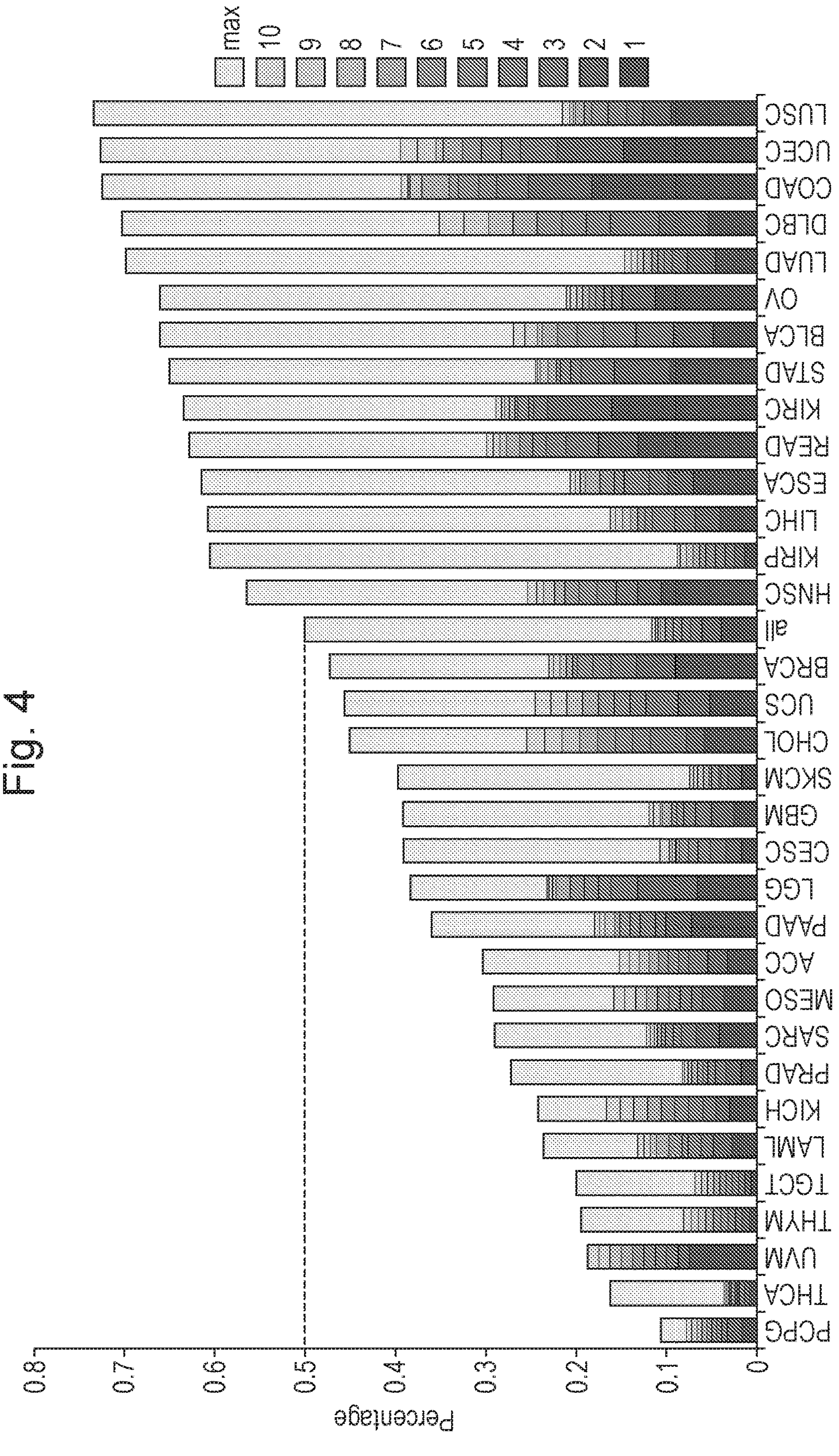
FIG. 4 For some cancers up to 70% of patients contain a recurrent NOP. TCGA cohort ratio of patients separated by tumor type that could be 'helped' using optimally selected peptides for genes encountered most often within a cancer. Coloring represents the ratio, using 1, 2 . . . 10 genes, or using all encountered genes (lightest shade)
Figure 5A:
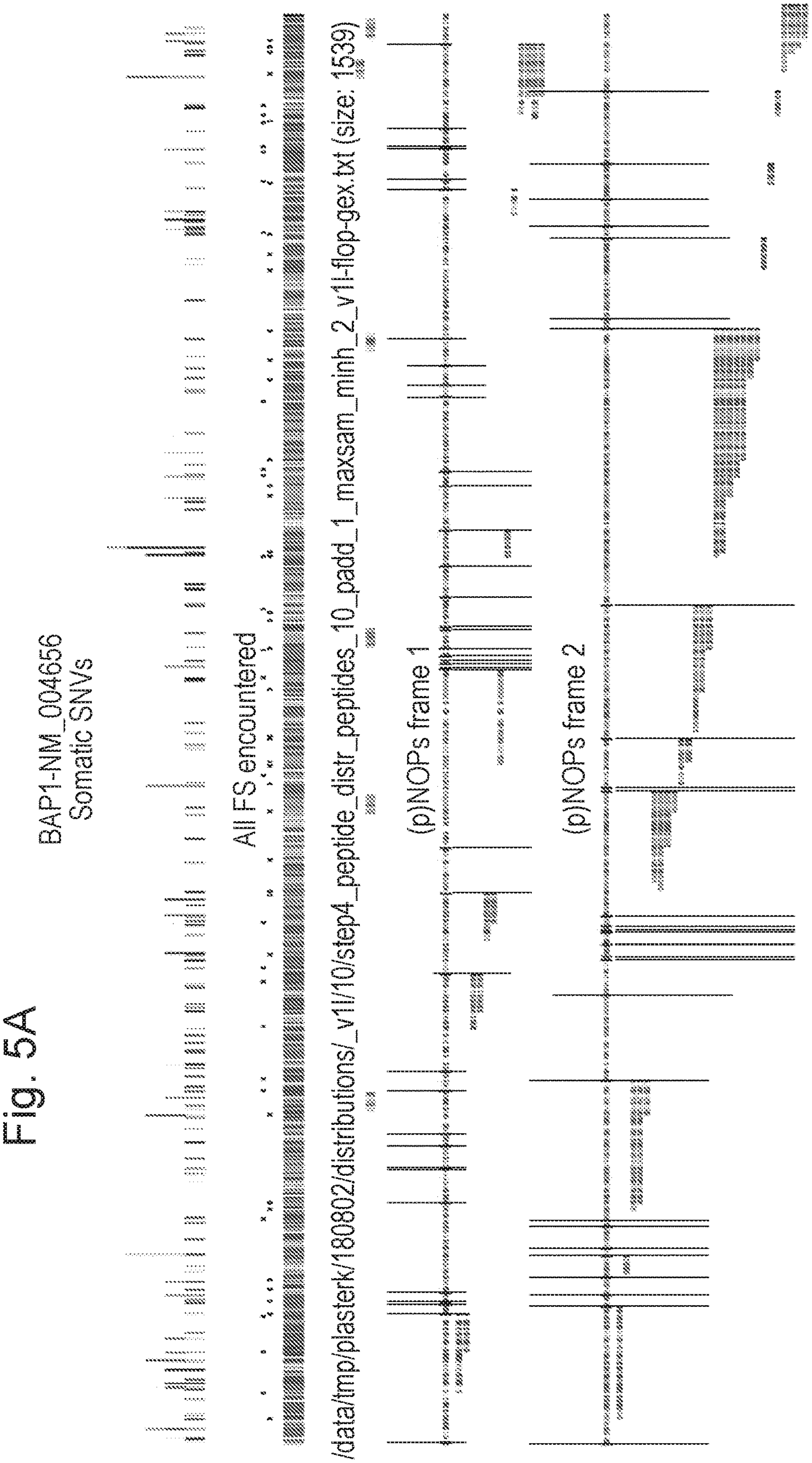
FIG. 5 Examples of NOPs. Selection of genes containing NOPs of 10 or more amino acids.
Figure 5B:
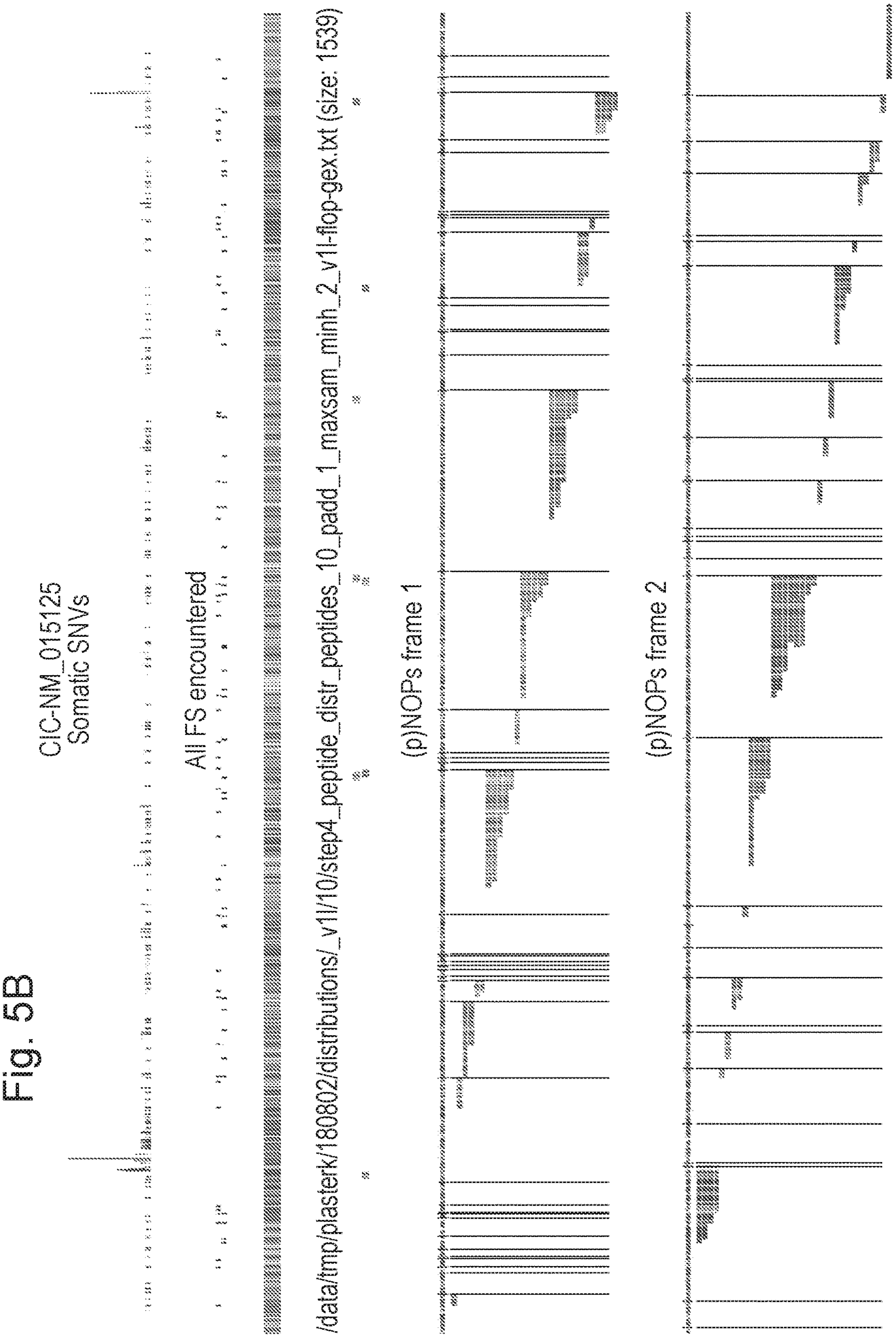
Figure 5C:
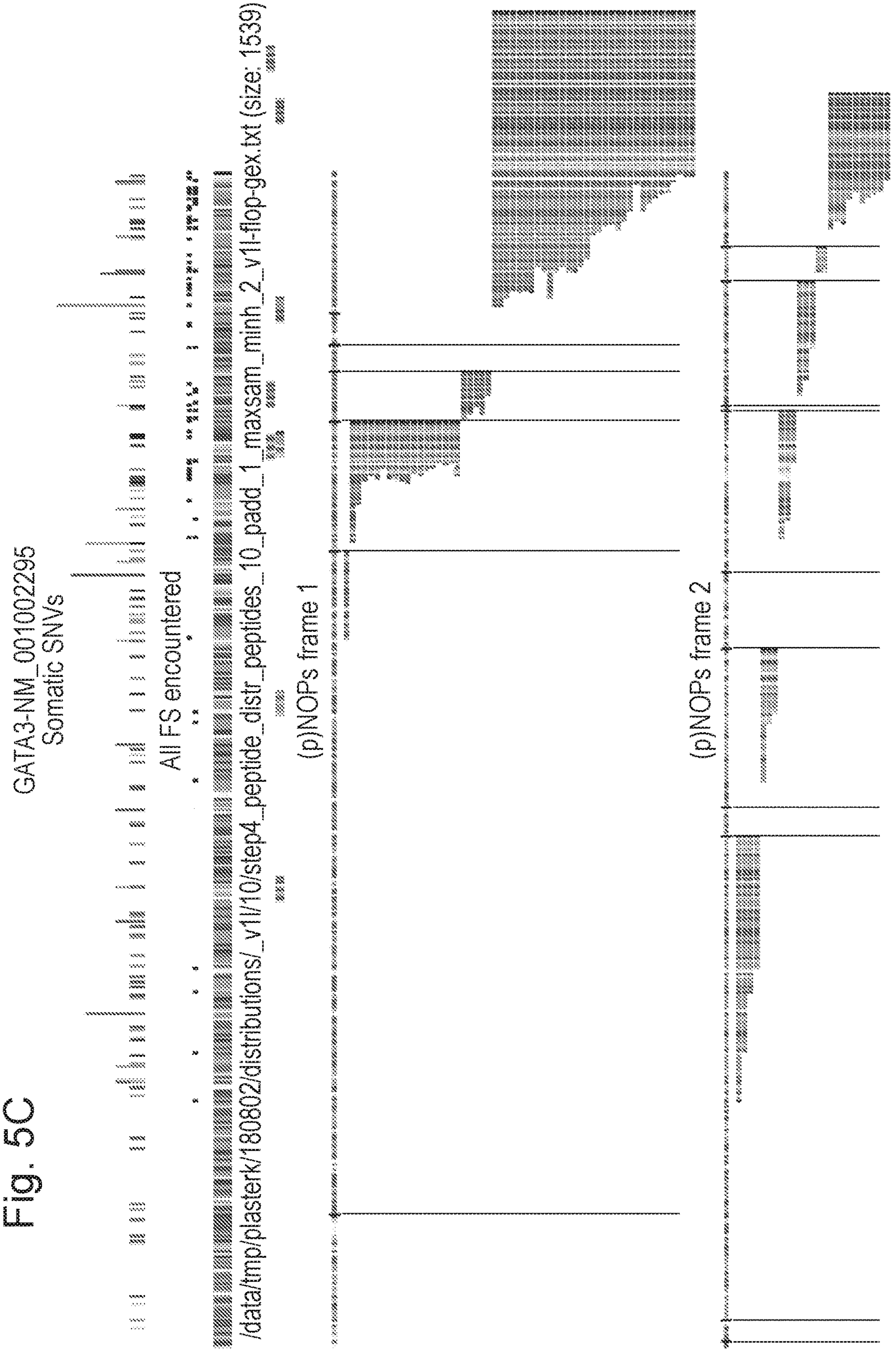
Figure 5D:
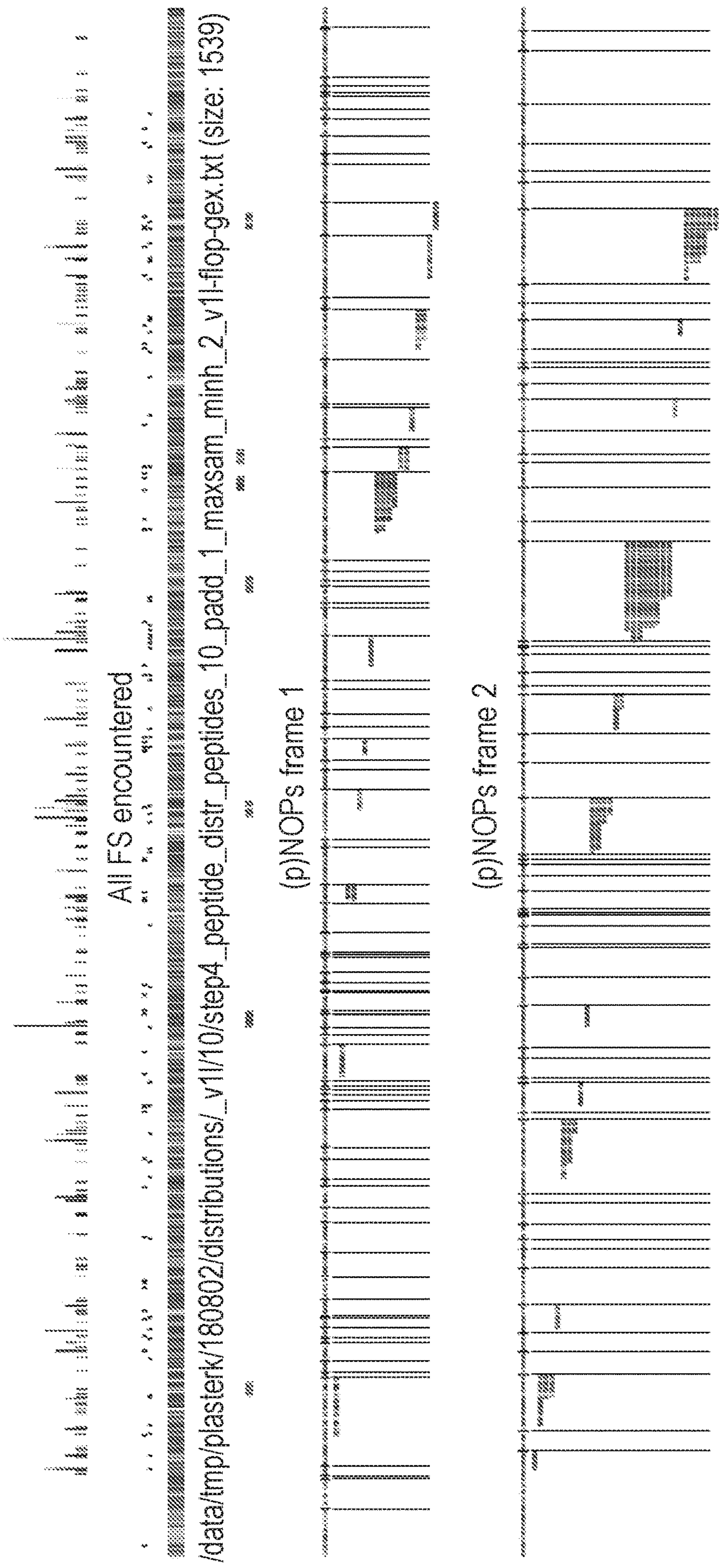
Figure 5E:
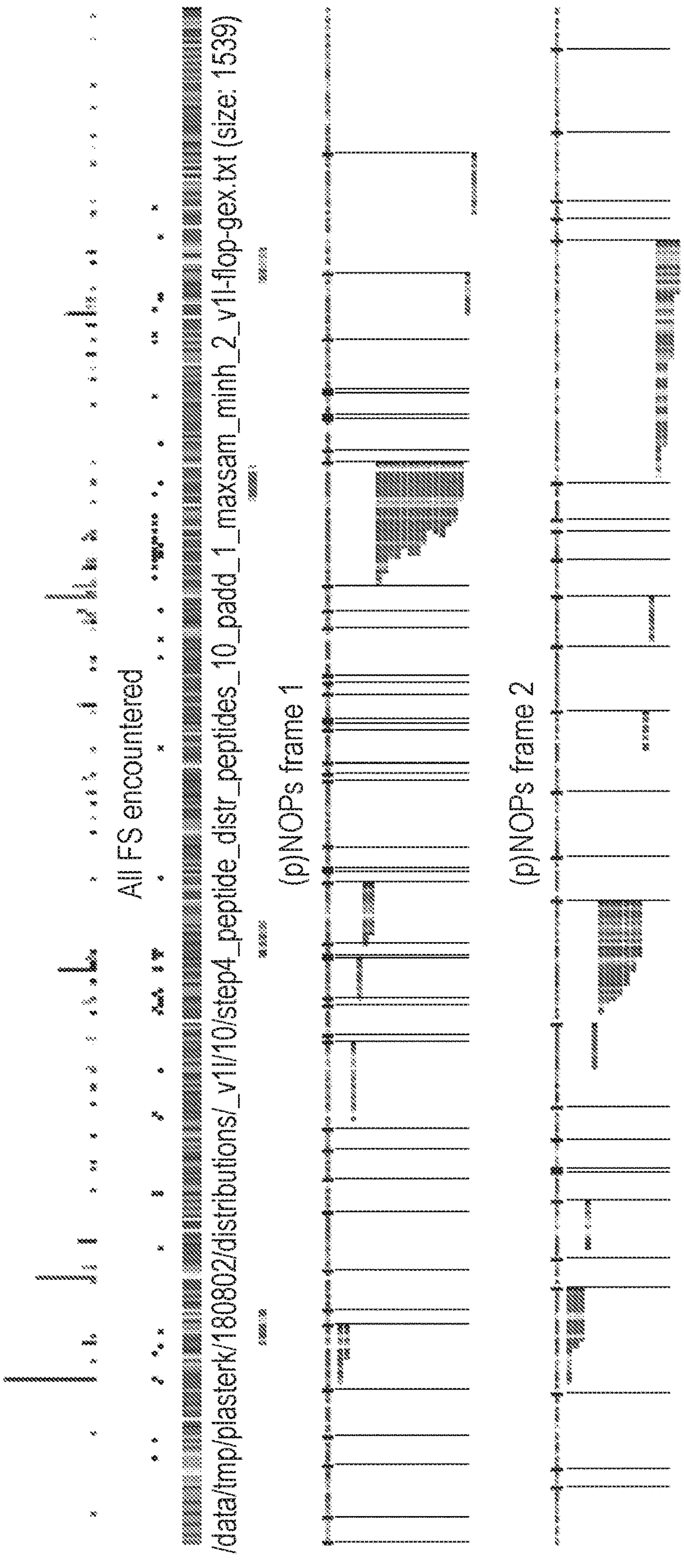
Figure 5F:
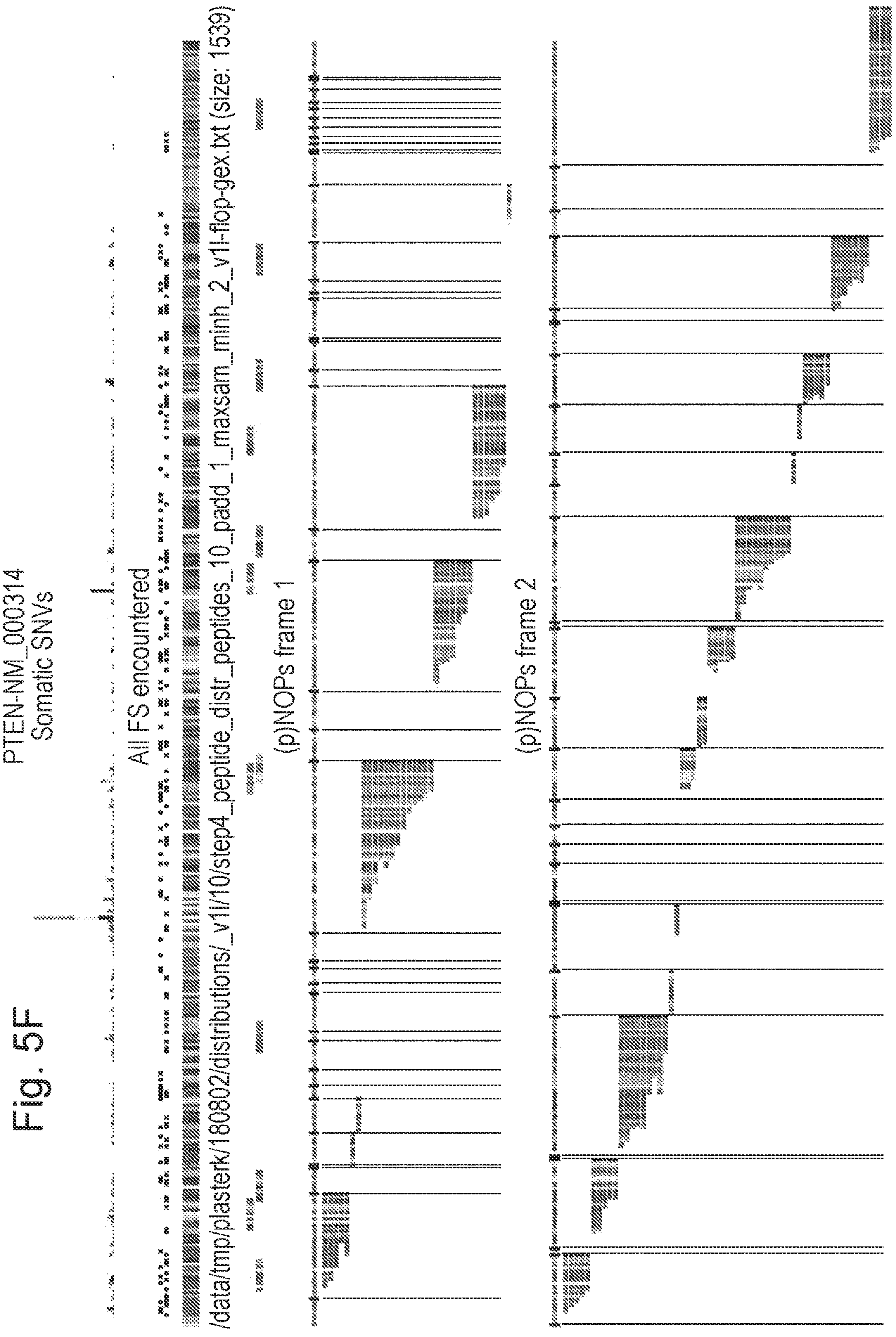
Figure 5G:
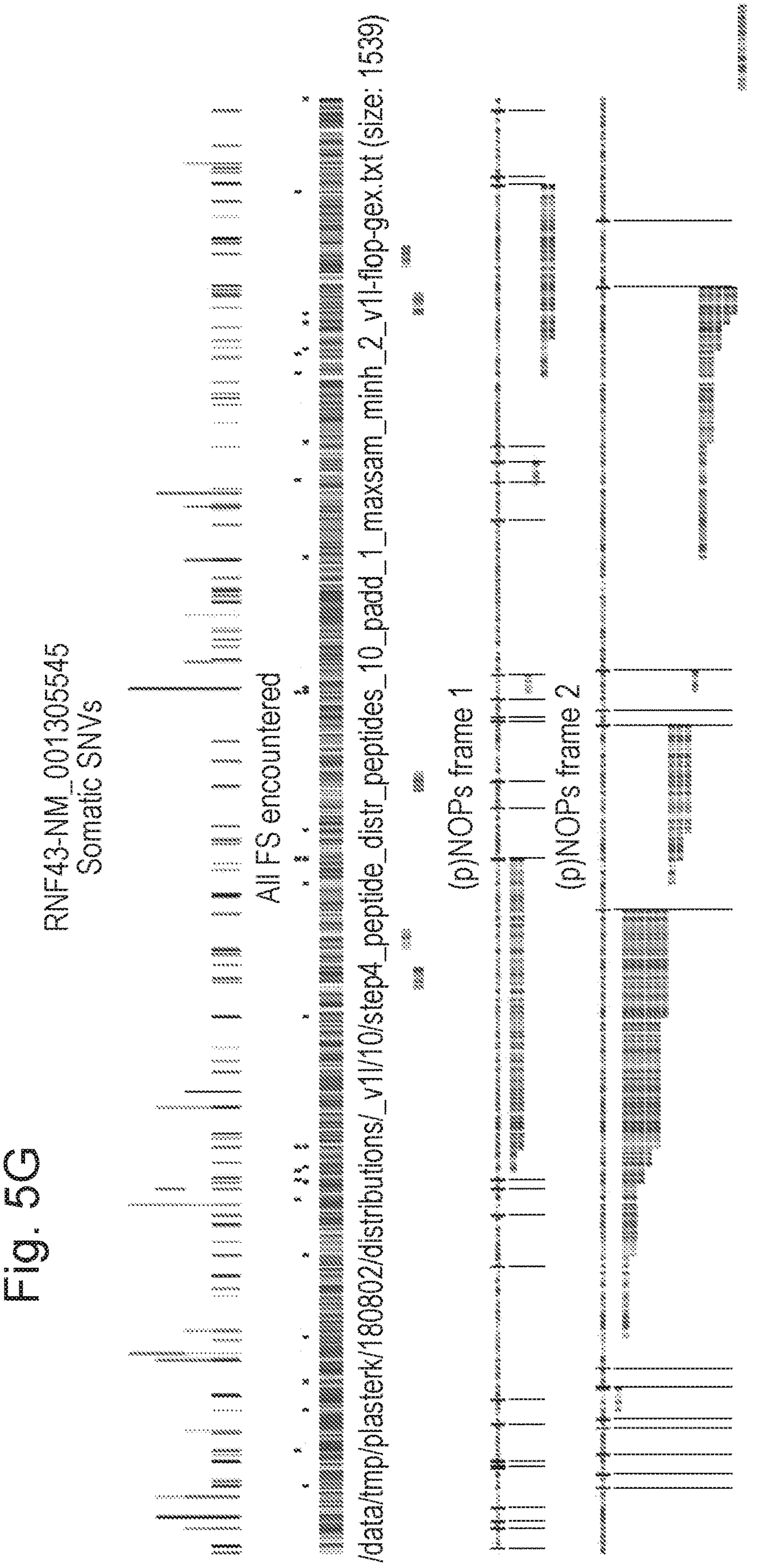
Figure 5H:
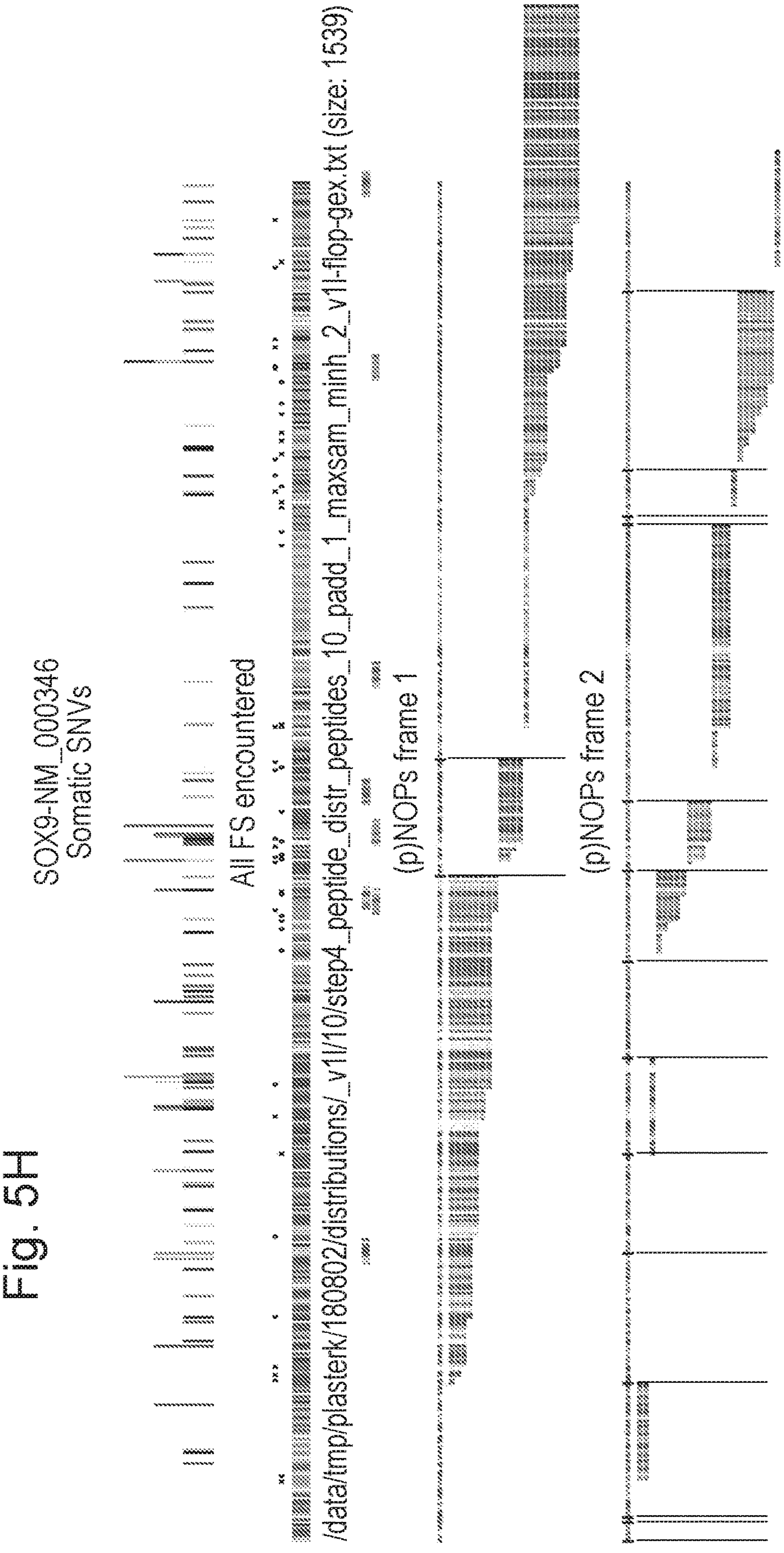
Figure 5I:
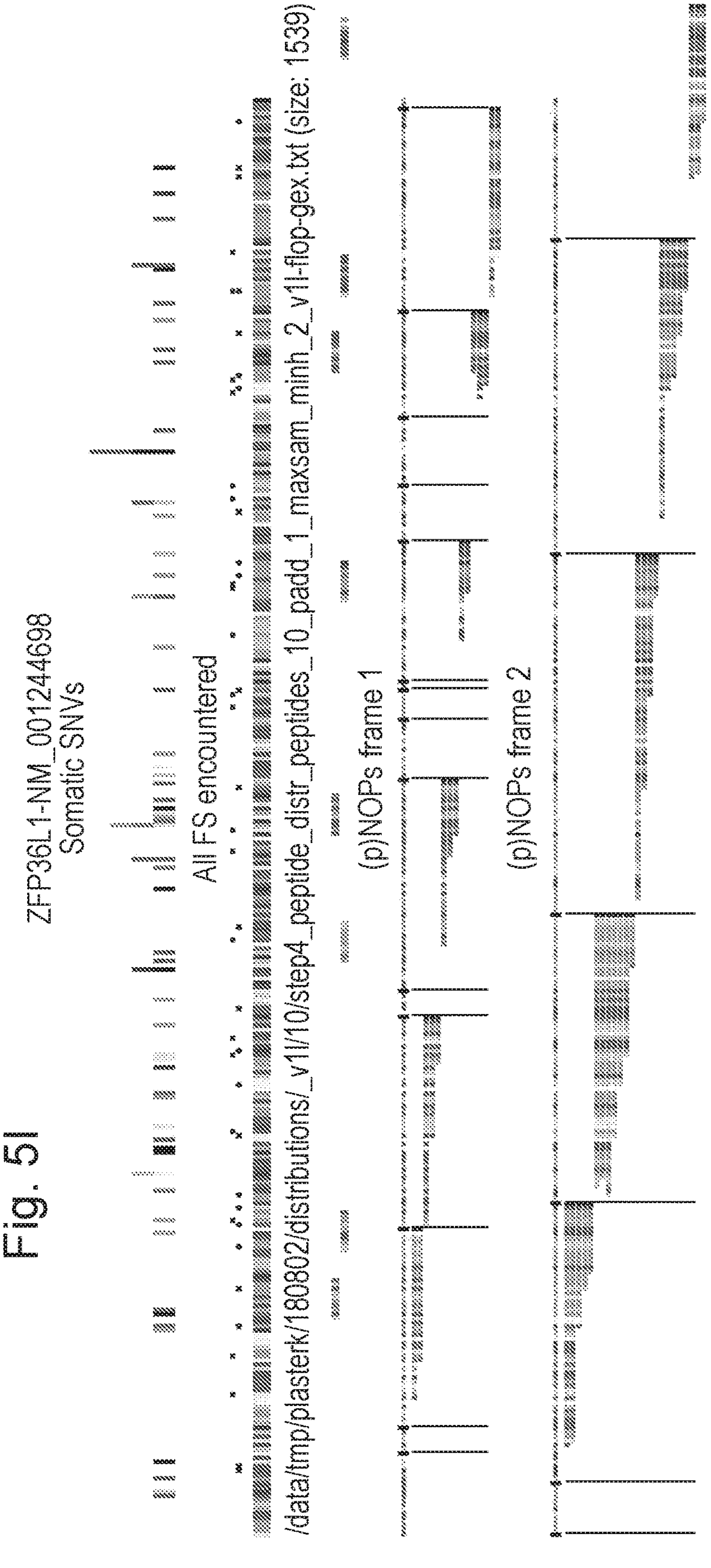
Figure 5J:
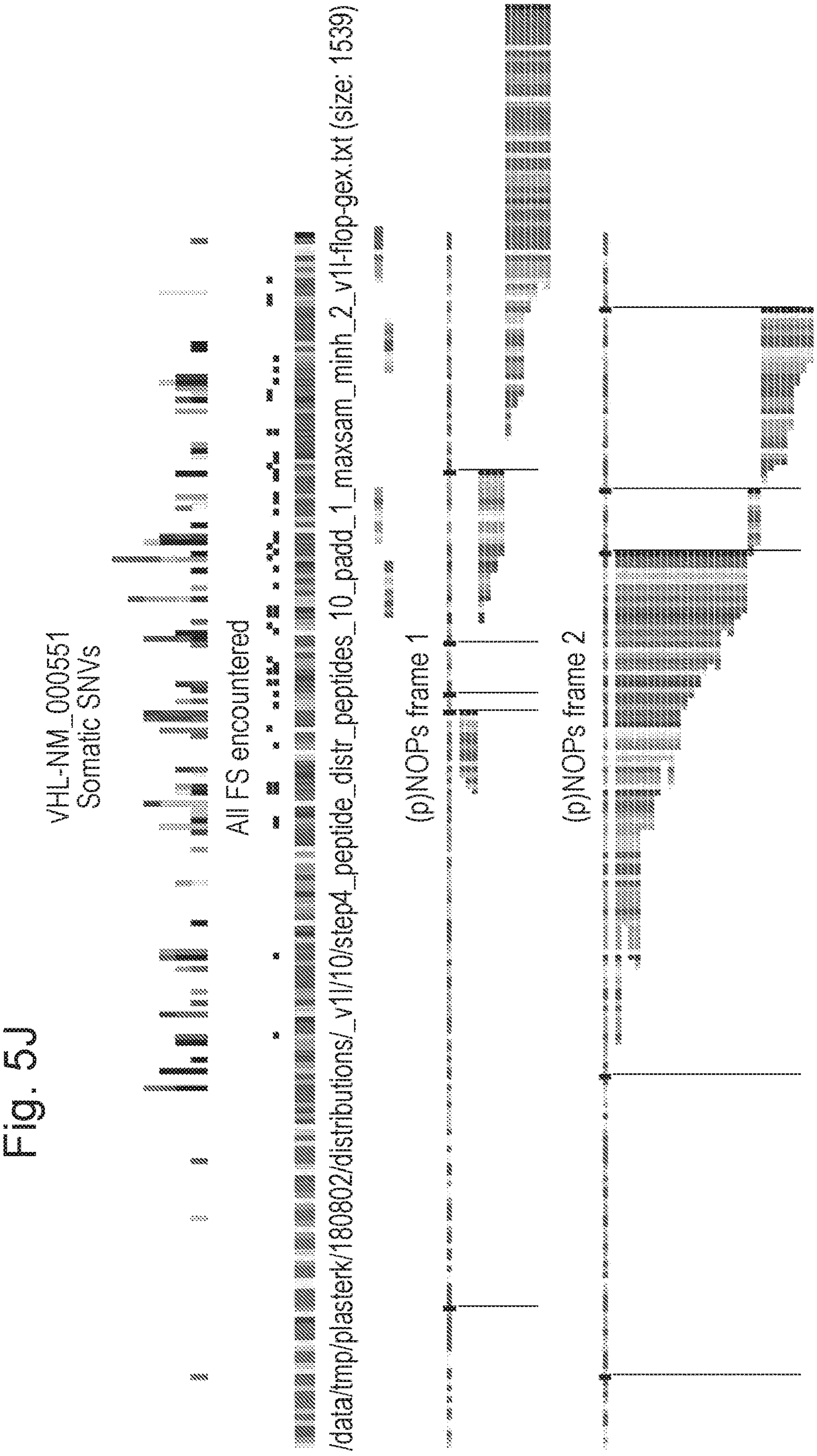
Figure 5K:
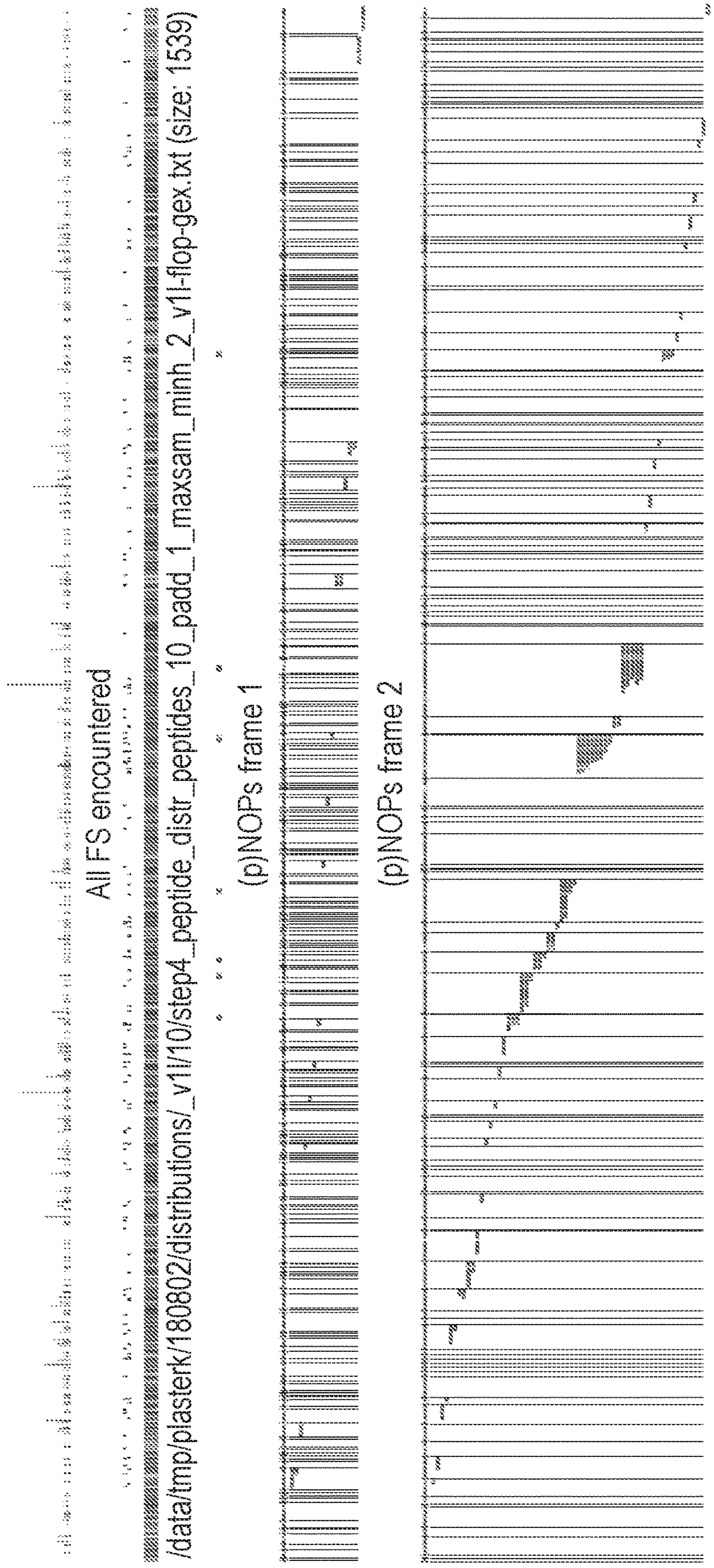
Figure 6A:
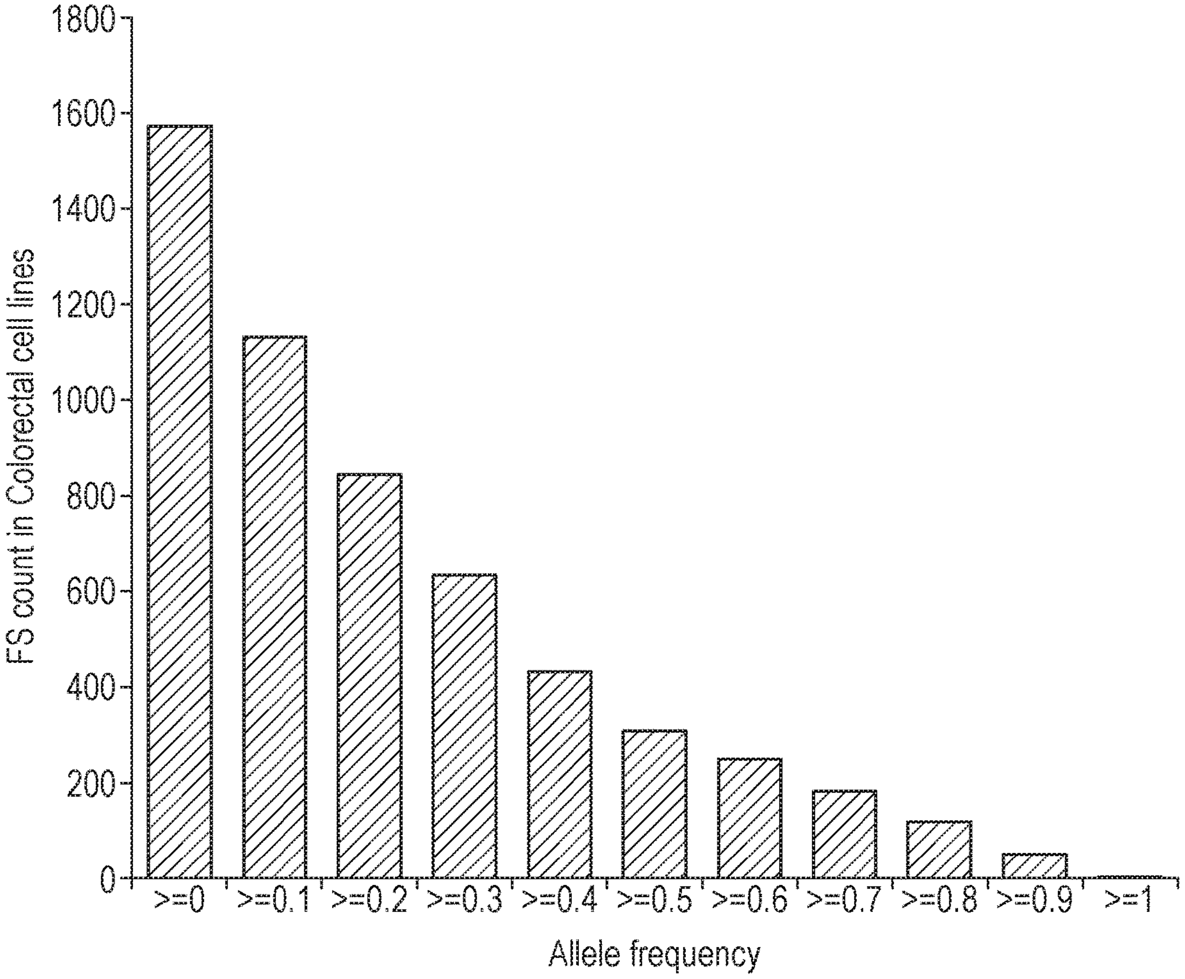
FIG. 6 Frame shift presence in mRNA from 58 CCLE colorectal cancer cell lines.
Figure 6B:
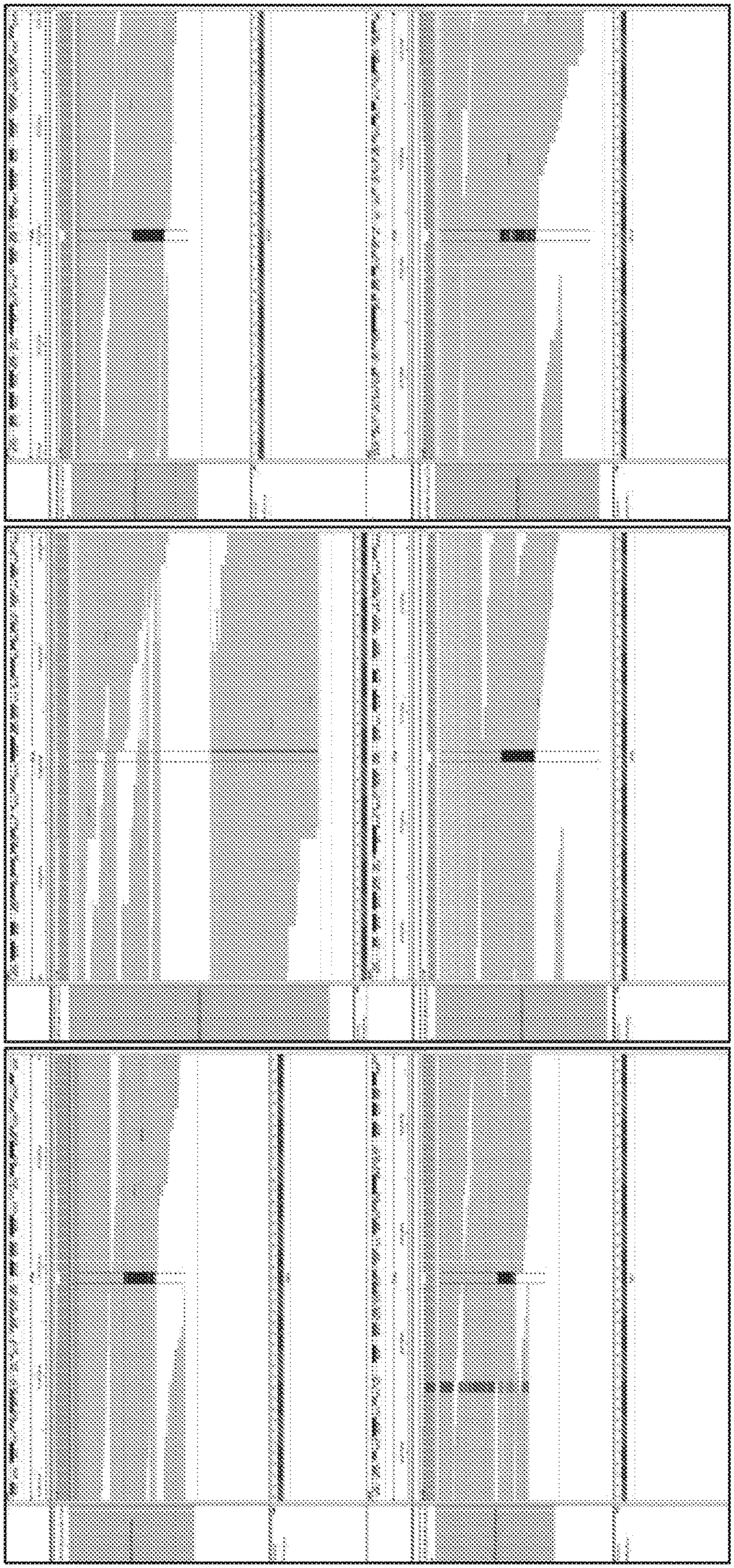

We have analyzed 10,186 cancer genomes from 33 tumor types of the 40 TCGA (The Cancer Genome Atlas[22]) and focused on the 143,444 frame shift mutations represented in this cohort. Translation of these mutations after re-annotation to a RefSeq annotation, starting in the protein reading frame, can lead to 70,439 unique peptides that are 10 or more amino acids in length (a cut off we have set at a size sufficient to shape a distinct epitope in the context of MHC (FIG. 1*a*). The list of genes most commonly represented in the cohort and containing such frame shift mutations is headed nearly exclusively by tumor driver genes, such as NF1, RB, BRCA2 (FIG. 1*b*) whose whole or partial loss of function apparently contributes to tumorigenesis. Note that a priori frame shift mutations are expected to result in loss of gene function more than a random SNV, and more independent of the precise position. NOPs initiated from a frameshift mutation and of a significant size are prevalent in tumors, and are enriched in cancer driver genes. Alignment of the translated NOP products onto the protein sequence reveals that a wide array of different frame shift mutations translate in a common downstream stretch of neo open reading frame peptides ('NOPs'), as dictated by the −1 and +1 alternative reading frames. While we initially screened for NOPs of ten or more amino acids, their open reading frame in the out-of-frame genome often extends far beyond that search window. As a result we see (FIG. 2) that hundreds of different frame shift mutations all at different sites in the gene nevertheless converge on only a handful of NOPs. Similar patterns are found in other common driver genes (FIG. 5). FIG. 2 illustrates that the precise location of a frame shift does not seem to matter much; the more or less straight slope of the series of mutations found in these 10,186 tumors indicates that it is not relevant for the biological effect (presumably reduction/loss of gene function) where the precise frame shift is, as long as translation stalls in the gene before the downstream remainder of the protein is expressed. As can also be seen in FIG. 2, all frame shift mutations alter the reading frame to one of the two alternative frames. Therefore, for potential immunogenicity the relevant information is the sequence of the alternative ORFs and more precisely, the encoded peptide sequence between 2 stop codons. We term these peptides 'proto Neo Open Reading Frame peptides' or pNOPs, and generated a full list of all thus defined out of frame protein encoding regions in the human genome, of 10 amino acids or longer. We refer to the total sum of all Neo-ORFs as the Neo-ORFeome. The Neo-ORFeome contains all the peptide potential that the human genome can generate after simple frame-shift induced mutations. The size of the Neo-ORFeome is 46.6 Mb. To investigate whether or not Nonsense Mediated Decay would wipe out frame shift mRNAs, we turned to a public repository containing read coverage for a large collection of cell lines (CCLE). We processed the data in a similar fashion as for the TCGA, identified the locations of frame shifts and subsequently found that, in line with the previous literature[23-25], at least a large proportion of expressed genes also contained the frame shift mutation within the expressed mRNAs (FIG. 6). On the mRNA level, NOPs can be detected in RNAseq data. We next investigated how the number of patients relates to the number of NOPs. We sorted 10-mer peptides from NOPs by the number of new patients that contain the queried peptide. Assessed per tumor type, frame shift mutations in genes with very low to absent mRNA expression were removed to avoid overestimation. Of note NOP sequences are sometimes also encountered in the normal ORFeome, presumably as result of naturally occurring isoforms (e,g, FIG. 7). Also these peptides were excluded. We can create a library of possible 'vaccines' that is optimally geared towards covering the TCGA cohort, a cohort large enough that, also looking at the data presented here, it is representative of future patients (FIG. 10). Using this strategy 30% of all patients can be covered with a fixed collection of only 1,244 peptides of length 10 (FIG. 3). Since tumors will regularly have more than 1 frame shift mutation, one can use a 'cocktail' of different NOPs to optimally attack a tumor. Indeed, given a library of 1,244 peptides, 27% of the covered TCGA patients contain 2 or more 'vaccine' candidates. In conclusion, using a limited pool with optimal patient inclusion of vaccines, a large proportion of patients is covered. Strikingly, using only 6 genes (TP53, ARID1A, KMT2D, GATA3, APC, PTEN), already 10% of the complete TCGA cohort is covered. Separating this by the various tumor types, we find that for some cancers (like Pheochromocytoma and Paraganglioma (PCPG) or Thyroid carcinoma (THCA)) the hit rate is low, while for others up to 39% can be covered even with only 10 genes (Colon adenocarcinoma (COAD) using 60 peptides, Uterine Corpus Endometrial Carcinoma (UCEC) using 90 peptides), FIG. 4. At saturation (using all peptides encountered more than once) 50% of TCGA is covered and more than 70% can be achieved for specific cancer types (COAD, UCEC, Lung squamous cell carcinoma (LUSC) 72%, 73%, 73% respectively). As could be expected, these roughly follow the mutational load in the respective cancer types. In addition some frame shifted genes are highly enriched in specific tumor types (e.g. VHL, GATA3. FIG. 8). We conclude that at saturating peptide coverage, using only very limited set of genes, a large cohort of patients can be provided with off the shelf vaccines. To validate the presence of NOPs, we used the targeted sequencing data on 10,129 patients from the MSK-IMPACT cohort 26. For the 341-410 genes assessed in this cohort, we obtained strikingly similar results in terms of genes frequently affected by frame shifts and the NOPs that they create (FIG. 9). Even within this limited set of genes, 86% of the library peptides (in genes targeted by MSK-IMPACT) were encountered in the patient set. Since some cancers, like glioblastoma or pancreatic cancer, show survival expectancies after diagnosis measured in months rather than years (e.g. see 27), it is of importance to move as much of the work load and time line to the moment before diagnosis. Since the time of whole exome sequencing after biopsy is currently technically days, and since the scan of a resulting sequence against a public database describing these NOPs takes seconds, and the shipment of a peptide of choice days, a vaccination can be done theoretically within days and practically within a few weeks after biopsy. This makes it attractive to generate a stored and quality controlled peptide vaccine library based on the data presented here, possibly with replicates stored on several locations in the world. The synthesis in advance will—by economics of scale—reduce costs, allow for proper regulatory oversight, and can be quality certified, in addition to saving the patient time and thus provide chances. The present invention will likely not replace other therapies, but be an additional option in the treatment repertoire. The advantages of scale also apply to other means of vaccination against these common neoantigens, by RNA- or DNA-based approaches (e.g. 28), or recombinant bacteria (e.g. 29). The present invention also provides neoantigen directed application of the CAR-T therapy (For recent review see 30, and references therein), where the T-cells are directed not against a cell-type specific antigens (such as CD19 or CD20), but against a tumor specific neoantigen as provided herein. E.g. once one functional T-cell against any of the common p53 NOPs (FIG. 2) is identified, the recognition domains can be engineered into T-cells for any future patient with such a NOP, and the constructs could similarly be deposited in an off-the-shelf library. In the present invention, we have identified that various frame shift mutations can result in a source for common neo open reading frame peptides, suitable as pre-synthesized vaccines. This may be combined with immune response stimulating measures such as but not limited checkpoint inhibition to help instruct our own immune system to defeat cancer.

Up to 5% of kidney cancers are a result of a heritable germline mutation. Von Hipple Lindau (VHL)-disease is a well known renal cancer disorder with a genetic basis (Schmidt and Linehan Semin Oncol. 2016 October; 43(5): 566-574). Germline mutations in the VHL gene, or other genes, such as BAP1, can predispose an individual to kidney cancer.

Thus, there is an opportunity for prophylactic vaccination to reduce the risk of kidney cancer in individuals with predisposition mutations in these genes. In addition, other non-genetic risk factors may play a role in development of kidney cancer, such as high blood pressure and smoking. A prophylactic vaccine would be of highest efficacy if it vaccinates against (i) strongly immunogenic antigens, and (ii) antigens that are expected to be present in a large proportion of kidney tumors (observed in patients with predisposition mutations).

We exploited a recent data source from the Hartwig Medical Foundation (see Priestley et al. 2019 at https://doi.org/10.1101/415133) for the presence of targetable neoantigens in kidney tumors in patients with germline mutations in a range of cancer predisposition genes. Amongst 106 kidney tumors, we found that 18 (17%) of the patients carrying those tumors have a mutation in one or more possible predisposition genes (Table 3).

TABLE 3 germline mutations in cancer predisposition genes observed in kidney cancer patients.

| Gene | Count |
| --- | --- |
| ATM | 1 |
| ATR | 1 |
| BRCA1 | 1 |
| BRIP1 | 1 |
| CBL | 1 |
| CHEK2 | 2 |
| DROSHA | 1 |
| FANCL | 2 |
| FH | 1 |
| FLCN | 1 |
| GJB2 | 2 |
| MUTYH | 1 |
| PRDM9 | 1 |
| RECQL | 1 |
| RECQL4 | 1 |
| SDHA | 1 |
| XPC | 1 |

Next, we explored the idea of using neo-open reading frame peptides, resulting from somatic frameshift mutations, as an attractive source of neoantigens in human cancers. Therefore, we calculated the number of kidney cancer patients in the HMF data resource with frameshift mutations leading to possible out of frame neo-peptides. Neo-peptides larger than or equal to 10 amino acids are most frequently found in VHL (12.3%) and PBRM1 (7.5%).

To explore the possibility for prophylactic vaccination of individuals at risk for kidney cancer based on germline predisposing mutations, we determined the genes for which out-of-frame peptide sequences are found among patients with germline predisposition mutations.

Out of all 18 kidney cancer patients with presumed germline predisposition mutations (in any possible predisposition gene), we found 4 (22%) patients that have a frameshift leading to a neo-peptide in VHL or PBRM1.

We conclude that a considerable fraction of kidney cancer patients with predisposing germline mutations, may benefit from vaccination against frameshift-induced neopeptides. With a peptide vaccine covering only 2 genes (VHL, PBRM1), for 22% of patients with germline mutations, kidney cancer development can possibly be prevented.

Methods

TCGA frameshift mutations-Frame shift mutations were retrieved from Varscan and mutect files per tumor type via https://portal.gdc.cancer.gov/. Frame shift mutations contained within these files were extracted using custom perl scripts and used for the further processing steps using HG38 as reference genome build.

CCLE frameshift mutations—For the CCLE cell line cohort, somatic mutations were retrieved from http://www-.broadinstitute.org/ccle/data/browseData?conversationPropagation=begin (CCLE_hybrid_capture1650_hg19_NoCommonSNPs_NoNeutralVariants_CDS_2012.02.20.maf). Frame shift mutations were extracted using custom perl scripts using hg19 as reference genome.

Refseq annotation—To have full control over the sequences used within our analyses, we downloaded the reference sequences from the NCBI website (2018 Feb. 27) and extracted mRNA and coding sequences from the gbff files using custom perl scripts. Subsequently, mRNA and every exon defined within the mRNA sequences were aligned to the genome (hg19 and hg38) using the BLAT suite. The best mapping locations from the psl files were subsequently used to place every mRNA on the genome, using the separate exons to perform fine placement of the exonic borders. Using this procedure we also keep track of the offsets to enable placement of the amino acid sequences onto the genome.

Mapping genome coordinate onto Refseq—To assess the effect of every mentioned frame shift mutation within the cohorts (CCLE or TCGA), we used the genome coordinates of the frameshifts to obtain the exact protein position on our reference sequence database, which were aligned to the genome builds. This step was performed using custom perl scripts taking into account the codon offsets and strand orientation, necessary for the translation step described below.

Translation of FS peptides—Using the reference sequence annotation and the positions on the genome where a frame shift mutation was identified, the frame shift mutations were used to translate peptides until a stop codon was encountered. The NOP sequences were recorded and used in downstream analyses as described in the text.

Verification of FS mRNA expression in the CCLE colorectal cancer cell lines—For a set of 59 colorectal cancer cell lines, the HG19 mapped bam files were downloaded from https://portal.gdc.cancer.gov/. Furthermore, the locations of FS mutations were retrieved from CCLE_hybrid_capture1650_hg19_NoCommonSNPs_NoNeutralVariants_CDS_201 2.02.20.maf (http://www.broadinstitute.org/ccle/data/browseData?conversationPropagation=beg in), by selection only frameshift entries. Entries were processed similarly to the TCGA data, but this time based on a HG19 reference genome. To get a rough indication that a particular location in the genome indeed contains an indel in the RNAseq data, we first extracted the count at the location of a frameshift by making use of the pileup function in samtools. Next we used the special tag XO: 1 to isolate reads that contain an indel in it. On those bam files we again used the pileup function to count the number of reads containing an indel (assuming that the indel would primarily be found at the frameshift instructed location). Comparison of those 2 values can then be interpreted as a percentage of indel at that particular location. To reduce spurious results, at least 10 reads needed to be detected at the FS location in the original bam file.

Defining peptide library—To define peptide libraries that are maximized on performance (covering as many patients with the least amount of peptides) we followed the following procedure. From the complete TCGA cohort, FS translated peptides of size 10 or more (up to the encountering of a stop codon) were cut to produce any possible 10-mer. Then in descending order of patients containing a 10-mer, a library was constructed. A new peptide was added only if an additional patient in the cohort was included. peptides were only considered if they were seen 2 or more times in the TCGA cohort, if they were not filtered for low expression (see Filtering for low expression section), and if the peptide was not encountered in the orfeome (see Filtering for peptide presence orfeome). In addition, since we expect frame shift mutations to occur randomly and be composed of a large array of events (insertions and deletions of any non triplet combination), frame shift mutations being encountered in more than 10 patients were omitted to avoid focusing on potential artefacts. Manual inspection indicated that these were cases with e.g. long stretches of Cs, where sequencing errors are common.

Filtering for low expression-Frameshift mutations within genes that are not expressed are not likely to result in the expression of a peptide. To take this into account we calculated the average expression of all genes per TCGA entity and arbitrarily defined a cutoff of 2 log 2 units as a minimal expression. Any frameshift mutation where the average expression within that particular entity was below the cutoff was excluded from the library. This strategy was followed, since mRNA gene expression data was not available for every TCGA sample that was represented in the sequencing data set. Expression data (RNASEQ v2) was pooled and downloaded from the R2 platform (http://r2.amc.nl). In current sequencing of new tumors with the goal of neoantigen identification such mRNA expression studies are routine and allow routine verification of presence of mutant alleles in the mRNA pool.

Filtering for peptide presence orfeome-Since for a small percentage of genes, different isoforms can actually make use of the shifted reading frame, or by chance a 10-mer could be present in any other gene, we verified the absence of any picked peptide from peptides that can be defined in any entry of the reference sequence collection, once converted to a collection of tiled 10-mers.

Generation of cohort coverage by all peptides per gene To generate overviews of the proportion of patients harboring exhaustive FS peptides starting from the most mentioned gene, we first pooled all peptides of size 10 by gene and recorded the largest group of patients per tumor entity. Subsequently we picked peptides identified in the largest set of patients and kept on adding a new peptide in descending order, but only when at least 1 new patient was added. Once all patients containing a peptide in the first gene was covered, we progressed to the next gene and repeated the procedure until no patient with FS mutations leading to a peptide of size 10 was left.

proto-NOP (pNOP) and Neo-ORFeome proto-NOPs are those peptide products that result from the translation of the gene products when the reading frame is shifted by −1 or +1 base (so out of frame). Collectively, these pNOPs form the Neo-Orfeome. As such we generated a pNOP reference base of any peptide with length of 10 or more amino acids, from the RefSeq collection of sequences. Two notes: the minimal length of 10 amino acids is a choice; if one were to set the minimal window at 8 amino acids the total numbers go up a bit, e.g. the 30% patient covery of the library goes up. On a second note: we limited our definition to ORFs that can become in frame after a single insertion deletion on that location; this includes obviously also longer insertion or deletion stretches than +1 or −1. The definition has not taken account more complex events that get an out-of-frame ORF in frame, such as mutations creating or deleting splice sites, or a combination of two frame shifts at different sites that result in bypass of a natural stop codon; these events may and will occur, but counting those in will make the definition of the Neo-ORFeome less well defined. For the magnitude of the numbers these rare events do not matter much.

Visualizing nops—Visualization of the nops was performed using custom perl scripts, which were assembled such that they can accept all the necessary input data structures such as protein sequence, frameshifted protein sequences, somatic mutation data, library definitions, and the peptide products from frameshift translations.

Detection of frameshift resulting neopeptides in breast cancer patients with cancer predisposition mutations—Somatic and germline mutation data were downloaded from the supplementary files attached to the manuscript posted here: https://www.biorxiv.org/content/biorxiv/early/2019/01/16/415133.full.pdf. Frameshift mutations were selected from the somatic mutation files and out-of-frame peptides were predicted using custom Perl and Python scripts, based on the human reference genome GRCh37. Out-of-frame peptides were selected based on their length (>=10 amino acids) and mapped against out of frame peptide sequences for each possible alternative transcript for genes present in the human genome, based on Ensembl annotation (ensembl.org).

REFERENCES

1 Schumacher T. N., & Schreiber R. D. Neoantigens in cancer immunotherapy. *Science.* 348, 69-74 (2015).
2 Gubin M. M., Artyomov M. N., Mardis E. R., & Schreiber R. D. Tumor neoantigens: building a framework for personalized cancer immunotherapy. *J Clin Invest.* 125, 3413-21 (2015).
3 Ward J. P., Gubin M. M., & Schreiber R. D. The Role of Neoantigens in Naturally Occurring and Therapeutically Induced Immune Responses to Cancer. *Adv Immunol.* 130, 25-74 (2016).
4 DeWeerdt S. Calling cancer's bluff with neoantigen vaccines. *Nature.* 552, S76-S77 (2017).
5 Guo C., et al. Therapeutic cancer vaccines: past, present, and future. *Adv Cancer Res.* 119, 421-75 (2013).
6 Overwijk W. W., Wang E., *Marincola* F. M., Rammensee H. G., & Restifo N. P. Mining the mutanome: developing highly personalized Immunotherapies based on mutational analysis of tumors. *J Immunother Cancer.* 1, 11 (2013).
7 Yamada A., Sasada T., Noguchi M., & Itoh K. Next-generation peptide vaccines for advanced cancer. *Cancer Sci.* 104, 15-21 (2013).
8 Ott P. A., et al. An immunogenic personal neoantigen vaccine for patients with melanoma. *Nature.* 547, 217-221 (2017).
9 Wirth T. C., & Kuhnel F. Neoantigen Targeting-Dawn of a New Era in Cancer Immunotherapy? *Front Immunol.* 8, 1848 (2017).
10 Yarchoan M., Hopkins A., & Jaffee E. M. Tumor Mutational Burden and Response Rate to PD-1 Inhibition. *N Engl J Med.* 377, 2500-2501 (2017).
11 Sahin U., et al. Personalized RNA mutanome vaccines mobilize poly-specific therapeutic immunity against cancer. *Nature.* 547, 222-226 (2017).
12 Linnebacher M., et al. Frameshift peptide-derived T-cell epitopes: a source of novel tumor-specific antigens. *Int J Cancer.* 93, 6-11 (2001).
13 Sonntag K., et al. Immune monitoring and TCR sequencing of CD4 T cells in a long term responsive patient with metastasized pancreatic ductal carcinoma treated with individualized, neoepitope derived multipeptide vaccines: a case report. *J Transl Med.* 16, 23 (2018).
14 MacArthur D. G., et al. A systematic survey of loss-of-function variants in human protein-coding genes. *Science.* 335, 823-8 (2012).
15 Turajlic S., et al. Insertion-and-deletion-derived tumour-specific neoantigens and the immunogenic phenotype: a pan-cancer analysis. *Lancet Oncol.* 18, 1009-1021 (2017).
16 Rammensee H., Bachmann J., Emmerich N. P., Bachor O. A., & Stevanovic S. SYFPEITHI: database for MHC ligands and peptide motifs. *Immunogenetics.* 50, 213-9 (1999).
17 Alvarez B., Barra C., Nielsen M., & Andreatta M. Computational Tools for the Identification and Interpretation of Sequence Motifs in Immunopeptidomes. *Proteomics.* 18, e1700252 (2018).
18 Andreatta M., et al. Accurate pan-specific prediction of peptide-MHC class II binding affinity with improved binding core identification. *Immunogenetics.* 67, 641-50 (2015).
19 Rizvi N. A., et al. Cancer immunology. Mutational landscape determines sensitivity to PD-1 blockade in non-small cell lung cancer. *Science.* 348, 124-8 (2015).
20 Prickett T. D., et al. Durable Complete Response from Metastatic Melanoma after Transfer of Autologous T Cells Recognizing 10 Mutated Tumor Antigens. *Cancer Immunol Res.* 4, 669-78 (2016).
21 Liu R., et al. H7N9 T-cell epitopes that mimic human sequences are less immunogenic and may induce Treg-mediated tolerance. *Hum Vaccin Immunother.* 11, 2241-52 (2015).
22 Weinstein J. N., et al. The Cancer Genome Atlas Pan-Cancer analysis project. *Nat Genet.* 45, 1113-20 (2013).
23 Lindeboom R. G., Supek F., & Lehner B. The rules and impact of nonsense-mediated mRNA decay in human cancers. *Nat Genet.* 48, 1112-8 (2016).
24 Longman D., Plasterk R. H., Johnstone I. L., & Caceres J. F. Mechanistic insights and identification of two novel factors in the *C. elegans* NMD pathway. *Genes Dev.* 21, 1075-85 (2007).
25 Nguyen L. S., Wilkinson M. F., & Gecz J. Nonsense-mediated mRNA decay: inter-individual variability and human disease. *Neurosci Biobehav Rev.* 46 Pt 2, 175-86 (2014).
26 Zehir A., et al. Mutational landscape of metastatic cancer revealed from prospective clinical sequencing of 10,000 patients. *Nat Med.* 23, 703-713 (2017).
27 Fest J., et al. Underestimation of pancreatic cancer in the national cancer registry *Eur J Cancer.* 72, 186-191 (2017).
28 Boisguerin V., et al. Translation of genomics-guided RNA-based personalised cancer vaccines: towards the bedside. *Br J Cancer.* 111, 1469-75 (2014).
29 Keenan B. P., et al. A *Listeria* vaccine and depletion of T-regulatory cells activate immunity against early stage pancreatic intraepithelial neoplasms and prolong survival of mice. *Gastroenterology.* 146, 1784-94.e6 (2014).
30 Ramello M. C., Haura E. B., & Abate-Daga D. CAR-T cells and combination therapies: What's next in the immunotherapy revolution? *Pharmacol Res.* 129, 194-203 (2018).
31 Giannakis, Marios, et al. "Genomic Correlates of Immune-Cell Infiltrates in Colorectal Carcinoma." Cell Reports, vol. 17, no. 4, October 2016, p. 1206.
32 Linnebacher, M., et al. "Frameshift Peptide-Derived T-Cell Epitopes: A Source of Novel Tumor-Specific Antigens." *International Journal of Cancer*. Journal International Du Cancer, vol. 93, no. 1, July 2001, pp. 6-11.

33 Maby, Pauline, et al. "Correlation between Density of CD8+ T-Cell Infiltrate in Microsatellite Unstable Colorectal Cancers and Frameshift Mutations: A Rationale for Personalized Immunotherapy." Cancer Research, vol. 75, no. 17, September 2015, pp. 3446-55.

34 Saeterdal, I., et al. "A TGF betaRII Frameshift-Mutation-Derived CTL Epitope Recognised by HLA-A2-Restricted CD8+ T Cells." Cancer Immunology, Immunotherapy: CII, vol. 50, no. 9, November 2001, pp. 469-76.

35 Turajlic, Samra, et al. "Insertion-and-Deletion-Derived Tumour-Specific Neoantigens and the Immunogenic Phenotype: A Pan-Cancer Analysis." The Lancet Oncology, vol. 18, no. 8, August 2017, pp. 1009-21.

36 Williams, David S., et al. "Nonsense Mediated Decay Resistant Mutations Are a Source of Expressed Mutant Proteins in Colon Cancer Cell Lines with Microsatellite Instability." PloS One, vol. 5, no. 12, December 2010, p. e16012.

The invention claimed is:

1. A vaccine or collection of vaccines for treating kidney cancer comprising:

(i) a peptide, or a collection of tiled peptides, having the amino acid sequence of SEQ ID NO: 1, or a fragment comprising at least 10 consecutive amino acids of SEQ ID NO: 1, or one or more nucleic acids encoding said peptide or collection of tiled peptides, wherein said peptide is a major histocompatibility complex class I (MHC-class I) binding peptide;

a peptide, or a collection of tiled peptides, having the amino acid sequence of SEQ ID NO: 3, or one or more nucleic acids encoding said peptide or collection of tiled peptides, wherein said peptide is a MHC-class I binding peptide; and a peptide, or a collection of tiled peptides, having the amino acid sequence of SEQ ID NO: 5, or a fragment comprising at least 10 consecutive amino acids of SEQ ID NO: 5 or one or more nucleic acids encoding said peptide or collection of tiled peptides, wherein said peptide is a major histocompatibility complex class I (MHC-class I) binding peptide; and wherein said vaccine or collection of vaccines further comprises a pharmaceutically acceptable excipient and an adjuvant or a therapeutic agent.

2. The vaccine or collection of vaccines of claim 1, wherein at least two of said peptides are linked.

3. The vaccine or collection of vaccines of 2, wherein said peptides are comprised within the same polypeptide.

4. The vaccine or collection of vaccines of claim 1, wherein the nucleic acid molecules encoding said peptides are comprised in one or more vectors.

5. The vaccine or collection of vaccines of claim 4, wherein said vector is a viral vector.

6. The vaccine or collection of vaccines of claim 1, wherein said vaccine or collection of vaccines comprises a therapeutic agent, wherein the therapeutic agent is a checkpoint inhibitor, a chemotherapeutic agent, or an antibody.

7. The vaccine or collection of vaccines of claim 1, wherein said vaccine or collection of vaccines comprises an immune-effective amount of adjuvant.

8. A method of treating an individual for kidney cancer or reducing the risk of developing said cancer, the method comprising administering to the individual in need thereof a vaccine selected from the vaccine or collection of vaccines of claim 1.

9. The vaccine or collection of vaccines of claim 1, wherein the nucleic acid molecules encoding said peptides are one or more RNA molecules.

10. The vaccine or collection of vaccines of claim 9, wherein the one or more RNA molecule is a mRNA.

11. The vaccine or collection of vaccines of claim 9, wherein the one or more RNA molecule is a RNA replicon.

* * * * *

SEQUENCE LISTING

<160> NUMBER OF SEQ ID NOS: 377

<210> SEQ ID NO 1
<211> LENGTH: 91
<212> TYPE: PRT
<213> ORGANISM: Artificial Sequence
<220> FEATURE:
<223> OTHER INFORMATION: pNOP42302 alt splice a

<400> SEQUENCE: 1

Thr Arg Ala Ser Pro Pro Arg Ser Ser Ser Ala Ile Ala Val Arg Ala
1 5 10 15

Ser Cys Cys Pro Tyr Gly Ser Thr Ser Thr Ala Ser Arg Ser Pro Thr
20 25 30

Gln Arg Cys Arg Leu Ala Arg Ala Ala Ala Ser Thr Ala Thr Glu Val
35 40 45

Thr Phe Gly Ser Ser Glu Met Gln Gly His Thr Met Gly Phe Trp Leu
50 55 60

Thr Lys Leu Asn Tyr Leu Cys His Leu Ser Met Leu Thr Asp Ser Leu
65 70 75 80

Phe Leu Pro Ile Ser His Cys Gln Cys Ile Leu
85 90

<210> SEQ ID NO 2
<211> LENGTH: 31
<212> TYPE: PRT
<213> ORGANISM: Artificial Sequence
<220> FEATURE:
<223> OTHER INFORMATION: pNOP279502

<400> SEQUENCE: 2

Ser Ser Leu Arg Ile Thr Gly Asp Trp Thr Ser Ser Gly Arg Ser Thr
1 5 10 15

Lys Ile Trp Lys Thr Thr Gln Met Cys Arg Lys Thr Trp Ser Gly
20 25 30

<210> SEQ ID NO 3
<211> LENGTH: 105
<212> TYPE: PRT
<213> ORGANISM: Artificial Sequence
<220> FEATURE:
<223> OTHER INFORMATION: pNOP29645 alt splice b

<400> SEQUENCE: 3

Arg Arg Arg Arg Gly Gly Val Gly Arg Arg Gly Val Arg Pro Gly Arg
1 5 10 15

Val Arg Pro Gly Gly Thr Gly Arg Arg Gly Gly Asp Gly Gly Arg Ala
20 25 30

Ala Ala Ala Arg Ala Ala Leu Gly Glu Leu Ala Arg Ala Leu Pro Gly
35 40 45

His Leu Leu Gln Ser Gln Ser Ala Arg Arg Ala Ala Arg Met Ala Gln
50 55 60

Leu Arg Arg Arg Ala Ala Ala Leu Pro Asn Ala Ala Ala Trp His Gly
65 70 75 80

Pro Pro His Pro Gln Leu Pro Ser Val Tyr Ser Glu Arg Ala Met Pro
85 90 95

Pro Gly Cys Pro Glu Pro Ser Gln Ala
100 105

<210> SEQ ID NO 4
<211> LENGTH: 104
<212> TYPE: PRT
<213> ORGANISM: Artificial Sequence
<220> FEATURE:
<223> OTHER INFORMATION: pNOP30388 alt splice b

<400> SEQUENCE: 4

Arg Arg Arg Arg Gly Gly Val Gly Arg Arg Gly Val Arg Pro Gly Arg
1 5 10 15

Val Arg Pro Gly Gly Thr Gly Arg Arg Gly Gly Asp Gly Gly Arg Ala
20 25 30

Ala Ala Ala Arg Ala Ala Leu Gly Glu Leu Ala Arg Ala Leu Pro Gly
35 40 45

His Leu Leu Gln Ser Gln Ser Ala Arg Arg Ala Ala Arg Met Ala Gln
50 55 60

Leu Arg Arg Arg Ala Ala Ala Leu Pro Asn Ala Ala Ala Trp His Gly
65 70 75 80

Pro Pro His Pro Gln Leu Pro Arg Ser Pro Leu Ala Leu Gln Arg Cys
85 90 95

Arg Asp Thr Arg Trp Ala Ser Gly
100

<210> SEQ ID NO 5
<211> LENGTH: 50
<212> TYPE: PRT
<213> ORGANISM: Artificial Sequence
<220> FEATURE:
<223> OTHER INFORMATION: pNOP140916 alt splice a

<400> SEQUENCE: 5

Thr Arg Ala Ser Pro Pro Arg Ser Ser Ser Ala Ile Ala Val Arg Ala
1 5 10 15

Ser Cys Cys Pro Tyr Gly Ser Thr Ser Thr Ala Ser Arg Ser Pro Thr
20 25 30

Gln Arg Cys Arg Leu Ala Arg Ala Ala Ala Ser Thr Ala Thr Glu Cys
35 40 45

Ile Leu
50

<210> SEQ ID NO 6
<211> LENGTH: 81
<212> TYPE: PRT
<213> ORGANISM: Artificial Sequence
<220> FEATURE:
<223> OTHER INFORMATION: pNOP54515

<400> SEQUENCE: 6

Glu Leu Gln Glu Thr Gly His Arg Gln Val Ala Leu Arg Arg Ser Gly
1 5 10 15

Arg Pro Pro Lys Cys Ala Glu Arg Pro Gly Ala Ala Asp Thr Gly Ala
20 25 30

```
His Cys Thr Ser Thr Asp Gly Arg Leu Lys Ile Ser Val Glu Thr Tyr
        35                  40                  45

Thr Val Ser Ser Gln Leu Leu Met Val Leu Met Ser Leu Asp Leu Asp
    50                  55                  60

Thr Gly Leu Val Pro Ser Leu Val Ser Lys Cys Leu Ile Leu Arg Val
65                  70                  75                  80

Lys


<210> SEQ ID NO 7
<211> LENGTH: 29
<212> TYPE: PRT
<213> ORGANISM: Artificial Sequence
<220> FEATURE:
<223> OTHER INFORMATION: pNOP301515

<400> SEQUENCE: 7

Arg Thr Ala Tyr Phe Cys Gln Tyr His Thr Ala Ser Val Tyr Ser Glu
1               5                   10                  15

Arg Ala Met Pro Pro Gly Cys Pro Glu Pro Ser Gln Ala
            20                  25


<210> SEQ ID NO 8
<211> LENGTH: 10
<212> TYPE: PRT
<213> ORGANISM: Artificial Sequence
<220> FEATURE:
<223> OTHER INFORMATION: pNOP700435

<400> SEQUENCE: 8

Lys Ser Asp Ala Ser Arg Leu Ser Gly Ala
1               5                   10


<210> SEQ ID NO 9
<211> LENGTH: 154
<212> TYPE: PRT
<213> ORGANISM: Artificial Sequence
<220> FEATURE:
<223> OTHER INFORMATION: pNOP10058 alt splice b

<400> SEQUENCE: 9

Arg Arg Arg Arg Gly Gly Val Gly Arg Arg Gly Val Arg Pro Gly Arg
1               5                   10                  15

Val Arg Pro Gly Gly Thr Gly Arg Arg Gly Gly Asp Gly Gly Arg Ala
            20                  25                  30

Ala Ala Ala Arg Ala Ala Leu Gly Glu Leu Ala Arg Ala Leu Pro Gly
        35                  40                  45

His Leu Leu Gln Ser Gln Ser Ala Arg Arg Ala Ala Arg Met Ala Gln
    50                  55                  60

Leu Arg Arg Arg Ala Ala Ala Leu Pro Asn Ala Ala Ala Trp His Gly
65                  70                  75                  80

Pro Pro His Pro Gln Leu Pro Ser Pro His Asp Ser Ser Gly Pro Val
                85                  90                  95

Leu Arg Ser Pro Cys Pro Arg Gly Glu His Ile Pro Pro Gly Glu Thr
            100                 105                 110

Asp Arg Cys Lys Asp Arg Asn Lys Pro Gly Ser Cys Trp Arg Arg Lys
        115                 120                 125

Ser Arg Pro Cys Val Ala Trp Glu Ile Asp Leu Pro Ala Cys Trp Glu
    130                 135                 140

Met Glu Gly Leu Arg Leu Cys Gly Phe Ser
145                 150
```

<210> SEQ ID NO 10
<211> LENGTH: 52
<212> TYPE: PRT
<213> ORGANISM: Artificial Sequence
<220> FEATURE:
<223> OTHER INFORMATION: pNOP128393

<400> SEQUENCE: 10

```
Ala Arg Arg Arg Gln Ala Ser Lys Ser Thr Ala Leu Lys Lys Thr Ala
1               5                   10                  15

Gly Arg Ser Arg Ala Pro Arg Ser Pro Ala Arg Lys Ser Pro Ala Arg
            20                  25                  30

Arg Asn Trp Ala Pro Arg Arg Arg Trp Arg Pro Gly Gly Arg Gly Pro
        35                  40                  45

Cys Cys Ala Arg
    50
```

<210> SEQ ID NO 11
<211> LENGTH: 49
<212> TYPE: PRT
<213> ORGANISM: Artificial Sequence
<220> FEATURE:
<223> OTHER INFORMATION: pNOP145743 alt splice a

<400> SEQUENCE: 11

```
Thr Arg Ala Ser Pro Pro Arg Ser Ser Ser Ala Ile Ala Val Arg Ala
1               5                   10                  15

Ser Cys Cys Pro Tyr Gly Ser Thr Ser Thr Ala Ser Arg Ser Pro Thr
            20                  25                  30

Gln Arg Cys Arg Leu Ala Arg Ala Ala Ala Ser Thr Ala Thr Glu Ser
        35                  40                  45

Ser
```

<210> SEQ ID NO 12
<211> LENGTH: 32
<212> TYPE: PRT
<213> ORGANISM: Artificial Sequence
<220> FEATURE:
<223> OTHER INFORMATION: pNOP265165

<400> SEQUENCE: 12

```
Leu Thr Cys Leu Leu Gly Asp Gly Gly Val Ala Val Val Trp Phe Gln
1               5                   10                  15

Leu Arg Ser Thr Ser Arg Arg Arg Lys Arg Ala Gly Trp Ser Arg Asn
            20                  25                  30
```

<210> SEQ ID NO 13
<211> LENGTH: 25
<212> TYPE: PRT
<213> ORGANISM: Artificial Sequence
<220> FEATURE:
<223> OTHER INFORMATION: pNOP352529

<400> SEQUENCE: 13

```
Asn Ala Pro Glu Gly Gly Glu Leu Gly Arg Gly Arg Gly Arg Arg Gly
1               5                   10                  15

Gly Gly Arg Arg Arg Arg Val Arg Pro
            20                  25
```

<210> SEQ ID NO 14
<211> LENGTH: 24

```
<212> TYPE: PRT
<213> ORGANISM: Artificial Sequence
<220> FEATURE:
<223> OTHER INFORMATION: pNOP369816

<400> SEQUENCE: 14

Gln Met Gln Arg Gln Glu Gln Ala Arg Val Met Leu Ala Pro Glu Glu
1               5                   10                  15

Pro Thr Val Cys Gly Val Gly Asn
            20


<210> SEQ ID NO 15
<211> LENGTH: 18
<212> TYPE: PRT
<213> ORGANISM: Artificial Sequence
<220> FEATURE:
<223> OTHER INFORMATION: pNOP472058

<400> SEQUENCE: 15

Gly Ala Leu Pro Gly Glu Gly Arg Glu Gln Asp Gly Val Gly Thr Ser
1               5                   10                  15

Gln Pro


<210> SEQ ID NO 16
<211> LENGTH: 16
<212> TYPE: PRT
<213> ORGANISM: Artificial Sequence
<220> FEATURE:
<223> OTHER INFORMATION: pNOP519384

<400> SEQUENCE: 16

His Arg Ser Ala Leu His Ile Asn Gly Trp Glu Ile Glu Asp Phe Cys
1               5                   10                  15


<210> SEQ ID NO 17
<211> LENGTH: 13
<212> TYPE: PRT
<213> ORGANISM: Artificial Sequence
<220> FEATURE:
<223> OTHER INFORMATION: pNOP614216

<400> SEQUENCE: 17

Ser Leu Pro Ser Trp Arg Thr His Ser Ser Trp Gly Asp
1               5                   10


<210> SEQ ID NO 18
<211> LENGTH: 12
<212> TYPE: PRT
<213> ORGANISM: Artificial Sequence
<220> FEATURE:
<223> OTHER INFORMATION: pNOP622782

<400> SEQUENCE: 18

Cys Pro Gly Gly Arg Arg Thr Gly Thr Arg Pro Arg
1               5                   10


<210> SEQ ID NO 19
<211> LENGTH: 90
<212> TYPE: PRT
<213> ORGANISM: Artificial Sequence
<220> FEATURE:
<223> OTHER INFORMATION: pNOP42654

<400> SEQUENCE: 19

Glu Thr Ser Ala Ser Cys Asn Ile Gln Ala Thr Ala Gly Tyr Tyr His
1               5                   10                  15
```

Ser Ser Ser Ile Ser Thr Tyr Ser Cys Ser Thr Ile Thr Ser Ser Asp
20 25 30

Ser Arg Ile Asn Asn Cys Arg Leu Thr Ala Leu Ile Ser Ala Ser Thr
35 40 45

Ala Ser Thr Cys Pro Ser His Asn Thr Leu Ile Thr Ser Thr Ser Asn
50 55 60

Arg Ala Ser Gly Leu Ala Thr Tyr Thr Asn Asn Ser Ser Asn Gly Ser
65 70 75 80

Thr Ser Thr Leu Thr Ser Arg Cys Ser Ser
85 90

<210> SEQ ID NO 20
<211> LENGTH: 96
<212> TYPE: PRT
<213> ORGANISM: Artificial Sequence
<220> FEATURE:
<223> OTHER INFORMATION: pNOP36509

<400> SEQUENCE: 20

Cys Leu Gly Phe Lys Pro Thr Val Cys Gln Cys Thr Ala Ala Val Leu
1 5 10 15

Ser Cys Thr Val Ser Ser Asn His Ile Leu Ser Arg Thr Asp Met Ser
20 25 30

Asn Ser Leu Trp Cys Asp Ile Thr Leu Phe Thr Asp Asn Ser Thr Asn
35 40 45

Cys Thr Glu Leu Cys Pro Ala Lys Ser Ser Val Tyr Pro Gly Ala Thr
50 55 60

Asp Phe His Ser Ser Ser Thr Arg Ser Gly Gly Thr Ala Ser Arg Ser
65 70 75 80

Ser Asp Tyr Asn Ser Cys Thr Arg Ala Ala Ser Ala Leu Ala Ala Ile
85 90 95

<210> SEQ ID NO 21
<211> LENGTH: 53
<212> TYPE: PRT
<213> ORGANISM: Artificial Sequence
<220> FEATURE:
<223> OTHER INFORMATION: pNOP127387

<400> SEQUENCE: 21

Ser Leu Gly Ser Ala Ala Pro Leu Ser Ser Gln Thr Lys Asn His Cys
1 5 10 15

Leu Thr Ser Gln Leu Glu Asp Ser Ser Arg Ser Arg Arg Glu Asp Leu
20 25 30

Leu Leu Pro Cys Asp His Lys Ala Asp Ser Val Gly Ser Ser Tyr Leu
35 40 45

Gly Lys Pro Arg Arg
50

<210> SEQ ID NO 22
<211> LENGTH: 44
<212> TYPE: PRT
<213> ORGANISM: Artificial Sequence
<220> FEATURE:
<223> OTHER INFORMATION: pNOP169956

<400> SEQUENCE: 22

Lys Pro Lys Tyr Leu Leu Gly Ser Lys Lys Ser Cys Gln Phe Ile Leu
1 5 10 15

Leu Ile Leu Lys Met Ser Gln Ile Ser Leu Gly Asn Arg Pro Leu Ser
            20                  25                  30

Lys Thr Gly Gln Ile Val Asp Trp Glu Lys Gln Asn
        35                  40

<210> SEQ ID NO 23
<211> LENGTH: 60
<212> TYPE: PRT
<213> ORGANISM: Artificial Sequence
<220> FEATURE:
<223> OTHER INFORMATION: pNOP102433

<400> SEQUENCE: 23

Tyr Thr Lys Thr Pro Ala Leu Leu Ser Cys Gln Cys Arg Pro Pro Ala
1               5                   10                  15

Gln Phe Arg Asp Arg Ile Ile Val Phe Gly Ile Gln Thr Asn Ser Leu
            20                  25                  30

Ser Val Tyr Ser Ser Ser Thr Leu Leu His Ser Leu Lys Gln Pro Tyr
        35                  40                  45

Ile Ile Lys Asp Arg His Val Gln Gln Ser Met Val
    50                  55                  60

<210> SEQ ID NO 24
<211> LENGTH: 45
<212> TYPE: PRT
<213> ORGANISM: Artificial Sequence
<220> FEATURE:
<223> OTHER INFORMATION: pNOP163115

<400> SEQUENCE: 24

Phe Ile Ser Thr Tyr Trp Glu Phe Arg Tyr Cys Phe Ile Ser Ser Glu
1               5                   10                  15

Ser Ser Thr Arg Asn Lys Gly Gly Gln Ser Asn Ser Leu Glu Met Arg
            20                  25                  30

Arg Glu His Ile Ser Ser Ser Gly Cys Ser Ala Lys Glu
        35                  40                  45

<210> SEQ ID NO 25
<211> LENGTH: 43
<212> TYPE: PRT
<213> ORGANISM: Artificial Sequence
<220> FEATURE:
<223> OTHER INFORMATION: pNOP175535

<400> SEQUENCE: 25

His His Leu Ile His Arg Gln Leu His Gln Leu Tyr Arg Val Met Pro
1               5                   10                  15

Ser Gln Val Phe Ser Ile Ser Arg Gly Asn Arg Phe Ser Gln Leu Ile
            20                  25                  30

His Lys Glu Trp Trp Tyr Ser Gln Pro Gln Gln
        35                  40

<210> SEQ ID NO 26
<211> LENGTH: 38
<212> TYPE: PRT
<213> ORGANISM: Artificial Sequence
<220> FEATURE:
<223> OTHER INFORMATION: pNOP212518

<400> SEQUENCE: 26

Gln Ile Ile Ser Trp Ile Cys Arg Pro Pro Leu Leu Pro Asn Gln Lys
1               5                   10                  15

```
Pro Leu Ser Tyr Leu Pro Thr Gly Arg Gln Leu Glu Ile Gln Lys Gly
            20                  25                  30

Arg Phe Ile Thr Thr Met
        35
```

<210> SEQ ID NO 27
<211> LENGTH: 35
<212> TYPE: PRT
<213> ORGANISM: Artificial Sequence
<220> FEATURE:
<223> OTHER INFORMATION: pNOP238211

<400> SEQUENCE: 27

```
Arg Leu Trp Asn Thr Cys Pro Phe Leu Leu Lys Ile Cys Trp Arg Lys
1               5                   10                  15

Ala Lys Tyr Phe Gln Leu Phe Asn Ala Gly Leu Arg Leu Arg Leu Leu
            20                  25                  30

Ser Leu Arg
        35
```

<210> SEQ ID NO 28
<211> LENGTH: 34
<212> TYPE: PRT
<213> ORGANISM: Artificial Sequence
<220> FEATURE:
<223> OTHER INFORMATION: pNOP244560

<400> SEQUENCE: 28

```
Lys Asn Leu Leu Met Lys Lys His His Pro Lys Met Lys Arg Arg Val
1               5                   10                  15

Cys Leu Met Trp Arg Val Lys Gly Ala Lys Asn Ser Gln Ile Lys Gln
            20                  25                  30

Trp Ile
```

<210> SEQ ID NO 29
<211> LENGTH: 28
<212> TYPE: PRT
<213> ORGANISM: Artificial Sequence
<220> FEATURE:
<223> OTHER INFORMATION: pNOP310885

<400> SEQUENCE: 29

```
Met Ser Lys Gln Ile Phe Pro Gln Lys Lys Lys Ile Pro Ile Leu Gly
1               5                   10                  15

Arg Met Lys Lys Phe Gln Ile Val Leu Arg Leu Val
            20                  25
```

<210> SEQ ID NO 30
<211> LENGTH: 16
<212> TYPE: PRT
<213> ORGANISM: Artificial Sequence
<220> FEATURE:
<223> OTHER INFORMATION: pNOP516328

<400> SEQUENCE: 30

```
Glu Val His Ala Glu Val Trp Gly Cys Leu Gln Thr Gln Arg Gly His
1               5                   10                  15
```

<210> SEQ ID NO 31
<211> LENGTH: 63
<212> TYPE: PRT
<213> ORGANISM: Artificial Sequence
<220> FEATURE:
<223> OTHER INFORMATION: pNOP91847

<400> SEQUENCE: 31

Leu Asp Arg Asn Tyr Pro Leu Trp Ser Lys His Ala Cys Phe His Gln
1 5 10 15

Met Asp Phe Arg Ile Leu Val Gly Ala Lys Lys Lys Thr Trp Met Ile
20 25 30

Pro Ala Cys Cys Ile Arg Ser Gln Lys Ala His Leu Glu Lys Gln Asn
35 40 45

Leu Trp Cys His His Thr Lys Ile Asn Ser Cys Leu Cys Gln Leu
50 55 60

<210> SEQ ID NO 32
<211> LENGTH: 52
<212> TYPE: PRT
<213> ORGANISM: Artificial Sequence
<220> FEATURE:
<223> OTHER INFORMATION: pNOP129693

<400> SEQUENCE: 32

Ile Arg Val Thr Val Gly Pro Gly Trp Glu Asp Gly Trp Ser Gly Lys
1 5 10 15

Thr Asp Ser Arg Glu Arg Lys Ser Cys Gly Pro Phe Cys Pro Thr Pro
20 25 30

Val Ser Thr Val Leu Leu Met Ile His His Pro Gly Glu Phe Asn Pro
35 40 45

Ala Asp Val Asn
50

<210> SEQ ID NO 33
<211> LENGTH: 50
<212> TYPE: PRT
<213> ORGANISM: Artificial Sequence
<220> FEATURE:
<223> OTHER INFORMATION: pNOP140653

<400> SEQUENCE: 33

Ser Arg Glu Arg His Gln Cys Pro Gln Val Gln His Trp Leu Gly Pro
1 5 10 15

Pro Val Ser Trp Met Thr Ser Gly Thr His Ser Asp Gly Arg Asn Val
20 25 30

Pro Ser Lys Gly Lys Cys His Val Thr Leu Ile Leu Leu Lys Lys Met
35 40 45

Phe Ile
50

<210> SEQ ID NO 34
<211> LENGTH: 48
<212> TYPE: PRT
<213> ORGANISM: Artificial Sequence
<220> FEATURE:
<223> OTHER INFORMATION: pNOP149559

<400> SEQUENCE: 34

Gln Ile Thr Gln Asn Leu His Val Lys Asn Ile Ser Arg Ala Ser Val
1 5 10 15

Ala Leu Val Gln Leu Leu Leu Ile Ile Leu Met Ile Tyr Ile Asn Leu
20 25 30

Leu Gly Val Gln Val Leu Leu His Leu Phe Arg Val Phe His Gln Glu
35 40 45

<210> SEQ ID NO 35
<211> LENGTH: 48
<212> TYPE: PRT
<213> ORGANISM: Artificial Sequence
<220> FEATURE:
<223> OTHER INFORMATION: pNOP151102

<400> SEQUENCE: 35

Val Val Thr Phe Leu Ile Gln Glu Arg Asp Leu Leu Pro Gly Arg Thr
1 5 10 15

Gly Val Ile Met Gly Tyr Leu Gly Asn Val Cys Lys Arg Leu Lys Lys
20 25 30

Lys Gly Ile Pro Tyr Cys Leu Lys Glu Glu Glu Asp Gln Lys Ser Leu
35 40 45

<210> SEQ ID NO 36
<211> LENGTH: 45
<212> TYPE: PRT
<213> ORGANISM: Artificial Sequence
<220> FEATURE:
<223> OTHER INFORMATION: pNOP164732

<400> SEQUENCE: 36

Leu Ser Val Pro Glu Ile Trp Lys Arg Ser Pro Glu Met Phe Leu Arg
1 5 10 15

Ile Ser Gln Leu Pro Gly Leu Pro Gly Arg Arg Lys Gln Ser Gln His
20 25 30

Gln Ser Ser Arg Arg Glu Asn Glu Glu Gly Thr Ile Ser
35 40 45

<210> SEQ ID NO 37
<211> LENGTH: 44
<212> TYPE: PRT
<213> ORGANISM: Artificial Sequence
<220> FEATURE:
<223> OTHER INFORMATION: pNOP172893 alt splice a

<400> SEQUENCE: 37

Thr Val Ser Glu Lys Thr Ala Cys Arg Cys Gly Ser His Thr His Arg
1 5 10 15

Lys Glu Arg Leu Gly Leu Glu Ser Cys Gln Arg Pro Ser Phe Glu His
20 25 30

Leu Cys Pro Arg Ile Leu Trp Arg Gly Thr Arg Ser
35 40

<210> SEQ ID NO 38
<211> LENGTH: 126
<212> TYPE: PRT
<213> ORGANISM: Artificial Sequence
<220> FEATURE:
<223> OTHER INFORMATION: pNOP18146

<400> SEQUENCE: 38

Arg Arg Tyr Ile Glu Phe Gln Arg Lys Val Lys Leu Lys Arg Lys Thr
1 5 10 15

Gln Gln Leu Asn Glu Glu Gly Met Leu Leu Ala Ser Glu Ile Lys His
20 25 30

Leu Pro Arg Arg Leu Leu Ile Gly Gln Glu Arg Glu Thr Gln Thr Ser
35 40 45

Lys Leu Lys Ile Lys Arg Lys Gly Asn Glu Glu Ala Pro Ser His His
50 55 60

Pro Leu Leu Pro Met Ser Gly Glu Gln Lys Gly Gln Met Thr Asp Met

```
65                  70                  75                  80

Ile His Gln Leu Leu Lys Arg Lys Tyr Glu Leu Lys Thr Ala Ile Asn
                85                  90                  95

Phe Leu Gln Arg Asn Ala Gly Ser Cys Leu Ser Lys Arg Trp Leu Asn
            100                 105                 110

Gly Arg Leu Arg Asn Asn Ser Asn Arg Cys Arg Thr Trp Glu
        115                 120                 125


<210> SEQ ID NO 39
<211> LENGTH: 41
<212> TYPE: PRT
<213> ORGANISM: Artificial Sequence
<220> FEATURE:
<223> OTHER INFORMATION: pNOP189678

<400> SEQUENCE: 39

Asn Phe Gly Ala Glu Thr Tyr Leu Ser Gly Thr His Thr Glu His Thr
1               5                   10                  15

Leu Thr Val Leu Pro Glu Val Leu Ser Gly Thr Ser Trp Ala Val Phe
            20                  25                  30

Val Val Asp Leu Asp Gly Arg Ala Arg
        35                  40


<210> SEQ ID NO 40
<211> LENGTH: 41
<212> TYPE: PRT
<213> ORGANISM: Artificial Sequence
<220> FEATURE:
<223> OTHER INFORMATION: pNOP191028

<400> SEQUENCE: 40

Arg Leu Thr Ile Ser Ser Arg Asp Met Glu Lys Lys Pro Arg Asn Val
1               5                   10                  15

Ser Ala Asp Gln Pro Ile Ala Gly Val Thr Trp Glu Glu Lys Thr Glu
            20                  25                  30

Ser Ala Ser Glu Gln Gln Glu Gly Lys
        35                  40


<210> SEQ ID NO 41
<211> LENGTH: 40
<212> TYPE: PRT
<213> ORGANISM: Artificial Sequence
<220> FEATURE:
<223> OTHER INFORMATION: pNOP197618

<400> SEQUENCE: 41

Gln Met Ile Val Lys Lys Arg Arg Ile Gly Ile Asn Arg Met Asp Pro
1               5                   10                  15

Ile Phe Gln Thr Ser Pro Ile Asn Phe Phe Tyr Pro Phe Arg Lys Thr
            20                  25                  30

Arg Gly Gln Cys Lys His Leu Lys
        35                  40


<210> SEQ ID NO 42
<211> LENGTH: 40
<212> TYPE: PRT
<213> ORGANISM: Artificial Sequence
<220> FEATURE:
<223> OTHER INFORMATION: pNOP198489

<400> SEQUENCE: 42

Ser Cys Ser Ala Leu Gly Gly Thr Phe Tyr Arg Thr Pro Phe Cys Pro
```

```
1               5                   10                  15

Ser Thr Ser Thr Ser Gly Ala Thr Cys Gly Ser Ser Cys Gly Ser Phe
            20                  25                  30

Gln Phe Pro Val Cys Gly Pro Glu
        35                  40


<210> SEQ ID NO 43
<211> LENGTH: 39
<212> TYPE: PRT
<213> ORGANISM: Artificial Sequence
<220> FEATURE:
<223> OTHER INFORMATION: pNOP201541 alt splice b

<400> SEQUENCE: 43

Glu Leu Pro Lys Thr Phe Leu Gln Lys Lys Pro Arg Asn Val Ser Ala
1               5                   10                  15

Asp Gln Pro Ile Ala Gly Val Thr Trp Glu Glu Lys Thr Glu Ser Ala
            20                  25                  30

Ser Glu Gln Gln Glu Gly Lys
        35


<210> SEQ ID NO 44
<211> LENGTH: 39
<212> TYPE: PRT
<213> ORGANISM: Artificial Sequence
<220> FEATURE:
<223> OTHER INFORMATION: pNOP204603

<400> SEQUENCE: 44

Pro Leu Pro Pro Thr Pro Ser Tyr Cys Trp Leu Leu Ser Ala Leu His
1               5                   10                  15

Leu Ile Phe Arg Lys Leu Ser Phe Leu Arg Ala Gly Met Leu Leu Tyr
            20                  25                  30

Ser Asn Leu Val Ser Ser Pro
        35


<210> SEQ ID NO 45
<211> LENGTH: 38
<212> TYPE: PRT
<213> ORGANISM: Artificial Sequence
<220> FEATURE:
<223> OTHER INFORMATION: pNOP208142

<400> SEQUENCE: 45

Ala Val Lys Lys Gln Val Leu Arg Arg Asn Pro His Asn Leu Lys Ala
1               5                   10                  15

Ser Phe Leu Val Gln Asn Leu Met Lys Ile Leu Tyr Gly Leu Leu Gln
            20                  25                  30

Val Lys Asp His Met Ile
        35


<210> SEQ ID NO 46
<211> LENGTH: 119
<212> TYPE: PRT
<213> ORGANISM: Artificial Sequence
<220> FEATURE:
<223> OTHER INFORMATION: pNOP21038

<400> SEQUENCE: 46

Gly Asn Leu His Asp Leu Lys Gln Thr Glu Met Ile Asn Ile Leu Ala
1               5                   10                  15

Ile Gln Asn Leu Lys Glu Ile Leu Gly Met Tyr Leu Pro Asp Val Asp
```

```
            20                  25                  30

Gln Lys Glu Ser Asp Gly Gly Ala Asp Leu Thr Leu Gly Leu Arg Glu
        35                  40                  45

Ala Leu Glu Leu Ile Tyr Pro Ile Pro Gly Gln Asn Asp Leu Ile Ile
    50                  55                  60

Met Thr Leu Ile Val Ala Thr Ile Gly Ala Pro Leu Ile Glu Arg Gly
65                  70                  75                  80

Arg Ala Ile Leu Gly His Thr Gln Ile Thr Glu His Glu Arg Val Leu
                85                  90                  95

Thr Gln Lys Lys Ser Ile Arg Arg His Thr Gln Gly Val Pro His Leu
            100                 105                 110

Ile Pro Leu Leu Thr Glu Thr
        115


<210> SEQ ID NO 47
<211> LENGTH: 38
<212> TYPE: PRT
<213> ORGANISM: Artificial Sequence
<220> FEATURE:
<223> OTHER INFORMATION: pNOP213911

<400> SEQUENCE: 47

Ser Gln Gly Arg Leu Ser Gly Ile Leu Leu Leu Gly Lys Ala Gln Glu
1               5                   10                  15

Met Met Pro Ala Leu Ser Met Lys Leu Arg Trp Thr Trp Glu Leu Gln
            20                  25                  30

His Met Met Lys Thr Pro
        35


<210> SEQ ID NO 48
<211> LENGTH: 37
<212> TYPE: PRT
<213> ORGANISM: Artificial Sequence
<220> FEATURE:
<223> OTHER INFORMATION: pNOP219165

<400> SEQUENCE: 48

Leu Asn Val Leu Leu Gly Val Gln Met Gly Ile Ile Val Pro Ile Asp
1               5                   10                  15

Gly Phe Arg Glu Asn Ser Met Gln Met Trp Lys Ser Tyr Ser Gln Lys
            20                  25                  30

Arg Lys Ala Gly Ala
        35


<210> SEQ ID NO 49
<211> LENGTH: 35
<212> TYPE: PRT
<213> ORGANISM: Artificial Sequence
<220> FEATURE:
<223> OTHER INFORMATION: pNOP237811

<400> SEQUENCE: 49

Gln Tyr Ser Lys Lys Pro Ser Pro Val Cys Cys Gly Cys Ala Lys Glu
1               5                   10                  15

Phe Tyr Phe Ala His Gly Arg Asn Lys Ser Leu Phe Phe Ser Glu Gln
            20                  25                  30

Ser Lys Leu
        35


<210> SEQ ID NO 50
```

<211> LENGTH: 34
<212> TYPE: PRT
<213> ORGANISM: Artificial Sequence
<220> FEATURE:
<223> OTHER INFORMATION: pNOP244795

<400> SEQUENCE: 50

Lys Trp Lys Leu Val Ile Pro Tyr Leu Leu Gln Lys Asn Leu Pro His
1               5                   10                  15

Gln Ser Gln Gly Trp Asn Trp Ala Lys Phe Ile Leu Arg Asn Ile Cys
            20                  25                  30

Phe Met

<210> SEQ ID NO 51
<211> LENGTH: 32
<212> TYPE: PRT
<213> ORGANISM: Artificial Sequence
<220> FEATURE:
<223> OTHER INFORMATION: pNOP261712

<400> SEQUENCE: 51

Asp Thr Thr Cys Gly Trp Leu Ala Leu Ile Arg Arg Ala Gln Lys Leu
1               5                   10                  15

Arg Leu Gly Leu Leu Ser Arg Lys Ala Phe Tyr His Val Ser Ala Thr
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: pNOP267031

<400> SEQUENCE: 52

Gln Val Lys Pro Val Leu Lys Leu Ile Ser Phe Ser Phe Ile Lys Glu
1               5                   10                  15

Gln Arg Arg Ile Arg Lys Phe Leu Leu His Ser Pro Val Glu Asn Lys
            20                  25                  30

<210> SEQ ID NO 53
<211> LENGTH: 31
<212> TYPE: PRT
<213> ORGANISM: Artificial Sequence
<220> FEATURE:
<223> OTHER INFORMATION: pNOP272114

<400> SEQUENCE: 53

Glu Gly Phe Lys His Thr Leu Thr Val Leu Pro Glu Val Leu Ser Gly
1               5                   10                  15

Thr Ser Trp Ala Val Phe Val Val Asp Leu Asp Gly Arg Ala Arg
            20                  25                  30

<210> SEQ ID NO 54
<211> LENGTH: 108
<212> TYPE: PRT
<213> ORGANISM: Artificial Sequence
<220> FEATURE:
<223> OTHER INFORMATION: pNOP27510 alt splice c

<400> SEQUENCE: 54

Ser Ser Cys Ser Arg Ser Arg Leu Arg Arg Trp Gly Ile Ser Thr Thr
1               5                   10                  15

Arg Ser Thr Arg Pro Leu Lys Lys Lys Lys Met Arg Gln Arg Leu Lys
            20                  25                  30

```
Met Cys Arg Lys Gln Val Ser Ser Lys Asp Gln Cys Ser Lys Val Leu
        35                  40                  45

Leu Leu Val Asp Phe Cys Pro Lys Ala Pro Lys Gln Lys Leu Ile Trp
    50                  55                  60

Lys Asn Arg Asp Asp Arg Arg Cys His Ser Ala Ser Ala Leu Gln Arg
65                  70                  75                  80

Lys Leu Cys Arg Ile Gly Phe Ser Leu His Leu Ala Met Lys Ser Lys
                85                  90                  95

Val Ile Leu Gln Thr Leu Gln Leu Tyr Leu Phe Arg
            100                 105


<210> SEQ ID NO 55
<211> LENGTH: 31
<212> TYPE: PRT
<213> ORGANISM: Artificial Sequence
<220> FEATURE:
<223> OTHER INFORMATION: pNOP277421

<400> SEQUENCE: 55

Gln Lys Glu Arg Arg Ile Asn Leu Ile Glu Ile Leu Ser Glu Cys Ser
1               5                   10                  15

Val Ser Val His Leu Phe Leu Lys Met Lys Glu Leu Lys Val Lys
            20                  25                  30


<210> SEQ ID NO 56
<211> LENGTH: 30
<212> TYPE: PRT
<213> ORGANISM: Artificial Sequence
<220> FEATURE:
<223> OTHER INFORMATION: pNOP292377

<400> SEQUENCE: 56

Tyr Asp Ser Ser His Glu Lys Pro Asp His Cys Leu Leu Leu His Leu
1               5                   10                  15

Ile Val Gly Phe Phe Leu Pro Tyr Thr Leu Tyr Ser Gly Ser
            20                  25                  30


<210> SEQ ID NO 57
<211> LENGTH: 28
<212> TYPE: PRT
<213> ORGANISM: Artificial Sequence
<220> FEATURE:
<223> OTHER INFORMATION: pNOP311275

<400> SEQUENCE: 57

Asn Pro Lys Met Asp Cys Glu Arg Thr Thr Glu Gly Trp Val Phe Tyr
1               5                   10                  15

His Gln Thr Gly Ser Phe Arg Leu Arg Val Asn Val
            20                  25


<210> SEQ ID NO 58
<211> LENGTH: 27
<212> TYPE: PRT
<213> ORGANISM: Artificial Sequence
<220> FEATURE:
<223> OTHER INFORMATION: pNOP329486

<400> SEQUENCE: 58

Thr Ser Lys Glu Lys Gln Arg Ser Ile Gln Lys Arg Asp Val Pro Val
1               5                   10                  15

His Arg Pro Val Pro Glu Pro Leu Pro Glu Thr
            20                  25
```

<210> SEQ ID NO 59
<211> LENGTH: 26
<212> TYPE: PRT
<213> ORGANISM: Artificial Sequence
<220> FEATURE:
<223> OTHER INFORMATION: pNOP331645

<400> SEQUENCE: 59

Ala Arg Gly Gly Ser Thr Gly Gly Ser Glu Thr Thr Ala Thr Asp Ala
1 5 10 15

Glu Pro Gly Asn Asp Ile Thr Thr Ala Leu
20 25

<210> SEQ ID NO 60
<211> LENGTH: 100
<212> TYPE: PRT
<213> ORGANISM: Artificial Sequence
<220> FEATURE:
<223> OTHER INFORMATION: pNOP33233

<400> SEQUENCE: 60

His His His Cys Pro Met Thr Leu Leu Val Ile Met Pro Arg Ile Ile
1 5 10 15

Pro Leu Leu Val Thr His Gln Val Ile Pro Cys Arg Pro Met Trp Ile
20 25 30

Pro Ala Thr Leu Met Leu Glu Arg Cys Ser Cys Pro His Pro Ala Trp
35 40 45

Thr Gln Cys Val Leu Leu Leu Leu Met Ile Met Leu Ser Pro Trp Trp
50 55 60

Asp Ile Leu Gln Asn Pro Phe Leu Pro Leu His Gln Tyr Gln Trp Cys
65 70 75 80

His Met Trp Gln Leu Leu Trp Lys Phe Pro Val Pro Ser Met Trp Pro
85 90 95

Arg Val Met Val
100

<210> SEQ ID NO 61
<211> LENGTH: 100
<212> TYPE: PRT
<213> ORGANISM: Artificial Sequence
<220> FEATURE:
<223> OTHER INFORMATION: pNOP33646

<400> SEQUENCE: 61

Ser Val Thr Val Val Val Met Pro Gln Lys Leu Cys Leu Gln Phe Met
1 5 10 15

Lys Ile Ile Leu Ala Leu Leu Lys Val Gln Met Met Lys Val Ile Gln
20 25 30

Lys Ile Gln Ile Arg Met Ile Ala Val Phe Gln Glu Thr Val Ser Ser
35 40 45

Leu Leu Trp Leu Cys Gln Arg Ile Leu Leu Cys Pro Trp Lys Lys Gln
50 55 60

Val Leu Val Leu Leu Gly Ala Val Lys Val Ile Asp Thr Ile Leu Thr
65 70 75 80

Ile Gly Lys Met Arg Asp Trp Ser Gln Gly Asp Ile Cys Met Arg Lys
85 90 95

Asn Leu Lys Val
100

<210> SEQ ID NO 62
<211> LENGTH: 26
<212> TYPE: PRT
<213> ORGANISM: Artificial Sequence
<220> FEATURE:
<223> OTHER INFORMATION: pNOP338557

<400> SEQUENCE: 62

```
Asn Thr Lys Pro Arg Ser Thr Leu Arg Ser Thr Cys Arg Ser Leu Gly
1               5                   10                  15

Leu Phe Thr Asn Pro Lys Arg Thr Leu Asn
            20                  25
```

<210> SEQ ID NO 63
<211> LENGTH: 26
<212> TYPE: PRT
<213> ORGANISM: Artificial Sequence
<220> FEATURE:
<223> OTHER INFORMATION: pNOP340580

<400> SEQUENCE: 63

```
Arg Lys Arg Lys Asn Cys Ser His Asn Ser Tyr Ser His Asn Ser Cys
1               5                   10                  15

Leu Asn Ala Lys Leu Ile Val Lys Pro Thr
            20                  25
```

<210> SEQ ID NO 64
<211> LENGTH: 26
<212> TYPE: PRT
<213> ORGANISM: Artificial Sequence
<220> FEATURE:
<223> OTHER INFORMATION: pNOP342316 alt splice c

<400> SEQUENCE: 64

```
Ser Ser Cys Ser Arg Ser Arg Leu Arg Arg Trp Gly Ile Ser Thr Thr
1               5                   10                  15

Arg Ser Thr Arg Pro Leu Ser Phe Leu Gly
            20                  25
```

<210> SEQ ID NO 65
<211> LENGTH: 26
<212> TYPE: PRT
<213> ORGANISM: Artificial Sequence
<220> FEATURE:
<223> OTHER INFORMATION: pNOP343672

<400> SEQUENCE: 65

```
Val Lys Glu Met Gly Ile Leu Val Arg Ile His Arg Val Leu Ile His
1               5                   10                  15

His Ser Thr His Leu Ile Leu Pro Pro Ser
            20                  25
```

<210> SEQ ID NO 66
<211> LENGTH: 25
<212> TYPE: PRT
<213> ORGANISM: Artificial Sequence
<220> FEATURE:
<223> OTHER INFORMATION: pNOP357840

<400> SEQUENCE: 66

```
Thr Leu Thr Gly Asn Leu Thr Ala Lys Trp Glu Glu Leu Pro Gln Leu
1               5                   10                  15

Lys Thr Leu Asn Ile Trp Leu Ala Ser
            20                  25
```

<210> SEQ ID NO 67
<211> LENGTH: 25
<212> TYPE: PRT
<213> ORGANISM: Artificial Sequence
<220> FEATURE:
<223> OTHER INFORMATION: pNOP358911

<400> SEQUENCE: 67

Trp Cys Ser Thr Pro Arg Leu Gln Arg Cys Cys Leu Ala Ser Ala Gly
1 5 10 15

Pro Arg Pro Ser Ser Gly Thr Glu Leu
20 25

<210> SEQ ID NO 68
<211> LENGTH: 25
<212> TYPE: PRT
<213> ORGANISM: Artificial Sequence
<220> FEATURE:
<223> OTHER INFORMATION: pNOP359043

<400> SEQUENCE: 68

Trp Leu Glu Leu Lys Leu Trp Ser Arg Asn Leu Pro Val Trp Asn Ser
1 5 10 15

Tyr Arg Thr His Thr His Ser Pro Ala
20 25

<210> SEQ ID NO 69
<211> LENGTH: 24
<212> TYPE: PRT
<213> ORGANISM: Artificial Sequence
<220> FEATURE:
<223> OTHER INFORMATION: pNOP360928

<400> SEQUENCE: 69

Cys Pro Ala Ser Ser Leu Cys Trp Leu Pro Thr Arg Leu Ser His Ala
1 5 10 15

Gly Leu Cys Gly Ser Gln Gln Pro
20

<210> SEQ ID NO 70
<211> LENGTH: 24
<212> TYPE: PRT
<213> ORGANISM: Artificial Sequence
<220> FEATURE:
<223> OTHER INFORMATION: pNOP362588

<400> SEQUENCE: 70

Phe Gly His Gln Thr Pro Gly Gln Leu Glu Arg Pro Lys Gly Gly Ile
1 5 10 15

Ser Asn Ser Lys Glu Lys Ser Asn
20

<210> SEQ ID NO 71
<211> LENGTH: 24
<212> TYPE: PRT
<213> ORGANISM: Artificial Sequence
<220> FEATURE:
<223> OTHER INFORMATION: pNOP371897

<400> SEQUENCE: 71

Ser Gly Gly Arg Ala Gly Arg Asp Ile Ser Ala Pro Arg Phe Ser Thr
1 5 10 15

Gly Trp Ala Leu Leu Cys His Gly

20

<210> SEQ ID NO 72
<211> LENGTH: 24
<212> TYPE: PRT
<213> ORGANISM: Artificial Sequence
<220> FEATURE:
<223> OTHER INFORMATION: pNOP372037

<400> SEQUENCE: 72

Ser Ile Arg Lys Cys Pro Cys Arg Gly Arg Gly Arg Ile Ala Val Thr
1 5 10 15

Thr Ala Thr Pro Thr Thr Ala Ala
20

<210> SEQ ID NO 73
<211> LENGTH: 24
<212> TYPE: PRT
<213> ORGANISM: Artificial Sequence
<220> FEATURE:
<223> OTHER INFORMATION: pNOP373154

<400> SEQUENCE: 73

Thr His Arg Pro His Leu Arg Leu His Arg Leu His Leu Pro Lys Pro
1 5 10 15

Gln His Ser His His Gln His Gln
20

<210> SEQ ID NO 74
<211> LENGTH: 23
<212> TYPE: PRT
<213> ORGANISM: Artificial Sequence
<220> FEATURE:
<223> OTHER INFORMATION: pNOP376360

<400> SEQUENCE: 74

Cys Asp Trp Ile Gly Ile Ile Pro Phe Gly Gln Ser Met His Ala Phe
1 5 10 15

Ile Lys Trp Ile Ser Glu Tyr
20

<210> SEQ ID NO 75
<211> LENGTH: 23
<212> TYPE: PRT
<213> ORGANISM: Artificial Sequence
<220> FEATURE:
<223> OTHER INFORMATION: pNOP377069

<400> SEQUENCE: 75

Asp Glu Ala Ala Ala Ala Ala Ala Ala Ser Glu Asp Gly Gly Phe Leu
1 5 10 15

Arg Pro Gly Ala Pro Asp Pro
20

<210> SEQ ID NO 76
<211> LENGTH: 23
<212> TYPE: PRT
<213> ORGANISM: Artificial Sequence
<220> FEATURE:
<223> OTHER INFORMATION: pNOP377612

<400> SEQUENCE: 76

Glu Asp Ile Leu Lys Ala Tyr Leu Ile Ser Phe Leu Phe Leu Gln Arg
1 5 10 15

Pro Lys Asp Ile Ile Leu Phe
20

<210> SEQ ID NO 77
<211> LENGTH: 23
<212> TYPE: PRT
<213> ORGANISM: Artificial Sequence
<220> FEATURE:
<223> OTHER INFORMATION: pNOP383516

<400> SEQUENCE: 77

Met Lys Glu Glu Lys Glu Asp Met Cys Ile Leu Leu Met Thr Gln Lys
1 5 10 15

Leu Tyr Phe Leu Leu Val Ile
20

<210> SEQ ID NO 78
<211> LENGTH: 22
<212> TYPE: PRT
<213> ORGANISM: Artificial Sequence
<220> FEATURE:
<223> OTHER INFORMATION: pNOP394982

<400> SEQUENCE: 78

Phe Gly Arg Thr Gly Thr Thr Glu Gly Val Ile Gln Leu Gln Pro Tyr
1 5 10 15

Lys Glu Asn Phe Ala Glu
20

<210> SEQ ID NO 79
<211> LENGTH: 22
<212> TYPE: PRT
<213> ORGANISM: Artificial Sequence
<220> FEATURE:
<223> OTHER INFORMATION: pNOP397465

<400> SEQUENCE: 79

Ile Ile Ala Cys Leu Asn Phe Leu Ile Leu Arg Val Met Gly Leu Ile
1 5 10 15

Val Gln Val Ile Gln Met
20

<210> SEQ ID NO 80
<211> LENGTH: 22
<212> TYPE: PRT
<213> ORGANISM: Artificial Sequence
<220> FEATURE:
<223> OTHER INFORMATION: pNOP399481

<400> SEQUENCE: 80

Leu Lys Asn Gln Leu Ile Arg Gly Phe Leu Ala Ala Lys Pro Lys Ile
1 5 10 15

Gln Thr Tyr Thr Val Leu
20

<210> SEQ ID NO 81
<211> LENGTH: 22
<212> TYPE: PRT
<213> ORGANISM: Artificial Sequence
<220> FEATURE:
<223> OTHER INFORMATION: pNOP407617

<400> SEQUENCE: 81

Val Phe Leu Pro Leu Val Arg Tyr His Met Trp Met Ala Cys Thr His
1 5 10 15

Gln Lys Ser Ser Glu Thr
20

<210> SEQ ID NO 82
<211> LENGTH: 22
<212> TYPE: PRT
<213> ORGANISM: Artificial Sequence
<220> FEATURE:
<223> OTHER INFORMATION: pNOP409009

<400> SEQUENCE: 82

Tyr Leu Ile Tyr Cys Arg Arg Ile Phe Pro Thr Lys Val Lys Gly Gly
1 5 10 15

Ile Gly Gln Asn Ser Phe
20

<210> SEQ ID NO 83
<211> LENGTH: 21
<212> TYPE: PRT
<213> ORGANISM: Artificial Sequence
<220> FEATURE:
<223> OTHER INFORMATION: pNOP418203

<400> SEQUENCE: 83

Met Asp Leu Leu Gly Gln Asn Leu Ile Trp Gln His Phe Ala Leu Leu
1 5 10 15

Lys Leu Met Leu Phe
20

<210> SEQ ID NO 84
<211> LENGTH: 21
<212> TYPE: PRT
<213> ORGANISM: Artificial Sequence
<220> FEATURE:
<223> OTHER INFORMATION: pNOP418296

<400> SEQUENCE: 84

Met Lys Lys Ser Asn Ser Leu Ile Leu Leu Val Tyr Arg His Leu Val
1 5 10 15

Gln Lys Val Val Asn
20

<210> SEQ ID NO 85
<211> LENGTH: 21
<212> TYPE: PRT
<213> ORGANISM: Artificial Sequence
<220> FEATURE:
<223> OTHER INFORMATION: pNOP424480

<400> SEQUENCE: 85

Ser Ser Ser Glu Gly Val Cys Thr Lys Gln Lys His Pro Leu Leu Phe
1 5 10 15

His Gly Pro Glu Glu
20

<210> SEQ ID NO 86
<211> LENGTH: 20
<212> TYPE: PRT
<213> ORGANISM: Artificial Sequence
<220> FEATURE:
<223> OTHER INFORMATION: pNOP429517

<400> SEQUENCE: 86

Cys Trp Lys Gly Ala Pro Ala His Thr Gln His Gly Pro Ser Val Phe

```
1               5                   10                  15

Ser Cys Ser Leu
            20


<210> SEQ ID NO 87
<211> LENGTH: 20
<212> TYPE: PRT
<213> ORGANISM: Artificial Sequence
<220> FEATURE:
<223> OTHER INFORMATION: pNOP429922

<400> SEQUENCE: 87

Asp Leu Leu Leu Arg Asp Gly Lys Lys Arg Gln Val Phe Phe Lys Thr
1               5                   10                  15

Arg Lys Arg Ile
            20


<210> SEQ ID NO 88
<211> LENGTH: 20
<212> TYPE: PRT
<213> ORGANISM: Artificial Sequence
<220> FEATURE:
<223> OTHER INFORMATION: pNOP432391

<400> SEQUENCE: 88

Gly Gln Gly Cys Cys Phe Ile Gln Ile Trp Ser Pro Ala Leu Ser Thr
1               5                   10                  15

Arg Arg Arg Lys
            20


<210> SEQ ID NO 89
<211> LENGTH: 20
<212> TYPE: PRT
<213> ORGANISM: Artificial Sequence
<220> FEATURE:
<223> OTHER INFORMATION: pNOP436619

<400> SEQUENCE: 89

Leu Gln Gly Pro Thr Ala Met Glu Gly Met Cys Gln Ala Arg Glu Asn
1               5                   10                  15

Ala Met Leu Leu
            20


<210> SEQ ID NO 90
<211> LENGTH: 20
<212> TYPE: PRT
<213> ORGANISM: Artificial Sequence
<220> FEATURE:
<223> OTHER INFORMATION: pNOP437076

<400> SEQUENCE: 90

Leu Trp Ser Leu Trp Trp Thr Gln Val Ser Ala Lys Cys Arg Thr Val
1               5                   10                  15

Trp Trp Asp Thr
            20


<210> SEQ ID NO 91
<211> LENGTH: 89
<212> TYPE: PRT
<213> ORGANISM: Artificial Sequence
<220> FEATURE:
<223> OTHER INFORMATION: pNOP44117

<400> SEQUENCE: 91
```

```
Met Glu Ile Glu Lys Lys Lys Met Arg Gln Arg Leu Lys Met Cys Arg
1               5                   10                  15

Lys Gln Val Ser Ser Lys Asp Gln Cys Ser Lys Val Leu Leu Leu Val
            20                  25                  30

Asp Phe Cys Pro Lys Ala Pro Lys Gln Lys Leu Ile Trp Lys Asn Arg
        35                  40                  45

Asp Asp Arg Arg Cys His Ser Ala Ser Ala Leu Gln Arg Lys Leu Cys
    50                  55                  60

Arg Ile Gly Phe Ser Leu His Leu Ala Met Lys Ser Lys Val Ile Leu
65                  70                  75                  80

Gln Thr Leu Gln Leu Tyr Leu Phe Arg
                85


<210> SEQ ID NO 92
<211> LENGTH: 20
<212> TYPE: PRT
<213> ORGANISM: Artificial Sequence
<220> FEATURE:
<223> OTHER INFORMATION: pNOP443088

<400> SEQUENCE: 92

Ser Ile Lys Lys Phe Leu Ser His Arg Ile Lys Tyr Lys Trp Ile Ser
1               5                   10                  15

Trp Gly Arg Ile
            20


<210> SEQ ID NO 93
<211> LENGTH: 19
<212> TYPE: PRT
<213> ORGANISM: Artificial Sequence
<220> FEATURE:
<223> OTHER INFORMATION: pNOP460543

<400> SEQUENCE: 93

Gln Arg Lys Ala Lys Lys Tyr Ser Glu Lys Arg Cys Pro Ser Ser Ser
1               5                   10                  15

Ser Ser Ala


<210> SEQ ID NO 94
<211> LENGTH: 19
<212> TYPE: PRT
<213> ORGANISM: Artificial Sequence
<220> FEATURE:
<223> OTHER INFORMATION: pNOP462663

<400> SEQUENCE: 94

Arg Val Ile Leu Lys Val Met Val Ser Phe Arg Thr Glu Arg Lys Leu
1               5                   10                  15

Glu Trp Arg


<210> SEQ ID NO 95
<211> LENGTH: 87
<212> TYPE: PRT
<213> ORGANISM: Artificial Sequence
<220> FEATURE:
<223> OTHER INFORMATION: pNOP46371

<400> SEQUENCE: 95

His Lys Lys Lys Lys Met Arg Gln Arg Leu Lys Met Cys Arg Lys Gln
1               5                   10                  15

Val Ser Ser Lys Asp Gln Cys Ser Lys Val Leu Leu Leu Val Asp Phe
            20                  25                  30
```

Cys Pro Lys Ala Pro Lys Gln Lys Leu Ile Trp Lys Asn Arg Asp Asp
35 40 45

Arg Arg Cys His Ser Ala Ser Ala Leu Gln Arg Lys Leu Cys Arg Ile
50 55 60

Gly Phe Ser Leu His Leu Ala Met Lys Ser Lys Val Ile Leu Gln Thr
65 70 75 80

Leu Gln Leu Tyr Leu Phe Arg
85

<210> SEQ ID NO 96
<211> LENGTH: 19
<212> TYPE: PRT
<213> ORGANISM: Artificial Sequence
<220> FEATURE:
<223> OTHER INFORMATION: pNOP464819

<400> SEQUENCE: 96

Thr Ile Ala Thr Leu Leu Cys Val Thr Leu Lys Leu Lys Ile Leu Ser
1 5 10 15

Leu Gln Leu

<210> SEQ ID NO 97
<211> LENGTH: 19
<212> TYPE: PRT
<213> ORGANISM: Artificial Sequence
<220> FEATURE:
<223> OTHER INFORMATION: pNOP467110

<400> SEQUENCE: 97

Trp Val Ile Trp Glu Met Phe Ala Arg Gly Ser Arg Arg Arg Glu Phe
1 5 10 15

His Ile Ala

<210> SEQ ID NO 98
<211> LENGTH: 19
<212> TYPE: PRT
<213> ORGANISM: Artificial Sequence
<220> FEATURE:
<223> OTHER INFORMATION: pNOP467219

<400> SEQUENCE: 98

Tyr Glu Gly Phe Leu Leu Gln Asn Gln Arg Phe Arg His Ile Leu Tyr
1 5 10 15

Phe Glu Arg

<210> SEQ ID NO 99
<211> LENGTH: 18
<212> TYPE: PRT
<213> ORGANISM: Artificial Sequence
<220> FEATURE:
<223> OTHER INFORMATION: pNOP470113

<400> SEQUENCE: 99

Asp Asn Arg Cys His Ser Lys Arg Lys Leu Leu Ser Phe His Glu Ser
1 5 10 15

Gln Leu

<210> SEQ ID NO 100
<211> LENGTH: 18
<212> TYPE: PRT
<213> ORGANISM: Artificial Sequence
<220> FEATURE:

<223> OTHER INFORMATION: pNOP472466

<400> SEQUENCE: 100

Gly His His Pro Ile Leu Asn Leu Ile Gly Thr Val Lys Leu Arg Pro
1 5 10 15

Leu Thr

<210> SEQ ID NO 101
<211> LENGTH: 18
<212> TYPE: PRT
<213> ORGANISM: Artificial Sequence
<220> FEATURE:
<223> OTHER INFORMATION: pNOP474911

<400> SEQUENCE: 101

Ile Ser Glu Arg Thr Thr Asn Tyr Asn Cys Thr Arg Ile Phe Arg Ser
1 5 10 15

Arg Tyr

<210> SEQ ID NO 102
<211> LENGTH: 18
<212> TYPE: PRT
<213> ORGANISM: Artificial Sequence
<220> FEATURE:
<223> OTHER INFORMATION: pNOP475195

<400> SEQUENCE: 102

Lys Cys Ala Glu Asn Arg Phe His Gln Arg Thr Asn Val Gln Arg Cys
1 5 10 15

Cys Phe

<210> SEQ ID NO 103
<211> LENGTH: 18
<212> TYPE: PRT
<213> ORGANISM: Artificial Sequence
<220> FEATURE:
<223> OTHER INFORMATION: pNOP475627

<400> SEQUENCE: 103

Lys Lys Phe Arg Val Phe Lys Ala Cys Arg Glu Arg Asn Asn Ser Arg
1 5 10 15

Ser Arg

<210> SEQ ID NO 104
<211> LENGTH: 18
<212> TYPE: PRT
<213> ORGANISM: Artificial Sequence
<220> FEATURE:
<223> OTHER INFORMATION: pNOP475977

<400> SEQUENCE: 104

Lys Pro His Glu Gly Leu Glu Lys Ala Gln Asp Ser Arg Ser Arg His
1 5 10 15

Leu Gln

<210> SEQ ID NO 105
<211> LENGTH: 18
<212> TYPE: PRT
<213> ORGANISM: Artificial Sequence
<220> FEATURE:
<223> OTHER INFORMATION: pNOP476615

<400> SEQUENCE: 105

```
Lys Tyr Val Gly Gly Lys Gln Ser Thr Ser Asn Tyr Ser Thr Leu Val
1               5                   10                  15

Ser Asp


<210> SEQ ID NO 106
<211> LENGTH: 18
<212> TYPE: PRT
<213> ORGANISM: Artificial Sequence
<220> FEATURE:
<223> OTHER INFORMATION: pNOP477103

<400> SEQUENCE: 106

Leu Ile Lys Ile Leu Lys Glu Lys Arg Leu Gly Leu Gln Leu His Gln
1               5                   10                  15

Ile Asp


<210> SEQ ID NO 107
<211> LENGTH: 18
<212> TYPE: PRT
<213> ORGANISM: Artificial Sequence
<220> FEATURE:
<223> OTHER INFORMATION: pNOP478859

<400> SEQUENCE: 107

Asn Phe Gln Gln Ala Leu Lys Arg Lys Glu Ile Leu Lys Arg Ala Gln
1               5                   10                  15

His Leu


<210> SEQ ID NO 108
<211> LENGTH: 18
<212> TYPE: PRT
<213> ORGANISM: Artificial Sequence
<220> FEATURE:
<223> OTHER INFORMATION: pNOP479862

<400> SEQUENCE: 108

Pro Glu Ala Ser Gly Arg Asp Tyr Lys Asp Phe Gly Thr Leu Ala His
1               5                   10                  15

Ser Tyr


<210> SEQ ID NO 109
<211> LENGTH: 18
<212> TYPE: PRT
<213> ORGANISM: Artificial Sequence
<220> FEATURE:
<223> OTHER INFORMATION: pNOP483413

<400> SEQUENCE: 109

Arg Arg Gly Glu Leu Gly Ser Thr Gly Trp Ile Pro Phe Phe Arg Pro
1               5                   10                  15

Val Arg


<210> SEQ ID NO 110
<211> LENGTH: 18
<212> TYPE: PRT
<213> ORGANISM: Artificial Sequence
<220> FEATURE:
<223> OTHER INFORMATION: pNOP485089

<400> SEQUENCE: 110

Ser Pro Phe Trp Asn Val Met Gly Cys Leu Cys Cys Gly Ser Gly Trp
1               5                   10                  15

Gln Ser
```

<210> SEQ ID NO 111
<211> LENGTH: 18
<212> TYPE: PRT
<213> ORGANISM: Artificial Sequence
<220> FEATURE:
<223> OTHER INFORMATION: pNOP486790

<400> SEQUENCE: 111

Thr Arg Lys Gly Cys Cys Trp Leu Gln Arg Ser Asn Thr Cys Pro Glu
1 5 10 15

Asp Ser

<210> SEQ ID NO 112
<211> LENGTH: 18
<212> TYPE: PRT
<213> ORGANISM: Artificial Sequence
<220> FEATURE:
<223> OTHER INFORMATION: pNOP488264

<400> SEQUENCE: 112

Trp Lys Met Val Arg Val Ser Leu Ile Lys Thr Arg Cys Ser Ala Tyr
1 5 10 15

Pro Gly

<210> SEQ ID NO 113
<211> LENGTH: 17
<212> TYPE: PRT
<213> ORGANISM: Artificial Sequence
<220> FEATURE:
<223> OTHER INFORMATION: pNOP497968

<400> SEQUENCE: 113

Lys Lys Met Ile Ser Lys Ile Glu Gly Leu Leu Lys Lys Gly Gly Arg
1 5 10 15

Lys

<210> SEQ ID NO 114
<211> LENGTH: 17
<212> TYPE: PRT
<213> ORGANISM: Artificial Sequence
<220> FEATURE:
<223> OTHER INFORMATION: pNOP503210

<400> SEQUENCE: 114

Pro Ser Gly Ser Pro Lys Phe Arg Gly Asn Arg Glu Ser Gln Asn Thr
1 5 10 15

Phe

<210> SEQ ID NO 115
<211> LENGTH: 17
<212> TYPE: PRT
<213> ORGANISM: Artificial Sequence
<220> FEATURE:
<223> OTHER INFORMATION: pNOP506077 alt splice d

<400> SEQUENCE: 115

Arg Arg Asn Asp Leu Val Arg Arg Ile Gln Thr His Thr His Ser Pro
1 5 10 15

Ala

<210> SEQ ID NO 116
<211> LENGTH: 16

<212> TYPE: PRT
<213> ORGANISM: Artificial Sequence
<220> FEATURE:
<223> OTHER INFORMATION: pNOP513180

<400> SEQUENCE: 116

Ala Ser Arg Tyr Phe Leu Lys Lys Arg Arg Phe Pro Tyr Trp Glu Gly
1 5 10 15

<210> SEQ ID NO 117
<211> LENGTH: 16
<212> TYPE: PRT
<213> ORGANISM: Artificial Sequence
<220> FEATURE:
<223> OTHER INFORMATION: pNOP515847

<400> SEQUENCE: 117

Glu Leu Pro Leu Ser Arg Glu Asp Ala Leu Phe Ser Ala Ile His Arg
1 5 10 15

<210> SEQ ID NO 118
<211> LENGTH: 16
<212> TYPE: PRT
<213> ORGANISM: Artificial Sequence
<220> FEATURE:
<223> OTHER INFORMATION: pNOP519358

<400> SEQUENCE: 118

His Arg His Ser Gln Glu Thr Asn Val Ser Gln Thr Glu Asn Tyr Lys
1 5 10 15

<210> SEQ ID NO 119
<211> LENGTH: 16
<212> TYPE: PRT
<213> ORGANISM: Artificial Sequence
<220> FEATURE:
<223> OTHER INFORMATION: pNOP528494

<400> SEQUENCE: 119

Arg Glu Lys Glu Thr Lys Lys Leu Pro Leu Thr Thr Leu Phe Cys Leu
1 5 10 15

<210> SEQ ID NO 120
<211> LENGTH: 16
<212> TYPE: PRT
<213> ORGANISM: Artificial Sequence
<220> FEATURE:
<223> OTHER INFORMATION: pNOP529595

<400> SEQUENCE: 120

Arg Pro Arg Lys Ser Pro Arg Gln Gln Lys Gln Thr Pro Pro Val Asn
1 5 10 15

<210> SEQ ID NO 121
<211> LENGTH: 16
<212> TYPE: PRT
<213> ORGANISM: Artificial Sequence
<220> FEATURE:
<223> OTHER INFORMATION: pNOP533091

<400> SEQUENCE: 121

Thr His Val Tyr Ala Ser Tyr Asp Cys Gly Leu Phe Gln Asn Ser Ser
1 5 10 15

<210> SEQ ID NO 122
<211> LENGTH: 15
<212> TYPE: PRT

<213> ORGANISM: Artificial Sequence
<220> FEATURE:
<223> OTHER INFORMATION: pNOP540029

<400> SEQUENCE: 122

Glu Gly Phe Ser Gly Trp Arg Ala Arg Ser Ser Asp Gly Lys Trp
1 5 10 15

<210> SEQ ID NO 123
<211> LENGTH: 15
<212> TYPE: PRT
<213> ORGANISM: Artificial Sequence
<220> FEATURE:
<223> OTHER INFORMATION: pNOP542259

<400> SEQUENCE: 123

Gly Leu Gly Phe Leu Pro Pro Asn Trp Phe Leu Gln Ala Gln Ser
1 5 10 15

<210> SEQ ID NO 124
<211> LENGTH: 15
<212> TYPE: PRT
<213> ORGANISM: Artificial Sequence
<220> FEATURE:
<223> OTHER INFORMATION: pNOP545135

<400> SEQUENCE: 124

Ile Ser Ser Ile Pro Ser Glu Arg Gln Gly Val Ser Ala Ser Thr
1 5 10 15

<210> SEQ ID NO 125
<211> LENGTH: 15
<212> TYPE: PRT
<213> ORGANISM: Artificial Sequence
<220> FEATURE:
<223> OTHER INFORMATION: pNOP546281

<400> SEQUENCE: 125

Lys Leu Val Ser Tyr Leu His Leu Asn Gln Lys Leu Thr Leu Lys
1 5 10 15

<210> SEQ ID NO 126
<211> LENGTH: 15
<212> TYPE: PRT
<213> ORGANISM: Artificial Sequence
<220> FEATURE:
<223> OTHER INFORMATION: pNOP547748

<400> SEQUENCE: 126

Leu His Gln Gly Ser Leu Ser Pro Cys Ser His Leu Lys Trp Leu
1 5 10 15

<210> SEQ ID NO 127
<211> LENGTH: 15
<212> TYPE: PRT
<213> ORGANISM: Artificial Sequence
<220> FEATURE:
<223> OTHER INFORMATION: pNOP549104

<400> SEQUENCE: 127

Met Cys Ile Trp Asn Gln Asn Gln Leu Tyr Val Ile Val Glu Ile
1 5 10 15

<210> SEQ ID NO 128
<211> LENGTH: 15
<212> TYPE: PRT
<213> ORGANISM: Artificial Sequence
<220> FEATURE:
<223> OTHER INFORMATION: pNOP550126

<400> SEQUENCE: 128

Asn Ile Val Glu Arg Tyr Ser Ile Ile Lys Ser Leu Lys Leu Glu
1 5 10 15

<210> SEQ ID NO 129
<211> LENGTH: 15
<212> TYPE: PRT
<213> ORGANISM: Artificial Sequence
<220> FEATURE:
<223> OTHER INFORMATION: pNOP550494

<400> SEQUENCE: 129

Asn Arg Ala Gln Arg Glu Gln Arg His Lys Thr Arg Arg Thr Tyr
1 5 10 15

<210> SEQ ID NO 130
<211> LENGTH: 15
<212> TYPE: PRT
<213> ORGANISM: Artificial Sequence
<220> FEATURE:
<223> OTHER INFORMATION: pNOP555604

<400> SEQUENCE: 130

Arg Ser Met His Glu Thr Lys Thr Ser Ile Thr Ile Ser Trp Pro
1 5 10 15

<210> SEQ ID NO 131
<211> LENGTH: 15
<212> TYPE: PRT
<213> ORGANISM: Artificial Sequence
<220> FEATURE:
<223> OTHER INFORMATION: pNOP560211

<400> SEQUENCE: 131

Val Lys Ile Ala Trp Thr Val Gln Ser Leu Met Gln Pro Val Ser
1 5 10 15

<210> SEQ ID NO 132
<211> LENGTH: 15
<212> TYPE: PRT
<213> ORGANISM: Artificial Sequence
<220> FEATURE:
<223> OTHER INFORMATION: pNOP562314

<400> SEQUENCE: 132

Tyr Ser Lys Pro Ser Ser Cys Thr Ser Ser Gly Arg Leu Asp Ser
1 5 10 15

<210> SEQ ID NO 133
<211> LENGTH: 14
<212> TYPE: PRT
<213> ORGANISM: Artificial Sequence
<220> FEATURE:
<223> OTHER INFORMATION: pNOP571897

<400> SEQUENCE: 133

Ile Thr Ala Val Asn Gln Ile Val Lys Pro Lys Asn Gly Leu
1 5 10

<210> SEQ ID NO 134
<211> LENGTH: 14
<212> TYPE: PRT
<213> ORGANISM: Artificial Sequence
<220> FEATURE:

<223> OTHER INFORMATION: pNOP573430

<400> SEQUENCE: 134

Lys Arg Lys Gly Trp Val Ser Ser Ser Ile Lys Ser Ile Lys
1 5 10

<210> SEQ ID NO 135
<211> LENGTH: 14
<212> TYPE: PRT
<213> ORGANISM: Artificial Sequence
<220> FEATURE:
<223> OTHER INFORMATION: pNOP582365

<400> SEQUENCE: 135

Arg Asn Arg Glu Glu Ser Gly Asn Phe Phe Tyr Thr Val Gln
1 5 10

<210> SEQ ID NO 136
<211> LENGTH: 14
<212> TYPE: PRT
<213> ORGANISM: Artificial Sequence
<220> FEATURE:
<223> OTHER INFORMATION: pNOP582849 alt splice d

<400> SEQUENCE: 136

Arg Arg Asn Asp Leu Val Arg Arg Ile Gln Trp Met Glu Ser
1 5 10

<210> SEQ ID NO 137
<211> LENGTH: 14
<212> TYPE: PRT
<213> ORGANISM: Artificial Sequence
<220> FEATURE:
<223> OTHER INFORMATION: pNOP585794

<400> SEQUENCE: 137

Ser Thr Val Arg Ile Leu Arg Thr Trp Ser Ala Met Arg Met
1 5 10

<210> SEQ ID NO 138
<211> LENGTH: 14
<212> TYPE: PRT
<213> ORGANISM: Artificial Sequence
<220> FEATURE:
<223> OTHER INFORMATION: pNOP588522

<400> SEQUENCE: 138

Val Thr Ala Gly Lys Val Thr Arg Ser Phe Arg Lys Arg Leu
1 5 10

<210> SEQ ID NO 139
<211> LENGTH: 13
<212> TYPE: PRT
<213> ORGANISM: Artificial Sequence
<220> FEATURE:
<223> OTHER INFORMATION: pNOP603675

<400> SEQUENCE: 139

Leu Leu Ala Arg Gln Trp Leu Leu Gly Ser Lys Ile Arg
1 5 10

<210> SEQ ID NO 140
<211> LENGTH: 13
<212> TYPE: PRT
<213> ORGANISM: Artificial Sequence
<220> FEATURE:
<223> OTHER INFORMATION: pNOP604883

<400> SEQUENCE: 140

Leu Tyr Glu Cys Ala Phe Gly Ile Lys Thr Ser Tyr Met
1 5 10

<210> SEQ ID NO 141
<211> LENGTH: 13
<212> TYPE: PRT
<213> ORGANISM: Artificial Sequence
<220> FEATURE:
<223> OTHER INFORMATION: pNOP605041

<400> SEQUENCE: 141

Met Phe Phe Ser Val Ser Lys Trp Gly Leu Leu Phe Gln
1 5 10

<210> SEQ ID NO 142
<211> LENGTH: 13
<212> TYPE: PRT
<213> ORGANISM: Artificial Sequence
<220> FEATURE:
<223> OTHER INFORMATION: pNOP605550

<400> SEQUENCE: 142

Asn Ala Glu Arg Thr His Leu Gln Phe Trp Met Gln Cys
1 5 10

<210> SEQ ID NO 143
<211> LENGTH: 13
<212> TYPE: PRT
<213> ORGANISM: Artificial Sequence
<220> FEATURE:
<223> OTHER INFORMATION: pNOP606242

<400> SEQUENCE: 143

Asn Leu Thr Leu Trp Val Thr Gln Ile Gln Arg Lys Pro
1 5 10

<210> SEQ ID NO 144
<211> LENGTH: 13
<212> TYPE: PRT
<213> ORGANISM: Artificial Sequence
<220> FEATURE:
<223> OTHER INFORMATION: pNOP613396

<400> SEQUENCE: 144

Ser Asp Cys Trp Ala Arg Val Gly Gly Trp Val Val Arg
1 5 10

<210> SEQ ID NO 145
<211> LENGTH: 13
<212> TYPE: PRT
<213> ORGANISM: Artificial Sequence
<220> FEATURE:
<223> OTHER INFORMATION: pNOP617878

<400> SEQUENCE: 145

Val Ile Trp Pro Pro Asn Ser Trp Thr Val Gly Lys Thr
1 5 10

<210> SEQ ID NO 146
<211> LENGTH: 12
<212> TYPE: PRT
<213> ORGANISM: Artificial Sequence
<220> FEATURE:
<223> OTHER INFORMATION: pNOP625134 alt splice b

<400> SEQUENCE: 146

Glu Leu Pro Lys Thr Phe Leu Arg Thr Pro Leu Ser
1 5 10

<210> SEQ ID NO 147
<211> LENGTH: 12
<212> TYPE: PRT
<213> ORGANISM: Artificial Sequence
<220> FEATURE:
<223> OTHER INFORMATION: pNOP625852

<400> SEQUENCE: 147

Glu Tyr Ile Ala Cys Ser Tyr Thr Thr Gln His Thr
1 5 10

<210> SEQ ID NO 148
<211> LENGTH: 12
<212> TYPE: PRT
<213> ORGANISM: Artificial Sequence
<220> FEATURE:
<223> OTHER INFORMATION: pNOP626121

<400> SEQUENCE: 148

Phe Ile Leu Phe Gln Val Arg Thr Ile Ser Leu Leu
1 5 10

<210> SEQ ID NO 149
<211> LENGTH: 12
<212> TYPE: PRT
<213> ORGANISM: Artificial Sequence
<220> FEATURE:
<223> OTHER INFORMATION: pNOP626457

<400> SEQUENCE: 149

Phe Arg Lys Gly Ile Cys Phe Gln Gly Glu Gln Ala
1 5 10

<210> SEQ ID NO 150
<211> LENGTH: 12
<212> TYPE: PRT
<213> ORGANISM: Artificial Sequence
<220> FEATURE:
<223> OTHER INFORMATION: pNOP629408

<400> SEQUENCE: 150

His Leu His Leu Leu Met Gln His His Tyr Gln Gln
1 5 10

<210> SEQ ID NO 151
<211> LENGTH: 12
<212> TYPE: PRT
<213> ORGANISM: Artificial Sequence
<220> FEATURE:
<223> OTHER INFORMATION: pNOP630920

<400> SEQUENCE: 151

Ile Arg Lys Arg Ala Thr Ala Glu Gln Ile Ser Leu
1 5 10

<210> SEQ ID NO 152
<211> LENGTH: 12
<212> TYPE: PRT
<213> ORGANISM: Artificial Sequence
<220> FEATURE:
<223> OTHER INFORMATION: pNOP632708

<400> SEQUENCE: 152

Lys Gln Ile Leu Ser Arg Thr Leu Tyr Leu Ile Val
1 5 10

<210> SEQ ID NO 153
<211> LENGTH: 12
<212> TYPE: PRT
<213> ORGANISM: Artificial Sequence
<220> FEATURE:
<223> OTHER INFORMATION: pNOP641668

<400> SEQUENCE: 153

Arg Phe Cys Thr Asp Phe Phe Lys Ser Lys Ile Thr
1 5 10

<210> SEQ ID NO 154
<211> LENGTH: 12
<212> TYPE: PRT
<213> ORGANISM: Artificial Sequence
<220> FEATURE:
<223> OTHER INFORMATION: pNOP645655

<400> SEQUENCE: 154

Ser Asn Ser Arg Thr Ser Thr Arg Phe Pro Asn Arg
1 5 10

<210> SEQ ID NO 155
<211> LENGTH: 12
<212> TYPE: PRT
<213> ORGANISM: Artificial Sequence
<220> FEATURE:
<223> OTHER INFORMATION: pNOP647445

<400> SEQUENCE: 155

Thr Gly Lys Asn Arg Ile Glu Phe Phe Phe Leu Leu
1 5 10

<210> SEQ ID NO 156
<211> LENGTH: 12
<212> TYPE: PRT
<213> ORGANISM: Artificial Sequence
<220> FEATURE:
<223> OTHER INFORMATION: pNOP648378

<400> SEQUENCE: 156

Thr Ser Gly Ser Gln Ala Asp Ser Arg Cys Tyr Glu
1 5 10

<210> SEQ ID NO 157
<211> LENGTH: 12
<212> TYPE: PRT
<213> ORGANISM: Artificial Sequence
<220> FEATURE:
<223> OTHER INFORMATION: pNOP649199

<400> SEQUENCE: 157

Val Lys Arg Glu Arg Pro Arg Gln Ala Asn Ser Lys
1 5 10

<210> SEQ ID NO 158
<211> LENGTH: 12
<212> TYPE: PRT
<213> ORGANISM: Artificial Sequence
<220> FEATURE:
<223> OTHER INFORMATION: pNOP649226

<400> SEQUENCE: 158

Val Leu Ala Thr Asp His Phe Pro Lys Gln Ala Arg
1 5 10

<210> SEQ ID NO 159
<211> LENGTH: 11
<212> TYPE: PRT
<213> ORGANISM: Artificial Sequence
<220> FEATURE:
<223> OTHER INFORMATION: pNOP652844

<400> SEQUENCE: 159

Ala Gln Lys Leu Thr Gln Thr Leu Pro Arg Asn
1 5 10

<210> SEQ ID NO 160
<211> LENGTH: 11
<212> TYPE: PRT
<213> ORGANISM: Artificial Sequence
<220> FEATURE:
<223> OTHER INFORMATION: pNOP661751

<400> SEQUENCE: 160

His Pro Gly His Cys Trp Leu Leu Pro Gln Gln
1 5 10

<210> SEQ ID NO 161
<211> LENGTH: 11
<212> TYPE: PRT
<213> ORGANISM: Artificial Sequence
<220> FEATURE:
<223> OTHER INFORMATION: pNOP662108

<400> SEQUENCE: 161

His Val Gly Lys Ile Val Leu Ile Val Phe Ser
1 5 10

<210> SEQ ID NO 162
<211> LENGTH: 11
<212> TYPE: PRT
<213> ORGANISM: Artificial Sequence
<220> FEATURE:
<223> OTHER INFORMATION: pNOP663661

<400> SEQUENCE: 162

Lys Ala Arg Met Ala Lys Arg Ile Leu Ile Asn
1 5 10

<210> SEQ ID NO 163
<211> LENGTH: 11
<212> TYPE: PRT
<213> ORGANISM: Artificial Sequence
<220> FEATURE:
<223> OTHER INFORMATION: pNOP663940

<400> SEQUENCE: 163

Lys Glu Arg Phe Phe Lys Lys Leu Arg Lys Lys
1 5 10

<210> SEQ ID NO 164
<211> LENGTH: 11
<212> TYPE: PRT
<213> ORGANISM: Artificial Sequence
<220> FEATURE:
<223> OTHER INFORMATION: pNOP665029

<400> SEQUENCE: 164

Lys Pro Gly Ala Gln Leu Ile Pro Ala Asn Gly 1 5 10

<210> SEQ ID NO 165
<211> LENGTH: 11
<212> TYPE: PRT
<213> ORGANISM: Artificial Sequence
<220> FEATURE:
<223> OTHER INFORMATION: pNOP668907

<400> SEQUENCE: 165

Met Pro Leu Lys Lys Glu Ile Ala Leu Val Ser
1 5 10

<210> SEQ ID NO 166
<211> LENGTH: 11
<212> TYPE: PRT
<213> ORGANISM: Artificial Sequence
<220> FEATURE:
<223> OTHER INFORMATION: pNOP675389

<400> SEQUENCE: 166

Arg Lys Cys Leu Phe Asn Arg Lys Lys Glu Glu
1 5 10

<210> SEQ ID NO 167
<211> LENGTH: 11
<212> TYPE: PRT
<213> ORGANISM: Artificial Sequence
<220> FEATURE:
<223> OTHER INFORMATION: pNOP676055

<400> SEQUENCE: 167

Arg Asn Arg Thr Ser Gly Val Thr Thr Pro Arg
1 5 10

<210> SEQ ID NO 168
<211> LENGTH: 11
<212> TYPE: PRT
<213> ORGANISM: Artificial Sequence
<220> FEATURE:
<223> OTHER INFORMATION: pNOP677462

<400> SEQUENCE: 168

Arg Trp Lys Glu Glu Ala Ser Ile Leu Gln Asn
1 5 10

<210> SEQ ID NO 169
<211> LENGTH: 11
<212> TYPE: PRT
<213> ORGANISM: Artificial Sequence
<220> FEATURE:
<223> OTHER INFORMATION: pNOP678458

<400> SEQUENCE: 169

Ser Ile Phe Ala Gln Arg His Gln Asn Lys Ser
1 5 10

<210> SEQ ID NO 170
<211> LENGTH: 11
<212> TYPE: PRT
<213> ORGANISM: Artificial Sequence
<220> FEATURE:
<223> OTHER INFORMATION: pNOP684868

<400> SEQUENCE: 170

Trp Ser Cys Pro Arg Asn Cys Val Tyr Ser Ser
1 5 10

<210> SEQ ID NO 171
<211> LENGTH: 10
<212> TYPE: PRT
<213> ORGANISM: Artificial Sequence
<220> FEATURE:
<223> OTHER INFORMATION: pNOP686009

<400> SEQUENCE: 171

Ala Ala Arg Arg Ala Ala Asn Leu Phe Phe
1 5 10

<210> SEQ ID NO 172
<211> LENGTH: 10
<212> TYPE: PRT
<213> ORGANISM: Artificial Sequence
<220> FEATURE:
<223> OTHER INFORMATION: pNOP687273

<400> SEQUENCE: 172

Ala Arg Arg Gln Gly Trp Gln Arg Gly Ser
1 5 10

<210> SEQ ID NO 173
<211> LENGTH: 10
<212> TYPE: PRT
<213> ORGANISM: Artificial Sequence
<220> FEATURE:
<223> OTHER INFORMATION: pNOP690677

<400> SEQUENCE: 173

Glu Cys Glu Thr Gln Asn Gln Gly Val His
1 5 10

<210> SEQ ID NO 174
<211> LENGTH: 10
<212> TYPE: PRT
<213> ORGANISM: Artificial Sequence
<220> FEATURE:
<223> OTHER INFORMATION: pNOP692910

<400> SEQUENCE: 174

Phe Arg Arg Thr Arg Asn Ser Asn Ile Glu
1 5 10

<210> SEQ ID NO 175
<211> LENGTH: 10
<212> TYPE: PRT
<213> ORGANISM: Artificial Sequence
<220> FEATURE:
<223> OTHER INFORMATION: pNOP696399

<400> SEQUENCE: 175

His Met Ile Ala Met Ile Val Leu Arg Asn
1 5 10

<210> SEQ ID NO 176
<211> LENGTH: 10
<212> TYPE: PRT
<213> ORGANISM: Artificial Sequence
<220> FEATURE:
<223> OTHER INFORMATION: pNOP698375

<400> SEQUENCE: 176

Ile Tyr Pro Phe Lys Thr Tyr Thr Gln Val
1 5 10

<210> SEQ ID NO 177
<211> LENGTH: 10
<212> TYPE: PRT
<213> ORGANISM: Artificial Sequence
<220> FEATURE:
<223> OTHER INFORMATION: pNOP698819

<400> SEQUENCE: 177

Lys Phe Asp Arg Ser Leu Lys Ile Cys Met
1               5                   10

<210> SEQ ID NO 178
<211> LENGTH: 10
<212> TYPE: PRT
<213> ORGANISM: Artificial Sequence
<220> FEATURE:
<223> OTHER INFORMATION: pNOP699449

<400> SEQUENCE: 178

Lys Lys Arg Lys Thr Arg Asn Leu Phe Arg
1               5                   10

<210> SEQ ID NO 179
<211> LENGTH: 10
<212> TYPE: PRT
<213> ORGANISM: Artificial Sequence
<220> FEATURE:
<223> OTHER INFORMATION: pNOP700367

<400> SEQUENCE: 179

Lys Arg Arg Arg Arg Thr Cys Ala Tyr Phe
1               5                   10

<210> SEQ ID NO 180
<211> LENGTH: 10
<212> TYPE: PRT
<213> ORGANISM: Artificial Sequence
<220> FEATURE:
<223> OTHER INFORMATION: pNOP700416

<400> SEQUENCE: 180

Lys Arg Tyr Ser Val Cys Ile Phe Pro Met
1               5                   10

<210> SEQ ID NO 181
<211> LENGTH: 10
<212> TYPE: PRT
<213> ORGANISM: Artificial Sequence
<220> FEATURE:
<223> OTHER INFORMATION: pNOP704029

<400> SEQUENCE: 181

Met Asn Cys Leu Phe Leu Ser Pro Asn Leu
1               5                   10

<210> SEQ ID NO 182
<211> LENGTH: 10
<212> TYPE: PRT
<213> ORGANISM: Artificial Sequence
<220> FEATURE:
<223> OTHER INFORMATION: pNOP709667

<400> SEQUENCE: 182

Gln Ser Gln Trp Pro Cys His Ile His Gln
1               5                   10

<210> SEQ ID NO 183
<211> LENGTH: 72
<212> TYPE: PRT
<213> ORGANISM: Artificial Sequence
<220> FEATURE:
<223> OTHER INFORMATION: pNOP71440

<400> SEQUENCE: 183

Val Gly Thr Ser Leu Lys Lys Ser Leu Leu Pro Arg Ile Ser Asn Leu
1 5 10 15

Thr Val Ala Met Glu Leu Val Val Asp Thr Ser Ile Ser Lys Met Gln
20 25 30

Asn Ser Met Val Gly His Val Ile Thr Gly Lys Ala Met Val Thr Gly
35 40 45

Ile Gln Asp Gln Val Asp Leu Leu Glu Leu Gly Leu Cys Met Ile Glu
50 55 60

Leu Lys Asp Lys Tyr Gln Ile Pro
65 70

<210> SEQ ID NO 184
<211> LENGTH: 10
<212> TYPE: PRT
<213> ORGANISM: Artificial Sequence
<220> FEATURE:
<223> OTHER INFORMATION: pNOP717155

<400> SEQUENCE: 184

Thr Phe Tyr Arg Gly Thr Pro Glu Val Val
1 5 10

<210> SEQ ID NO 185
<211> LENGTH: 10
<212> TYPE: PRT
<213> ORGANISM: Artificial Sequence
<220> FEATURE:
<223> OTHER INFORMATION: pNOP717203

<400> SEQUENCE: 185

Thr Gly Ile Pro Thr Arg Val Ile Ile Phe
1 5 10

<210> SEQ ID NO 186
<211> LENGTH: 68
<212> TYPE: PRT
<213> ORGANISM: Artificial Sequence
<220> FEATURE:
<223> OTHER INFORMATION: pNOP80237 alt splice a

<400> SEQUENCE: 186

Thr Val Ser Glu Lys Thr Ala Cys Arg Cys Gly Ser His Thr His Arg
1 5 10 15

Lys Glu Arg Leu Gly Leu Glu Ser Cys Gln Arg Pro Ser Phe Lys Arg
20 25 30

Ser Pro Glu Met Phe Leu Arg Ile Ser Gln Leu Pro Gly Leu Pro Gly
35 40 45

Arg Arg Lys Gln Ser Gln His Gln Ser Ser Arg Arg Glu Asn Glu Glu
50 55 60

Gly Thr Ile Ser
65

<210> SEQ ID NO 187
<211> LENGTH: 65
<212> TYPE: PRT

<213> ORGANISM: Artificial Sequence
<220> FEATURE:
<223> OTHER INFORMATION: pNOP85768

<400> SEQUENCE: 187

Cys Ser Lys Val Leu Leu Leu Val Asp Phe Cys Pro Lys Ala Pro Lys
1 5 10 15

Gln Lys Leu Ile Trp Lys Asn Arg Asp Asp Arg Arg Cys His Ser Ala
20 25 30

Ser Ala Leu Gln Arg Lys Leu Cys Arg Ile Gly Phe Ser Leu His Leu
35 40 45

Ala Met Lys Ser Lys Val Ile Leu Gln Thr Leu Gln Leu Tyr Leu Phe
50 55 60

Arg
65

<210> SEQ ID NO 188
<211> LENGTH: 63
<212> TYPE: PRT
<213> ORGANISM: Artificial Sequence
<220> FEATURE:
<223> OTHER INFORMATION: pNOP91732

<400> SEQUENCE: 188

Lys Glu Asn Leu Lys Gly Leu Gln Lys Met Lys Gln Leu Lys Asp Val
1 5 10 15

Val Leu Pro Leu Met Asn Trp Asp Ser Asp Glu Gly His His Ile Leu
20 25 30

Ser Met Thr Val Val Leu Pro Val Ile Asn Leu Pro Phe Gln Asn Leu
35 40 45

Tyr Pro Ser Leu Ile Asn Leu Lys Ile Leu Ser Val Val Gln Asn
50 55 60

<210> SEQ ID NO 189
<211> LENGTH: 60
<212> TYPE: PRT
<213> ORGANISM: Artificial Sequence
<220> FEATURE:
<223> OTHER INFORMATION: pNOP100723

<400> SEQUENCE: 189

Leu Leu Thr Ser Ser Phe Phe Leu Thr Met Gln Ser Pro Ile Ile Ser
1 5 10 15

Gln Ile Leu Leu Asn Ile Lys Pro Leu Ala Asn Ser Gly Ile Cys Thr
20 25 30

Phe Glu Gln Glu Met Ser Leu Phe Arg Lys Glu Lys Gln Met Thr Lys
35 40 45

Met Met Met Lys Met Gly Lys Thr Ile Arg Ala Gln
50 55 60

<210> SEQ ID NO 190
<211> LENGTH: 51
<212> TYPE: PRT
<213> ORGANISM: Artificial Sequence
<220> FEATURE:
<223> OTHER INFORMATION: pNOP136779

<400> SEQUENCE: 190

Trp Val Ala Ile Arg Gln Ala Phe His Leu Cys Arg Ala Gln Leu Met
1 5 10 15

Ala Leu Leu Ala Trp Ala Ala Cys Ser His Phe Thr Leu Gly Gly Leu

```
            20                  25                  30

His Pro Thr Ile Phe Arg Gln Val Cys Leu Ala Ser Arg Ala Ser His
        35                  40                  45

His Arg Val
    50


<210> SEQ ID NO 191
<211> LENGTH: 47
<212> TYPE: PRT
<213> ORGANISM: Artificial Sequence
<220> FEATURE:
<223> OTHER INFORMATION: pNOP152717

<400> SEQUENCE: 191

Gly Leu Gln His Gln Val Glu Val His Met Asp Asn Arg Trp Glu Phe
1               5                   10                  15

Trp Gly Leu Gln Gly Ser Arg His His Leu His Ile Pro Ala His Ile
            20                  25                  30

Gln Leu Asp Pro Leu Ser Tyr Ser Ser Gln Gln His Pro Cys Leu
        35                  40                  45


<210> SEQ ID NO 192
<211> LENGTH: 125
<212> TYPE: PRT
<213> ORGANISM: Artificial Sequence
<220> FEATURE:
<223> OTHER INFORMATION: pNOP18284

<400> SEQUENCE: 192

Ala Ser Val Trp Ser Cys Leu Ser Arg Asn Thr Leu Ser Tyr Ala Gln
1               5                   10                  15

Lys Thr Ser Glu Met Arg Met Phe Leu Ser Val Asn His Gly Ile Leu
            20                  25                  30

Pro Lys Pro Asn Leu Leu Arg Lys Leu Asn Cys Gly Pro Cys Pro Ser
        35                  40                  45

Ala Gln Ser Gly Leu Ser Leu Gly Met Cys Leu Cys Leu Trp Phe Ala
    50                  55                  60

Trp Pro Leu Tyr Leu Gln Met Gln Ile Lys Val Met Met Arg Arg Ile
65                  70                  75                  80

Gln Thr Thr Gln Arg Thr Val Glu Leu Lys Thr Ile Leu Thr Trp Lys
                85                  90                  95

Arg Lys Lys Lys Met Ser Leu Trp Lys Cys Pro Met Val Asn Gln Val
            100                 105                 110

Ala Thr Thr Leu Ser Ser Ser Ile Thr Met Thr Cys Gly
        115                 120                 125


<210> SEQ ID NO 193
<211> LENGTH: 58
<212> TYPE: PRT
<213> ORGANISM: Artificial Sequence
<220> FEATURE:
<223> OTHER INFORMATION: pNOP108150

<400> SEQUENCE: 193

Arg Leu Ala Thr Val Ser Ser Ser Ser Pro Met Ala Trp Cys Val Leu
1               5                   10                  15

Val Trp Ala Glu Leu Lys Lys Tyr Gly Phe Glu Met Glu Leu His Ile
            20                  25                  30

Phe Met Ala Pro Ser Ser Phe Thr Gln Lys Lys Gln Ser Met Ser Pro
        35                  40                  45
```

```
Gln Lys Cys Ser Thr Lys Lys Lys Tyr Phe
    50                  55


<210> SEQ ID NO 194
<211> LENGTH: 49
<212> TYPE: PRT
<213> ORGANISM: Artificial Sequence
<220> FEATURE:
<223> OTHER INFORMATION: pNOP143190

<400> SEQUENCE: 194

Ile Leu Leu Pro Cys Ala Met Asn Ser Ile Ile Pro Ser Glu Thr Ile
1               5                   10                  15

Arg Met Asn Arg Ala Asp Phe Ser Val Ser Ser Ser Leu Gly His Gln
            20                  25                  30

Ser Glu Glu Ile Asn Gln Thr Ile Met Lys Trp Phe Leu Ser Pro Leu
        35                  40                  45

Thr


<210> SEQ ID NO 195
<211> LENGTH: 48
<212> TYPE: PRT
<213> ORGANISM: Artificial Sequence
<220> FEATURE:
<223> OTHER INFORMATION: pNOP146830

<400> SEQUENCE: 195

Cys Ser Gly Met Pro Gly Thr Ile Met Arg Arg Ala Pro Arg Phe Ile
1               5                   10                  15

Met Met His Ile Ser Trp Arg Ser Tyr Ser Arg Arg Lys Gly Lys Ser
            20                  25                  30

Trp Ala His Cys Leu Met Met Met Thr Trp Leu Leu Pro Asn Ser Ser
        35                  40                  45


<210> SEQ ID NO 196
<211> LENGTH: 34
<212> TYPE: PRT
<213> ORGANISM: Artificial Sequence
<220> FEATURE:
<223> OTHER INFORMATION: pNOP245326 alt splice a

<400> SEQUENCE: 196

Leu Arg Pro Asn Thr Gln Thr Thr Leu Ser Gly Ser Ser Ala Ala Trp
1               5                   10                  15

Trp Gly Gln Asn Gly Glu Ile Leu Arg Gln Pro Arg Lys Gln Asn Met
            20                  25                  30

Lys Ala


<210> SEQ ID NO 197
<211> LENGTH: 29
<212> TYPE: PRT
<213> ORGANISM: Artificial Sequence
<220> FEATURE:
<223> OTHER INFORMATION: pNOP297770

<400> SEQUENCE: 197

Leu Gly Arg Met Leu Lys Ile Ile Ala Thr Val Gly Leu Ile Tyr Phe
1               5                   10                  15

Lys Ser Ile Cys Leu Lys Tyr Trp Asn Glu Gln Glu Gly
            20                  25
```

<210> SEQ ID NO 198
<211> LENGTH: 29
<212> TYPE: PRT
<213> ORGANISM: Artificial Sequence
<220> FEATURE:
<223> OTHER INFORMATION: pNOP302582

<400> SEQUENCE: 198

Ser Thr Lys Met Leu Leu Phe Tyr Thr Lys Ser Cys Leu Lys His Ala
1               5                   10                  15

Glu Thr Trp Arg Glu Met Arg Thr Leu Met Ser Gln Met
            20                  25

<210> SEQ ID NO 199
<211> LENGTH: 27
<212> TYPE: PRT
<213> ORGANISM: Artificial Sequence
<220> FEATURE:
<223> OTHER INFORMATION: pNOP323570

<400> SEQUENCE: 199

Leu Gln Ile His Gln Asp Val Ser Leu Ala Asn Phe Phe Arg Asn Cys
1               5                   10                  15

Leu Leu Lys Cys Asn Ile Gln Ile Ile Met Gln
            20                  25

<210> SEQ ID NO 200
<211> LENGTH: 87
<212> TYPE: PRT
<213> ORGANISM: Artificial Sequence
<220> FEATURE:
<223> OTHER INFORMATION: pNOP46601 alt splice b

<400> SEQUENCE: 200

Asn Glu Lys Lys Lys Lys Glu Lys Leu Lys Arg Val Lys Ile Pro Leu
1               5                   10                  15

Val Leu Gln Ala Ser Gln Ala Tyr Ile Ala His Thr Ala Arg Thr Val
            20                  25                  30

Ala Leu Lys Thr Ala Cys Thr Met Leu Glu Ile Thr Ser Met Trp Asn
        35                  40                  45

Leu Gln Arg Pro Thr Tyr Asn His Ile Ser Ser Val Leu Lys Asp Cys
    50                  55                  60

Gly Arg Ile Gln Leu Lys Lys Lys Phe Leu Arg Val Thr Ile Thr Thr
65                  70                  75                  80

Lys Phe Gln Leu Val Lys Phe
                85

<210> SEQ ID NO 201
<211> LENGTH: 50
<212> TYPE: PRT
<213> ORGANISM: Artificial Sequence
<220> FEATURE:
<223> OTHER INFORMATION: pNOP139958

<400> SEQUENCE: 201

Gln Val Leu His Thr Val Lys Ala Ala Leu Val Lys Arg Glu Ile Pro
1               5                   10                  15

Leu Ala Ser Ile Thr Val Ile Lys Glu Gln Tyr Lys Glu Val Val Tyr
            20                  25                  30

Gln Gln Leu Gln Trp His Phe Asn Met Ala Gln Lys Val Lys Lys Met
        35                  40                  45

Leu Leu

50

<210> SEQ ID NO 202
<211> LENGTH: 47
<212> TYPE: PRT
<213> ORGANISM: Artificial Sequence
<220> FEATURE:
<223> OTHER INFORMATION: pNOP154131

<400> SEQUENCE: 202

Asn Phe Ser Ser Phe Leu Leu Lys Phe Val Met Asn Ser Ala Lys Met
1               5                   10                  15

Glu Arg Phe Phe Phe His Arg His Ser Ala Ile Pro Gln Asn Ile Cys
            20                  25                  30

Ile Met Met Trp Arg Lys Arg Glu Arg Lys Asn Cys Gln Lys Lys
        35                  40                  45

<210> SEQ ID NO 203
<211> LENGTH: 41
<212> TYPE: PRT
<213> ORGANISM: Artificial Sequence
<220> FEATURE:
<223> OTHER INFORMATION: pNOP188417

<400> SEQUENCE: 203

His Val Phe Ser Glu Ser Val Leu Cys Cys His Ser Arg Thr Ser Ser
1               5                   10                  15

Pro Ala Gly Gln Leu Lys Tyr Gln Lys Met Thr Phe Cys Phe Val Arg
            20                  25                  30

Ala Ala Thr Met Arg Ala Thr Ser Arg
        35                  40

<210> SEQ ID NO 204
<211> LENGTH: 32
<212> TYPE: PRT
<213> ORGANISM: Artificial Sequence
<220> FEATURE:
<223> OTHER INFORMATION: pNOP264907

<400> SEQUENCE: 204

Leu Asn Leu Phe Thr Ile Cys Leu Gln Arg Lys Asn Thr Leu Ile Ile
1               5                   10                  15

Thr Ser Lys Leu Lys Cys Pro Tyr His Tyr Asn Arg Ser Glu Gln Asn
            20                  25                  30

<210> SEQ ID NO 205
<211> LENGTH: 29
<212> TYPE: PRT
<213> ORGANISM: Artificial Sequence
<220> FEATURE:
<223> OTHER INFORMATION: pNOP303604

<400> SEQUENCE: 205

Val Ile Lys Glu Gln Tyr Lys Glu Val Val Tyr Gln Gln Leu Gln Trp
1               5                   10                  15

His Phe Asn Met Ala Gln Lys Val Lys Lys Met Leu Leu
            20                  25

<210> SEQ ID NO 206
<211> LENGTH: 27
<212> TYPE: PRT
<213> ORGANISM: Artificial Sequence
<220> FEATURE:
<223> OTHER INFORMATION: pNOP324121

<400> SEQUENCE: 206

Met Met Lys Phe Thr Thr Ser Glu Asn Gln Leu Phe Leu Arg Arg Ser
1 5 10 15

His His Leu Cys Trp Lys Arg Arg Ser Ser Cys
20 25

<210> SEQ ID NO 207
<211> LENGTH: 24
<212> TYPE: PRT
<213> ORGANISM: Artificial Sequence
<220> FEATURE:
<223> OTHER INFORMATION: pNOP367819

<400> SEQUENCE: 207

Asn Cys Ser Lys Leu Cys Arg Gln Arg Arg Lys Ser Leu Pro Gly Glu
1 5 10 15

Thr Ile Ser Arg Thr Glu Thr Ala
20

<210> SEQ ID NO 208
<211> LENGTH: 22
<212> TYPE: PRT
<213> ORGANISM: Artificial Sequence
<220> FEATURE:
<223> OTHER INFORMATION: pNOP396093

<400> SEQUENCE: 208

Gly Pro Thr Pro Arg Leu Leu Phe Arg Gly Ala Gln Pro Pro Gly Gly
1 5 10 15

Asp Arg Met Glu Lys Ser
20

<210> SEQ ID NO 209
<211> LENGTH: 17
<212> TYPE: PRT
<213> ORGANISM: Artificial Sequence
<220> FEATURE:
<223> OTHER INFORMATION: pNOP504975

<400> SEQUENCE: 209

Arg Gly Asn Asp Arg Arg His Glu Ala Asp Val Pro Glu Cys Gln Ala
1 5 10 15

Leu

<210> SEQ ID NO 210
<211> LENGTH: 16
<212> TYPE: PRT
<213> ORGANISM: Artificial Sequence
<220> FEATURE:
<223> OTHER INFORMATION: pNOP520755

<400> SEQUENCE: 210

Lys Glu His Lys Lys Ala Ala Asn Glu Asn Leu Ile Gln Cys Cys Ser
1 5 10 15

<210> SEQ ID NO 211
<211> LENGTH: 15
<212> TYPE: PRT
<213> ORGANISM: Artificial Sequence
<220> FEATURE:
<223> OTHER INFORMATION: pNOP547617

<400> SEQUENCE: 211

Leu Gly Lys Gly Lys Arg Arg Cys Pro Cys Gly Asn Val Gln Trp
1 5 10 15

<210> SEQ ID NO 212
<211> LENGTH: 15
<212> TYPE: PRT
<213> ORGANISM: Artificial Sequence
<220> FEATURE:
<223> OTHER INFORMATION: pNOP548688

<400> SEQUENCE: 212

Leu Ser Ile Thr Ser Ala Met Thr Asn Met Leu Val Lys Arg Glu
1 5 10 15

<210> SEQ ID NO 213
<211> LENGTH: 13
<212> TYPE: PRT
<213> ORGANISM: Artificial Sequence
<220> FEATURE:
<223> OTHER INFORMATION: pNOP592499

<400> SEQUENCE: 213

Cys Leu Ile Met Pro Val His Thr Met Ser Arg Ser Leu
1 5 10

<210> SEQ ID NO 214
<211> LENGTH: 13
<212> TYPE: PRT
<213> ORGANISM: Artificial Sequence
<220> FEATURE:
<223> OTHER INFORMATION: pNOP613848

<400> SEQUENCE: 214

Ser His Ser Cys Ser Tyr Lys Ser Ile Arg Thr Ser His
1 5 10

<210> SEQ ID NO 215
<211> LENGTH: 66
<212> TYPE: PRT
<213> ORGANISM: Artificial Sequence
<220> FEATURE:
<223> OTHER INFORMATION: pNOP83912

<400> SEQUENCE: 215

Lys Met Phe Asn His Ile Ile Thr Phe Leu Leu Tyr Arg Ser Ile Lys
1 5 10 15

Ser Cys Gly Ser Val Ala Ile Leu Val Thr Gly Gly Gly Gly Lys Glu
20 25 30

Gln Arg Arg Ile Ile Phe Ile Ala Phe Tyr Cys Thr Ser Gln Gly His
35 40 45

Phe Tyr Ile Arg Thr Leu Leu Ile Ser Tyr Phe Asn Leu Phe Val Ile
50 55 60

Leu Ser
65

<210> SEQ ID NO 216
<211> LENGTH: 48
<212> TYPE: PRT
<213> ORGANISM: Artificial Sequence
<220> FEATURE:
<223> OTHER INFORMATION: pNOP150133

<400> SEQUENCE: 216

Arg Ser Trp Ile Pro Trp Val Pro Arg Glu Glu Glu Leu Pro Pro Leu
1 5 10 15

Pro Ala Val Ser Ala Gly Thr Leu Met Met Gly Thr Ile Leu Cys Gln
20 25 30

His Gln Ala Gln Ala Gly Lys Gly Gly Asp Phe Pro Ile Phe Gln Leu
35 40 45

<210> SEQ ID NO 217
<211> LENGTH: 47
<212> TYPE: PRT
<213> ORGANISM: Artificial Sequence
<220> FEATURE:
<223> OTHER INFORMATION: pNOP155811

<400> SEQUENCE: 217

Ser Trp Ile Pro Trp Val Pro Arg Glu Glu Glu Leu Pro Pro Leu Pro
1 5 10 15

Ala Val Ser Ala Gly Thr Leu Met Met Gly Thr Ile Leu Cys Gln His
20 25 30

Gln Ala Gln Ala Gly Lys Gly Gly Asp Phe Pro Ile Phe Gln Leu
35 40 45

<210> SEQ ID NO 218
<211> LENGTH: 44
<212> TYPE: PRT
<213> ORGANISM: Artificial Sequence
<220> FEATURE:
<223> OTHER INFORMATION: pNOP170046

<400> SEQUENCE: 218

Lys Ser Tyr Ser Met Leu Phe Leu Lys Leu Glu Ser Gln Val Gln Ala
1 5 10 15

Glu Asp Phe Val Thr Tyr Leu Trp Leu Asn His Pro Lys Arg Thr Ile
20 25 30

Leu Ile Ile Ile Lys Ser Ser Trp Ser Gln Trp Thr
35 40

<210> SEQ ID NO 219
<211> LENGTH: 43
<212> TYPE: PRT
<213> ORGANISM: Artificial Sequence
<220> FEATURE:
<223> OTHER INFORMATION: pNOP179578

<400> SEQUENCE: 219

Trp Val Pro Arg Glu Glu Glu Leu Pro Pro Leu Pro Ala Val Ser Ala
1 5 10 15

Gly Thr Leu Met Met Gly Thr Ile Leu Cys Gln His Gln Ala Gln Ala
20 25 30

Gly Lys Gly Gly Asp Phe Pro Ile Phe Gln Leu
35 40

<210> SEQ ID NO 220
<211> LENGTH: 42
<212> TYPE: PRT
<213> ORGANISM: Artificial Sequence
<220> FEATURE:
<223> OTHER INFORMATION: pNOP180157

<400> SEQUENCE: 220

Cys Ala Gln Phe Ser His Leu Gln Ala Ser Ser Lys Ile Ala Ala Ser
1 5 10 15

Tyr Ala Gly Lys Glu Glu Arg Ala Cys Gln Glu Arg Arg Tyr Arg Gly
20 25 30

```
Arg Arg Gln His Asp Leu Phe Ser His Leu
        35                  40


<210> SEQ ID NO 221
<211> LENGTH: 125
<212> TYPE: PRT
<213> ORGANISM: Artificial Sequence
<220> FEATURE:
<223> OTHER INFORMATION: pNOP18247 alt splice c

<400> SEQUENCE: 221

Ala Ala Gly Glu Arg Ala Ser Ser Thr Ala Thr Ala Ala Glu Cys Phe
1               5                   10                  15

Ser Pro Ser Arg His Pro Cys Gly Gly Ser His Gly Gly Gly Ala Thr
            20                  25                  30

Thr Asn Thr Asn Gly Asp Ala Gln Ser Ala Val Asp Thr Cys Cys Arg
        35                  40                  45

Cys Asp Glu Pro Arg Ser Gly Pro Tyr Gly Arg Asp Ser Ser Thr Arg
    50                  55                  60

Trp Lys Ser Ile Trp Thr Thr Gly Gly Ser Phe Gly Ala Ser Arg Ala
65                  70                  75                  80

Ala Gly Thr Thr Ser Ile Ser Arg Pro Thr Ser Ser Trp Thr Pro Cys
                85                  90                  95

His Thr Ala Ala Asn Asn Thr His Val Cys Ser Ser Pro Thr Lys Asp
            100                 105                 110

Pro Ala Ala Ser Ser Leu Arg Gly Leu Pro Glu Ile His
        115                 120                 125


<210> SEQ ID NO 222
<211> LENGTH: 41
<212> TYPE: PRT
<213> ORGANISM: Artificial Sequence
<220> FEATURE:
<223> OTHER INFORMATION: pNOP189150

<400> SEQUENCE: 222

Leu Leu His Ala Met Lys Arg Glu Ser Gln Lys Gln Lys Ala Ser Leu
1               5                   10                  15

Pro Leu Trp Met Phe Gln Ile Leu Phe Ile Ser Phe Met Thr Gln Leu
            20                  25                  30

Gly Val Val Gly Ile Thr Lys Gly Ser
        35                  40


<210> SEQ ID NO 223
<211> LENGTH: 41
<212> TYPE: PRT
<213> ORGANISM: Artificial Sequence
<220> FEATURE:
<223> OTHER INFORMATION: pNOP189879

<400> SEQUENCE: 223

Asn Thr Leu Lys Asp Ser Val Arg Ser Pro Thr Ala Leu Ala Ser Gly
1               5                   10                  15

Ile Arg His Trp Gln Leu Glu Asp Ala Thr Ser Ile Cys Arg Lys Asn
            20                  25                  30

Arg Arg Ala Ala Tyr Pro Leu Thr Gly
        35                  40


<210> SEQ ID NO 224
<211> LENGTH: 40
```

<212> TYPE: PRT
<213> ORGANISM: Artificial Sequence
<220> FEATURE:
<223> OTHER INFORMATION: pNOP196761 alt splice d

<400> SEQUENCE: 224

Asn Glu Glu Thr Gly Phe Ser Arg Arg Trp Leu Cys Ser Gly Lys Ala
1 5 10 15

Glu Glu Val Gly Phe His Gly Phe Gln Glu Lys Lys Ser Tyr Leu Pro
20 25 30

Phe Gln Gln Cys Gln Arg Gly Leu
35 40

<210> SEQ ID NO 225
<211> LENGTH: 39
<212> TYPE: PRT
<213> ORGANISM: Artificial Sequence
<220> FEATURE:
<223> OTHER INFORMATION: pNOP200354

<400> SEQUENCE: 225

Ala Gly Pro His Ala Leu His Thr Pro Thr Val Tyr Pro Lys Val Cys
1 5 10 15

Gln Arg Gln Cys Lys Glu Gly Arg Leu Gln Thr Glu Asn Gln His Glu
20 25 30

Trp Leu His Pro Val Gln Gln
35

<210> SEQ ID NO 226
<211> LENGTH: 37
<212> TYPE: PRT
<213> ORGANISM: Artificial Sequence
<220> FEATURE:
<223> OTHER INFORMATION: pNOP217261

<400> SEQUENCE: 226

Gly Ala Tyr Arg Ser Gln Asp His Cys Pro Glu Asp Thr Glu Trp Lys
1 5 10 15

Leu Gln Lys Tyr Ser Cys Asn Gly Gln Arg Tyr Arg Ser Pro Arg Lys
20 25 30

Lys Cys Gln Asn Leu
35

<210> SEQ ID NO 227
<211> LENGTH: 37
<212> TYPE: PRT
<213> ORGANISM: Artificial Sequence
<220> FEATURE:
<223> OTHER INFORMATION: pNOP219611 alt splice d

<400> SEQUENCE: 227

Asn Glu Glu Thr Gly Phe Ser Arg Arg Trp Leu Cys Ser Glu Glu Val
1 5 10 15

Gly Phe His Gly Phe Gln Glu Lys Lys Ser Tyr Leu Pro Phe Gln Gln
20 25 30

Cys Gln Arg Gly Leu
35

<210> SEQ ID NO 228
<211> LENGTH: 36
<212> TYPE: PRT
<213> ORGANISM: Artificial Sequence
<220> FEATURE:

<223> OTHER INFORMATION: pNOP227023 alt splice e

<400> SEQUENCE: 228

Lys Val Glu Met Met Ile Leu Lys Arg Trp Glu Lys Lys Ile Val Ser
1               5                   10                  15

Leu Pro Gln Ser Leu Pro Lys Ala Val Gln Arg Arg Lys Ala Pro Asn
            20                  25                  30

Gly Lys Ser Thr
        35

<210> SEQ ID NO 229
<211> LENGTH: 36
<212> TYPE: PRT
<213> ORGANISM: Artificial Sequence
<220> FEATURE:
<223> OTHER INFORMATION: pNOP227832 alt splice d

<400> SEQUENCE: 229

Asn Glu Glu Thr Gly Phe Ser Arg Arg Trp Leu Cys Ser Glu Val Gly
1               5                   10                  15

Phe His Gly Phe Gln Glu Lys Lys Ser Tyr Leu Pro Phe Gln Gln Cys
            20                  25                  30

Gln Arg Gly Leu
        35

<210> SEQ ID NO 230
<211> LENGTH: 34
<212> TYPE: PRT
<213> ORGANISM: Artificial Sequence
<220> FEATURE:
<223> OTHER INFORMATION: pNOP245327 alt splice a

<400> SEQUENCE: 230

Leu Arg Pro Asn Thr Gln Thr Thr Leu Ser Gly Ser Ser Ala Ala Trp
1               5                   10                  15

Trp Gly Gln Asn Gly Glu Ile Leu Arg Gln Pro Arg Lys Gln Asn Met
            20                  25                  30

Lys Val

<210> SEQ ID NO 231
<211> LENGTH: 33
<212> TYPE: PRT
<213> ORGANISM: Artificial Sequence
<220> FEATURE:
<223> OTHER INFORMATION: pNOP258302 alt splice f

<400> SEQUENCE: 231

Ser Leu Gln Pro Pro Leu Ile Leu Val Val Pro Lys Glu Lys Gly Thr
1               5                   10                  15

Leu Met Thr Val Arg Cys Trp Val Ser Gly Gly Tyr Pro Val Lys Arg
            20                  25                  30

Thr

<210> SEQ ID NO 232
<211> LENGTH: 108
<212> TYPE: PRT
<213> ORGANISM: Artificial Sequence
<220> FEATURE:
<223> OTHER INFORMATION: pNOP27190

<400> SEQUENCE: 232

His Gly Gln His Ala Ala Thr Ser Pro Trp Gly Ala Ser Thr Pro Pro

```
1               5                   10                  15

Ser Ser Ala Arg Cys Ala Trp Pro Pro Gly His Pro Thr Thr Gly Cys
            20                  25                  30

Asp Glu Pro Arg Ser Gly Pro Tyr Gly Arg Asp Ser Ser Thr Arg Trp
        35                  40                  45

Lys Ser Ile Trp Thr Thr Gly Gly Ser Phe Gly Ala Ser Arg Ala Ala
    50                  55                  60

Gly Thr Thr Ser Ile Ser Arg Pro Thr Ser Ser Trp Thr Pro Cys His
65                  70                  75                  80

Thr Ala Ala Asn Asn Thr His Val Cys Ser Ser Pro Thr Lys Asp Pro
                85                  90                  95

Ala Ala Ser Ser Leu Arg Gly Leu Pro Glu Ile His
            100                 105


<210> SEQ ID NO 233
<211> LENGTH: 31
<212> TYPE: PRT
<213> ORGANISM: Artificial Sequence
<220> FEATURE:
<223> OTHER INFORMATION: pNOP280248

<400> SEQUENCE: 233

Thr Val Asp His Ala His Gln Leu Ser Gln Val Cys Pro Ser Gly Cys
1               5                   10                  15

Ala Ser Ala Cys Gly Ser Arg Gly Leu Cys Ile Cys Lys Cys Arg
            20                  25                  30


<210> SEQ ID NO 234
<211> LENGTH: 30
<212> TYPE: PRT
<213> ORGANISM: Artificial Sequence
<220> FEATURE:
<223> OTHER INFORMATION: pNOP291935

<400> SEQUENCE: 234

Trp Ala Pro Phe Cys Val Asn Thr Arg Pro Lys Gln Glu Lys Glu Glu
1               5                   10                  15

Thr Phe Gln Ser Ser Asn Cys Arg Ser Tyr Cys Arg Val Pro
            20                  25                  30


<210> SEQ ID NO 235
<211> LENGTH: 29
<212> TYPE: PRT
<213> ORGANISM: Artificial Sequence
<220> FEATURE:
<223> OTHER INFORMATION: pNOP296775

<400> SEQUENCE: 235

Ile Ser Ser Gln Lys Met Pro Lys Leu Ile Met Ser Leu Ala Leu Lys
1               5                   10                  15

Tyr Ser Arg Met Gln Ile Gln Leu Lys Lys Tyr Phe Ile
            20                  25


<210> SEQ ID NO 236
<211> LENGTH: 29
<212> TYPE: PRT
<213> ORGANISM: Artificial Sequence
<220> FEATURE:
<223> OTHER INFORMATION: pNOP303912

<400> SEQUENCE: 236

Val Tyr Pro Lys Val Cys Gln Arg Gln Cys Lys Glu Gly Arg Leu Gln
```

1 5 10 15

Thr Glu Asn Gln His Glu Trp Leu His Pro Val Gln Gln
20 25

<210> SEQ ID NO 237
<211> LENGTH: 28
<212> TYPE: PRT
<213> ORGANISM: Artificial Sequence
<220> FEATURE:
<223> OTHER INFORMATION: pNOP314359

<400> SEQUENCE: 237

Ser Gly Arg Asn Leu Pro His Asp Met Tyr Ser Arg Lys Val Cys Cys
1 5 10 15

Val Val Ile Gln Gly Leu Pro Leu Leu Gln Ala Asn
20 25

<210> SEQ ID NO 238
<211> LENGTH: 27
<212> TYPE: PRT
<213> ORGANISM: Artificial Sequence
<220> FEATURE:
<223> OTHER INFORMATION: pNOP320508

<400> SEQUENCE: 238

Gly Leu Ser Cys Pro Lys Cys Asp Phe Ala Asp Ser Arg Ala Tyr Pro
1 5 10 15

Gln Ser Phe Cys Val Ser His Glu Ser Ser Gly
20 25

<210> SEQ ID NO 239
<211> LENGTH: 27
<212> TYPE: PRT
<213> ORGANISM: Artificial Sequence
<220> FEATURE:
<223> OTHER INFORMATION: pNOP324586

<400> SEQUENCE: 239

Asn Leu Leu Leu Gln Lys Thr Asn Cys Ser Ser Glu Gly Ala Ile Thr
1 5 10 15

Phe Ala Gly Lys Glu Asp Pro Val Ala Arg Ser
20 25

<210> SEQ ID NO 240
<211> LENGTH: 26
<212> TYPE: PRT
<213> ORGANISM: Artificial Sequence
<220> FEATURE:
<223> OTHER INFORMATION: pNOP336473

<400> SEQUENCE: 240

Lys Gln His Val Pro Cys Trp Arg Leu Arg Leu Cys Gly Thr Cys Arg
1 5 10 15

Gly Gln Pro Thr Thr Thr Tyr Arg Leu Tyr
20 25

<210> SEQ ID NO 241
<211> LENGTH: 24
<212> TYPE: PRT
<213> ORGANISM: Artificial Sequence
<220> FEATURE:
<223> OTHER INFORMATION: pNOP364497

<400> SEQUENCE: 241

His Val Ala Glu Gly Trp Arg Leu Cys Leu His Gln Val Pro Trp Pro
1 5 10 15

Gly Ala Ser Ser Cys Gly Gln Asn
20

<210> SEQ ID NO 242
<211> LENGTH: 24
<212> TYPE: PRT
<213> ORGANISM: Artificial Sequence
<220> FEATURE:
<223> OTHER INFORMATION: pNOP365921

<400> SEQUENCE: 242

Lys Ser Met Gly Ser Arg Trp Ser Cys Ile Phe Leu Trp Pro His Leu
1 5 10 15

His Ser Pro Arg Arg Asn Arg Ala
20

<210> SEQ ID NO 243
<211> LENGTH: 24
<212> TYPE: PRT
<213> ORGANISM: Artificial Sequence
<220> FEATURE:
<223> OTHER INFORMATION: pNOP370708

<400> SEQUENCE: 243

Arg Lys Ser Thr Phe Phe Ser Thr Leu Pro Val Phe Ser Ser Leu Leu
1 5 10 15

Glu Gly Asp Pro Gly Ala Ala Ser
20

<210> SEQ ID NO 244
<211> LENGTH: 23
<212> TYPE: PRT
<213> ORGANISM: Artificial Sequence
<220> FEATURE:
<223> OTHER INFORMATION: pNOP380983

<400> SEQUENCE: 244

Ile Ser Arg Pro Leu Pro Arg Gly Tyr Arg Met Glu Ala Thr Lys Val
1 5 10 15

Phe Met Gln Trp Pro Lys Ile
20

<210> SEQ ID NO 245
<211> LENGTH: 23
<212> TYPE: PRT
<213> ORGANISM: Artificial Sequence
<220> FEATURE:
<223> OTHER INFORMATION: pNOP386577

<400> SEQUENCE: 245

Arg Gly Arg Val Arg Ser Arg Lys His His Phe Leu Tyr Gly Cys Phe
1 5 10 15

Lys Ser Phe Leu Ser Ala Leu
20

<210> SEQ ID NO 246
<211> LENGTH: 93
<212> TYPE: PRT
<213> ORGANISM: Artificial Sequence
<220> FEATURE:
<223> OTHER INFORMATION: pNOP39757 alt splice b

<400> SEQUENCE: 246

Asn Glu Lys Lys Lys Lys Glu Lys Leu Lys Arg Val Lys Ile Pro Leu
1 5 10 15

Val Leu Gln Ala Ser Gln Ala Tyr Ile Ala His Thr Ala Arg Thr Val
20 25 30

Ala Leu Lys Thr Ala Cys Thr Met Leu Glu Ile Thr Ser Met Trp Asn
35 40 45

Leu Gln Arg Pro Thr Tyr Asn His Ile Ser Ser Val Leu Lys Asp Cys
50 55 60

Gly Arg Ile Gln Leu Val Lys Asn Gly Cys Met Ala Val Gly Phe Thr
65 70 75 80

Asp Gln Met Lys His Ser Thr Trp Leu His Glu Asn Phe
85 90

<210> SEQ ID NO 247
<211> LENGTH: 22
<212> TYPE: PRT
<213> ORGANISM: Artificial Sequence
<220> FEATURE:
<223> OTHER INFORMATION: pNOP407746

<400> SEQUENCE: 247

Val Lys Ser Ser Asn Glu Asp Ser Ile Gln Leu Gly Cys Ser Gln Thr
1 5 10 15

Asp Arg Ser Phe Thr Gln
20

<210> SEQ ID NO 248
<211> LENGTH: 92
<212> TYPE: PRT
<213> ORGANISM: Artificial Sequence
<220> FEATURE:
<223> OTHER INFORMATION: pNOP40838 alt splice b

<400> SEQUENCE: 248

Asn Glu Lys Lys Lys Lys Glu Leu Lys Arg Val Lys Ile Pro Leu Val
1 5 10 15

Leu Gln Ala Ser Gln Ala Tyr Ile Ala His Thr Ala Arg Thr Val Ala
20 25 30

Leu Lys Thr Ala Cys Thr Met Leu Glu Ile Thr Ser Met Trp Asn Leu
35 40 45

Gln Arg Pro Thr Tyr Asn His Ile Ser Ser Val Leu Lys Asp Cys Gly
50 55 60

Arg Ile Gln Leu Val Lys Asn Gly Cys Met Ala Val Gly Phe Thr Asp
65 70 75 80

Gln Met Lys His Ser Thr Trp Leu His Glu Asn Phe
85 90

<210> SEQ ID NO 249
<211> LENGTH: 21
<212> TYPE: PRT
<213> ORGANISM: Artificial Sequence
<220> FEATURE:
<223> OTHER INFORMATION: pNOP416668

<400> SEQUENCE: 249

Lys Ser Ser Thr Arg Arg Ser Phe Ile Ser Asn Tyr Asn Gly Thr Ser
1 5 10 15

Ile Trp Leu Arg Lys
20

<210> SEQ ID NO 250
<211> LENGTH: 21
<212> TYPE: PRT
<213> ORGANISM: Artificial Sequence
<220> FEATURE:
<223> OTHER INFORMATION: pNOP425265

<400> SEQUENCE: 250

Thr Leu Gln Lys Trp Arg Asp Ser Ser Phe Thr Gly Thr Gln Leu Tyr
1               5                   10                  15

His Lys Thr Phe Ala
            20

<210> SEQ ID NO 251
<211> LENGTH: 20
<212> TYPE: PRT
<213> ORGANISM: Artificial Sequence
<220> FEATURE:
<223> OTHER INFORMATION: pNOP434493

<400> SEQUENCE: 251

Lys Ala His Gly His Gly Lys Asn Ser Lys Ser His Asp Gly Gln Gln
1               5                   10                  15

Val Pro Arg Tyr
            20

<210> SEQ ID NO 252
<211> LENGTH: 19
<212> TYPE: PRT
<213> ORGANISM: Artificial Sequence
<220> FEATURE:
<223> OTHER INFORMATION: pNOP448870

<400> SEQUENCE: 252

Cys Leu Lys Met Pro Asn Ala Ile Met Cys Pro Ile Gln Pro Ser Thr
1               5                   10                  15

Ser Glu Phe

<210> SEQ ID NO 253
<211> LENGTH: 19
<212> TYPE: PRT
<213> ORGANISM: Artificial Sequence
<220> FEATURE:
<223> OTHER INFORMATION: pNOP449322

<400> SEQUENCE: 253

Cys Thr Tyr Pro Gly Glu Val Thr Gln Gly Glu Lys Glu Arg Ala Gly
1               5                   10                  15

Pro Thr Ala

<210> SEQ ID NO 254
<211> LENGTH: 19
<212> TYPE: PRT
<213> ORGANISM: Artificial Sequence
<220> FEATURE:
<223> OTHER INFORMATION: pNOP452067

<400> SEQUENCE: 254

Gly Lys Met Leu Gln Arg Phe Phe Ser Arg Asn Ser Cys Cys Gly Ser
1               5                   10                  15

Gln Leu Ser

<210> SEQ ID NO 255

<211> LENGTH: 19
<212> TYPE: PRT
<213> ORGANISM: Artificial Sequence
<220> FEATURE:
<223> OTHER INFORMATION: pNOP453139

<400> SEQUENCE: 255

His Gly Phe Gln Glu Lys Lys Ser Tyr Leu Pro Phe Gln Gln Cys Gln
1               5                   10                  15

Arg Gly Leu

<210> SEQ ID NO 256
<211> LENGTH: 19
<212> TYPE: PRT
<213> ORGANISM: Artificial Sequence
<220> FEATURE:
<223> OTHER INFORMATION: pNOP460219

<400> SEQUENCE: 256

Gln Lys Phe Leu Leu Trp Ile Pro Thr Phe Leu Thr Asn His Pro Leu
1               5                   10                  15

His Leu Thr

<210> SEQ ID NO 257
<211> LENGTH: 19
<212> TYPE: PRT
<213> ORGANISM: Artificial Sequence
<220> FEATURE:
<223> OTHER INFORMATION: pNOP461097

<400> SEQUENCE: 257

Arg Phe Leu Trp Cys Cys Arg Pro Leu Arg Leu Thr Ser His Ile Gln
1               5                   10                  15

Pro Gly Leu

<210> SEQ ID NO 258
<211> LENGTH: 18
<212> TYPE: PRT
<213> ORGANISM: Artificial Sequence
<220> FEATURE:
<223> OTHER INFORMATION: pNOP471164

<400> SEQUENCE: 258

Glu Arg Gln Ala Asp Glu Glu Ile Gln Arg Ile Glu Glu Val Phe Thr
1               5                   10                  15

Leu Cys

<210> SEQ ID NO 259
<211> LENGTH: 18
<212> TYPE: PRT
<213> ORGANISM: Artificial Sequence
<220> FEATURE:
<223> OTHER INFORMATION: pNOP475150

<400> SEQUENCE: 259

Lys Ala Lys Gly Pro Thr Pro Pro Trp Gln Met Pro Ser Gly Ala Phe
1               5                   10                  15

Glu Ile

<210> SEQ ID NO 260
<211> LENGTH: 18
<212> TYPE: PRT
<213> ORGANISM: Artificial Sequence
<220> FEATURE:

<223> OTHER INFORMATION: pNOP475643

<400> SEQUENCE: 260

Lys Lys Lys Phe Leu Arg Val Thr Ile Thr Thr Lys Phe Gln Leu Val
1 5 10 15

Lys Phe

<210> SEQ ID NO 261
<211> LENGTH: 18
<212> TYPE: PRT
<213> ORGANISM: Artificial Sequence
<220> FEATURE:
<223> OTHER INFORMATION: pNOP484932 alt splice f

<400> SEQUENCE: 261

Ser Leu Gln Pro Pro Leu Ile Leu Val Val Pro Lys Glu Lys Val Lys
1 5 10 15

Arg Thr

<210> SEQ ID NO 262
<211> LENGTH: 17
<212> TYPE: PRT
<213> ORGANISM: Artificial Sequence
<220> FEATURE:
<223> OTHER INFORMATION: pNOP489695

<400> SEQUENCE: 262

Ala Gly Val Phe Asp Leu Gln Arg Cys Ser Cys Ser Thr Gln Ser Pro
1 5 10 15

Ala

<210> SEQ ID NO 263
<211> LENGTH: 17
<212> TYPE: PRT
<213> ORGANISM: Artificial Sequence
<220> FEATURE:
<223> OTHER INFORMATION: pNOP499515

<400> SEQUENCE: 263

Leu Lys Glu Lys Tyr Phe Phe Leu His Ile Thr Ser Leu Leu Gln Leu
1 5 10 15

Thr

<210> SEQ ID NO 264
<211> LENGTH: 17
<212> TYPE: PRT
<213> ORGANISM: Artificial Sequence
<220> FEATURE:
<223> OTHER INFORMATION: pNOP501126

<400> SEQUENCE: 264

Asn Ala His Ile Thr Thr Thr Asp Pro Asn Lys Thr Glu Glu Ser Arg
1 5 10 15

Ile

<210> SEQ ID NO 265
<211> LENGTH: 17
<212> TYPE: PRT
<213> ORGANISM: Artificial Sequence
<220> FEATURE:
<223> OTHER INFORMATION: pNOP505051

<400> SEQUENCE: 265

```
Arg His Asp Gly Trp Leu Ser Ala Arg Pro Ser Thr Phe Ala Gly Pro
1               5                   10                  15

Ser


<210> SEQ ID NO 266
<211> LENGTH: 16
<212> TYPE: PRT
<213> ORGANISM: Artificial Sequence
<220> FEATURE:
<223> OTHER INFORMATION: pNOP513619

<400> SEQUENCE: 266

Cys Gly Glu Arg Glu Lys Gly Lys Ile Ala Lys Arg Asn Arg Gly Arg
1               5                   10                  15


<210> SEQ ID NO 267
<211> LENGTH: 83
<212> TYPE: PRT
<213> ORGANISM: Artificial Sequence
<220> FEATURE:
<223> OTHER INFORMATION: pNOP51984 alt splice a

<400> SEQUENCE: 267

Leu Arg Pro Asn Thr Gln Thr Thr Leu Ser Gly Ser Ser Ala Ala Trp
1               5                   10                  15

Trp Gly Gln Asn Gly Glu Ile Leu Arg Gln Pro Arg Lys Gln Asn Met
            20                  25                  30

Lys Ser Gly Gln Leu Lys Leu Leu Ser Ser Arg Arg Glu Ser Glu Gln
        35                  40                  45

His Ser Asn Ser Ser Arg Val Leu Leu Pro Glu Gln Ala Pro Leu Trp
    50                  55                  60

Gly Leu Ser Trp Gly Trp Cys His His Gln His Gln Trp Gly Cys Ser
65                  70                  75                  80

Ile Ser Ser


<210> SEQ ID NO 268
<211> LENGTH: 16
<212> TYPE: PRT
<213> ORGANISM: Artificial Sequence
<220> FEATURE:
<223> OTHER INFORMATION: pNOP521733

<400> SEQUENCE: 268

Lys Arg Leu Lys Leu Asn Ile Met Lys Trp Leu Ser Gln Val Phe Glu
1               5                   10                  15


<210> SEQ ID NO 269
<211> LENGTH: 16
<212> TYPE: PRT
<213> ORGANISM: Artificial Sequence
<220> FEATURE:
<223> OTHER INFORMATION: pNOP531143

<400> SEQUENCE: 269

Ser Ile Gly Thr Ser Lys Lys Asp Glu Ser Asp Arg Phe Arg Asn Ile
1               5                   10                  15


<210> SEQ ID NO 270
<211> LENGTH: 16
<212> TYPE: PRT
<213> ORGANISM: Artificial Sequence
<220> FEATURE:
<223> OTHER INFORMATION: pNOP535461
```

<400> SEQUENCE: 270

Trp Pro Thr Ser Thr Lys Ile Leu Thr Leu Trp Leu Arg Thr Leu Ser
1 5 10 15

<210> SEQ ID NO 271
<211> LENGTH: 15
<212> TYPE: PRT
<213> ORGANISM: Artificial Sequence
<220> FEATURE:
<223> OTHER INFORMATION: pNOP548322

<400> SEQUENCE: 271

Leu Pro His Gln Arg Pro Ser Gly Phe Phe Thr Gln Arg Pro Thr
1 5 10 15

<210> SEQ ID NO 272
<211> LENGTH: 15
<212> TYPE: PRT
<213> ORGANISM: Artificial Sequence
<220> FEATURE:
<223> OTHER INFORMATION: pNOP550107

<400> SEQUENCE: 272

Asn Ile Pro Pro Gly Tyr Thr Lys Ile Ser Arg Lys Arg Ser Phe
1 5 10 15

<210> SEQ ID NO 273
<211> LENGTH: 15
<212> TYPE: PRT
<213> ORGANISM: Artificial Sequence
<220> FEATURE:
<223> OTHER INFORMATION: pNOP554243

<400> SEQUENCE: 273

Arg Ile Phe Ser Ser Leu Leu Glu Gly Asp Pro Gly Ala Ala Ser
1 5 10 15

<210> SEQ ID NO 274
<211> LENGTH: 15
<212> TYPE: PRT
<213> ORGANISM: Artificial Sequence
<220> FEATURE:
<223> OTHER INFORMATION: pNOP555796

<400> SEQUENCE: 274

Arg Thr Ile Leu Ile Arg Gly Val Ala Ala Ser Val Pro Tyr Phe
1 5 10 15

<210> SEQ ID NO 275
<211> LENGTH: 14
<212> TYPE: PRT
<213> ORGANISM: Artificial Sequence
<220> FEATURE:
<223> OTHER INFORMATION: pNOP566375

<400> SEQUENCE: 275

Glu Gly Ser Pro Pro Gln Cys His Ile Ser Glu Ala Ser Leu
1 5 10

<210> SEQ ID NO 276
<211> LENGTH: 14
<212> TYPE: PRT
<213> ORGANISM: Artificial Sequence
<220> FEATURE:
<223> OTHER INFORMATION: pNOP574911

<400> SEQUENCE: 276

Leu Leu Lys Ser Pro Trp Thr Trp Lys Lys Phe Glu Val Thr
1 5 10

<210> SEQ ID NO 277
<211> LENGTH: 14
<212> TYPE: PRT
<213> ORGANISM: Artificial Sequence
<220> FEATURE:
<223> OTHER INFORMATION: pNOP577711

<400> SEQUENCE: 277

Asn Ser Arg Gln Val Cys Gly His Val Cys Gln Gly Ile Leu
1 5 10

<210> SEQ ID NO 278
<211> LENGTH: 14
<212> TYPE: PRT
<213> ORGANISM: Artificial Sequence
<220> FEATURE:
<223> OTHER INFORMATION: pNOP585233

<400> SEQUENCE: 278

Ser Arg Leu Gln Thr Leu Gly Phe Val Pro Ser Asn Lys Lys
1 5 10

<210> SEQ ID NO 279
<211> LENGTH: 13
<212> TYPE: PRT
<213> ORGANISM: Artificial Sequence
<220> FEATURE:
<223> OTHER INFORMATION: pNOP590879

<400> SEQUENCE: 279

Ala His Lys Asn Val Leu Gln Lys Arg Ser Ile Ser Glu
1 5 10

<210> SEQ ID NO 280
<211> LENGTH: 13
<212> TYPE: PRT
<213> ORGANISM: Artificial Sequence
<220> FEATURE:
<223> OTHER INFORMATION: pNOP592931

<400> SEQUENCE: 280

Cys Ser Gly Thr Pro Ser Thr Phe Ala Lys His Thr Thr
1 5 10

<210> SEQ ID NO 281
<211> LENGTH: 78
<212> TYPE: PRT
<213> ORGANISM: Artificial Sequence
<220> FEATURE:
<223> OTHER INFORMATION: pNOP60025

<400> SEQUENCE: 281

Arg Cys Asp Glu Pro Arg Ser Gly Pro Tyr Gly Arg Asp Ser Ser Thr
1 5 10 15

Arg Trp Lys Ser Ile Trp Thr Thr Gly Gly Ser Phe Gly Ala Ser Arg
20 25 30

Ala Ala Gly Thr Thr Ser Ile Ser Arg Pro Thr Ser Ser Trp Thr Pro
35 40 45

Cys His Thr Ala Ala Asn Asn Thr His Val Cys Ser Ser Pro Thr Lys
50 55 60

Asp Pro Ala Ala Ser Ser Leu Arg Gly Leu Pro Glu Ile His 65 70 75

<210> SEQ ID NO 282
<211> LENGTH: 13
<212> TYPE: PRT
<213> ORGANISM: Artificial Sequence
<220> FEATURE:
<223> OTHER INFORMATION: pNOP601294

<400> SEQUENCE: 282

Lys Ile Lys Ile His Asp Ser Asn Ala Ala Glu Thr Lys
1 5 10

<210> SEQ ID NO 283
<211> LENGTH: 13
<212> TYPE: PRT
<213> ORGANISM: Artificial Sequence
<220> FEATURE:
<223> OTHER INFORMATION: pNOP603087

<400> SEQUENCE: 283

Leu Asp Glu Asn Pro Thr Glu Thr Lys Asn Gly Arg Val
1 5 10

<210> SEQ ID NO 284
<211> LENGTH: 13
<212> TYPE: PRT
<213> ORGANISM: Artificial Sequence
<220> FEATURE:
<223> OTHER INFORMATION: pNOP617063

<400> SEQUENCE: 284

Thr Ser Phe Ser Thr Ser Ala Ser Asp Pro Pro Gly Gln
1 5 10

<210> SEQ ID NO 285
<211> LENGTH: 13
<212> TYPE: PRT
<213> ORGANISM: Artificial Sequence
<220> FEATURE:
<223> OTHER INFORMATION: pNOP617777

<400> SEQUENCE: 285

Val Gly Arg Val Ala Phe Leu Leu Lys Asn Gln Asn Thr
1 5 10

<210> SEQ ID NO 286
<211> LENGTH: 13
<212> TYPE: PRT
<213> ORGANISM: Artificial Sequence
<220> FEATURE:
<223> OTHER INFORMATION: pNOP617867

<400> SEQUENCE: 286

Val Ile Arg Met Met Arg Glu Asp Ala Thr Ala Ile Leu
1 5 10

<210> SEQ ID NO 287
<211> LENGTH: 12
<212> TYPE: PRT
<213> ORGANISM: Artificial Sequence
<220> FEATURE:
<223> OTHER INFORMATION: pNOP622052

<400> SEQUENCE: 287

Ala Trp Leu Ser Ser Ile Gln Gly Cys Lys Phe Asn
1 5 10

<210> SEQ ID NO 288
<211> LENGTH: 12
<212> TYPE: PRT
<213> ORGANISM: Artificial Sequence
<220> FEATURE:
<223> OTHER INFORMATION: pNOP626183

<400> SEQUENCE: 288

Phe Lys Ser Leu Ser Thr Ile Phe Leu Cys Gln Ser
1 5 10

<210> SEQ ID NO 289
<211> LENGTH: 12
<212> TYPE: PRT
<213> ORGANISM: Artificial Sequence
<220> FEATURE:
<223> OTHER INFORMATION: pNOP626974 alt splice g

<400> SEQUENCE: 289

Gly Asp Trp Leu Phe Glu Ala Leu Val Val Leu Trp
1 5 10

<210> SEQ ID NO 290
<211> LENGTH: 12
<212> TYPE: PRT
<213> ORGANISM: Artificial Sequence
<220> FEATURE:
<223> OTHER INFORMATION: pNOP627099

<400> SEQUENCE: 290

Gly Phe Pro Leu Asp Leu Ser Cys Leu Thr Thr Ile
1 5 10

<210> SEQ ID NO 291
<211> LENGTH: 12
<212> TYPE: PRT
<213> ORGANISM: Artificial Sequence
<220> FEATURE:
<223> OTHER INFORMATION: pNOP632437

<400> SEQUENCE: 291

Lys Met Val Val Trp Leu Leu Val Leu Pro Thr Lys
1 5 10

<210> SEQ ID NO 292
<211> LENGTH: 76
<212> TYPE: PRT
<213> ORGANISM: Artificial Sequence
<220> FEATURE:
<223> OTHER INFORMATION: pNOP63453

<400> SEQUENCE: 292

Gln Val Gly Ser Asp Thr Gly Ser Ser Lys Thr Arg Arg Pro Phe Val
1 5 10 15

Glu Arg Thr Gly Glu Pro Pro Thr Leu Ser Leu Ala Glu Lys Gln Arg
20 25 30

Gly Pro His His His Gly Arg Cys Pro Leu Ala Pro Ser Arg Phe Asp
35 40 45

Ala Pro Gly His Pro Gln His Ser Pro Ser Ile Gln Pro Arg Lys Cys
50 55 60

Leu Ile Thr Ser Leu Arg Phe Phe Tyr Ile Glu Ala
65 70 75

<210> SEQ ID NO 293
<211> LENGTH: 12
<212> TYPE: PRT
<213> ORGANISM: Artificial Sequence
<220> FEATURE:
<223> OTHER INFORMATION: pNOP647364

<400> SEQUENCE: 293

Thr Phe Leu Pro Phe Ala Phe Lys Glu Lys Ile Pro
1 5 10

<210> SEQ ID NO 294
<211> LENGTH: 11
<212> TYPE: PRT
<213> ORGANISM: Artificial Sequence
<220> FEATURE:
<223> OTHER INFORMATION: pNOP656432

<400> SEQUENCE: 294

Glu Glu Tyr Arg Gln Leu Arg Gly Gln Ser Ser
1 5 10

<210> SEQ ID NO 295
<211> LENGTH: 11
<212> TYPE: PRT
<213> ORGANISM: Artificial Sequence
<220> FEATURE:
<223> OTHER INFORMATION: pNOP659059 alt splice g

<400> SEQUENCE: 295

Gly Asp Trp Leu Phe Glu Ala Leu Val Val Leu
1 5 10

<210> SEQ ID NO 296
<211> LENGTH: 11
<212> TYPE: PRT
<213> ORGANISM: Artificial Sequence
<220> FEATURE:
<223> OTHER INFORMATION: pNOP660715

<400> SEQUENCE: 296

Gly Thr Lys Ala Lys Lys Ser Thr Arg Leu Leu
1 5 10

<210> SEQ ID NO 297
<211> LENGTH: 11
<212> TYPE: PRT
<213> ORGANISM: Artificial Sequence
<220> FEATURE:
<223> OTHER INFORMATION: pNOP662459

<400> SEQUENCE: 297

Ile Gly Gln Ile Gln Lys Tyr Met Lys Met Gln
1 5 10

<210> SEQ ID NO 298
<211> LENGTH: 11
<212> TYPE: PRT
<213> ORGANISM: Artificial Sequence
<220> FEATURE:
<223> OTHER INFORMATION: pNOP669764

<400> SEQUENCE: 298

Asn His Leu Gly Ala Asn Gly Leu Glu Asn Asn
1 5 10

<210> SEQ ID NO 299

<211> LENGTH: 11
<212> TYPE: PRT
<213> ORGANISM: Artificial Sequence
<220> FEATURE:
<223> OTHER INFORMATION: pNOP679970

<400> SEQUENCE: 299

Ser Ser Arg Ala Arg Phe Arg Gln Lys Thr Leu
1 5 10

<210> SEQ ID NO 300
<211> LENGTH: 10
<212> TYPE: PRT
<213> ORGANISM: Artificial Sequence
<220> FEATURE:
<223> OTHER INFORMATION: pNOP694253

<400> SEQUENCE: 300

Gly Leu His Pro Thr Trp Leu Gln Pro Asp
1 5 10

<210> SEQ ID NO 301
<211> LENGTH: 10
<212> TYPE: PRT
<213> ORGANISM: Artificial Sequence
<220> FEATURE:
<223> OTHER INFORMATION: pNOP698245

<400> SEQUENCE: 301

Ile Thr Val Phe Cys Gln Asn Gln Ile Phe
1 5 10

<210> SEQ ID NO 302
<211> LENGTH: 10
<212> TYPE: PRT
<213> ORGANISM: Artificial Sequence
<220> FEATURE:
<223> OTHER INFORMATION: pNOP700951

<400> SEQUENCE: 302

Lys Trp Lys Ser Met Met Met Leu Ile Cys
1 5 10

<210> SEQ ID NO 303
<211> LENGTH: 10
<212> TYPE: PRT
<213> ORGANISM: Artificial Sequence
<220> FEATURE:
<223> OTHER INFORMATION: pNOP710206

<400> SEQUENCE: 303

Arg Cys Ser Arg Thr Ser Ala Val Phe Tyr
1 5 10

<210> SEQ ID NO 304
<211> LENGTH: 10
<212> TYPE: PRT
<213> ORGANISM: Artificial Sequence
<220> FEATURE:
<223> OTHER INFORMATION: pNOP712256

<400> SEQUENCE: 304

Arg Arg Cys Cys Phe Ser Cys Cys Thr Leu
1 5 10

<210> SEQ ID NO 305
<211> LENGTH: 10

<212> TYPE: PRT
<213> ORGANISM: Artificial Sequence
<220> FEATURE:
<223> OTHER INFORMATION: pNOP712598

<400> SEQUENCE: 305

Arg Arg Ser Trp Ser Ser Phe Leu Lys Pro
1 5 10

<210> SEQ ID NO 306
<211> LENGTH: 10
<212> TYPE: PRT
<213> ORGANISM: Artificial Sequence
<220> FEATURE:
<223> OTHER INFORMATION: pNOP713384

<400> SEQUENCE: 306

Arg Trp Ala Arg Gln Ser Gly His Ser Asp
1 5 10

<210> SEQ ID NO 307
<211> LENGTH: 10
<212> TYPE: PRT
<213> ORGANISM: Artificial Sequence
<220> FEATURE:
<223> OTHER INFORMATION: pNOP713614

<400> SEQUENCE: 307

Ser Ala Ile Ser Arg Leu Leu Cys Asn Asn
1 5 10

<210> SEQ ID NO 308
<211> LENGTH: 10
<212> TYPE: PRT
<213> ORGANISM: Artificial Sequence
<220> FEATURE:
<223> OTHER INFORMATION: pNOP717507

<400> SEQUENCE: 308

Thr Lys Thr Arg Arg Arg Lys Lys Arg Ser
1 5 10

<210> SEQ ID NO 309
<211> LENGTH: 64
<212> TYPE: PRT
<213> ORGANISM: Artificial Sequence
<220> FEATURE:
<223> OTHER INFORMATION: pNOP88057 alt splice c

<400> SEQUENCE: 309

Ala Ala Gly Glu Arg Ala Ser Ser Thr Ala Thr Ala Ala Glu Cys Phe
1 5 10 15

Ser Pro Ser Arg His Pro Cys Gly Gly Ser His Gly Gly Gly Ala Thr
20 25 30

Thr Asn Thr Asn Gly Asp Ala Gln Ser Ala Val Asp Thr Cys Cys Arg
35 40 45

His Asp Gly Trp Leu Ser Ala Arg Pro Ser Thr Phe Ala Gly Pro Ser
50 55 60

<210> SEQ ID NO 310
<211> LENGTH: 63
<212> TYPE: PRT
<213> ORGANISM: Artificial Sequence
<220> FEATURE:
<223> OTHER INFORMATION: pNOP91822 alt splice e

<400> SEQUENCE: 310

Lys Val Glu Met Met Ile Leu Lys Arg Trp Glu Lys Lys Ile Val Arg
1               5                   10                  15

Ser Leu Asn Leu Leu Leu Tyr Leu Ser Phe Arg Pro Pro Trp Pro Val
            20                  25                  30

Ser Trp Thr Ser Cys Pro Thr His Pro His Ser Leu Pro Gln Ser Leu
        35                  40                  45

Pro Lys Ala Val Gln Arg Arg Lys Ala Pro Asn Gly Lys Ser Thr
    50                  55                  60

<210> SEQ ID NO 311
<211> LENGTH: 140
<212> TYPE: PRT
<213> ORGANISM: Artificial Sequence
<220> FEATURE:
<223> OTHER INFORMATION: pNOP13160

<400> SEQUENCE: 311

Ala Val Leu Leu Met Gly Asn Cys Gln Cys Cys Ser Pro Thr Pro Ser
1               5                   10                  15

Thr Ser Trp Leu Arg Ser Ser Lys Ser Pro Arg Arg Thr Ser Gln Phe
            20                  25                  30

Leu Cys Pro Ser Arg Leu Ala Ala Gly Leu Gly Val Arg Leu Trp Gln
        35                  40                  45

Cys Pro His Thr Arg Ser Pro His Pro Pro Pro Ala Met Arg Val Gln
    50                  55                  60

Thr Arg Pro Leu Arg Ser Ala Val Leu Ser Thr Arg His Cys Ala Arg
65                  70                  75                  80

Leu Ser Ala Gln Pro Thr Arg Arg Gly Pro Pro Ala Leu Ser Pro Pro
                85                  90                  95

Thr Ser Pro Arg Cys Phe Leu Glu Arg Met Thr Ala Cys Cys Val Leu
            100                 105                 110

Thr Ala Tyr Ala Thr Thr Val Leu Ser Val Ile Trp Val Leu Ser Ser
        115                 120                 125

Ala Gln Ala Cys Cys Thr Trp Leu Arg Met Gly Cys
    130                 135                 140

<210> SEQ ID NO 312
<211> LENGTH: 43
<212> TYPE: PRT
<213> ORGANISM: Artificial Sequence
<220> FEATURE:
<223> OTHER INFORMATION: pNOP179558

<400> SEQUENCE: 312

Trp Ser Arg Thr Ser Pro Cys Gly Gly Ala Lys Gly Ser Ala Ser Ala
1               5                   10                  15

Gly Ser Thr Ser Ser Gly Ser Leu Thr Gly Gly Asn Ala Leu Ala Pro
            20                  25                  30

Thr Arg Pro Ser Ala Ser Glu Asp Cys Trp Pro
        35                  40

<210> SEQ ID NO 313
<211> LENGTH: 22
<212> TYPE: PRT
<213> ORGANISM: Artificial Sequence
<220> FEATURE:
<223> OTHER INFORMATION: pNOP403156

<400> SEQUENCE: 313

Gln Arg Gly Trp Glu Ser Gly Cys Gly Ser Ala His Thr Leu Ala Ala
1 5 10 15

Leu Thr His Pro Gln Gln
20

<210> SEQ ID NO 314
<211> LENGTH: 42
<212> TYPE: PRT
<213> ORGANISM: Artificial Sequence
<220> FEATURE:
<223> OTHER INFORMATION: pNOP185542

<400> SEQUENCE: 314

Val His Leu His Leu Tyr Leu His Ala Gly Ser Gly Arg His Ala Gly
1 5 10 15

Gln Pro Ser Gly Ala Glu His Leu Arg Ala Ala Ala Pro Arg Gly Gln
20 25 30

His Arg Pro Ala Pro Gln Ala Ala Glu Ala
35 40

<210> SEQ ID NO 315
<211> LENGTH: 67
<212> TYPE: PRT
<213> ORGANISM: Artificial Sequence
<220> FEATURE:
<223> OTHER INFORMATION: pNOP82605

<400> SEQUENCE: 315

Thr Ile Thr Ile Met Pro Ser Pro Pro Cys Arg Arg Lys Lys Thr Trp
1 5 10 15

Arg Gln Val Trp Ala Ala Ala Glu Phe Gln Ser Ala His Pro Ser Ser
20 25 30

Thr Gln Met Met Arg Met Thr Met Arg Met Thr Arg Arg Met Thr Cys
35 40 45

Arg Thr Pro Thr Leu Pro Leu Gly Ile Arg Gly Arg Glu Gln Gly Ser
50 55 60

Gln Gly His
65

<210> SEQ ID NO 316
<211> LENGTH: 49
<212> TYPE: PRT
<213> ORGANISM: Artificial Sequence
<220> FEATURE:
<223> OTHER INFORMATION: pNOP144488 alt splice a

<400> SEQUENCE: 316

Pro Trp Ala Leu Gly Gly Gly Arg Gly Val Asp Arg Gln Gly Pro Ala
1 5 10 15

Gly His His Gly Ala Tyr Arg Pro Arg His Cys Arg Gly Ala Leu Pro
20 25 30

Arg His Pro Leu Gln Pro Asp Gly Ser Gly Ala Arg Pro Gln Asp Gln
35 40 45

Val

<210> SEQ ID NO 317
<211> LENGTH: 24
<212> TYPE: PRT
<213> ORGANISM: Artificial Sequence
<220> FEATURE:
<223> OTHER INFORMATION: pNOP372160

<400> SEQUENCE: 317

Ser Leu Gln Ala Ala Ala Ser Met Gly Phe Thr Pro Thr Pro Leu Pro
1 5 10 15

Leu Ser Ser Gly Cys Arg Pro Phe
20

<210> SEQ ID NO 318
<211> LENGTH: 22
<212> TYPE: PRT
<213> ORGANISM: Artificial Sequence
<220> FEATURE:
<223> OTHER INFORMATION: pNOP396500

<400> SEQUENCE: 318

Gly Val Gln Val Ser Gln Gln Gln Val Pro Ala Gly Ala Gly Ser Lys
1 5 10 15

Gln Gly Pro Cys Ser Leu
20

<210> SEQ ID NO 319
<211> LENGTH: 90
<212> TYPE: PRT
<213> ORGANISM: Artificial Sequence
<220> FEATURE:
<223> OTHER INFORMATION: pNOP42739

<400> SEQUENCE: 319

Gly Gln Pro His Arg Trp Cys Arg Gly Gly Gly Trp Phe Met Arg Thr
1 5 10 15

Ser Pro Ile Pro Gln Pro Ser Gln Gln Thr Gln Ala Ser Gly Glu Ala
20 25 30

Ser Arg Gln Gln Pro Gln Trp Gly Ser Pro Gln Pro His Ser His Cys
35 40 45

Pro Ala Ala Ala Gly Leu Ser Arg Gln Ser Gln Leu Cys Gln Val Pro
50 55 60

His Ala Gly Gly Arg Arg Pro Gly Gly Arg Cys Gly Pro Gln Pro Ser
65 70 75 80

Ser Ser Pro Pro Thr Pro Ala Val Leu Arg
85 90

<210> SEQ ID NO 320
<211> LENGTH: 17
<212> TYPE: PRT
<213> ORGANISM: Artificial Sequence
<220> FEATURE:
<223> OTHER INFORMATION: pNOP492413

<400> SEQUENCE: 320

Glu Ala Gln Arg Val Pro Glu Gly Pro Leu Asn Ser Ser Val His Gln
1 5 10 15

Asp

<210> SEQ ID NO 321
<211> LENGTH: 75
<212> TYPE: PRT
<213> ORGANISM: Artificial Sequence
<220> FEATURE:
<223> OTHER INFORMATION: pNOP64587 alt splice b

<400> SEQUENCE: 321

Gly Trp Gly Ala Glu Ser Pro Gly Ala Asp Arg Gly Trp Glu Gly Phe 1 5 10 15

Leu Ala Leu His Gln Thr Asn Pro Arg Gln Pro Gly Val Gln Gln Pro
20 25 30

Ser Gly Glu Gly Gly Arg Gly Ser His Gly Gln Gln Arg Glu Asp Gly
35 40 45

Asp Gly Glu Ala Trp Arg Ala Leu Glu Trp Gly Glu Ile Leu Thr Gln
50 55 60

Gly Ala Ala Gly Thr Ala Glu Val Cys Gly Gly
65 70 75

<210> SEQ ID NO 322
<211> LENGTH: 63
<212> TYPE: PRT
<213> ORGANISM: Artificial Sequence
<220> FEATURE:
<223> OTHER INFORMATION: pNOP91275

<400> SEQUENCE: 322

Phe Arg Pro Thr Ser Leu Lys Ser His Ser Cys Leu Arg Ser Pro Ser
1 5 10 15

Gln Pro Ala Thr Ser Pro Arg Trp Cys Trp Lys Gln Thr Gly Pro Leu
20 25 30

Gln Pro Leu Arg Ala Thr Thr Gln Met Val Gln Arg Arg Arg Leu Val
35 40 45

His Ala His Lys Pro His Pro Thr Ala Leu Pro Thr Asn Pro Ser
50 55 60

<210> SEQ ID NO 323
<211> LENGTH: 60
<212> TYPE: PRT
<213> ORGANISM: Artificial Sequence
<220> FEATURE:
<223> OTHER INFORMATION: pNOP100199 alt splice b

<400> SEQUENCE: 323

Gly Trp Gly Ala Glu Ser Pro Gly Ala Asp Arg Gly Trp Glu Gly Phe
1 5 10 15

Leu Ala Leu His Gln Thr Asn Pro Arg Gln Pro Gly Val Gln Gln Pro
20 25 30

Ser Gly Glu Gly Gly Arg Gly Ser His Gly Gln Gln Arg Glu Asp Gly
35 40 45

Asp Gly Ala Ala Gly Thr Ala Glu Val Cys Gly Gly
50 55 60

<210> SEQ ID NO 324
<211> LENGTH: 46
<212> TYPE: PRT
<213> ORGANISM: Artificial Sequence
<220> FEATURE:
<223> OTHER INFORMATION: pNOP159625

<400> SEQUENCE: 324

Pro Ala Glu Thr Leu Ser Pro Leu Gln Gly Gln Ala Pro Val Arg Thr
1 5 10 15

Ala Gly Pro Asp Ser Ala Ala His Ser Cys Arg Val Ala Leu Thr Arg
20 25 30

Val Leu Pro Cys Pro Thr Ser Pro Phe Pro Ser Ile Thr Glu
35 40 45

<210> SEQ ID NO 325

<211> LENGTH: 45
<212> TYPE: PRT
<213> ORGANISM: Artificial Sequence
<220> FEATURE:
<223> OTHER INFORMATION: pNOP163874

<400> SEQUENCE: 325

His Val Leu Cys Pro Pro Ala Asp Thr Gln Leu Leu Cys Asn Ser Cys
1 5 10 15

Leu Ala Glu Arg Ala Pro Glu Leu Gln Gln Arg Gly Pro Gly Thr His
20 25 30

Pro Glu Ser His Glu Gly Leu His Gln Gly Phe Gln Pro
35 40 45

<210> SEQ ID NO 326
<211> LENGTH: 45
<212> TYPE: PRT
<213> ORGANISM: Artificial Sequence
<220> FEATURE:
<223> OTHER INFORMATION: pNOP165665 alt splice c

<400> SEQUENCE: 326

Gln Arg Val Gly Arg Val Pro Arg Pro Pro Ser Asp Gln Ser Lys Ala
1 5 10 15

Ala Arg Gly Pro Ala Ala Gln Trp Arg Arg Arg Ser Trp Lys Pro Arg
20 25 30

Thr Ala Glu Arg Arg Arg Gly Trp Ser Cys Trp His Cys
35 40 45

<210> SEQ ID NO 327
<211> LENGTH: 43
<212> TYPE: PRT
<213> ORGANISM: Artificial Sequence
<220> FEATURE:
<223> OTHER INFORMATION: pNOP178195 alt splice d

<400> SEQUENCE: 327

Arg Ser Thr Pro Leu Thr Met Gly Pro Gly Gly Arg Thr Arg Ser Gly
1 5 10 15

Gln Thr Arg Pro Gly Gly Ser Ser Trp Ser Val Ser Ala Ser Pro Leu
20 25 30

Gln Gly Ser Pro Thr Thr Thr Ser Ala Ser Thr
35 40

<210> SEQ ID NO 328
<211> LENGTH: 43
<212> TYPE: PRT
<213> ORGANISM: Artificial Sequence
<220> FEATURE:
<223> OTHER INFORMATION: pNOP178196 alt splice d

<400> SEQUENCE: 328

Arg Ser Thr Pro Leu Thr Met Gly Pro Gly Gly Arg Thr Arg Ser Gly
1 5 10 15

Gln Thr Arg Pro Gly Gly Ser Ser Trp Ser Val Ser Ala Ser Pro Leu
20 25 30

Gln Gly Ser Ser Met Arg Pro Gly Cys Met Cys
35 40

<210> SEQ ID NO 329
<211> LENGTH: 40
<212> TYPE: PRT
<213> ORGANISM: Artificial Sequence
<220> FEATURE:
<223> OTHER INFORMATION: pNOP194903

<400> SEQUENCE: 329

Gly Gln Ala Ala Cys Ala Glu Gly Glu Pro Ser Asp Ser Thr Arg Gly
1               5                   10                  15

Ser Ala Ala Ala Asp Lys Ser Asn Thr Ala Arg Ala Asp Ser Asp Pro
            20                  25                  30

Gln Val Ser Arg Val Thr Ala Ala
        35                  40

<210> SEQ ID NO 330
<211> LENGTH: 40
<212> TYPE: PRT
<213> ORGANISM: Artificial Sequence
<220> FEATURE:
<223> OTHER INFORMATION: pNOP197712 alt splice c

<400> SEQUENCE: 330

Gln Arg Val Gly Arg Val Pro Arg Pro Pro Ser Asp Gln Ser Lys Ala
1               5                   10                  15

Ala Arg Gly Pro Ala Ala Gln Trp Arg Arg Arg Ser Trp Lys Pro Arg
            20                  25                  30

Thr Ala Glu Arg Arg Arg Gly Trp
        35                  40

<210> SEQ ID NO 331
<211> LENGTH: 37
<212> TYPE: PRT
<213> ORGANISM: Artificial Sequence
<220> FEATURE:
<223> OTHER INFORMATION: pNOP216613

<400> SEQUENCE: 331

Asp Arg Gln Cys Phe Gln Leu Ala Thr Ala Leu Ala Tyr Pro Leu Ser
1               5                   10                  15

Gln Pro Asp Ala Ala Leu Gln Pro Cys His Leu Pro His Leu Gln Gly
            20                  25                  30

Ala Phe Trp Arg Gly
        35

<210> SEQ ID NO 332
<211> LENGTH: 36
<212> TYPE: PRT
<213> ORGANISM: Artificial Sequence
<220> FEATURE:
<223> OTHER INFORMATION: pNOP229607

<400> SEQUENCE: 332

Arg Arg Gly Arg Ser Ser Arg Leu Met Thr Arg Glu Gly Pro Thr Thr
1               5                   10                  15

Thr Met Ser Ser Ser Ala Pro Leu Ser Pro Cys Trp Leu Arg Lys Ala
            20                  25                  30

Cys Trp Pro Thr
        35

<210> SEQ ID NO 333
<211> LENGTH: 36
<212> TYPE: PRT
<213> ORGANISM: Artificial Sequence
<220> FEATURE:
<223> OTHER INFORMATION: pNOP231133 alt splice e

<400> SEQUENCE: 333

Val Gly Arg Asn Thr His Pro Ser Cys Leu Leu Leu Val Gly Leu Cys
1 5 10 15

Cys Trp Pro Ala Pro Ile Arg Gly Ala Met Leu Gly Phe Gly Arg Ser
20 25 30

Cys Trp His Cys
35

<210> SEQ ID NO 334
<211> LENGTH: 31
<212> TYPE: PRT
<213> ORGANISM: Artificial Sequence
<220> FEATURE:
<223> OTHER INFORMATION: pNOP277235 alt splice a

<400> SEQUENCE: 334

Pro Trp Ala Leu Gly Gly Gly Arg Gly Val Asp Arg Gln Gly Pro Ala
1 5 10 15

Gly His His Gly Ala Tyr Arg Pro Arg His Cys Arg Asp Gln Val
20 25 30

<210> SEQ ID NO 335
<211> LENGTH: 98
<212> TYPE: PRT
<213> ORGANISM: Artificial Sequence
<220> FEATURE:
<223> OTHER INFORMATION: pNOP34900 alt splice b

<400> SEQUENCE: 335

Gly Trp Gly Ala Glu Ser Pro Gly Ala Asp Arg Gly Trp Glu Gly Phe
1 5 10 15

Leu Ala Leu His Gln Thr Asn Pro Arg Gln Pro Gly Val Gln Gln Pro
20 25 30

Ser Gly Glu Gly Gly Arg Gly Ser His Gly Gln Gln Arg Glu Asp Gly
35 40 45

Asp Gly Glu Ala Trp Arg Ala Leu Glu Trp Gly Glu Ile Leu Thr Gln
50 55 60

Ala Ala Tyr Cys Ser Trp Gly Phe Val Ala Gly Pro Pro Arg Ser Glu
65 70 75 80

Val Gln Cys Trp Val Leu Ala Gly Ala Ala Gly Thr Ala Glu Val Cys
85 90 95

Gly Gly

<210> SEQ ID NO 336
<211> LENGTH: 21
<212> TYPE: PRT
<213> ORGANISM: Artificial Sequence
<220> FEATURE:
<223> OTHER INFORMATION: pNOP410821

<400> SEQUENCE: 336

Cys Ser Ala Asp His Gly Gly Val Pro Leu Cys Gln Leu Cys Ala Tyr
1 5 10 15

His Arg Pro Ala Leu
20

<210> SEQ ID NO 337
<211> LENGTH: 17
<212> TYPE: PRT
<213> ORGANISM: Artificial Sequence
<220> FEATURE:

<223> OTHER INFORMATION: pNOP508542

<400> SEQUENCE: 337

Ser Val Trp Arg Leu Arg Leu Gln Thr Met Arg Arg Ala Ser Arg Arg
1               5                   10                  15

Arg

<210> SEQ ID NO 338
<211> LENGTH: 17
<212> TYPE: PRT
<213> ORGANISM: Artificial Sequence
<220> FEATURE:
<223> OTHER INFORMATION: pNOP511363

<400> SEQUENCE: 338

Trp Gln Trp Cys Pro Thr Ala Gly Ser Ser Met Arg Pro Gly Cys Met
1               5                   10                  15

Cys

<210> SEQ ID NO 339
<211> LENGTH: 16
<212> TYPE: PRT
<213> ORGANISM: Artificial Sequence
<220> FEATURE:
<223> OTHER INFORMATION: pNOP516062

<400> SEQUENCE: 339

Glu Gln Arg Ile Cys Asp Trp Gln Cys Pro Gly Val Gly Gln Gly Pro
1               5                   10                  15

<210> SEQ ID NO 340
<211> LENGTH: 83
<212> TYPE: PRT
<213> ORGANISM: Artificial Sequence
<220> FEATURE:
<223> OTHER INFORMATION: pNOP51715 alt splice b

<400> SEQUENCE: 340

Gly Trp Gly Ala Glu Ser Pro Gly Ala Asp Arg Gly Trp Glu Gly Phe
1               5                   10                  15

Leu Ala Leu His Gln Thr Asn Pro Arg Gln Pro Gly Val Gln Gln Pro
            20                  25                  30

Ser Gly Glu Gly Gly Arg Gly Ser His Gly Gln Gln Arg Glu Asp Gly
        35                  40                  45

Asp Ala Ala Tyr Cys Ser Trp Gly Phe Val Ala Gly Pro Pro Arg Ser
    50                  55                  60

Glu Val Gln Cys Trp Val Leu Ala Gly Ala Ala Gly Thr Ala Glu Val
65                  70                  75                  80

Cys Gly Gly

<210> SEQ ID NO 341
<211> LENGTH: 15
<212> TYPE: PRT
<213> ORGANISM: Artificial Sequence
<220> FEATURE:
<223> OTHER INFORMATION: pNOP543182

<400> SEQUENCE: 341

Gly Val Pro Gln Gly Gly Gly Arg Glu Glu Glu Glu Val Gln Asp
1               5                   10                  15

<210> SEQ ID NO 342

```
<211> LENGTH: 15
<212> TYPE: PRT
<213> ORGANISM: Artificial Sequence
<220> FEATURE:
<223> OTHER INFORMATION: pNOP560984

<400> SEQUENCE: 342

Trp Ala Thr Val Ser Ala Ala Ala Gln His His Gln Arg Leu Gly
1               5                   10                  15


<210> SEQ ID NO 343
<211> LENGTH: 14
<212> TYPE: PRT
<213> ORGANISM: Artificial Sequence
<220> FEATURE:
<223> OTHER INFORMATION: pNOP568350

<400> SEQUENCE: 343

Gly Glu Gly Asn Arg Glu Ala Arg Gly Ile Glu Arg Phe Cys
1               5                   10


<210> SEQ ID NO 344
<211> LENGTH: 13
<212> TYPE: PRT
<213> ORGANISM: Artificial Sequence
<220> FEATURE:
<223> OTHER INFORMATION: pNOP613742

<400> SEQUENCE: 344

Ser Gly Ser Cys His Gln His Arg Pro Ala Ala Pro Gly
1               5                   10


<210> SEQ ID NO 345
<211> LENGTH: 13
<212> TYPE: PRT
<213> ORGANISM: Artificial Sequence
<220> FEATURE:
<223> OTHER INFORMATION: pNOP617773 alt splice e

<400> SEQUENCE: 345

Val Gly Arg Asn Thr His Pro Arg Ser Cys Trp His Cys
1               5                   10


<210> SEQ ID NO 346
<211> LENGTH: 10
<212> TYPE: PRT
<213> ORGANISM: Artificial Sequence
<220> FEATURE:
<223> OTHER INFORMATION: pNOP706421

<400> SEQUENCE: 346

Pro Cys Gln Ala Arg Ala Thr Pro Pro Pro
1               5                   10


<210> SEQ ID NO 347
<211> LENGTH: 10
<212> TYPE: PRT
<213> ORGANISM: Artificial Sequence
<220> FEATURE:
<223> OTHER INFORMATION: pNOP716714

<400> SEQUENCE: 347

Thr Ala Ala Ala Trp Thr Trp Asp Pro Pro
1               5                   10


<210> SEQ ID NO 348
<211> LENGTH: 10
```

<212> TYPE: PRT
<213> ORGANISM: Artificial Sequence
<220> FEATURE:
<223> OTHER INFORMATION: pNOP722094

<400> SEQUENCE: 348

Tyr Pro Thr Leu Val Gln Leu Met Pro Cys
1               5                   10

<210> SEQ ID NO 349
<211> LENGTH: 70
<212> TYPE: PRT
<213> ORGANISM: Artificial Sequence
<220> FEATURE:
<223> OTHER INFORMATION: pNOP75322

<400> SEQUENCE: 349

Arg Thr Ser Pro Arg Val Ser Ala Leu Arg Ala Lys Asp Met Arg Leu
1               5                   10                  15

Ala Met Pro Arg Ser Trp Pro Arg Pro Ile Ile Ala Met Pro Gly Pro
            20                  25                  30

Ser His Ala Thr Ser Leu Arg Ser Arg Met Ala Leu Val Gln Cys Gly
        35                  40                  45

Pro Trp Arg Arg Ser Thr Leu Ser Ala Met Cys Leu Ser Gln Ala Gly
    50                  55                  60

Ser Leu Ser Trp Met Gly
65                  70

<210> SEQ ID NO 350
<211> LENGTH: 69
<212> TYPE: PRT
<213> ORGANISM: Artificial Sequence
<220> FEATURE:
<223> OTHER INFORMATION: pNOP76739

<400> SEQUENCE: 350

Ile Arg Ala Gly Trp Ser Trp Arg Ala Thr Gln Ala Ser Ser Pro Cys
1               5                   10                  15

Ser Trp Lys Ile Ser Val Ser Arg Gly Cys Lys Trp Arg Arg Ser Thr
            20                  25                  30

Thr Phe Arg Ala Asn Val Arg Ala Leu Tyr Met Asp Leu Ser Ser Cys
        35                  40                  45

Ser Asn Gly Ser Lys Ser Ala Gly Pro Gly Glu Arg Ser Leu Pro Trp
    50                  55                  60

Trp Met Ile Arg Pro
65

<210> SEQ ID NO 351
<211> LENGTH: 68
<212> TYPE: PRT
<213> ORGANISM: Artificial Sequence
<220> FEATURE:
<223> OTHER INFORMATION: pNOP79648 alt splice c

<400> SEQUENCE: 351

Gln Arg Val Gly Arg Val Pro Arg Pro Pro Ser Asp Gln Ser Lys Ala
1               5                   10                  15

Ala Arg Gly Pro Ala Ala Gln Trp Arg Arg Arg Ser Trp Lys Pro Arg
            20                  25                  30

Thr Ala Glu Arg Arg Arg Gly Cys Cys Leu Leu Leu Val Gly Leu Cys
        35                  40                  45

Cys Trp Pro Ala Pro Ile Arg Gly Ala Met Leu Gly Phe Gly Arg Ser
    50                  55                  60

Cys Trp His Cys
65

<210> SEQ ID NO 352
<211> LENGTH: 64
<212> TYPE: PRT
<213> ORGANISM: Artificial Sequence
<220> FEATURE:
<223> OTHER INFORMATION: pNOP88716

<400> SEQUENCE: 352

Gly Leu Ala Gly Ala Gly Glu Arg Pro Arg Pro Leu His Pro Ala Arg
1               5                   10                  15

Gly Arg Phe Arg Cys Gln Gly Gly Ala Ser Gly Gly Asp Leu Arg Pro
            20                  25                  30

Ser Glu Gln Met Ser Gly Pro Cys Ile Trp Ile Tyr Leu Pro Val Gln
        35                  40                  45

Met Asp Arg Arg Ala Pro Val Pro Ala Lys Gly Leu Tyr Leu Gly Gly
    50                  55                  60

<210> SEQ ID NO 353
<211> LENGTH: 140
<212> TYPE: PRT
<213> ORGANISM: Artificial Sequence
<220> FEATURE:
<223> OTHER INFORMATION: pNOP13160

<400> SEQUENCE: 353

Ala Val Leu Leu Met Gly Asn Cys Gln Cys Cys Ser Pro Thr Pro Ser
1               5                   10                  15

Thr Ser Trp Leu Arg Ser Ser Lys Ser Pro Arg Arg Thr Ser Gln Phe
            20                  25                  30

Leu Cys Pro Ser Arg Leu Ala Ala Gly Leu Gly Val Arg Leu Trp Gln
        35                  40                  45

Cys Pro His Thr Arg Ser Pro His Pro Pro Pro Ala Met Arg Val Gln
    50                  55                  60

Thr Arg Pro Leu Arg Ser Ala Val Leu Ser Thr Arg His Cys Ala Arg
65                  70                  75                  80

Leu Ser Ala Gln Pro Thr Arg Arg Gly Pro Pro Ala Leu Ser Pro Pro
                85                  90                  95

Thr Ser Pro Arg Cys Phe Leu Glu Arg Met Thr Ala Cys Cys Val Leu
            100                 105                 110

Thr Ala Tyr Ala Thr Thr Val Leu Ser Val Ile Trp Val Leu Ser Ser
        115                 120                 125

Ala Gln Ala Cys Cys Thr Trp Leu Arg Met Gly Cys
    130                 135                 140

<210> SEQ ID NO 354
<211> LENGTH: 43
<212> TYPE: PRT
<213> ORGANISM: Artificial Sequence
<220> FEATURE:
<223> OTHER INFORMATION: pNOP179558

<400> SEQUENCE: 354

Trp Ser Arg Thr Ser Pro Cys Gly Gly Ala Lys Gly Ser Ala Ser Ala
1               5                   10                  15

Gly Ser Thr Ser Ser Gly Ser Leu Thr Gly Gly Asn Ala Leu Ala Pro

```
            20                  25                  30

Thr Arg Pro Ser Ala Ser Glu Asp Cys Trp Pro
        35                  40


<210> SEQ ID NO 355
<211> LENGTH: 22
<212> TYPE: PRT
<213> ORGANISM: Artificial Sequence
<220> FEATURE:
<223> OTHER INFORMATION: pNOP403156

<400> SEQUENCE: 355

Gln Arg Gly Trp Glu Ser Gly Cys Gly Ser Ala His Thr Leu Ala Ala
1               5                   10                  15

Leu Thr His Pro Gln Gln
            20


<210> SEQ ID NO 356
<211> LENGTH: 60
<212> TYPE: PRT
<213> ORGANISM: Artificial Sequence
<220> FEATURE:
<223> OTHER INFORMATION: pNOP100723

<400> SEQUENCE: 356

Leu Leu Thr Ser Ser Phe Phe Leu Thr Met Gln Ser Pro Ile Ile Ser
1               5                   10                  15

Gln Ile Leu Leu Asn Ile Lys Pro Leu Ala Asn Ser Gly Ile Cys Thr
            20                  25                  30

Phe Glu Gln Glu Met Ser Leu Phe Arg Lys Glu Lys Gln Met Thr Lys
        35                  40                  45

Met Met Met Lys Met Gly Lys Thr Ile Arg Ala Gln
    50                  55                  60


<210> SEQ ID NO 357
<211> LENGTH: 125
<212> TYPE: PRT
<213> ORGANISM: Artificial Sequence
<220> FEATURE:
<223> OTHER INFORMATION: pNOP18284

<400> SEQUENCE: 357

Ala Ser Val Trp Ser Cys Leu Ser Arg Asn Thr Leu Ser Tyr Ala Gln
1               5                   10                  15

Lys Thr Ser Glu Met Arg Met Phe Leu Ser Val Asn His Gly Ile Leu
            20                  25                  30

Pro Lys Pro Asn Leu Leu Arg Lys Leu Asn Cys Gly Pro Cys Pro Ser
        35                  40                  45

Ala Gln Ser Gly Leu Ser Leu Gly Met Cys Leu Cys Leu Trp Phe Ala
    50                  55                  60

Trp Pro Leu Tyr Leu Gln Met Gln Ile Lys Val Met Met Arg Arg Ile
65                  70                  75                  80

Gln Thr Thr Gln Arg Thr Val Glu Leu Lys Thr Ile Leu Thr Trp Lys
                85                  90                  95

Arg Lys Lys Lys Met Ser Leu Trp Lys Cys Pro Met Val Asn Gln Val
            100                 105                 110

Ala Thr Thr Leu Ser Ser Ser Ile Thr Met Thr Cys Gly
        115                 120                 125


<210> SEQ ID NO 358
```

<211> LENGTH: 47
<212> TYPE: PRT
<213> ORGANISM: Artificial Sequence
<220> FEATURE:
<223> OTHER INFORMATION: pNOP152717

<400> SEQUENCE: 358

Gly Leu Gln His Gln Val Glu Val His Met Asp Asn Arg Trp Glu Phe
1 5 10 15

Trp Gly Leu Gln Gly Ser Arg His His Leu His Ile Pro Ala His Ile
20 25 30

Gln Leu Asp Pro Leu Ser Tyr Ser Ser Gln Gln His Pro Cys Leu
35 40 45

<210> SEQ ID NO 359
<211> LENGTH: 51
<212> TYPE: PRT
<213> ORGANISM: Artificial Sequence
<220> FEATURE:
<223> OTHER INFORMATION: pNOP136779

<400> SEQUENCE: 359

Trp Val Ala Ile Arg Gln Ala Phe His Leu Cys Arg Ala Gln Leu Met
1 5 10 15

Ala Leu Leu Ala Trp Ala Ala Cys Ser His Phe Thr Leu Gly Gly Leu
20 25 30

His Pro Thr Ile Phe Arg Gln Val Cys Leu Ala Ser Arg Ala Ser His
35 40 45

His Arg Val
50

<210> SEQ ID NO 360
<211> LENGTH: 90
<212> TYPE: PRT
<213> ORGANISM: Artificial Sequence
<220> FEATURE:
<223> OTHER INFORMATION: pNOP42654

<400> SEQUENCE: 360

Glu Thr Ser Ala Ser Cys Asn Ile Gln Ala Thr Ala Gly Tyr Tyr His
1 5 10 15

Ser Ser Ser Ile Ser Thr Tyr Ser Cys Ser Thr Ile Thr Ser Ser Asp
20 25 30

Ser Arg Ile Asn Asn Cys Arg Leu Thr Ala Leu Ile Ser Ala Ser Thr
35 40 45

Ala Ser Thr Cys Pro Ser His Asn Thr Leu Ile Thr Ser Thr Ser Asn
50 55 60

Arg Ala Ser Gly Leu Ala Thr Tyr Thr Asn Asn Ser Ser Asn Gly Ser
65 70 75 80

Thr Ser Thr Leu Thr Ser Arg Cys Ser Ser
85 90

<210> SEQ ID NO 361
<211> LENGTH: 96
<212> TYPE: PRT
<213> ORGANISM: Artificial Sequence
<220> FEATURE:
<223> OTHER INFORMATION: pNOP36509

<400> SEQUENCE: 361

Cys Leu Gly Phe Lys Pro Thr Val Cys Gln Cys Thr Ala Ala Val Leu
1 5 10 15

```
Ser Cys Thr Val Ser Ser Asn His Ile Leu Ser Arg Thr Asp Met Ser
            20                  25                  30

Asn Ser Leu Trp Cys Asp Ile Thr Leu Phe Thr Asp Asn Ser Thr Asn
        35                  40                  45

Cys Thr Glu Leu Cys Pro Ala Lys Ser Ser Val Tyr Pro Gly Ala Thr
    50                  55                  60

Asp Phe His Ser Ser Ser Thr Arg Ser Gly Gly Thr Ala Ser Arg Ser
65                  70                  75                  80

Ser Asp Tyr Asn Ser Cys Thr Arg Ala Ala Ser Ala Leu Ala Ala Ile
                85                  90                  95
```

<210> SEQ ID NO 362
<211> LENGTH: 91
<212> TYPE: PRT
<213> ORGANISM: Artificial Sequence
<220> FEATURE:
<223> OTHER INFORMATION: pNOP42302

<400> SEQUENCE: 362

```
Thr Arg Ala Ser Pro Pro Arg Ser Ser Ser Ala Ile Ala Val Arg Ala
1               5                   10                  15

Ser Cys Cys Pro Tyr Gly Ser Thr Ser Thr Ala Ser Arg Ser Pro Thr
            20                  25                  30

Gln Arg Cys Arg Leu Ala Arg Ala Ala Ala Ser Thr Ala Thr Glu Val
        35                  40                  45

Thr Phe Gly Ser Ser Glu Met Gln Gly His Thr Met Gly Phe Trp Leu
    50                  55                  60

Thr Lys Leu Asn Tyr Leu Cys His Leu Ser Met Leu Thr Asp Ser Leu
65                  70                  75                  80

Phe Leu Pro Ile Ser His Cys Gln Cys Ile Leu
                85                  90
```

<210> SEQ ID NO 363
<211> LENGTH: 31
<212> TYPE: PRT
<213> ORGANISM: Artificial Sequence
<220> FEATURE:
<223> OTHER INFORMATION: pNOP279502

<400> SEQUENCE: 363

```
Ser Ser Leu Arg Ile Thr Gly Asp Trp Thr Ser Ser Gly Arg Ser Thr
1               5                   10                  15

Lys Ile Trp Lys Thr Thr Gln Met Cys Arg Lys Thr Trp Ser Gly
            20                  25                  30
```

<210> SEQ ID NO 364
<211> LENGTH: 105
<212> TYPE: PRT
<213> ORGANISM: Artificial Sequence
<220> FEATURE:
<223> OTHER INFORMATION: pNOP29645

<400> SEQUENCE: 364

```
Arg Arg Arg Arg Gly Gly Val Gly Arg Arg Gly Val Arg Pro Gly Arg
1               5                   10                  15

Val Arg Pro Gly Gly Thr Gly Arg Arg Gly Gly Asp Gly Gly Arg Ala
            20                  25                  30

Ala Ala Ala Arg Ala Ala Leu Gly Glu Leu Ala Arg Ala Leu Pro Gly
        35                  40                  45
```

```
His Leu Leu Gln Ser Gln Ser Ala Arg Arg Ala Ala Arg Met Ala Gln
    50                  55                  60

Leu Arg Arg Arg Ala Ala Ala Leu Pro Asn Ala Ala Ala Trp His Gly
65                  70                  75                  80

Pro Pro His Pro Gln Leu Pro Ser Val Tyr Ser Glu Arg Ala Met Pro
                85                  90                  95

Pro Gly Cys Pro Glu Pro Ser Gln Ala
            100                 105
```

<210> SEQ ID NO 365
<211> LENGTH: 104
<212> TYPE: PRT
<213> ORGANISM: Artificial Sequence
<220> FEATURE:
<223> OTHER INFORMATION: pNOP30388

<400> SEQUENCE: 365

```
Arg Arg Arg Arg Gly Gly Val Gly Arg Arg Gly Val Arg Pro Gly Arg
1               5                   10                  15

Val Arg Pro Gly Gly Thr Gly Arg Arg Gly Gly Asp Gly Gly Arg Ala
            20                  25                  30

Ala Ala Ala Arg Ala Ala Leu Gly Glu Leu Ala Arg Ala Leu Pro Gly
        35                  40                  45

His Leu Leu Gln Ser Gln Ser Ala Arg Arg Ala Ala Arg Met Ala Gln
    50                  55                  60

Leu Arg Arg Arg Ala Ala Ala Leu Pro Asn Ala Ala Ala Trp His Gly
65                  70                  75                  80

Pro Pro His Pro Gln Leu Pro Arg Ser Pro Leu Ala Leu Gln Arg Cys
                85                  90                  95

Arg Asp Thr Arg Trp Ala Ser Gly
            100
```

<210> SEQ ID NO 366
<211> LENGTH: 50
<212> TYPE: PRT
<213> ORGANISM: Artificial Sequence
<220> FEATURE:
<223> OTHER INFORMATION: pNOP140916

<400> SEQUENCE: 366

```
Thr Arg Ala Ser Pro Pro Arg Ser Ser Ser Ala Ile Ala Val Arg Ala
1               5                   10                  15

Ser Cys Cys Pro Tyr Gly Ser Thr Ser Thr Ala Ser Arg Ser Pro Thr
            20                  25                  30

Gln Arg Cys Arg Leu Ala Arg Ala Ala Ala Ser Thr Ala Thr Glu Cys
        35                  40                  45

Ile Leu
    50
```

<210> SEQ ID NO 367
<211> LENGTH: 81
<212> TYPE: PRT
<213> ORGANISM: Artificial Sequence
<220> FEATURE:
<223> OTHER INFORMATION: pNOP54515

<400> SEQUENCE: 367

```
Glu Leu Gln Glu Thr Gly His Arg Gln Val Ala Leu Arg Arg Ser Gly
1               5                   10                  15

Arg Pro Pro Lys Cys Ala Glu Arg Pro Gly Ala Ala Asp Thr Gly Ala
```

```
            20                  25                  30

His Cys Thr Ser Thr Asp Gly Arg Leu Lys Ile Ser Val Glu Thr Tyr
        35                  40                  45

Thr Val Ser Ser Gln Leu Leu Met Val Leu Met Ser Leu Asp Leu Asp
    50                  55                  60

Thr Gly Leu Val Pro Ser Leu Val Ser Lys Cys Leu Ile Leu Arg Val
65                  70                  75                  80

Lys


<210> SEQ ID NO 368
<211> LENGTH: 29
<212> TYPE: PRT
<213> ORGANISM: Artificial Sequence
<220> FEATURE:
<223> OTHER INFORMATION: pNOP301515

<400> SEQUENCE: 368

Arg Thr Ala Tyr Phe Cys Gln Tyr His Thr Ala Ser Val Tyr Ser Glu
1               5                   10                  15

Arg Ala Met Pro Pro Gly Cys Pro Glu Pro Ser Gln Ala
            20                  25


<210> SEQ ID NO 369
<211> LENGTH: 10
<212> TYPE: PRT
<213> ORGANISM: Artificial Sequence
<220> FEATURE:
<223> OTHER INFORMATION: pNOP700435

<400> SEQUENCE: 369

Lys Ser Asp Ala Ser Arg Leu Ser Gly Ala
1               5                   10


<210> SEQ ID NO 370
<211> LENGTH: 23
<212> TYPE: DNA
<213> ORGANISM: Artificial Sequence
<220> FEATURE:
<223> OTHER INFORMATION: sequence comprising a linker amino acid
      encoding sequence
<220> FEATURE:
<221> NAME/KEY: CDS
<222> LOCATION: (1)..(21)

<400> SEQUENCE: 370

cta tac agg cga atg aga tta tg                                       23
Leu Tyr Arg Arg Met Arg Leu
1               5


<210> SEQ ID NO 371
<211> LENGTH: 7
<212> TYPE: PRT
<213> ORGANISM: Artificial Sequence
<220> FEATURE:
<223> OTHER INFORMATION: Synthetic Construct

<400> SEQUENCE: 371

Leu Tyr Arg Arg Met Arg Leu
1               5


<210> SEQ ID NO 372
<211> LENGTH: 23
<212> TYPE: DNA
<213> ORGANISM: Artificial Sequence
<220> FEATURE:
```

```
<223> OTHER INFORMATION: sequence comprising a linker amino acid
      encoding sequence
<220> FEATURE:
<221> NAME/KEY: CDS
<222> LOCATION: (2)..(22)

<400> SEQUENCE: 372

c tat aca ggc gaa tga gat tat g                                    23
  Tyr Thr Gly Glu     Asp Tyr
  1                   5


<210> SEQ ID NO 373
<211> LENGTH: 4
<212> TYPE: PRT
<213> ORGANISM: Artificial Sequence
<220> FEATURE:
<223> OTHER INFORMATION: Synthetic Construct

<400> SEQUENCE: 373

Tyr Thr Gly Glu
1


<210> SEQ ID NO 374
<211> LENGTH: 66
<212> TYPE: DNA
<213> ORGANISM: Artificial Sequence
<220> FEATURE:
<223> OTHER INFORMATION: p21.3 seq
<220> FEATURE:
<221> NAME/KEY: CDS
<222> LOCATION: (1)..(66)

<400> SEQUENCE: 374

gca gtt ggg ctc cgc gcc gtg gag cag cag cag ctc cgc cac tcg ggc      48
Ala Val Gly Leu Arg Ala Val Glu Gln Gln Gln Leu Arg His Ser Gly
1               5                   10                  15

gct gcc cat cat cat gac                                              66
Ala Ala His His His Asp
            20


<210> SEQ ID NO 375
<211> LENGTH: 22
<212> TYPE: PRT
<213> ORGANISM: Artificial Sequence
<220> FEATURE:
<223> OTHER INFORMATION: Synthetic Construct

<400> SEQUENCE: 375

Ala Val Gly Leu Arg Ala Val Glu Gln Gln Gln Leu Arg His Ser Gly
1               5                   10                  15

Ala Ala His His His Asp
            20


<210> SEQ ID NO 376
<211> LENGTH: 63
<212> TYPE: DNA
<213> ORGANISM: Artificial Sequence
<220> FEATURE:
<223> OTHER INFORMATION: frameshift
<220> FEATURE:
<221> NAME/KEY: CDS
<222> LOCATION: (1)..(63)

<400> SEQUENCE: 376

cag ttg ggc tcc gcg ccg tgg agc agc agc agc tcc gcc act cgg gcg      48
Gln Leu Gly Ser Ala Pro Trp Ser Ser Ser Ser Ser Ala Thr Arg Ala
1               5                   10                  15
```

-continued

```
ctg ccc atc atc atg                                              63
Leu Pro Ile Ile Met
            20


<210> SEQ ID NO 377
<211> LENGTH: 21
<212> TYPE: PRT
<213> ORGANISM: Artificial Sequence
<220> FEATURE:
<223> OTHER INFORMATION: Synthetic Construct

<400> SEQUENCE: 377

Gln Leu Gly Ser Ala Pro Trp Ser Ser Ser Ser Ser Ala Thr Arg Ala
1               5                   10                  15

Leu Pro Ile Ile Met
            20
```